(12) United States Patent
Thompson et al.

(10) Patent No.: US 11,911,044 B2
(45) Date of Patent: *Feb. 27, 2024

(54) RESECTION LINE GUIDE FOR A MEDICAL PROCEDURE AND METHOD OF USING SAME

(71) Applicant: Standard Bariatrics, Inc., Cincinnati, OH (US)

(72) Inventors: Jonathan R. Thompson, Cincinnati, OH (US); Ryan Weitzel, Liberty Township, OH (US); Bennie Thompson, Blue Ash, OH (US); Richard P. Nuchols, Williamsburg, OH (US)

(*) Notice: Subject to any disclaimer, the term of this patent is extended or adjusted under 35 U.S.C. 154(b) by 410 days.

This patent is subject to a terminal disclaimer.

(21) Appl. No.: 17/227,557

(22) Filed: Apr. 12, 2021

(65) Prior Publication Data

US 2021/0228213 A1    Jul. 29, 2021

Related U.S. Application Data

(63) Continuation of application No. 16/353,837, filed on Mar. 14, 2019, now Pat. No. 10,987,108, which is a
(Continued)

(51) Int. Cl.
*A61B 17/12* (2006.01)
*A61B 17/122* (2006.01)
(Continued)

(52) U.S. Cl.
CPC ...... *A61B 17/122* (2013.01); *A61B 17/00234* (2013.01); *A61B 17/068* (2013.01);
(Continued)

(58) Field of Classification Search
CPC .......... A61B 17/2909; A61B 17/00234; A61B 17/22; A61B 17/122; A61B 17/068;
(Continued)

(56) References Cited

U.S. PATENT DOCUMENTS

| 848,126 | A | 3/1907 | Roosevelt |
| 1,413,896 | A | 4/1922 | Harold |

(Continued)

FOREIGN PATENT DOCUMENTS

| CA | 2663002 A1 | 10/2009 |
| EP | 140552 A2 | 5/1985 |

(Continued)

OTHER PUBLICATIONS

De Petz, A; Aseptic Technic of Stomach Resections; 86 Annals of Surgery 388; Sep. 1927; 5 pages.

(Continued)

*Primary Examiner* — Erich G Herbermann

(57) ABSTRACT

A clamp for a medical procedure includes a first clamp member, a second clamp member, a hinge, a biasing member, a shaft, and an actuator. The hinge couples the first ends of the first and second clamp members such that the first clamp member is pivotable relative to the second clamp member. The biasing member couples the second ends of the first and second clamp members and is configured to apply a clamping force. The distal end of the shaft and the biasing member are fixedly coupled with at least one of the first clamp member or the second clamp member for a duration of the medical procedure. The actuator is operatively coupled with the biasing member such that the actuator selectively tensions the biasing member to provide the clamping force.

19 Claims, 60 Drawing Sheets

Related U.S. Application Data continuation of application No. 15/105,198, filed as application No. PCT/US2014/070869 on Dec. 17, 2014, now Pat. No. 10,278,707.

(60) Provisional application No. 62/046,700, filed on Sep. 5, 2014, provisional application No. 61/917,342, filed on Dec. 17, 2013.

(51) Int. Cl.

| | | |
|---|---|---|
| *A61B 17/00* | (2006.01) | |
| *A61F 5/00* | (2006.01) | |
| *A61B 17/068* | (2006.01) | |
| A61B 17/072 | (2006.01) | |
| A61B 17/29 | (2006.01) | |
| A61B 17/32 | (2006.01) | |
| A61B 5/107 | (2006.01) | |
| A61B 90/00 | (2016.01) | |

(52) U.S. Cl.
CPC ...... *A61B 17/12009* (2013.01); *A61F 5/0083* (2013.01); *A61B 5/1076* (2013.01); *A61B 17/07207* (2013.01); *A61B 17/1227* (2013.01); *A61B 2017/0046* (2013.01); *A61B 2017/00066* (2013.01); *A61B 2017/00115* (2013.01); *A61B 2017/00314* (2013.01); *A61B 2017/00358* (2013.01); *A61B 2017/00407* (2013.01); *A61B 2017/00818* (2013.01); *A61B 2017/00867* (2013.01); *A61B 2017/00876* (2013.01); *A61B 2017/00902* (2013.01); *A61B 2017/00991* (2013.01); *A61B 2017/07285* (2013.01); *A61B 2017/2927* (2013.01); *A61B 2017/2929* (2013.01); *A61B 2017/2946* (2013.01); *A61B 2017/320052* (2013.01); *A61B 2090/061* (2016.02); *A61B 2090/0807* (2016.02)

(58) Field of Classification Search
CPC ........ A61B 17/12009; A61B 17/07207; A61B 17/1227; A61B 2017/2919; A61B 2017/2927; A61B 2017/320052; A61B 2017/00818; A61B 2017/00066; A61B 2017/00115; A61B 2017/00314; A61B 2017/00358; A61B 2017/00407; A61B 2017/0046; A61B 2017/00867; A61B 2017/00876; A61B 2017/00902; A61B 2017/00991; A61B 2017/07285; A61B 2017/2929; A61B 2017/2946; A61B 2090/061; A61B 2090/0807; A61B 5/1076; A61F 5/0083; A61F 5/0086

See application file for complete search history.

(56) References Cited

U.S. PATENT DOCUMENTS

| | | | |
|---|---|---|---|
| 2,659,371 A | 11/1953 | Schnee | |
| 2,686,520 A | 8/1954 | Jarvis et al. | |
| 3,017,637 A | 1/1962 | Sampson | |
| 3,490,675 A | 1/1970 | Green et al. | |
| 3,551,987 A | 1/1971 | Wilkinson | |
| 3,877,434 A | 4/1975 | Ferguson | |
| 4,216,891 A | 8/1980 | Behlke | |
| 4,269,190 A | 5/1981 | Behney | |
| 4,319,576 A | 3/1982 | Rothfuss | |
| 4,354,628 A | 10/1982 | Green | |
| 4,442,964 A | 4/1984 | Becht | |
| 4,458,681 A | 7/1984 | Hopkins | |
| 4,494,057 A | 1/1985 | Hotta | |
| 4,520,817 A | 6/1985 | Green | |
| 4,527,724 A | 7/1985 | Chow et al. | |
| 4,558,699 A | 12/1985 | Bashour | |
| 4,605,001 A | 8/1986 | Rothfuss et al. | |
| 4,605,004 A | 8/1986 | Di Giovanni et al. | |
| 4,608,981 A | 9/1986 | Rothfuss et al. | |
| 4,610,383 A | 9/1986 | Rothfuss et al. | |
| 4,617,928 A | 10/1986 | Alfranca | |
| 4,632,290 A | 12/1986 | Green et al. | |
| 4,633,861 A | 1/1987 | Chow et al. | |
| 4,676,774 A | 6/1987 | Semm et al. | |
| 4,679,557 A | 7/1987 | Opie et al. | |
| 4,705,038 A | 11/1987 | Sjostrom et al. | |
| 4,784,137 A | 11/1988 | Kulik et al. | |
| 4,803,985 A | 2/1989 | Hill | |
| 4,819,853 A | 4/1989 | Green | |
| 4,848,637 A | 7/1989 | Pruitt | |
| 4,930,503 A | 6/1990 | Pruitt | |
| 4,935,006 A | 6/1990 | Hasson | |
| 4,941,623 A | 7/1990 | Pruitt | |
| 4,951,861 A | 8/1990 | Schulze et al. | |
| 4,976,721 A | 12/1990 | Blasnik et al. | |
| 4,978,049 A | 12/1990 | Green | |
| 5,040,715 A | 8/1991 | Green et al. | |
| 5,136,220 A | 8/1992 | Philipp | |
| 5,152,744 A | 10/1992 | Krause et al. | |
| 5,176,651 A | 1/1993 | Allgood et al. | |
| 5,205,459 A | 4/1993 | Brinkerhoff et al. | |
| 5,219,111 A | 6/1993 | Bilotti et al. | |
| 5,221,036 A | 6/1993 | Takase | |
| 5,222,961 A | 6/1993 | Nakao et al. | |
| 5,258,009 A | 11/1993 | Conners | |
| 5,295,977 A | 3/1994 | Cohen | |
| 5,307,976 A | 5/1994 | Olson et al. | |
| 5,308,576 A | 5/1994 | Green et al. | |
| 5,312,410 A | 5/1994 | Miller et al. | |
| 5,327,914 A | 7/1994 | Shlain | |
| 5,333,772 A | 8/1994 | Rothfuss et al. | |
| 5,345,949 A | 9/1994 | Shlain | |
| 5,389,098 A | 2/1995 | Tsuruta et al. | |
| 5,395,030 A | 3/1995 | Kuramoto et al. | |
| 5,395,034 A | 3/1995 | Allen et al. | |
| 5,413,267 A | 5/1995 | Solyntjes et al. | |
| 5,415,334 A | 5/1995 | Williamson et al. | |
| 5,431,323 A | 7/1995 | Smith et al. | |
| 5,443,475 A | 8/1995 | Auerbach et al. | |
| 5,452,836 A | 9/1995 | Huitema et al. | |
| 5,452,837 A | 9/1995 | Williamson et al. | |
| 5,456,401 A | 10/1995 | Green et al. | |
| 5,465,895 A | 11/1995 | Knodel et al. | |
| 5,465,896 A | 11/1995 | Allen et al. | |
| 5,469,840 A | 11/1995 | Tanii et al. | |
| 5,470,006 A | 11/1995 | Rodak | |
| 5,470,009 A | 11/1995 | Rodak | |
| 5,480,089 A | 1/1996 | Blewett | |
| 5,485,952 A | 1/1996 | Fontayne | |
| 5,487,500 A | 1/1996 | Knodel et al. | |
| 5,496,333 A | 3/1996 | Sackier et al. | |
| 5,503,638 A | 4/1996 | Cooper et al. | |
| 5,507,426 A | 4/1996 | Young et al. | |
| 5,507,773 A | 4/1996 | Huitema et al. | |
| 5,514,098 A | 5/1996 | Pfoslgraf et al. | |
| 5,531,744 A | 7/1996 | Nardella et al. | |
| 5,549,621 A | 8/1996 | Bessler et al. | |
| 5,551,622 A | 9/1996 | Yoon | |
| 5,554,169 A | 9/1996 | Green et al. | |
| 5,560,530 A | 10/1996 | Bolanos et al. | |
| 5,562,702 A | 10/1996 | Huitema et al. | |
| 5,571,116 A | 11/1996 | Bolanos et al. | |
| 5,571,131 A | 11/1996 | Ek et al. | |
| 5,586,711 A | 12/1996 | Plyley et al. | |
| 5,597,107 A | 1/1997 | Knodel et al. | |
| 5,630,540 A | 5/1997 | Blewett | |
| 5,632,432 A | 5/1997 | Schulze et al. | |
| 5,636,780 A | 6/1997 | Green et al. | |
| 5,655,698 A | 8/1997 | Yoon | |
| 5,662,667 A | 9/1997 | Knodel | |
| 5,676,674 A | 10/1997 | Bolanos et al. | |
| 5,689,159 A | 11/1997 | Culp et al. | |
| 5,697,542 A | 12/1997 | Knodel et al. | |
| 5,702,409 A | 12/1997 | Rayburn et al. | |

(56) References Cited

U.S. PATENT DOCUMENTS

| | | |
|---|---|---|
| 5,704,534 A | 1/1998 | Huitema et al. |
| 5,707,369 A | 1/1998 | Vaitekunas |
| 5,732,871 A | 3/1998 | Clark et al. |
| 5,762,256 A | 6/1998 | Mastri et al. |
| 5,779,130 A | 7/1998 | Alesi et al. |
| 5,779,132 A | 7/1998 | Knodel et al. |
| 5,782,396 A | 7/1998 | Mastri et al. |
| 5,797,538 A | 8/1998 | Heaton et al. |
| 5,810,240 A | 9/1998 | Robertson |
| 5,814,055 A | 9/1998 | Knodel et al. |
| 5,819,240 A | 10/1998 | Kara |
| 5,820,009 A | 10/1998 | Melling et al. |
| 5,865,361 A | 2/1999 | Milliman et al. |
| 5,868,760 A | 2/1999 | Mcguckin, Jr. |
| 5,871,135 A | 2/1999 | Williamson, IV et al. |
| 5,901,895 A | 5/1999 | Heaton et al. |
| 5,902,312 A | 5/1999 | Frater et al. |
| 5,954,259 A | 9/1999 | Viola et al. |
| 5,964,394 A | 10/1999 | Robertson |
| 5,980,248 A | 11/1999 | Kusakabe et al. |
| 5,988,479 A | 11/1999 | Palmer |
| 6,032,849 A | 3/2000 | Mastri et al. |
| 6,048,330 A | 4/2000 | Atala |
| 6,099,551 A | 8/2000 | Gabbay |
| 6,264,087 B1 | 7/2001 | Whitman |
| 6,270,507 B1 | 8/2001 | Callicrate |
| 6,315,184 B1 | 11/2001 | Whitman |
| 6,325,810 B1 | 12/2001 | Hamilton et al. |
| 6,345,754 B1 | 2/2002 | Jeng |
| 6,439,541 B1 | 8/2002 | Nosel et al. |
| 6,488,196 B1 | 12/2002 | Fenton |
| 6,505,768 B2 | 1/2003 | Whitman |
| 6,511,490 B2 | 1/2003 | Robert |
| 6,616,446 B1 | 9/2003 | Schmid |
| 6,716,233 B1 | 4/2004 | Whitman |
| 6,769,590 B2 | 8/2004 | Vresh et al. |
| 6,793,652 B1 | 9/2004 | Whitman et al. |
| 6,835,199 B2 | 12/2004 | Mcguckin et al. |
| RE38,708 E | 3/2005 | Bolanos et al. |
| 6,953,138 B1 | 10/2005 | Dworak et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,025,791 B2 | 4/2006 | Levine et al. |
| 7,032,799 B2 | 4/2006 | Viola et al. |
| 7,037,344 B2 | 5/2006 | Kagan et al. |
| 7,044,353 B2 | 5/2006 | Mastri et al. |
| 7,070,083 B2 | 7/2006 | Jankowski |
| 7,128,253 B2 | 10/2006 | Mastri et al. |
| 7,134,587 B2 | 11/2006 | Schwemberger et al. |
| 7,175,648 B2 | 2/2007 | Nakao |
| 7,207,472 B2 | 4/2007 | Wukusick et al. |
| 7,225,964 B2 | 6/2007 | Mastri et al. |
| 7,229,428 B2 | 6/2007 | Gannoe et al. |
| 7,235,089 B1 | 6/2007 | Mcguckin, Jr. |
| 7,258,262 B2 | 8/2007 | Mastri et al. |
| 7,278,562 B2 | 10/2007 | Mastri et al. |
| 7,278,563 B1 | 10/2007 | Green |
| 7,288,100 B2 | 10/2007 | Molina Trigueros |
| 7,308,998 B2 | 12/2007 | Mastri et al. |
| RE40,237 E | 4/2008 | Bilotti et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,076 B2 | 8/2008 | Racenet et al. |
| 7,422,138 B2 | 9/2008 | Bilotti et al. |
| 7,434,716 B2 | 10/2008 | Viola |
| 7,434,717 B2 | 10/2008 | Shelton, IV et al. |
| 7,438,209 B1 | 10/2008 | Hess et al. |
| 7,455,676 B2 | 11/2008 | Holsten et al. |
| 7,467,740 B2 | 12/2008 | Shelton, IV et al. |
| 7,472,815 B2 | 1/2009 | Shelton, IV et al. |
| 7,481,349 B2 | 1/2009 | Holsten et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,549,654 B2 | 6/2009 | Anderson et al. |
| 7,565,993 B2 | 7/2009 | Milliman et al. |
| 7,588,175 B2 | 9/2009 | Timm et al. |
| 7,588,176 B2 | 9/2009 | Timm et al. |
| 7,588,177 B2 | 9/2009 | Racenet |
| 7,604,151 B2 | 10/2009 | Hess et al. |
| 7,617,961 B2 | 11/2009 | Viola |
| 7,635,074 B2 | 12/2009 | Olson et al. |
| 7,641,091 B2 | 1/2010 | Olson et al. |
| 7,645,285 B2 | 1/2010 | Cosgrove et al. |
| 7,658,312 B2 | 2/2010 | Vidal et al. |
| 7,665,647 B2 | 2/2010 | Shelton, IV et al. |
| 7,669,746 B2 | 3/2010 | Shelton, IV |
| 7,669,747 B2 | 3/2010 | Weisenburgh et al. |
| 7,673,781 B2 | 3/2010 | Swayze et al. |
| 7,673,782 B2 | 3/2010 | Hess et al. |
| 7,690,547 B2 | 4/2010 | Racenet et al. |
| 7,694,864 B2 | 4/2010 | Okada et al. |
| 7,704,264 B2 | 4/2010 | Ewers et al. |
| 7,708,684 B2 | 5/2010 | Demarais et al. |
| 7,717,312 B2 | 5/2010 | Beetel |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,744,613 B2 | 6/2010 | Ewers et al. |
| 7,758,493 B2 | 7/2010 | Gingras |
| 7,770,774 B2 | 8/2010 | Mastri et al. |
| 7,775,967 B2 | 8/2010 | Gertner |
| D624,182 S | 9/2010 | Thouement |
| 7,793,812 B2 | 9/2010 | Moore et al. |
| 7,794,475 B2 | 9/2010 | Hess et al. |
| 7,815,092 B2 | 10/2010 | Whitman et al. |
| 7,819,896 B2 | 10/2010 | Racenet |
| 7,828,188 B2 | 11/2010 | Jankowski |
| 7,837,079 B2 | 11/2010 | Holsten et al. |
| 7,846,149 B2 | 12/2010 | Jankowski |
| 7,857,184 B2 | 12/2010 | Viola |
| 7,866,525 B2 | 1/2011 | Scirica |
| 7,866,528 B2 | 1/2011 | Olson et al. |
| 7,871,416 B2 | 1/2011 | Phillips |
| 7,891,531 B1 | 2/2011 | Ward |
| 7,891,533 B2 | 2/2011 | Green et al. |
| 7,913,893 B2 | 3/2011 | Mastri et al. |
| 7,918,869 B2 | 4/2011 | Saadat et al. |
| 7,934,630 B2 | 5/2011 | Shelton, IV et al. |
| 7,955,340 B2 | 6/2011 | Michlitsch et al. |
| 7,959,050 B2 | 6/2011 | Smith et al. |
| 7,963,907 B2 | 6/2011 | Gertner |
| 7,966,799 B2 | 6/2011 | Morgan et al. |
| 7,992,757 B2 | 8/2011 | Wheeler et al. |
| 7,997,469 B2 | 8/2011 | Olson et al. |
| 8,016,176 B2 | 9/2011 | Kasvikis et al. |
| 8,020,741 B2 | 9/2011 | Cole et al. |
| 8,028,884 B2 | 10/2011 | Sniffin et al. |
| 8,033,442 B2 | 10/2011 | Racenet et al. |
| 8,034,077 B2 | 10/2011 | Smith et al. |
| 8,052,697 B2 | 11/2011 | Phillips |
| 8,056,788 B2 | 11/2011 | Mastri et al. |
| 8,061,577 B2 | 11/2011 | Racenet et al. |
| 8,062,236 B2 | 11/2011 | Soltz |
| 8,066,168 B2 | 11/2011 | Vidal et al. |
| 8,070,034 B1 | 12/2011 | Knodel |
| 8,070,036 B1 | 12/2011 | Knodel |
| 8,087,563 B2 | 1/2012 | Milliman et al. |
| 8,091,756 B2 | 1/2012 | Viola |
| 8,096,459 B2 | 1/2012 | Ortiz et al. |
| 8,113,406 B2 | 2/2012 | Holsten et al. |
| 8,132,704 B2 | 3/2012 | Whitman et al. |
| 8,141,762 B2 | 3/2012 | Bedi et al. |
| 8,147,506 B2 | 4/2012 | Ortiz et al. |
| 8,167,186 B2 | 5/2012 | Racenet et al. |
| 8,172,122 B2 | 5/2012 | Kasvikis et al. |
| 8,186,560 B2 | 5/2012 | Hess et al. |
| 8,196,795 B2 | 6/2012 | Moore et al. |

(56) References Cited

U.S. PATENT DOCUMENTS

| | | |
|---|---|---|
| 8,205,780 B2 | 6/2012 | Sorrentino et al. |
| 8,210,415 B2 | 7/2012 | Ward |
| 8,216,159 B1 | 7/2012 | Leiboff |
| 8,220,690 B2 | 7/2012 | Hess et al. |
| 8,226,602 B2 | 7/2012 | Quijana et al. |
| 8,245,898 B2 | 8/2012 | Smith et al. |
| 8,252,009 B2 | 8/2012 | Weller et al. |
| 8,256,655 B2 | 9/2012 | Sniffin et al. |
| 8,276,801 B2 | 10/2012 | Zemlok et al. |
| 8,292,153 B2 | 10/2012 | Jankowski |
| 8,308,725 B2 | 11/2012 | Bell et al. |
| 8,317,070 B2 | 11/2012 | Hueil et al. |
| 8,322,455 B2 | 12/2012 | Shelton, IV et al. |
| 8,328,061 B2 | 12/2012 | Kasvikis |
| 8,328,064 B2 | 12/2012 | Racenet et al. |
| 8,343,175 B2 | 1/2013 | Ewers et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,436 B2 | 1/2013 | Kasvikis |
| 8,360,297 B2 | 1/2013 | Shelton, IV et al. |
| 8,365,973 B1 | 2/2013 | White et al. |
| 8,365,976 B2 | 2/2013 | Hess et al. |
| 8,382,775 B1 | 2/2013 | Bender et al. |
| 8,393,513 B2 | 3/2013 | Jankowski |
| 8,393,514 B2 | 3/2013 | Shelton, IV et al. |
| 8,403,956 B1 | 3/2013 | Thompson et al. |
| 8,408,442 B2 | 4/2013 | Racenet et al. |
| 8,424,739 B2 | 4/2013 | Racenet et al. |
| 8,439,244 B2 | 5/2013 | Holcomb et al. |
| 8,439,246 B1 | 5/2013 | Knodel |
| 8,449,460 B2 | 5/2013 | Duke et al. |
| 8,449,560 B2 | 5/2013 | Roth et al. |
| 8,453,912 B2 | 6/2013 | Mastri et al. |
| 8,453,914 B2 | 6/2013 | Laurent et al. |
| 8,464,923 B2 | 6/2013 | Shelton, IV |
| 8,465,507 B2 | 6/2013 | Cosgrove et al. |
| 8,469,252 B2 | 6/2013 | Holcomb et al. |
| 8,469,977 B2 | 6/2013 | Balbierz et al. |
| 8,479,969 B2 | 7/2013 | Shelton, IV |
| 8,485,412 B2 | 7/2013 | Shelton, IV et al. |
| 8,496,155 B2 | 7/2013 | Knodel |
| 8,496,156 B2 | 7/2013 | Sniffin et al. |
| 8,499,993 B2 | 8/2013 | Shelton, IV et al. |
| 8,523,041 B2 | 9/2013 | Ishitsuki et al. |
| 8,529,585 B2 | 9/2013 | Jacobs et al. |
| 8,540,128 B2 | 9/2013 | Shelton, IV et al. |
| 8,540,130 B2 | 9/2013 | Moore et al. |
| 8,544,712 B2 | 10/2013 | Jankowski |
| 8,561,872 B2 | 10/2013 | Wheeler et al. |
| 8,573,465 B2 | 11/2013 | Shelton, IV |
| 8,574,243 B2 | 11/2013 | Saadat et al. |
| 8,579,176 B2 | 11/2013 | Smith et al. |
| 8,579,178 B2 | 11/2013 | Holsten et al. |
| 8,590,762 B2 | 11/2013 | Hess et al. |
| 8,596,513 B2 | 12/2013 | Olson et al. |
| 8,608,043 B2 | 12/2013 | Scirica |
| 8,608,046 B2 | 12/2013 | Laurent et al. |
| 8,613,384 B2 | 12/2013 | Pastorelli et al. |
| 8,616,431 B2 | 12/2013 | Timm et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |
| 8,663,245 B2 | 3/2014 | Francischelli et al. |
| 8,668,130 B2 | 3/2014 | Hess et al. |
| 8,672,208 B2 | 3/2014 | Hess et al. |
| 8,672,830 B2 | 3/2014 | Dlugos, Jr. et al. |
| 8,701,958 B2 | 4/2014 | Shelton, IV et al. |
| 8,714,429 B2 | 5/2014 | Demmy |
| 8,720,766 B2 | 5/2014 | Hess et al. |
| 8,727,197 B2 | 5/2014 | Hess et al. |
| 8,727,199 B2 | 5/2014 | Wenchell |
| 8,733,613 B2 | 5/2014 | Huitema et al. |
| 8,740,035 B2 | 6/2014 | Mastri et al. |
| 8,758,392 B2 | 6/2014 | Crainich |
| 8,763,875 B2 | 7/2014 | Morgan et al. |
| 8,800,838 B2 | 8/2014 | Shelton, IV |
| 8,800,840 B2 | 8/2014 | Jankowski |
| 8,801,732 B2 | 8/2014 | Harris et al. |
| 8,808,161 B2 | 8/2014 | Gregg |
| 8,808,325 B2 | 8/2014 | Hess et al. |
| 8,840,004 B2 | 9/2014 | Holsten et al. |
| 8,852,218 B2 | 10/2014 | Hughett, Sr. et al. |
| 8,864,009 B2 | 10/2014 | Shelton, IV et al. |
| 8,882,766 B2 | 11/2014 | Couture |
| 8,899,465 B2 | 12/2014 | Shelton, IV et al. |
| 8,925,788 B2 | 1/2015 | Hess et al. |
| 8,945,163 B2 | 2/2015 | Voegele et al. |
| 8,956,390 B2 | 2/2015 | Shah et al. |
| 8,973,804 B2 | 3/2015 | Hess et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,998,058 B2 | 4/2015 | Moore et al. |
| 9,011,437 B2 | 4/2015 | Woodruff |
| 9,016,541 B2 | 4/2015 | Viola et al. |
| 9,033,203 B2 | 5/2015 | Woodard, Jr. et al. |
| 9,050,084 B2 | 6/2015 | Schmid et al. |
| 9,066,721 B2 | 6/2015 | Ichihara et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,119,627 B2 | 9/2015 | Cosgrove et al. |
| 9,138,226 B2 | 9/2015 | Racenet et al. |
| 9,149,325 B2 | 10/2015 | Worrell et al. |
| 9,155,528 B2 | 10/2015 | Bender et al. |
| 9,168,039 B1 | 10/2015 | Knodel |
| 9,179,911 B2 | 11/2015 | Morgan et al. |
| 9,180,035 B2 | 11/2015 | Stack et al. |
| 9,211,120 B2 | 12/2015 | Scheib et al. |
| 9,216,019 B2 | 12/2015 | Schmid et al. |
| 9,254,131 B2 | 2/2016 | Soltz et al. |
| 9,289,206 B2 | 3/2016 | Hess et al. |
| 9,289,207 B2 | 3/2016 | Shelton, IV |
| 9,307,981 B2 | 4/2016 | Mikkaichi et al. |
| 9,314,362 B2 | 4/2016 | Bender et al. |
| 9,326,768 B2 | 5/2016 | Shelton, IV |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,408,604 B2 | 8/2016 | Shelton, IV et al. |
| 9,433,411 B2 | 9/2016 | Racenet et al. |
| 9,439,633 B2 | 9/2016 | O'Dea |
| 9,498,219 B2 | 11/2016 | Moore et al. |
| 9,549,733 B2 | 1/2017 | Knodel |
| 9,561,032 B2 | 2/2017 | Shelton, IV et al. |
| 9,603,595 B2 | 3/2017 | Shelton, IV et al. |
| 9,603,598 B2 | 3/2017 | Shelton, IV et al. |
| 9,615,952 B2 | 4/2017 | Scott et al. |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,687,237 B2 | 6/2017 | Schmid et al. |
| 9,693,816 B2 | 7/2017 | Orszulak |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,093 B2 | 8/2017 | Farascioni et al. |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,795,380 B2 | 10/2017 | Shelton, IV et al. |
| 9,801,627 B2 | 10/2017 | Harris et al. |
| 9,801,628 B2 | 10/2017 | Harris et al. |
| 9,801,630 B2 | 10/2017 | Harris et al. |
| 9,808,246 B2 | 11/2017 | Shelton, IV et al. |
| 9,808,257 B2 | 11/2017 | Armenteros et al. |
| 9,820,742 B2 | 11/2017 | Covach et al. |

(56) References Cited

U.S. PATENT DOCUMENTS

| | | |
|---|---|---|
| 9,827,002 B2 | 11/2017 | Hausen et al. |
| 9,844,370 B2 | 12/2017 | Viola et al. |
| 9,848,873 B2 | 12/2017 | Shelton, IV |
| 9,848,875 B2 | 12/2017 | Aronhalt et al. |
| 9,848,878 B2 | 12/2017 | Racenet et al. |
| 9,855,040 B2 | 1/2018 | Kostrzewski |
| 9,861,366 B2 | 1/2018 | Aranyi |
| 9,872,682 B2 | 1/2018 | Hess et al. |
| 9,901,344 B2 | 2/2018 | Moore et al. |
| 9,901,346 B2 | 2/2018 | Moore et al. |
| 9,913,646 B2 | 3/2018 | Shelton, IV |
| 9,924,947 B2 | 3/2018 | Shelton, IV et al. |
| 9,936,953 B2 | 4/2018 | Thompson et al. |
| 9,937,001 B2 | 4/2018 | Nakamura |
| 9,980,729 B2 | 5/2018 | Moore et al. |
| 9,999,426 B2 | 6/2018 | Moore et al. |
| 9,999,431 B2 | 6/2018 | Shelton, IV et al. |
| 10,004,505 B2 | 6/2018 | Moore et al. |
| 10,045,780 B2 | 8/2018 | Adams et al. |
| 10,085,751 B2 | 10/2018 | Overmyer |
| 10,085,754 B2 | 10/2018 | Sniffin et al. |
| 10,130,360 B2 | 11/2018 | Olson et al. |
| 10,130,363 B2 | 11/2018 | Huitema et al. |
| 10,172,616 B2 | 1/2019 | Murray et al. |
| 10,194,912 B2 | 2/2019 | Scheib et al. |
| 10,226,250 B2 | 3/2019 | Beckman et al. |
| 10,231,734 B2 | 3/2019 | Thompson et al. |
| 10,238,517 B2 | 3/2019 | Gingras |
| 10,245,032 B2 | 4/2019 | Shelton, IV |
| 10,258,334 B2 | 4/2019 | Adams et al. |
| 10,265,073 B2 | 4/2019 | Scheib et al. |
| 10,278,695 B2 | 5/2019 | Milo |
| 10,278,699 B2 | 5/2019 | Thompson et al. |
| 10,278,707 B2 | 5/2019 | Thompson et al. |
| 10,285,712 B2 | 5/2019 | Cosgrove, III et al. |
| 10,285,837 B1 | 5/2019 | Thompson et al. |
| 10,292,706 B2 | 5/2019 | Jankowski |
| 10,307,161 B2 | 6/2019 | Jankowski |
| 10,307,163 B2 | 6/2019 | Moore et al. |
| 10,314,580 B2 | 6/2019 | Scheib et al. |
| 10,314,589 B2 | 6/2019 | Shelton, IV et al. |
| 10,342,538 B2 | 7/2019 | Racenet et al. |
| 10,383,628 B2 | 8/2019 | Kang et al. |
| 10,390,826 B2 | 8/2019 | Badawi |
| 10,405,856 B2 | 9/2019 | Knodel |
| 10,405,860 B2 | 9/2019 | Thompson et al. |
| 10,420,559 B2 | 9/2019 | Marczyk et al. |
| 10,420,560 B2 | 9/2019 | Shelton, IV et al. |
| 10,441,283 B1 | 10/2019 | Thompson et al. |
| 10,456,571 B2 | 10/2019 | Cairns |
| 10,470,911 B2 | 11/2019 | Thompson et al. |
| 10,485,540 B2 | 11/2019 | Hodgkinson et al. |
| 10,499,912 B2 | 12/2019 | Scheib et al. |
| 10,537,325 B2 | 1/2020 | Bakos et al. |
| 10,542,986 B2 | 1/2020 | Thompson et al. |
| 10,548,597 B2 | 2/2020 | Dunki-Jacobs et al. |
| 10,610,226 B2 | 4/2020 | Shelton et al. |
| 10,624,638 B2 | 4/2020 | Thompson et al. |
| 10,687,807 B2 | 6/2020 | Simms et al. |
| 10,687,810 B2 | 6/2020 | Shelton et al. |
| 10,687,814 B2 | 6/2020 | Dunki-Jacobs et al. |
| 10,716,564 B2 | 7/2020 | Shelton, IV |
| 10,758,231 B2 | 9/2020 | Harris et al. |
| 10,849,623 B2 | 12/2020 | Dunki-Jacobs et al. |
| 10,912,562 B2 | 2/2021 | Dunki-Jacobs et al. |
| 10,966,721 B2 | 4/2021 | Dunki-Jacobs et al. |
| 10,987,108 B2 | 4/2021 | Thompson et al. |
| 11,173,060 B2 | 11/2021 | Thompson et al. |
| 11,197,672 B2 | 12/2021 | Dunki-Jacobs et al. |
| 2001/0044656 A1 | 11/2001 | Williamson, IV et al. |
| 2002/0143346 A1 | 10/2002 | Mcguckin, Jr. et al. |
| 2003/0125734 A1 | 7/2003 | Mollenauer |
| 2003/0135091 A1 | 7/2003 | Nakazawa et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0006372 A1 | 1/2004 | Racenet et al. |
| 2004/0068267 A1 | 4/2004 | Harvie et al. |
| 2004/0181239 A1 | 9/2004 | Dorn et al. |
| 2004/0215216 A1 | 10/2004 | Gannoe et al. |
| 2005/0006432 A1 | 1/2005 | Racenet et al. |
| 2005/0080444 A1 | 4/2005 | Kraemer et al. |
| 2005/0139633 A1 | 6/2005 | Wukusick et al. |
| 2005/0203547 A1 | 9/2005 | Weller et al. |
| 2005/0203548 A1 | 9/2005 | Weller et al. |
| 2005/0256533 A1 | 11/2005 | Roth et al. |
| 2006/0011698 A1 | 1/2006 | Okada et al. |
| 2006/0016853 A1 | 1/2006 | Racenet |
| 2006/0020277 A1 | 1/2006 | Gostout et al. |
| 2006/0036267 A1 | 2/2006 | Saadat et al. |
| 2006/0041270 A1 | 2/2006 | Lenker et al. |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | Mcguckin et al. |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0034667 A1 | 2/2007 | Holsten et al. |
| 2007/0039997 A1 | 2/2007 | Mather et al. |
| 2007/0056932 A1 | 3/2007 | Whitman et al. |
| 2007/0075114 A1 | 4/2007 | Shelton et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0213743 A1 | 9/2007 | Mcguckin, Jr. |
| 2007/0246505 A1 | 10/2007 | Pace-Floridia et al. |
| 2007/0262116 A1 | 11/2007 | Hueil et al. |
| 2008/0015631 A1 | 1/2008 | Lee et al. |
| 2008/0023522 A1 | 1/2008 | Olson et al. |
| 2008/0033457 A1 | 2/2008 | Francischelli et al. |
| 2008/0035702 A1 | 2/2008 | Holsten et al. |
| 2008/0041918 A1 | 2/2008 | Holsten et al. |
| 2008/0058716 A1 | 3/2008 | Dubrul et al. |
| 2008/0078800 A1 | 4/2008 | Hess et al. |
| 2008/0082124 A1 | 4/2008 | Hess et al. |
| 2008/0087707 A1 | 4/2008 | Jankowski |
| 2008/0097332 A1 | 4/2008 | Greenhalgh et al. |
| 2008/0149684 A1 | 6/2008 | Viola |
| 2008/0164297 A1 | 7/2008 | Holsten et al. |
| 2008/0169329 A1 | 7/2008 | Shelton et al. |
| 2008/0169332 A1 | 7/2008 | Shelton et al. |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2008/0294179 A1 | 11/2008 | Balbierz et al. |
| 2008/0308602 A1 | 12/2008 | Timm et al. |
| 2009/0001122 A1 | 1/2009 | Prommersberger et al. |
| 2009/0001130 A1 | 1/2009 | Hess et al. |
| 2009/0012556 A1 | 1/2009 | Boudreaux et al. |
| 2009/0020584 A1 | 1/2009 | Soltz et al. |
| 2009/0078739 A1 | 3/2009 | Viola |
| 2009/0095791 A1 | 4/2009 | Eskaros et al. |
| 2009/0101692 A1 | 4/2009 | Whitman et al. |
| 2009/0134200 A1 | 5/2009 | Tarinelli et al. |
| 2009/0173766 A1 | 7/2009 | Wenchell |
| 2009/0209946 A1 | 8/2009 | Swayze et al. |
| 2009/0209986 A1* | 8/2009 | Stewart ............... A61B 17/122 606/157 |
| 2009/0212088 A1 | 8/2009 | Okada et al. |
| 2009/0255974 A1 | 10/2009 | Viola |
| 2009/0261144 A1 | 10/2009 | Sniffin et al. |
| 2009/0308907 A1 | 12/2009 | Nalagatla et al. |
| 2010/0010512 A1 | 1/2010 | Taylor et al. |
| 2010/0072255 A1 | 3/2010 | Olson et al. |
| 2010/0072258 A1 | 3/2010 | Farascioni et al. |
| 2010/0108739 A1 | 5/2010 | Holsten et al. |
| 2010/0114124 A1 | 5/2010 | Kelleher et al. |
| 2010/0121356 A1 | 5/2010 | Hartmann et al. |

(56) References Cited

U.S. PATENT DOCUMENTS

| | | |
|---|---|---|
| 2010/0137904 A1 | 6/2010 | Wenchell |
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0004062 A1 | 1/2011 | Asai et al. |
| 2011/0017800 A1 | 1/2011 | Viola |
| 2011/0036888 A1 | 2/2011 | Pribanic et al. |
| 2011/0046437 A1* | 2/2011 | Kassab .............. A61F 5/0013 606/157 |
| 2011/0046653 A1 | 2/2011 | Addington et al. |
| 2011/0071555 A1 | 3/2011 | Mcbrayer et al. |
| 2011/0084113 A1 | 4/2011 | Bedi et al. |
| 2011/0087169 A1 | 4/2011 | Parihar et al. |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 7/2011 | Gagner et al. |
| 2011/0186614 A1 | 8/2011 | Kasvikis |
| 2011/0190791 A1 | 8/2011 | Jacobs et al. |
| 2011/0208211 A1 | 8/2011 | Whitfield et al. |
| 2011/0226837 A1 | 9/2011 | Baxter, III et al. |
| 2011/0278343 A1 | 11/2011 | Knodel et al. |
| 2011/0290851 A1 | 12/2011 | Shelton, IV |
| 2011/0315739 A1 | 12/2011 | Sniffin et al. |
| 2012/0035631 A1* | 2/2012 | Hughett, Sr ....... A61B 17/1285 606/157 |
| 2012/0059400 A1 | 3/2012 | Williamson, IV et al. |
| 2012/0080494 A1 | 4/2012 | Thompson et al. |
| 2012/0116379 A1 | 5/2012 | Yates et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0234899 A1 | 9/2012 | Scheib et al. |
| 2012/0234900 A1 | 9/2012 | Swayze |
| 2012/0248169 A1 | 10/2012 | Widenhouse et al. |
| 2012/0277525 A1 | 11/2012 | O'Dea |
| 2012/0286022 A1 | 11/2012 | Olson et al. |
| 2012/0289979 A1 | 11/2012 | Eskaros et al. |
| 2013/0062394 A1 | 3/2013 | Smith et al. |
| 2013/0075447 A1 | 3/2013 | Weisenburgh, II et al. |
| 2013/0075450 A1 | 3/2013 | Schmid et al. |
| 2013/0092718 A1 | 4/2013 | Soltz et al. |
| 2013/0105549 A1 | 5/2013 | Holsten et al. |
| 2013/0131440 A1 | 5/2013 | Gabriel |
| 2013/0146638 A1 | 6/2013 | Mandakolathur Vasudevan et al. |
| 2013/0146641 A1 | 6/2013 | Shelton, IV et al. |
| 2013/0146642 A1 | 6/2013 | Shelton, IV et al. |
| 2013/0153625 A1 | 6/2013 | Felder et al. |
| 2013/0153634 A1 | 6/2013 | Carter et al. |
| 2013/0153642 A1 | 6/2013 | Felder et al. |
| 2013/0161374 A1 | 6/2013 | Swayze et al. |
| 2013/0165774 A1 | 6/2013 | Nocca |
| 2013/0172929 A1 | 7/2013 | Hess et al. |
| 2013/0193190 A1 | 8/2013 | Carter et al. |
| 2013/0214025 A1 | 8/2013 | Zemlok et al. |
| 2013/0245652 A1 | 9/2013 | Cosgrove et al. |
| 2013/0256372 A1 | 10/2013 | Baxter, III et al. |
| 2013/0256375 A1 | 10/2013 | Shelton, IV et al. |
| 2013/0256377 A1 | 10/2013 | Schmid et al. |
| 2013/0284791 A1 | 10/2013 | Olson et al. |
| 2013/0306704 A1 | 11/2013 | Balbierz et al. |
| 2013/0327809 A1 | 12/2013 | Shelton, IV et al. |
| 2013/0334288 A1 | 12/2013 | Shelton, IV |
| 2013/0341374 A1 | 12/2013 | Shelton, IV et al. |
| 2014/0005678 A1 | 1/2014 | Shelton, IV et al. |
| 2014/0008412 A1 | 1/2014 | Zemlok et al. |
| 2014/0018722 A1 | 1/2014 | Scott et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0081176 A1 | 3/2014 | Hassan |
| 2014/0082497 A1 | 3/2014 | Chalouhi et al. |
| 2014/0107698 A1 | 4/2014 | Inge |
| 2014/0110457 A1 | 4/2014 | Zhang et al. |
| 2014/0114121 A1 | 4/2014 | Trivedi |
| 2014/0131418 A1 | 5/2014 | Kostrzewski |
| 2014/0131419 A1 | 5/2014 | Bettuchi |
| 2014/0144968 A1 | 5/2014 | Shelton, IV |
| 2014/0148731 A1 | 5/2014 | Radl et al. |
| 2014/0171744 A1 | 6/2014 | Racenet et al. |
| 2014/0183242 A1 | 7/2014 | Farascioni et al. |
| 2014/0184519 A1 | 7/2014 | Benchenaa et al. |
| 2014/0191015 A1 | 7/2014 | Shelton, IV |
| 2014/0214025 A1 | 7/2014 | Worrell et al. |
| 2014/0231489 A1 | 8/2014 | Balbierz et al. |
| 2014/0239037 A1 | 8/2014 | Boudreaux et al. |
| 2014/0257353 A1 | 9/2014 | Whitman et al. |
| 2014/0263570 A1 | 9/2014 | Hopkins et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0133740 A1 | 5/2015 | Dierking et al. |
| 2015/0157318 A1 | 6/2015 | Beardsley et al. |
| 2015/0173746 A1 | 6/2015 | Baxter, III et al. |
| 2015/0173755 A1 | 6/2015 | Baxter, III et al. |
| 2015/0173762 A1 | 6/2015 | Shelton, IV et al. |
| 2015/0209034 A1 | 7/2015 | Viola et al. |
| 2015/0265276 A1 | 9/2015 | Huitema et al. |
| 2015/0297224 A1 | 10/2015 | Hall et al. |
| 2015/0297227 A1 | 10/2015 | Huitema et al. |
| 2015/0320423 A1 | 11/2015 | Aranyi |
| 2015/0351764 A1 | 12/2015 | Shelton, IV |
| 2016/0058447 A1 | 3/2016 | Posada et al. |
| 2016/0058594 A1 | 3/2016 | Armenteros et al. |
| 2016/0066916 A1 | 3/2016 | Overmyer et al. |
| 2016/0067074 A1 | 3/2016 | Thompson et al. |
| 2016/0089148 A1 | 3/2016 | Harris et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0213302 A1 | 7/2016 | Frushour |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0256152 A1 | 9/2016 | Kostrzewski |
| 2016/0262744 A1 | 9/2016 | Milo et al. |
| 2016/0262750 A1 | 9/2016 | Hausen et al. |
| 2016/0262921 A1 | 9/2016 | Balbierz et al. |
| 2016/0270792 A1 | 9/2016 | Sniffin et al. |
| 2016/0287251 A1 | 10/2016 | Shelton, IV |
| 2016/0296272 A1 | 10/2016 | Heard |
| 2016/0324527 A1 | 11/2016 | Thompson et al. |
| 2016/0354085 A1 | 12/2016 | Shelton, IV et al. |
| 2016/0367250 A1 | 12/2016 | Racenet et al. |
| 2017/0007248 A1 | 1/2017 | Shelton, IV et al. |
| 2017/0014125 A1 | 1/2017 | Shelton, IV et al. |
| 2017/0027633 A1 | 2/2017 | Wham |
| 2017/0055981 A1 | 3/2017 | Vendely et al. |
| 2017/0055991 A1 | 3/2017 | Kang |
| 2017/0056016 A1 | 3/2017 | Barton et al. |
| 2017/0086847 A1 | 3/2017 | Dinardo et al. |
| 2017/0095251 A1 | 4/2017 | Thompson et al. |
| 2017/0105728 A1 | 4/2017 | Scheib et al. |
| 2017/0172571 A1 | 6/2017 | Thompson et al. |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2017/0360447 A1 | 12/2017 | Armenteros et al. |
| 2017/0367697 A1 | 12/2017 | Shelton, IV et al. |
| 2018/0014826 A1 | 1/2018 | Scheib et al. |
| 2018/0036000 A1 | 2/2018 | Terada et al. |
| 2018/0036005 A1 | 2/2018 | Covach et al. |
| 2018/0092641 A1 | 4/2018 | Aranyi |
| 2018/0168594 A1 | 6/2018 | Shelton, IV et al. |
| 2018/0168620 A1 | 6/2018 | Huang et al. |
| 2018/0168633 A1 | 6/2018 | Shelton, IV et al. |

(56) References Cited

U.S. PATENT DOCUMENTS

| | | |
|---|---|---|
| 2018/0199939 A1 | 7/2018 | Thompson et al. |
| 2018/0199941 A1 | 7/2018 | Thompson et al. |
| 2018/0235625 A1 | 8/2018 | Shelton, IV et al. |
| 2018/0235626 A1 | 8/2018 | Shelton, IV et al. |
| 2018/0280020 A1 | 10/2018 | Hess et al. |
| 2018/0317905 A1 | 11/2018 | Olson et al. |
| 2019/0000455 A1 | 1/2019 | Adams et al. |
| 2019/0046186 A1 | 2/2019 | Dunki-Jacobs et al. |
| 2019/0046189 A1 | 2/2019 | Dunki-Jacobs et al. |
| 2019/0046190 A1 | 2/2019 | Dunki-Jacobs et al. |
| 2019/0046191 A1 | 2/2019 | Dunki-Jacobs et al. |
| 2019/0046192 A1 | 2/2019 | Dunki-Jacobs et al. |
| 2019/0046193 A1 | 2/2019 | Dunki-Jacobs et al. |
| 2019/0105042 A1 | 4/2019 | Huitema et al. |
| 2019/0133577 A1 | 5/2019 | Weadock et al. |
| 2019/0150924 A1 | 5/2019 | Thompson et al. |
| 2019/0209173 A1 | 7/2019 | Thompson et al. |
| 2019/0209175 A1 | 7/2019 | Thompson et al. |
| 2019/0224029 A1 | 7/2019 | Thompson et al. |
| 2019/0261985 A1 | 8/2019 | Adams et al. |
| 2019/0261991 A1 | 8/2019 | Beckman et al. |
| 2019/0269408 A1 | 9/2019 | Jankowski |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0307450 A1 | 10/2019 | Thompson et al. |
| 2019/0343519 A1 | 11/2019 | Thompson et al. |
| 2019/0380742 A1 | 12/2019 | Hall et al. |
| 2019/0388092 A1 | 12/2019 | Thompson et al. |
| 2020/0008964 A1 | 1/2020 | Thompson et al. |
| 2020/0015822 A1 | 1/2020 | Marczyk et al. |
| 2020/0054326 A1 | 2/2020 | Harris et al. |
| 2020/0100790 A1 | 4/2020 | Dinardo et al. |
| 2020/0205810 A1 | 7/2020 | Posey et al. |
| 2020/0205827 A1 | 7/2020 | Bakos et al. |
| 2020/0206805 A1 | 7/2020 | Nalagatla et al. |
| 2020/0214703 A1 | 7/2020 | Thompson et al. |
| 2020/0229818 A1 | 7/2020 | Thompson et al. |
| 2020/0268385 A1 | 8/2020 | Dunki-Jacobs et al. |
| 2020/0297344 A1 | 9/2020 | Dunki-Jacobs et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305873 A1 | 10/2020 | Dunki-Jacobs et al. |
| 2020/0390443 A1 | 12/2020 | Thompson et al. |
| 2021/0128335 A1 | 5/2021 | Thompson et al. |
| 2021/0177411 A1 | 6/2021 | Williams |
| 2021/0369330 A1 | 12/2021 | Brandt |
| 2021/0393319 A1 | 12/2021 | Shelton, IV |

FOREIGN PATENT DOCUMENTS

| | | |
|---|---|---|
| EP | 399699 A1 | 11/1990 |
| EP | 503662 A1 | 9/1992 |
| EP | 666057 A2 | 8/1995 |
| EP | 669104 A1 | 8/1995 |
| EP | 1090592 A1 | 4/2001 |
| EP | 1616526 A1 | 1/2006 |
| EP | 1722691 A1 | 11/2006 |
| EP | 1769766 A1 | 4/2007 |
| EP | 1774916 A1 | 4/2007 |
| EP | 1806101 A1 | 7/2007 |
| EP | 1875868 A1 | 1/2008 |
| EP | 1875870 A1 | 1/2008 |
| EP | 1938759 A2 | 7/2008 |
| EP | 2005896 A2 | 12/2008 |
| EP | 2005897 A2 | 12/2008 |
| EP | 2005898 A2 | 12/2008 |
| EP | 2005899 A2 | 12/2008 |
| EP | 2005900 A2 | 12/2008 |
| EP | 2005901 A1 | 12/2008 |
| EP | 2019633 A1 | 2/2009 |
| EP | 2090247 A1 | 8/2009 |
| EP | 2111803 A2 | 10/2009 |
| EP | 2245993 A2 | 11/2010 |
| EP | 2319424 A1 | 5/2011 |
| EP | 2382928 A1 | 11/2011 |
| FR | 2731895 A1 | 9/1996 |
| GB | 2298905 A | 9/1996 |
| WO | 0154594 A1 | 8/2001 |
| WO | 2002060328 A1 | 8/2002 |
| WO | 03094747 A1 | 11/2003 |
| WO | 2007009099 A2 | 1/2007 |
| WO | 2007019268 A2 | 2/2007 |
| WO | 2007102152 A2 | 9/2007 |
| WO | 2008039238 A1 | 4/2008 |
| WO | 2008039249 A1 | 4/2008 |
| WO | 2008039250 A1 | 4/2008 |
| WO | 2008039270 A1 | 4/2008 |
| WO | 2008042021 A1 | 4/2008 |
| WO | 2008042022 A1 | 4/2008 |
| WO | 2008042043 A1 | 4/2008 |
| WO | 2008042044 A2 | 4/2008 |
| WO | 2008042045 A2 | 4/2008 |
| WO | 2008094210 A1 | 8/2008 |
| WO | 2008141288 A1 | 11/2008 |
| WO | 2009038550 A1 | 3/2009 |
| WO | 2010011661 A1 | 1/2010 |
| WO | 2011044032 A2 | 4/2011 |
| WO | 2011094700 A1 | 8/2011 |
| WO | 2012125615 A2 | 9/2012 |
| WO | 2012141679 A1 | 10/2012 |
| WO | 2013151888 A1 | 10/2013 |
| WO | 2014026170 A2 | 2/2014 |
| WO | 2014085099 A1 | 6/2014 |
| WO | 2015063609 A2 | 5/2015 |
| WO | 2015153324 A1 | 10/2015 |
| WO | 2015153340 A2 | 10/2015 |
| WO | 2016033221 A1 | 3/2016 |

OTHER PUBLICATIONS

Parker, G.; A New Stomach Clamp; 26 Postgrad Med. J. 550; Oct. 1950; 1 page.

Harrah, J. D.; A Lung Clamp for Use with Mechanical Staplers; 28 The Annals of Thoracic Surgery 489; Nov. 1979; 2 pages.

Steichen, F. M. et al.; Stapling in Surgery; Figures 1-11C; Year Book Medical Publishers, Inc.; 1984; 3 pages.

Regan, J. P. et al.; Early Experience with Two-Stage Laparoscopic Roux-en-Y Gastric Bypass as an Alternative in the Super-Super Obese Patient; Obes Surg; 13(6):861-4; Dec. 1, 2003; abstract only; 2 pages.

AtriCure, Inc.; 510(k) Summary for AtriClip LAA Exclusion System with preloaded Gillinov-Cosgrove Clip; published Jun. 10, 2010; 6 pages.

Jacobs, M. et al.; Laparoscopic sleeve gastrectomy: a retrospective review of 1- and 2-year results; Surg Endosc. Apr. 2010; 24(4): 781-5; doi: 10.1007/s00464-009-0619-8; Epub Aug. 19, 2009; abstract only; 2 pages.

LAAx, Inc.; 510(k) Summary for TigerPaw(R) System; published Oct. 29, 2010; 6 pages.

Zuckerman, B. D., Food and Drug Administration; Letter to AtriCure, Inc. Addressing Indication for Use of AtriClip LAA Exclusion System w/Pre-loaded Gillnov-Cosgrove Clip; Jun. 10, 2010; 3 pages.

Dept. of Health and Human Services; CMS Description of Open Left Atrial Appendage Occlusion with "U" Fastener Implant; Mar. 9, 2011; 1 page.

Pfiedler Enterprises; Science of Stapling: Urban Legend and Fact; Jun. 4, 2012; 38 pages.

Parikh, M. et al.; Surgical Strategies That May Decrease Leak After Laparoscopic Sleeve Gastrectomy; 257 Annals of Surgery 231; Feb. 2013; 7 pages.

International Search Report and Written Opinion of the International Searching Authority received in International Patent App. No. PCT/US2014/070869; mailed Apr. 21, 2015; 17 pages.

International Preliminary Report on Patentability and Written Opinion of the International Searching Authority received In International Patent App. No. PCT/US2015/048740; dated Mar. 7, 2017; 8 pages.

(56) References Cited

OTHER PUBLICATIONS

International Search Report and Written Opinion of the International Searching Authority received in International Patent App. No. PCT/US2015/022904; mailed Jun. 25, 2015; 6 pages.
International Search Report and Written Opinion of the International Searching Authority received in International Patent App. No. PCT/US2015/022990; mailed Sep. 30, 2015; 10 pages.
International Search Report and Written Opinion of the International Searching Authority received in International Patent App. No. PCT/US2015/048740; mailed Feb. 17, 2016; 12 pages.
European Search Report received in European U.S. Appl. No. 15/774,247; dated Dec. 23, 2016; 11 pages.
Supplementary Partial European Search Report received in European U.S. Appl. No. 14/872,137; dated Dec. 12, 2016; 5 pages.
Examination Report received in Australian Application No. 2016208416; dated May 18, 2017; 4 pages.
Supplementary European Search Report received in European U.S. Appl. No. 14/872,137; dated Mar. 28, 2017; 15 pages.
Supplementary European Search Report received in European U.S. Appl. No. 15/772,561; dated Mar. 15, 2017; 8 pages.
Examination Report received in Australian Application No. 2018203527; dated Oct. 22, 2018; 5 pages.
Examination Report received in European U.S. Appl. No. 15/772,561; dated Oct. 29, 2018; 7 pages.
International Preliminary Report on Patentability and Written Opinion of the International Searching Authority received In Application No. PCT/US2018/046743; dated Feb. 18, 2020; 17 pages.
International Search Report and Written Opinion of the International Searching Authority received in International Patent App. No. PCT/US2018/046743; mailed Dec. 4, 2018; 20 pages.
Search Report received in Chinese Application No. 201480075706.2; dated Nov. 28, 2018; 3 pages.
Examination Report received in Australian Application No. 2015241193; dated Dec. 11, 2018; 5 pages.
Examination Report received in Australian Application No. 2015241267; dated Feb. 25, 2019; 6 pages.
International Search Report and Written Opinion of the International Searching Authority received in International Patent Appln. No. PCT/US2022/021250; mailed Jun. 10, 2022; 12 pages.
Communication pursuant to Article 94(3) EPC received in European Patent Appln. No. 18 845 739.4; mailed Apr. 28, 2022; 9 pages.
Examination Report received in Australian Patent Appln. No. 2022204678; mailed Jul. 7, 2022; 4 pages.

\* cited by examiner

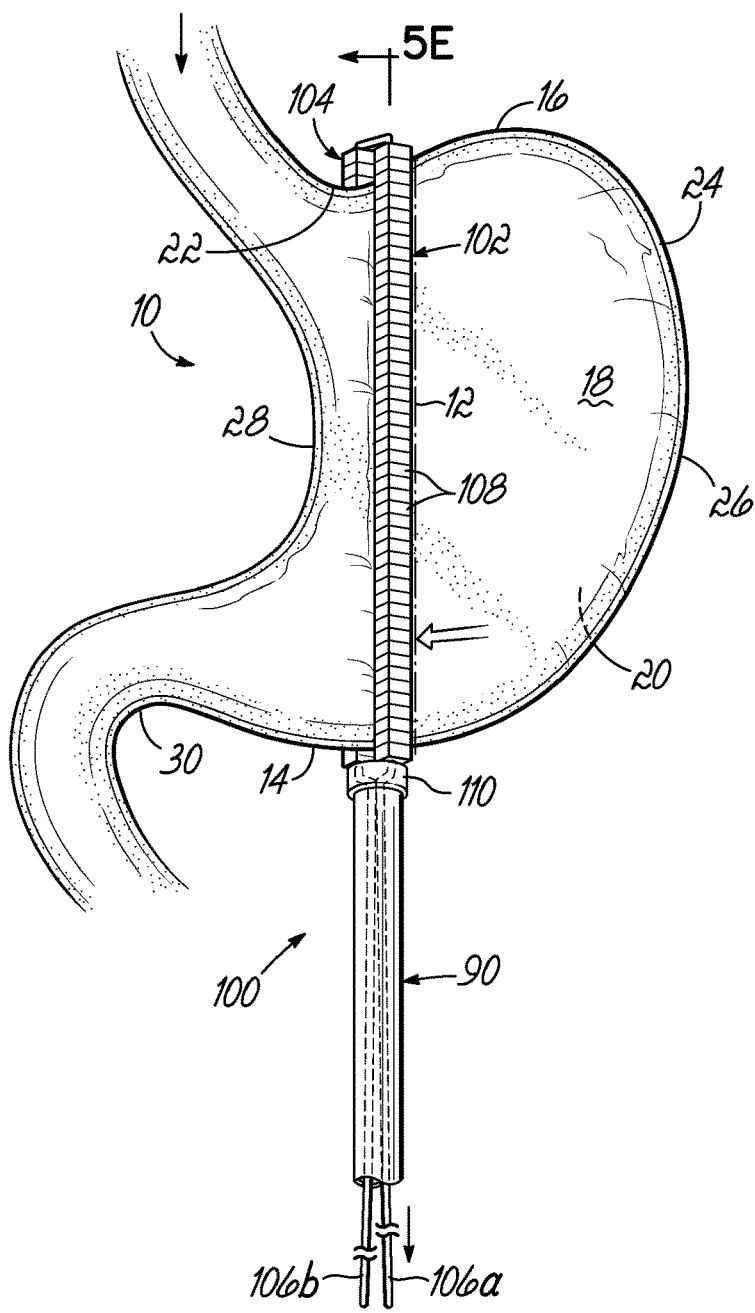
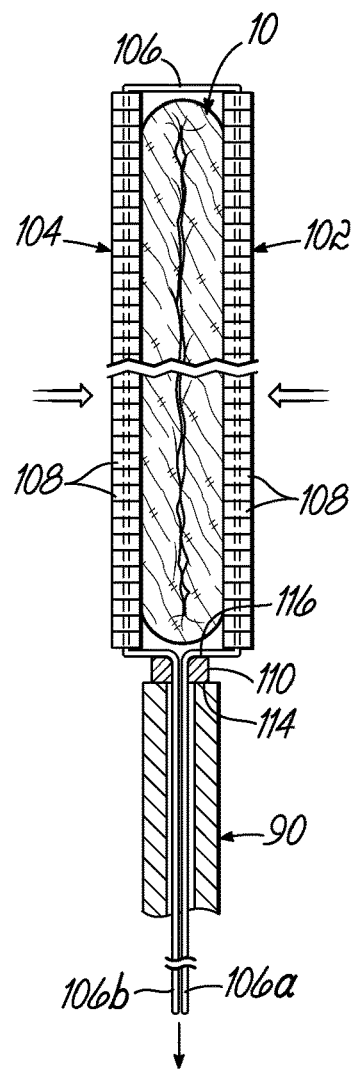
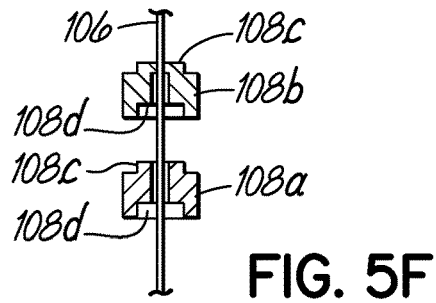
FIG. 5D
FIG. 5E
FIG. 5F

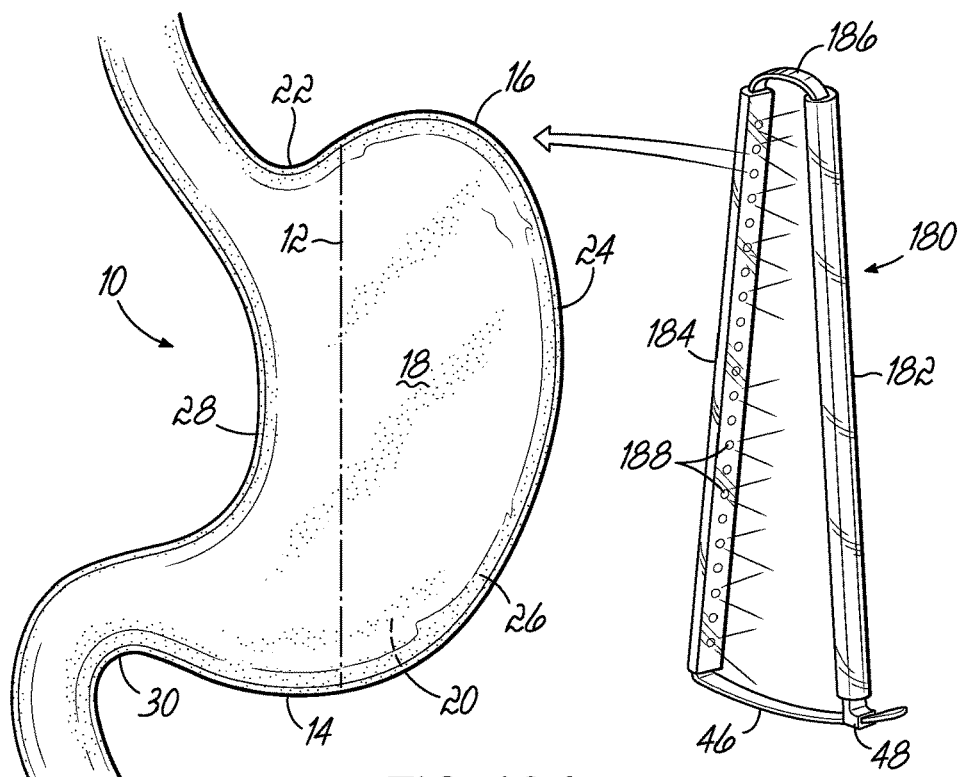
FIG. 10A
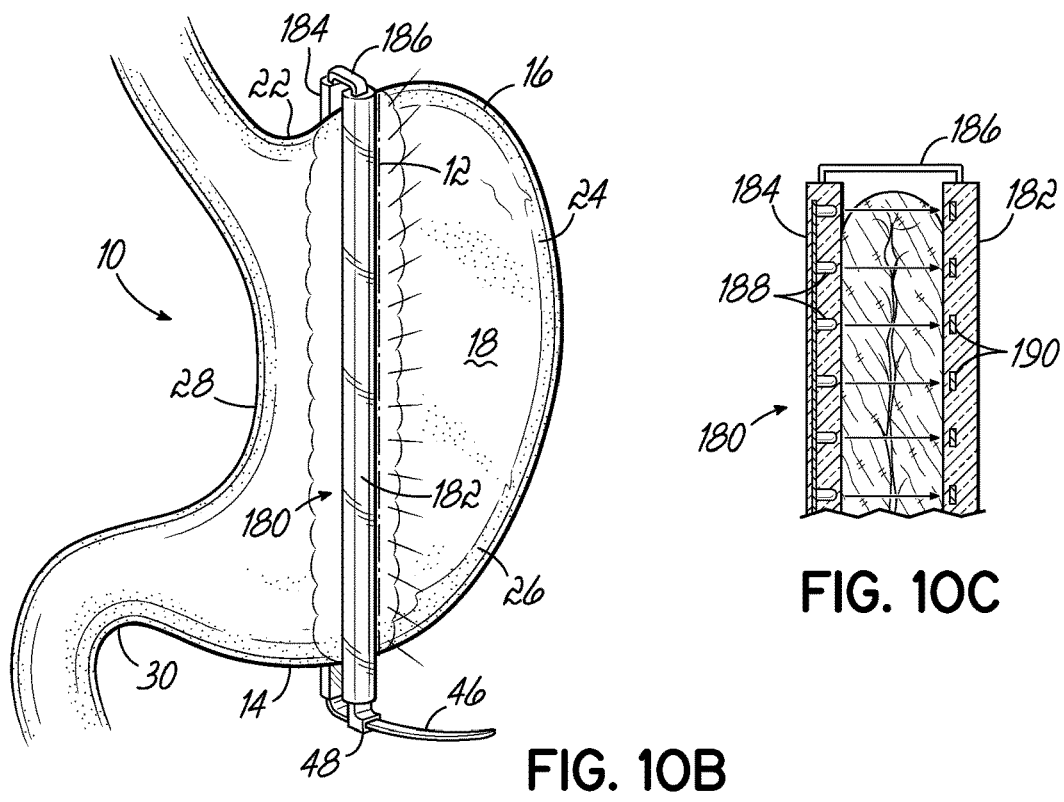
FIG. 10C
FIG. 10B

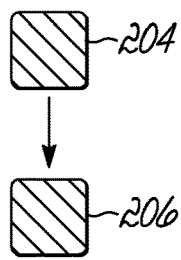 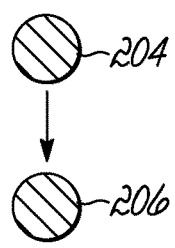 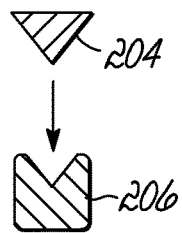 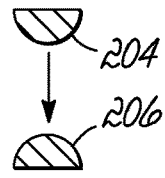
FIG. 12A     FIG. 12B     FIG. 12C     FIG. 12D
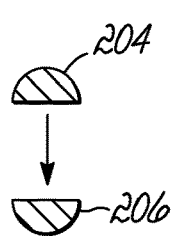 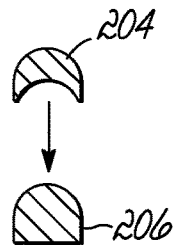 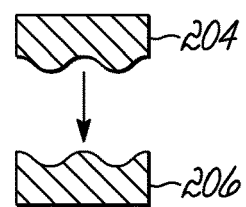
FIG. 12E     FIG. 12F     FIG. 12G
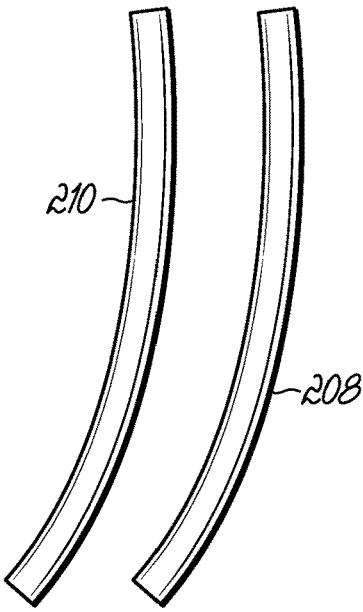 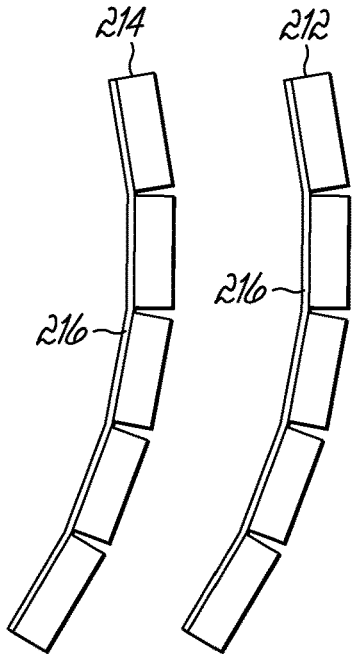
FIG. 13A     FIG. 13B

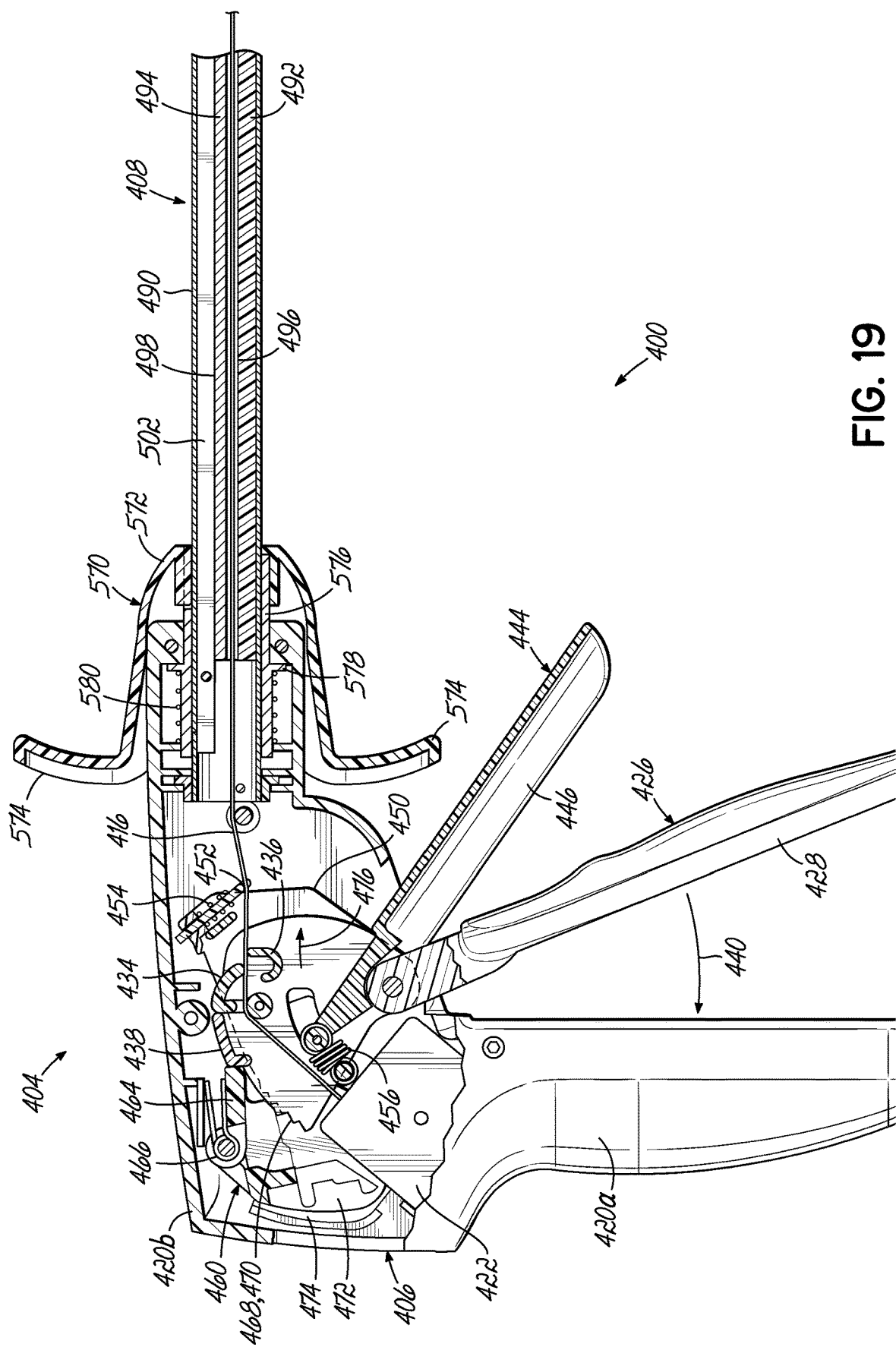

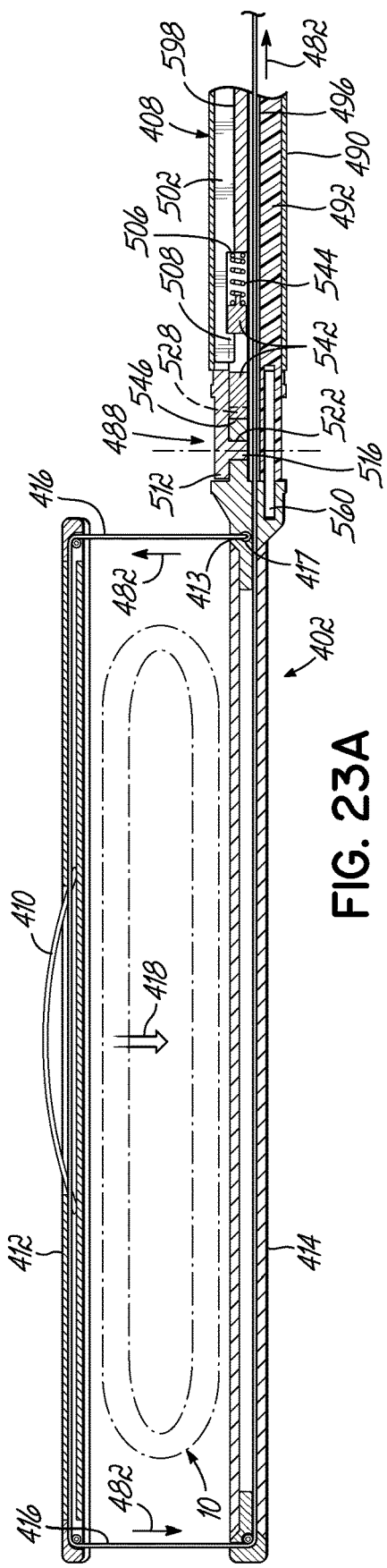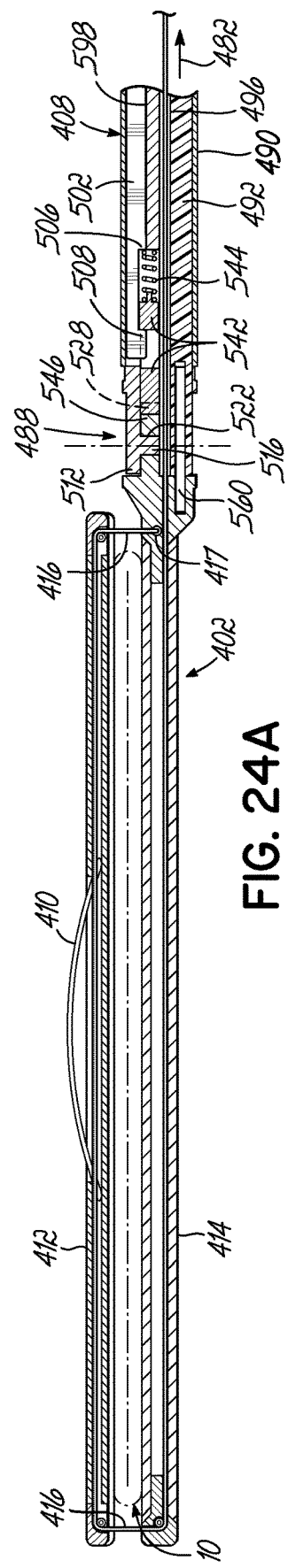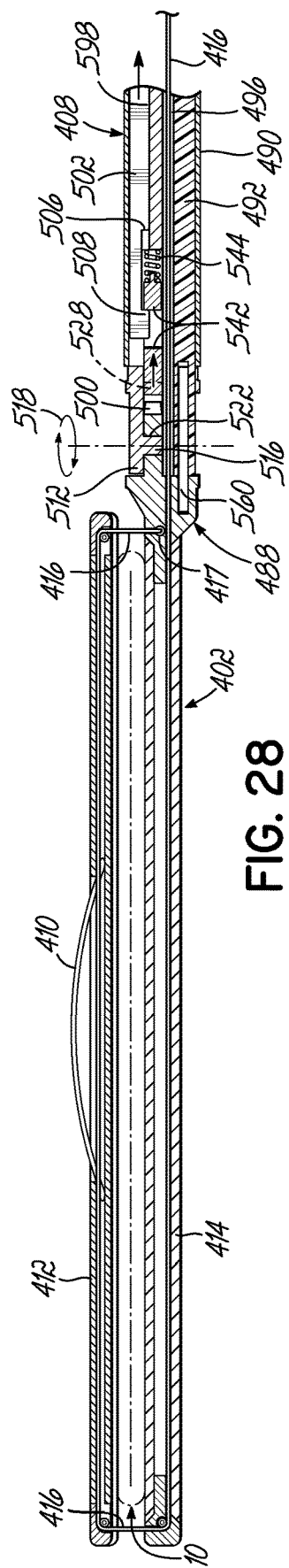

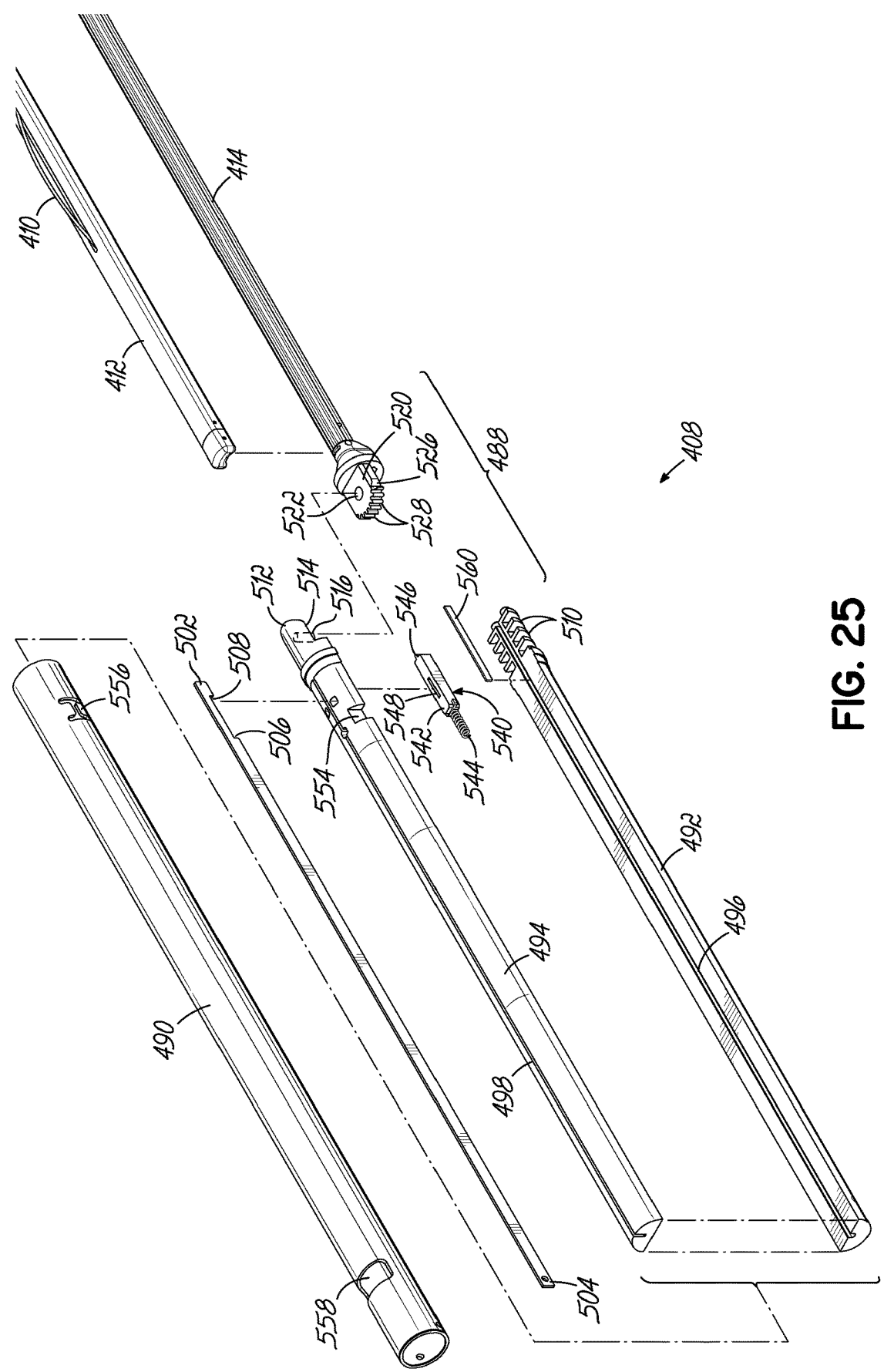

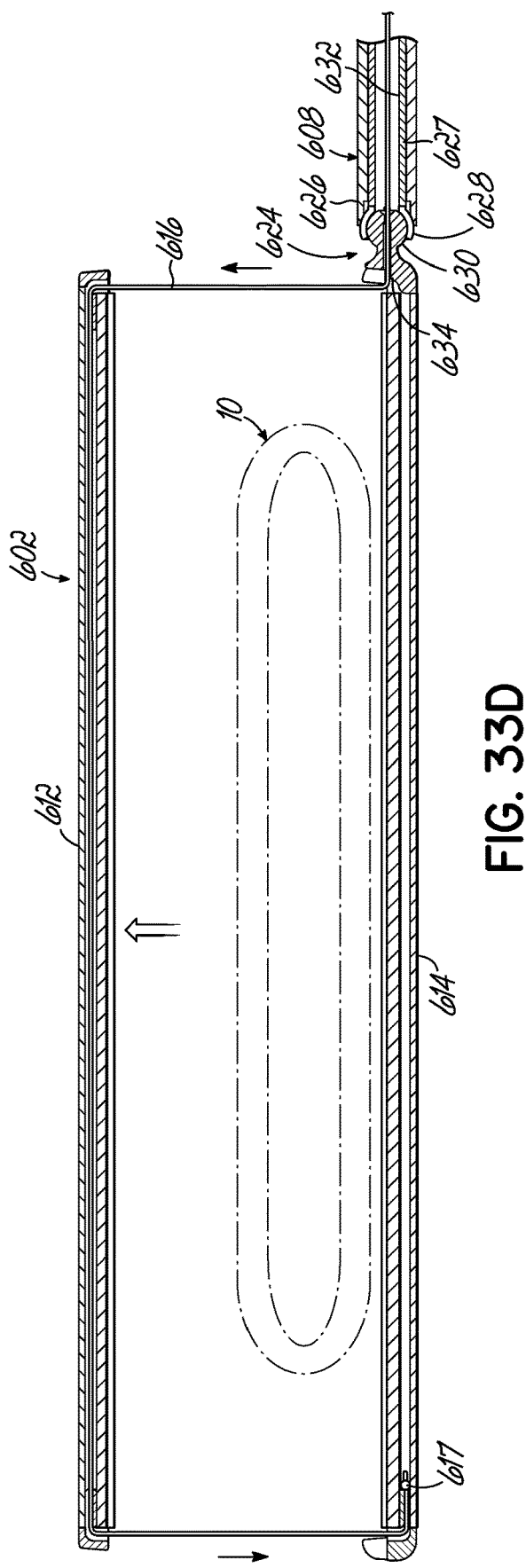
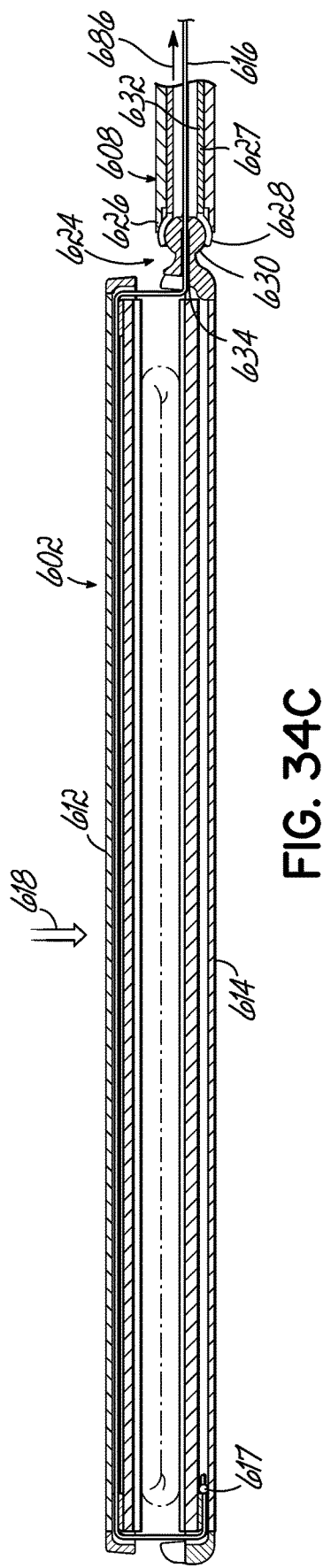
FIG. 33D
FIG. 34C

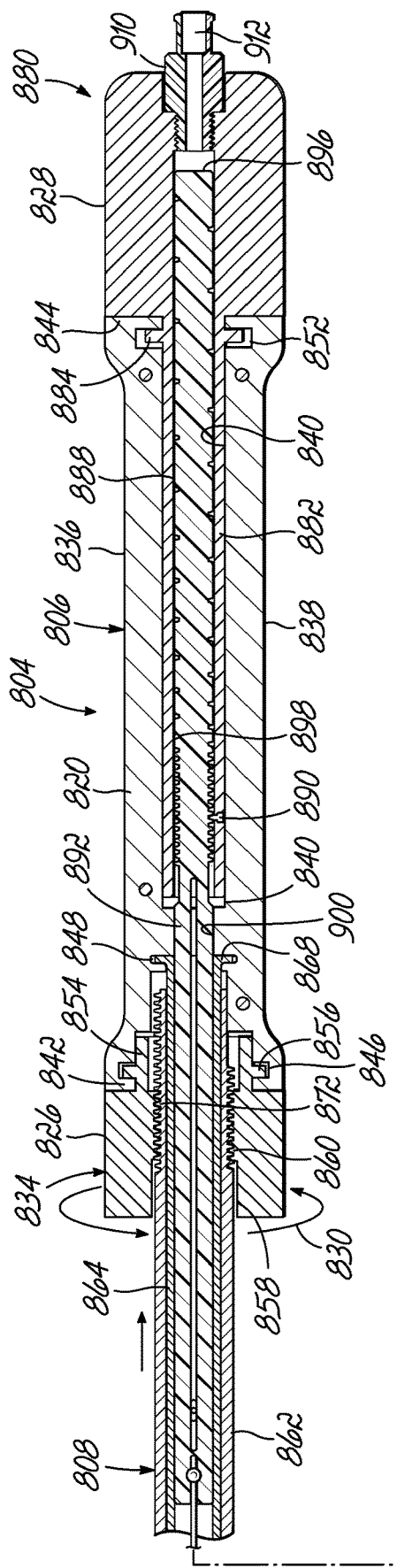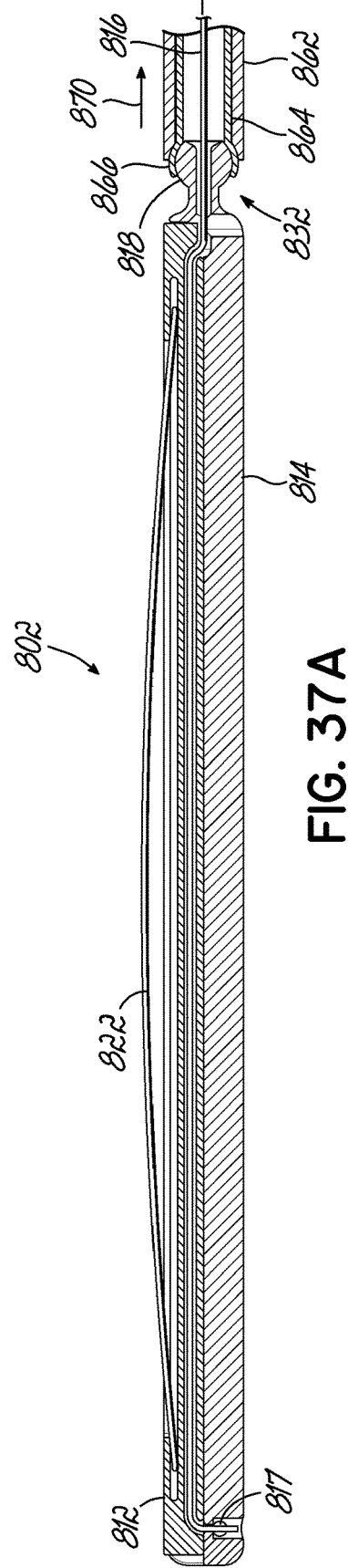
FIG. 37A

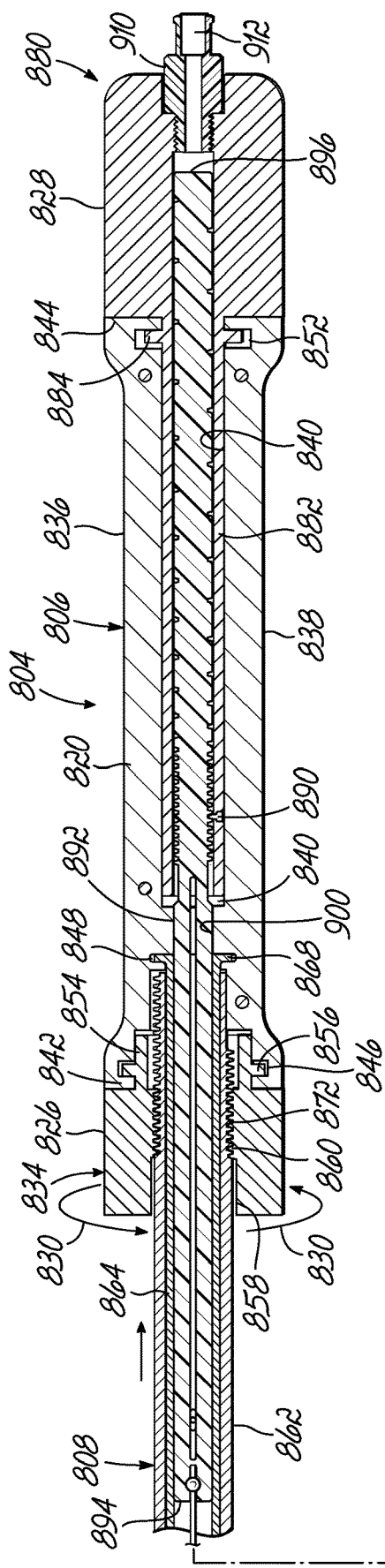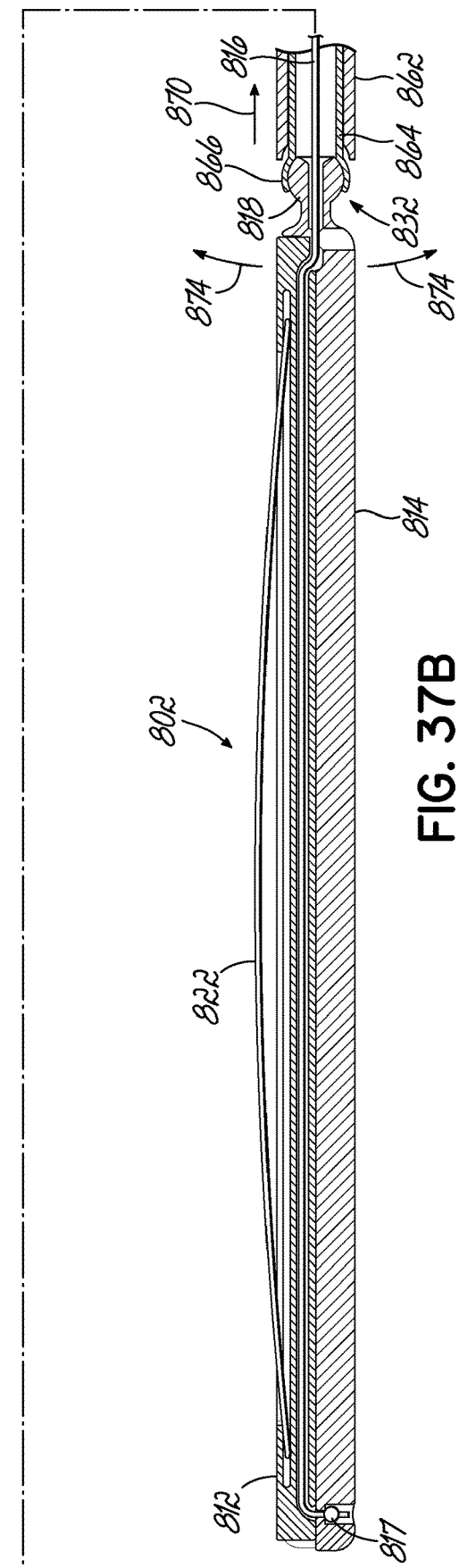
FIG. 37B

RESECTION LINE GUIDE FOR A MEDICAL PROCEDURE AND METHOD OF USING SAME

REFERENCE TO RELATED APPLICATIONS

The present application is a continuation of U.S. application Ser. No. 16/353,837, filed Mar. 14, 2019, which is a continuation of U.S. application Ser. No. 15/105,198, filed Jun. 16, 2016, which is a National Stage Entry of PCT/US2014/070869, filed Dec. 17, 2014, which claims the priority of U.S. provisional patent application Ser. No. 62/046,700, filed Sep. 5, 2014, and U.S. provisional patent application Ser. No. 61/917,342, filed Dec. 17, 2013, each of which are incorporated herein by reference in its entirety.

TECHNICAL FIELD

The technology relates to medical procedures, and more particularly to apparatuses and methods of using a resection line guide in various medical procedures.

BACKGROUND

Obesity, as a disease, affects a significant portion of the world's population. Obesity often leads to multiple chronic medical conditions and premature death from cardiovascular events and cancer. The U.S. Centers for Disease Control and Prevention ("CDC") reports that over 33% of the U.S. population is obese, with a body mass index ("BMI") of over 30, and another 35-40% of the population is overweight, with a BMI of 25-30. The CDC reports that the percent of the population being either overweight or obese by 2018 will be 75%. The CDC also reports that obesity directly costs the U.S. economy $147 billion currently, and projects that the costs will approach $315 billion by 2020. The increase in obesity and the financial impact on the local economy is not limited to the United States but impacts many countries throughout the world.

Obesity has environmental, genetic, and behavioral origins but is intractable to most medical and behavioral interventions. Weight loss, or bariatric, surgery seems to be the only effective long-term treatment option for patients with a BMI greater than 35. Despite the 20 million patients who are eligible for weight loss surgery in the United States, the number of procedures per year has plateaued at about 200,000, essentially eliminating any meaningful public health effect of the surgery.

In recent years, laparoscopic vertical sleeve gastrectomy has emerged as a procedure that is safe and effective for patients who are eligible for weight loss surgery. Since its introduction in 2003 as a stand-alone surgery, vertical sleeve gastrectomy has been studied extensively. It is now widely accepted as the surgery that should be offered to most morbidly obese patients over laparoscopic adjustable gastric banding and laparoscopic Roux-en-Y gastric bypass. The surgery has been adopted by most bariatric surgeons and is now one of the most commonly used procedures to achieve effective weight loss.

During a vertical sleeve gastrectomy, approximately 80% of the stomach is removed and the remaining pouch is based on the less distensible lesser curve of the stomach. The fundus of the stomach, which is formed by the upper curvature of the organ, is the most crucial portion of the stomach that is removed. The resultant gastric pouch generally should be about 80 mL to about 820 mL in volume, should not be narrowed at the incisura angularis, should be as straight as possible to avoid obstruction from spiraling or zigzagging, should be about 0.5 cm to about 2 cm away from the gastroesophageal junction, and should be about 2 cm to about 10 cm away from the pylorus.

A vertical sleeve gastrectomy is typically performed using standard laparoscopic equipment. The greater curvature of the stomach is mobilized by using vessel-sealing devices to seal the gastric branches of the gastroepiploic vessels and the short gastric vessels. The posterior adhesions of the stomach are also divided so the stomach is fully mobilized while the blood supply to the lesser curvature remains intact. The left crus of the diaphragm is an important landmark to ensure the fundus has been fully mobilized.

Following mobilization of the stomach and repair of any hiatal hernia that may be present, a calibration tube or bougie is typically introduced into the stomach through the mouth. The bougie is inserted through the mouth, down the esophagus, and into the stomach, where it is used as a point of reference in order to help align the initial staple fire. The bougie acts as a left-hand landmark, which the surgeon uses to visualize the path of the staple line. A surgeon creating a sleeve gastrectomy staple line will estimate 2.0 cm away from the lesser curvature of the stomach and visually orient the stapler. As constant diameter bougies cannot be used to facilitate orienting the stapler, only surgeon experience and estimation is used. At the top of the staple line, it is important to not divide part of the esophagus or the 'sling fibers' of the cardia, which participate in the physiologic anti-reflux action of the lower esophageal sphincter. Surgeons must use visual cues to ensure that the staple line is a safe distance away from the gastroesophageal junction.

Resection is accomplished by a series of applications of a laparoscopic linear surgical stapler. The staplers that are most commonly used for sleeve gastrectomy are 60 mm in length and include an integrated cutting blade. Each staple application places three rows of overlapping staples into the tissue on either side of the cutting blade. For sleeve gastrectomy, the average number of staple fires per procedure is 4 to 6 in order to create a continuous resection line. This results in a resection line that is approximately 15 cm to about 36 cm on average. Currently, surgeon training, experience, and trial and error are the only tools used to aid the surgeon in determining the path of the resection line in a vertical sleeve gastrectomy. Only after applying the stapler to begin creating the resection line is the resultant stomach anatomy demonstrated. Before beginning stapling, the surgeon must attempt to envision the resultant anatomy of the stomach. Further, the surgeon must actively and accurately control the stapler during the resection to produce the desired resection line. Because the thickness of the stomach tissue varies at the antrum, the body and the fundus, different staple leg lengths are typically used. This requires the stapler to be removed from the patient between firings to load the stapler with a new staple cartridge having staples with an appropriate leg length.

There is wide variability in the size and type of calibration tube, or bougie, used by surgeons to size the remaining gastric sleeve. Some surgeons use an endoscope (30 French or 1 cm in diameter) while others use a large mercury-weighted bougie (60 French or 2 cm in diameter). In a large meta-analysis, there was no difference in weight loss when bougie sizes of less than 40 and greater than 40 were used. The resection line is important in sleeve gastrectomy because the amount of weight loss and subsequent medical complications may be a direct result of the quality of the resultant anatomy. The resultant anatomy is determined by the resection line created by the surgeon during the gastrectomy. Negative consequences related to the quality of the resection line may include, for example, gastroesophageal reflux, weight loss failure, weight regain, food intolerance, resection line bleed, and leak.

Leaks are the most concerning complication of a vertical sleeve gastrectomy. In large pooled databases, the leak rate is approximately 0.3 to 2%. Leak is thought to be prevented by making a straight resection line that avoids crossing staple cartridge applications, has no narrow segments (particularly at the incisura angularis), is about 1 cm from the gastroesophageal junction, and has a squared-off final application. Generally speaking, leak is not prevented by oversewing the resection line or using buttress material in the resection line. Leak is thought to be more a result of poor resultant stomach anatomy. Poor anatomy is a direct result of the shortcomings of the calibration equipment and technique used to create the resection line. Conventional calibration tubes specifically designed for use in a sleeve gastrectomy may provide some user benefits, but fail to reliably produce the proper geometry of the resultant anatomy from the vertical sleeve gastrectomy.

Accordingly, new apparatuses and methods are needed to address the shortcomings of existing apparatuses and methods. More particularly, new apparatuses and methods are needed that improve the consistency and quality of the resection line created during a medical procedure, such as a vertical sleeve gastrectomy.

SUMMARY

A guide for guiding a medical instrument during a medical procedure on an anatomical structure that addresses these and other shortcomings includes a first clamp member configured to be positioned on a first side of the anatomical structure and a second clamp member configured to be positioned on a second side of the anatomical structure generally opposite that of the first side. The first and second clamp members are configured to provide a clamping force on the anatomical structure to secure the guide to the anatomical structure. At least one of the clamp members is configured to cooperate with the medical instrument in order to guide and support the medical instrument during the medical procedure.

In an exemplary embodiment, the first and second clamp members are operatively coupled together adjacent at least one of a first end and a second end of the first and second clamp members. The first and second clamp members may be operatively coupled together by a hinge joint, a flexible ratchet, a flexible member, a biasing member, or combinations thereof.

In another embodiment, at least one of the clamp members includes an alignment surface configured to engage with the medical instrument in order to guide and support the medical instrument during the medical procedure. Additionally, both the alignment surface of at least one of the clamp members and the medical instrument may include at least one connector, the connectors being configured to movably couple the at least one of the clamp members and the medical instrument.

In an exemplary embodiment, the guide is configured to provide a variable clamping force on the anatomical structure. The guide may be configured to provide a first stage clamping force on the anatomical structure, the first stage clamping force configured to couple the guide to the anatomical structure while permitting the clamp members to be moved relative to the anatomical structure. Further, the guide may be configured to provide a second stage clamping force on the anatomical structure greater than the first stage clamping force, the second stage clamping force configured to substantially prevent the guide from moving relative to the anatomical structure during the medical procedure.

In another embodiment, the guide further includes at least one flexible member operatively coupled to the first and second clamp members. The flexible member is configured to be tensioned so as to provide at least a portion of the clamping force on the anatomical structure. At least one of the first and second clamp members may be moveably coupled to the at least one flexible member. More specifically, at least one of the first and second clamp members may be slidably coupled to at least one flexible member. In one embodiment, at least one flexible member extends through the first and second clamp members along substantially an entire longitudinal length of the first and second clamp members.

In an alternate embodiment, a first flexible member and a second flexible member are operatively coupled to the first and second clamp members. Further, the guide may be configured to provide a clamping force at a first end of the clamp members that is different from a clamping force at a second end of the clamp members. In one embodiment, the first and second flexible members may be individually tensioned. Additionally, a distance between the clamp members at the first end may be different from a distance between the clamp members at the second end.

Additionally, the first and second flexible members may be operatively coupled to the first and second clamp members and the guide is configured to provide a clamping force at a first longitudinal side of the clamp members that is different from a clamping force at a second longitudinal side of the clamp members. The first and second flexible members may extend through the first and second clamp members along substantially an entire longitudinal length of the first and second clamp members and the first and second flexible members may be individually tensioned.

In an exemplary embodiment, the guide further includes a tensioning device for tensioning the at least one flexible member and thereby provide at least a portion of the clamping force on the anatomical structure. The tensioning device may include a cinch tube having a distal tip, wherein the at least one flexible member extends into the cinch tube, and wherein the distal tip is configured to engage against the guide as the flexible member is pulled so as to induce a tension in the flexible member and thereby provide a clamping force on the anatomical structure.

In another embodiment, at least one of the first and second clamp members includes a plurality of clamp segments that collectively form the at least one of the first and second clamp members. Adjacent clamp segments may be separate elements configured to be in abutting contact with each other when the at least one flexible member is tensioned. Further, the adjacent clamp segments may include an interlock feature. The clamp segments that form the at least one of the first and second clamp members may be moveably coupled to the at least one flexible member.

In an exemplary embodiment, the first and second clamp members are biased towards each other to provide at least a portion of the clamping force on the anatomical structure. At least one of the first and second clamp members may include a biasing mechanism for biasing the first and second clamp members towards each other. The biasing mechanism may include, for example, an elastic band, shape memory element, or spring.

In another embodiment, the guide further includes a hinge joint for coupling the first and second clamp members. The hinge joint may be formed by a living hinge, include a selectively formable hinge, or be formed by a spring hinge configured to bias the first and second clamp members away from each other. The guide may further include at least one flexible member operatively coupled to the first and second clamp members, wherein the flexible member is configured to be tensioned so as to provide at least a portion of the clamping force on the anatomical structure. The at least one flexible member may couple to the first and second clamp members at an end thereof opposite to the hinge joint.

In an exemplary embodiment, the guide includes magnetic characteristics such that at least a portion of the clamping force of the guide on the anatomical structure is due to magnetic attraction forces.

In another embodiment, at least one of the first and second clamp members include at least one connector configured to couple the at least one of the first and second clamp members with a laparoscopic instrument. The connector may be a tab configured to be grasped by the laparoscopic instrument.

In a further embodiment, each of the first and second clamp members has a longitudinal shape that is generally linear or generally curved. At least one of the first and second clamp members may be telescopic for adjusting a length of the at least one of the first and second clamp members. At least one of the first and second clamp members may include a plurality of serially arranged segments. Each of the first and second clamp members may have a cross-sectional shape that is selected from the group consisting of rectangular, circular, crescent, wavy, half-moon, v-shaped, or a combination thereof.

In an exemplary embodiment, the guide is configured to indicate at least one of a length of the anatomical structure, a thickness of the anatomical structure, a distance of the guide from an anatomical landmark, and the clamping force being provided by the guide.

A stabilizing device for stabilizing an anatomical structure during a medical procedure may include a first clamp member configured to be positioned on a first side of the anatomical structure and a second clamp member configured to be positioned on a second side of the anatomical structure generally opposite that of the first side where the first and second clamp members are configured to provide a clamping force on the anatomical structure to secure the stabilizing device to the anatomical structure. The first and second clamp members may be operatively coupled together adjacent at least one of a first end and a second end of the first and second clamp members In an exemplary embodiment, the stabilizing device may be configured to provide a first stage clamping force on the anatomical structure, the first stage clamping force configured to couple the stabilizing device to the anatomical structure while permitting the clamp members to be moved relative to the anatomical structure. The stabilizing device may be further configured to provide a second stage clamping force on the anatomical structure greater than the first stage clamping force, the second stage clamping force configured to substantially prevent the stabilizing device from moving relative to the anatomical structure during the medical procedure.

In a further embodiment, the stabilizing device may further include at least one flexible member operatively coupled to the first and second clamp members, wherein the flexible member is configured to be tensioned so as to provide at least a portion of the clamping force on the anatomical structure. At least one of the first and second clamp members may be moveably coupled to the at least one flexible member.

In another embodiment, the clamping force at the first end of the clamp members is different from the clamping force at the second end of the clamp members. Further, a distance between the clamp members at the first end may be different from a distance between the clamp members at the second end.

A method of resecting at least a portion of an anatomical structure during a medical procedure includes positioning a guide in an abdominal cavity adjacent to the anatomical structure, clamping the guide to the anatomical structure to secure the position of the guide relative to the anatomical structure, and resecting the portion of the anatomical structure along a resection line defined at least in part by the guide using a medical instrument guided and supported by the guide.

Positioning a guide in an abdominal cavity adjacent to the anatomical structure may include positioning a first clamp member and a second clamp member in the abdominal cavity adjacent the anatomical structure.

In an exemplary embodiment, clamping the guide to the anatomical structure further comprises applying a first-stage clamping force on the anatomical structure, the first stage clamping force configured to couple the guide to the anatomical structure while permitting the guide to be moved relative to the anatomical structure. Further, clamping the guide may include applying a second-stage clamping force on the anatomical structure greater than the first-stage clamping force, the second stage clamping force configured to substantially prevent the guide from moving relative to the anatomical structure during the medical procedure.

In another embodiment, the first and second clamp members are operatively coupled by at least one flexible member and clamping the guide to the anatomical structure further comprises tensioning the at least one flexible member.

In one embodiment, the guide includes an alignment surface and resecting the portion of the anatomical structure further comprises engaging an aspect of the medical instrument to the alignment surface to guide and support the medical instrument during use.

In an exemplary embodiment, the method further includes measuring or estimating at least one of a length of the anatomical structure, a thickness of the anatomical structure, a distance of the guide from an anatomical landmark, and the clamping force being provided by the guide.

A method of stabilizing at least a portion of an anatomical structure during a medical procedure includes positioning a stabilizing device in an abdominal cavity adjacent to the anatomical structure, and coupling the stabilizing device to the anatomical structure to stabilize the position of the stabilizing device relative to the anatomical structure.

In one embodiment, coupling the stabilizing device to the anatomical structure further may include applying a first-stage clamping force on the anatomical structure, the first stage clamping force configured to couple the stabilizing device to the anatomical structure while permitting the stabilizing device to be moved relative to the anatomical structure. Further, the method may include applying a second-stage clamping force on the anatomical structure greater than the first-stage clamping force, the second stage clamping force configured to substantially prevent the stabilizing device from moving relative to the anatomical structure during the medical procedure.

In another embodiment, the first and second clamp members may be operatively coupled by at least one flexible member and coupling the stabilizing device to the anatomical structure further includes tensioning the at least one flexible member.

A medical device for performing a medical procedure may include a manipulator including a shaft, a resection line guide being coupled to the shaft and being configured to clamp an anatomical structure in the human body, and a flexible member operably coupled to the manipulator and extending through the shaft to the resection line guide, wherein the manipulator is configured to place the flexible member in tension so that the resection line guide imposes a clamping force on the anatomical structure. The resection line guide may be movable relative to the shaft.

In an embodiment, the manipulator may include a spring reel for letting out a length of the flexible member and/or taking up a length of the flexible member. Further, the manipulator may include a housing and a brake mechanism at least partially within the housing, the brake mechanism being operable for selectively stopping relative movement between the flexible member and the spring reel.

In another embodiment, the manipulator may include a housing, a clamping mechanism operable to selectively apply tension to the flexible member in an engaged position, and a stop and release mechanism for maintaining the clamping mechanism in the engaged position.

A medical device for performing a medical procedure may include a manipulator including a shaft, a stabilizing device being coupled to the shaft and being configured to clamp an anatomical structure in the human body, and a flexible member operably coupled to the manipulator and extending through the shaft to the stabilizing device, wherein the manipulator is configured to place the flexible member in tension so that the stabilizing device imposes a clamping force on the anatomical structure.

In one embodiment, the stabilizing device may be configured to provide a first stage clamping force on the anatomical structure, the first stage clamping force configured to couple the stabilizing device to the anatomical structure while permitting the clamp members to be moved relative to the anatomical structure. The stabilizing device may be further configured to provide a second stage clamping force on the anatomical structure greater than the first stage clamping force, the second stage clamping force configured to substantially prevent the stabilizing device from moving relative to the anatomical structure during the medical procedure.

A method of clamping at least a portion of an anatomical structure during a medical procedure with a medical device including a manipulator operably coupled to a resection line guide having a first clamp member movably coupled to a second clamp member with a flexible member may include inserting the resection line guide into a patient, positioning the first clamp member and the second clamp member adjacent the anatomical structure, retracting the flexible member at the manipulator to draw the first clamp member and the second clamp member toward one another and into contact with the anatomical structure, tensioning the flexible member at the manipulator to forcibly clamp the anatomical structure between the first clamp member and the second clamp member, and resecting a portion of the anatomical structure along the resection line guide.

A method of stabilizing at least a portion of an anatomical structure during a medical procedure with a medical device including a manipulator operably coupled to a stabilizing device having a first clamp member movably coupled to a second clamp member with a flexible member may include inserting the stabilizing device into a patient, positioning the first clamp member and the second clamp member adjacent to the anatomical structure, retracting the flexible member at the manipulator to draw the first clamp member and the second clamp member toward one another and into contact with the anatomical structure, and tensioning the flexible member at the manipulator to forcibly clamp the anatomical structure between the first clamp member and the second clamp member.

BRIEF DESCRIPTION OF THE DRAWINGS

The accompanying drawings, which are incorporated in and constitute a part of this specification, illustrate embodiments and, together with a general description given above, and the detailed description given below, serve to explain the invention.

FIG. 5D is an elevation view of the resection line guide FIG. 5A placed around a stomach.

FIG. 5E is a cross-sectional view of the resection line guide shown in FIG. 5D.

FIG. 5F is a cross-sectional view of a portion of the resection line guide according to another embodiment.

FIG. 10A is an elevation view of a resection line guide according to another embodiment.

FIG. 10B is an elevation view of the resection line guide of FIG. 10A placed around a stomach.

FIG. 10C is a partial cross-sectional view of the resection line guide of FIG. 10B.

FIGS. 12A-12G illustrate cross-sectional views of two clamp members of a resection line guide according to various embodiments.

FIGS. 13A-13D are elevation views of two clamp members of a resection line guide according to various embodiments.

FIG. 19 is a partial cross-sectional view of a manipulator of the medical device of FIG. 14 depicting engagement of a mechanism according to an embodiment.

FIG. 23A is a schematic cross-sectional view of a resection line guide of FIG. 16 in an opened position.

FIG. 24A is a schematic cross-sectional view of the resection line guide of FIG. 16 in a closed position.

FIG. 25 is an exploded perspective view of a shaft of one embodiment of a manipulator.

FIG. 28 is a schematic cross-sectional view of the resection line guide of FIG. 16 illustrating manipulation of the joint shown in FIGS. 27A and 27B.

FIG. 33D is a cross-sectional view of the resection line guide of the medical device of FIG. 30 depicting the resection line guide in an opened position.

FIG. 34C is a cross-sectional view of the resection line guide of the medical device of FIG. 30 depicting the resection line guide in a closed position.

FIGS. 37A and 37B are cross-sectional views of the medical device of FIG. 35 depicting engagement of a mechanism according to an embodiment.

DETAILED DESCRIPTION

In its broadest aspects, embodiments of the present invention are directed to a resection line guide for directing the application of a resection line during a surgical procedure involving the resection of at least a part of an anatomical structure. In an exemplary embodiment, the resection line guide may be used in a vertical sleeve gastrectomy procedure. The resection line guide is a supplement to current practices of a sleeve gastrectomy, including the laparoscopic access, mobilization of the greater curvature of the stomach and multiple applications of a laparoscopic stapler to create the resection line. Laparoscopic surgery is surgery inside of the abdominal cavity performed at a distance by the surgeon. Laparoscopic surgery instrumentation is designed to fit through small incisions in the abdominal wall, typically 5 mm to 15 mm in diameter. The abdominal access sites are maintained by cannulae, or trocars, that are designed to maintain pressure in the abdominal cavity with valves that seal around an instrument shaft. Devices and methods for performing laparoscopic surgery are well known in the prior art.

While embodiments discussed below involve the use of the resection line guide to guide and support a medical instrument during a medical procedure, it should be recognized that the resection line guide may act as a surgical clamp independent of its use as a guide to a medical instrument. Further, while embodiments discussed below involve the use of the resection line guide in a vertical sleeve gastrectomy procedure, the resection line guide may also be used in other procedures involving anatomical structures, such as organs other than the stomach or soft tissue. For example, the resection line guide may be used in a parencymal resection, lung volume reduction surgery, or other procedures involving the lung. Further, the resection line guide may be useful in an anatomic resection such as a lobectomy, a non-anatomic parencymal resection, or other procedures involving the liver. Moreover, a surgeon or other medical professional may benefit from using the resection line guide in a partial nephrectomy, total nephrectomy, or other procedures involving the kidney. During procedures involving an anatomical structure, the tissue of the anatomical structure may be sealed. Tissue may be sealed by any method known in the art, such as, for example, stapling, suturing, gluing, and welding. Thus, while aspects of the present invention may be illustrated in the context of a vertical sleeve gastrectomy, it should be appreciated that aspects of the disclosed technology may provide a benefit in a host of medical procedures on anatomical structures and be adapted for use in such medical procedures.

Figure 1:
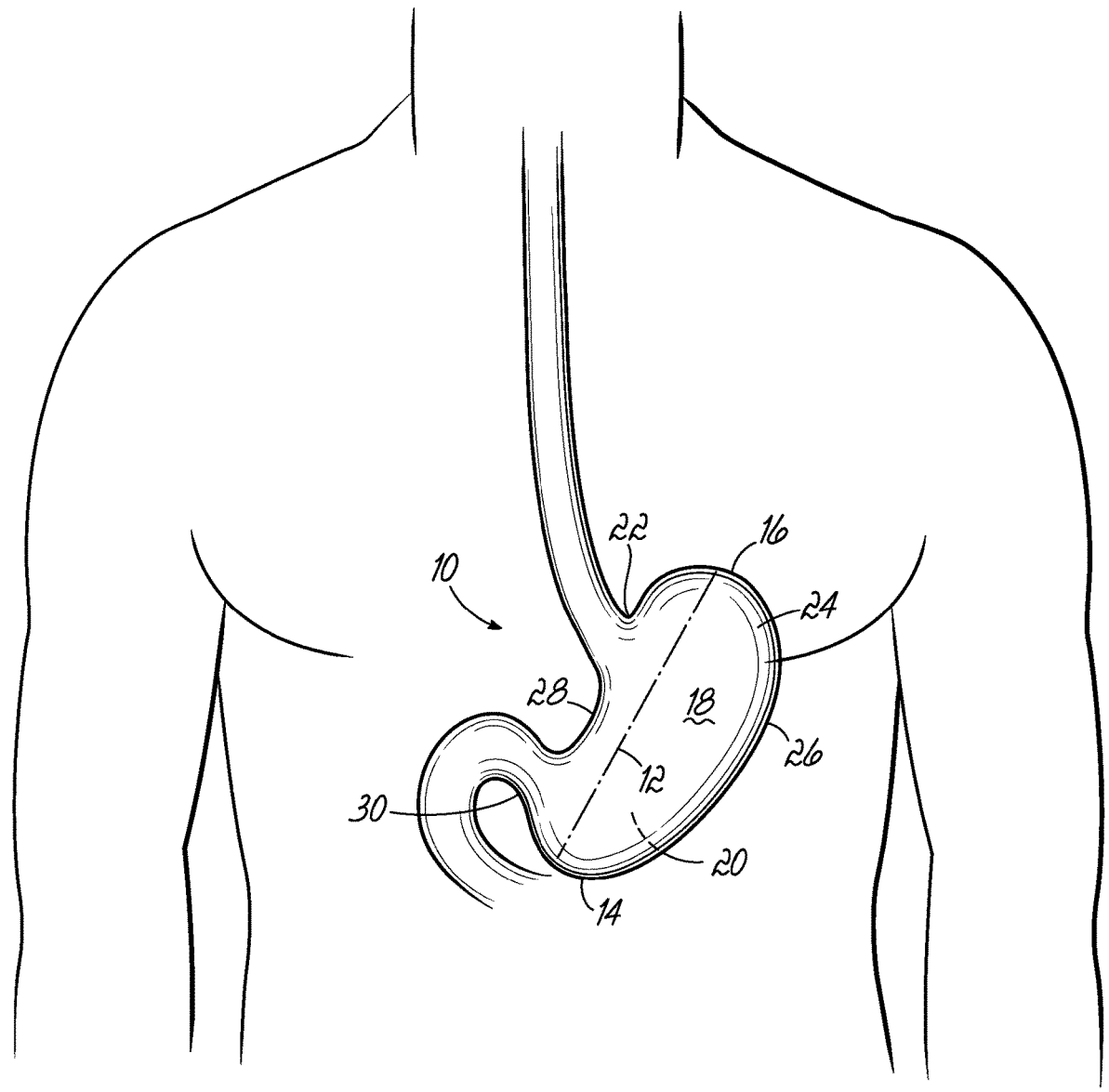
FIG. 1 depicts the anatomy of a stomach.

Now referring to the figures, FIG. 1 illustrates the anatomy of the stomach 10 and a resection line 12, where the resection line 12 represents a resection line for a vertical sleeve gastrectomy. The stomach 10 generally includes a proximal end 14, a distal end 16, an anterior side 18, and a posterior side 20. As used herein, the proximal and distal ends 14, 16 of the stomach are described from the perspective of the operative surgeon. The gastroesophageal junction 22 opens into the stomach 10 and is a common landmark in bariatric surgeries. The fundus 24 and the section of the stomach defined by the greater curvature 26 are generally the parts of the stomach 10 removed during a vertical sleeve gastrectomy. The remaining pouch is generally defined by the lesser curvature 28 and the resection line 12 and presents a stomach with a significantly reduced volume. As described above, the desired location of the resection line 12 is about 0.5 to 2 cm away from the gastroesophageal junction 22 and about 2 to 10 cm away from the pylorus 30. In accordance with aspects of the disclosed technology, resection line guides as described herein aid in forming high quality, consistent resection lines during a medical procedure, such as a vertical sleeve gastrectomy. In this regard, the resection line guides provide an accurate visual indication of the resection line and further provide a stabilizing engagement surface along which medical staplers may be guided during a resection procedure. The visualization and guiding aspects of the disclosed resection line guides are believed to result in high quality and consistent resection lines that are significantly improved over resection lines produced by current methodologies.

Figure 2A:
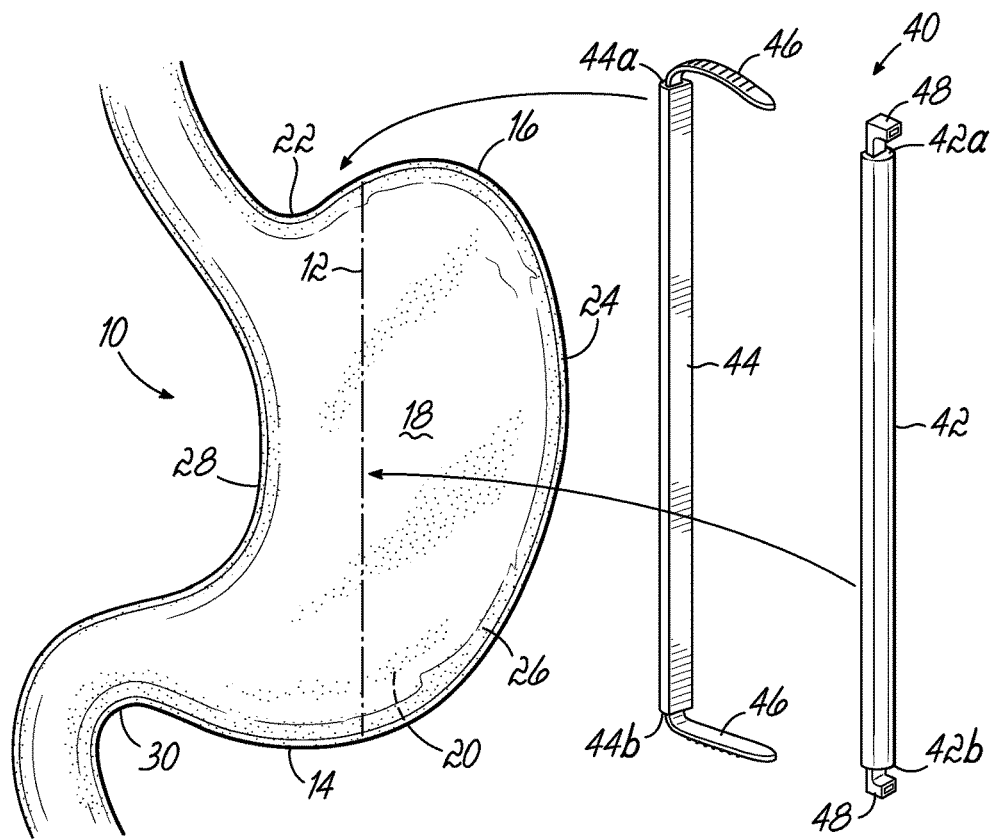
FIG. 2A is an elevation view of a resection line guide according to one embodiment.

Various embodiments of the present invention may include a resection line guide including two clamp members capable of being operatively coupled to each other and movable relative to each other so as to provide a clamping force on an anatomical structure, such as a stomach. The ability of the resection line guides to generate a clamping force allows the device to be reliably positioned relative to the anatomical structure in order to eliminate or reduce the likelihood of undesirable movements of the device during a stapling operation. In this regard, FIG. 2A illustrates an exemplary embodiment where a resection line guide 40 includes a first clamp member 42 generally positionable on the anterior side 18 of the stomach 10, and a second clamp member 44 generally positionable on the posterior side 20 of the stomach 10, where the first clamp member 42 and the second clamp member 44 may be configured to be operatively coupled to effectuate a clamping force on the stomach 10. In other words, once the clamp members are coupled, the first clamp member 42 and the second clamp member 44 essentially operate as a surgical clamping device for purposes described in more detail below. It should be realized that aspects of the present invention are not limited to the illustrated arrangement, where the first clamp member 42 is on the anterior side 18 of the stomach 10 and the second clamp member 44 is on the posterior side 20. In an alternative embodiment, for example, the arrangement may be reversed such that the first clamp member 42 is on the posterior side 20 of the stomach 10 and the second clamp member 44 is on the anterior side 18 of the stomach 10 (not shown). Other alternative arrangements may also be possible.

Figure 2B:
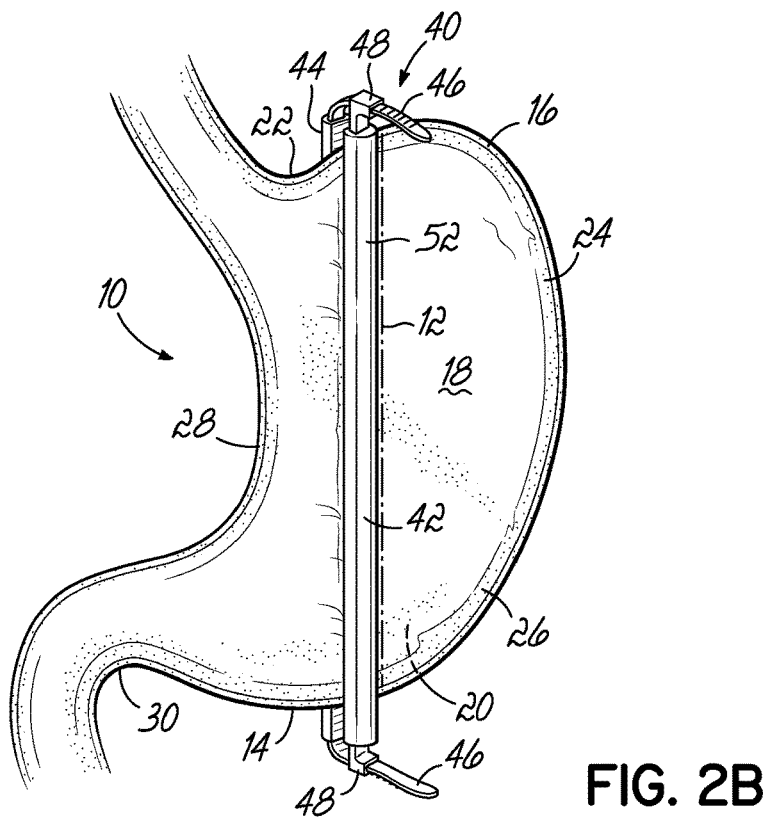
FIG. 2B is an elevation view of the resection line guide of FIG. 2A positioned on the stomach.

As noted above, the first and second clamp members 42, 44 may be configured to be operatively coupled to each other to effectuate a clamping force on an anatomical structure. In one embodiment, as illustrated in FIG. 2B, the clamp members 42, 44 couple together at both the proximal end 14 and distal end 16 of the stomach 10. The clamp members 42, 44 may be coupled together using a variety of methods and engagement elements, such as that described below. By way of example, the proximal and distal ends of one the clamp members may include a projection or pin that can be engaged or received by the proximal and distal ends of the other clamp member, respectively. Alternatively, the clamp members may be configured to connect using magnets, a clip-in connection, or other types of connections or connectors that are generally well known in the art. The connection method used at the proximal and distal ends of the clamp members do not need to be similar. By way of example, the distal ends of the clamp members may be configured to connect using a clip-in connection, while the proximal end of one of the clamp members may be configured to slide through an opening on the proximal end of the other clamp member, where the opening is capable of receiving and gripping the proximal end of the one clamp member. Accordingly, there are many ways to couple the clamp members and the invention should not be limited to a certain type of connection.

In this regard, FIG. 2B illustrates the resection line guide 40 placed around the stomach 10 with the clamp members 42, 44 coupled together at both the proximal and distal ends 14, 16 of the stomach 10. Using laparoscopic instruments, the second clamp member 44 may be inserted under (posterior to) the stomach 10 so that the distal end 44a of the second clamp member 44 generally extends beyond the distal end 16 of the stomach 10 and the proximal end 44b generally extends beyond the proximal end 14 of the stomach. Next, the first clamp member 42 may be inserted over (anterior to) the stomach 10 using laparoscopic instruments, for example, so that the distal end 42a of the first clamp member 42 generally extends beyond the distal end 16 of the stomach 10 and the proximal end 42b generally extends beyond the proximal end 14 of the stomach 10. The resection line guide 40 may be put in place and used with or without having to mobilize the greater curvature. For example, a surgeon may prefer to leave the greater curvature 26 attached to the omentum (not shown), which could improve stability of the stomach 10 during stapling.

In accordance with the present embodiment, the distal end 44a of the second clamp member 44 may be received through the distal end 42a of the first clamp member 42. Similarly, the proximal end 44b of the second clamp member 44 may be received through the proximal end 42b of the first clamp member 42. In this regard, the distal and proximal ends 44a, 44b may include a serrated tab 46 and the distal and proximal ends 42a, 42b may include a passage or bore 48 having an opening through which the serrated tabs 46 may pass. Collectively, the tab 46 and bore 48 operate as a flexible ratchet capable of bringing the clamp members 42, 44 together to generate a clamping force. The bores 48 may be configured to prevent the serrated tabs 46 from moving backwards through the openings. The clamp members 42, 44 may be further manipulated so as to provide a sufficient clamping force on the stomach 10 to effectively prevent or minimize the guide 40 from moving, but without damaging the clamped tissue. For example, conventional graspers may be used to pull the tabs 46 through the bores 48. Although not shown, the resection line guide 40 may include a release mechanism in the flexible ratchet that allows the tab 46 to be released from the bore 48 and thereby separate the two clamp members 42, 44. It should be appreciated that the flexible ratchet may take other forms other than that described above.

More particularly, and in one aspect, the resection line guide 40 may be positioned relative to the stomach 10 using a two-stage clamping process. In the first clamping stage, the first and second clamp members 42, 44 may be configured to provide a certain amount of resistance to movement of the resection line guide 40 relative to the stomach 10. For example, the range of clamping force (or clamping pressure) in the first stage may be about 0.5 g/mm$^2$ to about 4 g/mm$^2$. This resistance is configured to prevent undesirable or unintentional movements of the resection line guide 40, but yet permit the surgeon to move the resection line guide 40 to a desired position relative to the stomach 10 without significant difficulty. In the second clamping stage, and with the resection line guide 40 in the desired location relative to the stomach 10, the clamping force of the resection line guide 40 may be increased to effectively prevent or minimize the guide 40 from moving relative to the stomach 10. For example, the clamping force (or clamping pressure) in the second stage may be about 4 g/mm$^2$ to about 12 g/mm$^2$. In an exemplary embodiment, the clamping force (or clamping pressure) in the second stage may be about 8 g/mm$^2$. The upper limit to which the resection line guide 40 may be clamped is selected so as to avoid any damage to the underlying tissue being clamped. This upper limit may be, for example, about 12 g/mm$^2$. Additionally, the value of about 4 g/mm$^2$ represents a threshold clamping force below which constitutes the first stage clamping and above which constitutes the second stage clamping. It should be recognized that these values are merely exemplary and the particular values may depend on several factors, including the anatomical structure being clamped as well as other factors. Thus, the invention should not be limited to the range of values provided herein.

In an advantageous aspect, when the resection line guide 40 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach shape and volume defined by the lesser curvature 28 and the resection line 12 will likely be prior to cutting tissue. If the surgeon is not satisfied with the indication of the expected stomach shape and volume, the surgeon may adjust and manipulate the location and alignment of the resection line guide 40 prior to stapling and cutting the stomach 10. This is in contrast to current procedures, where the resection line is generally not well visualized prior to activating the stapler, thus the ultimate outcome is less certain. It should be appreciated that the resection line guide 40 should be positioned such that it does not provide lateral stretching or tension of the stomach 10, which may create an undesirable environment for stapling and cutting. Using a resection line guide, such as resection line guide 40, ensures proper alignment of the resection line 12 so that the final cut with the stapler removes the fundus 24 portion, is a safe distance away from both the lesser curvature 28 and the gastroesophageal junction 22, and is squared off at the fundus 24 of the stomach to prevent or reduce the likelihood of necrotic tissue development.

Figure 2C:
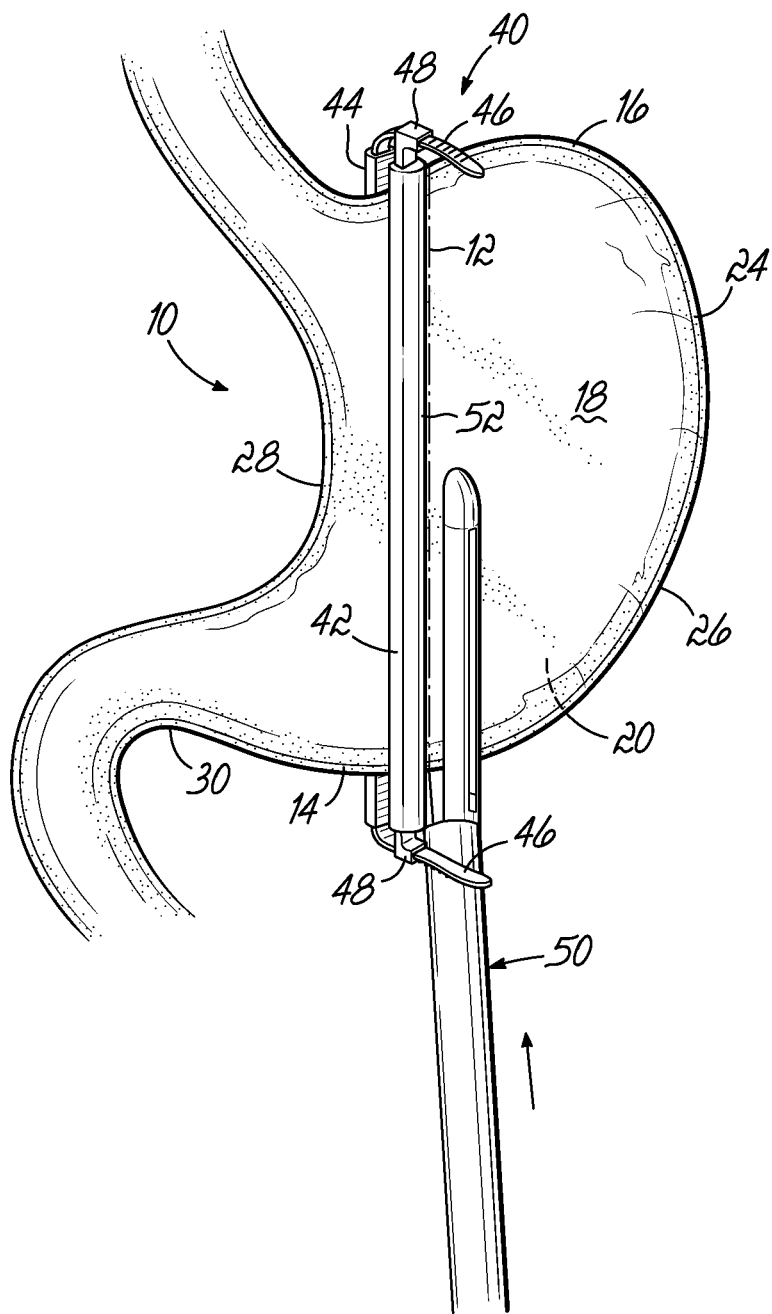
FIG. 2C is an elevation view of a surgical stapler placed next to the resection line guide of FIG. 2A.
Figure 2D:
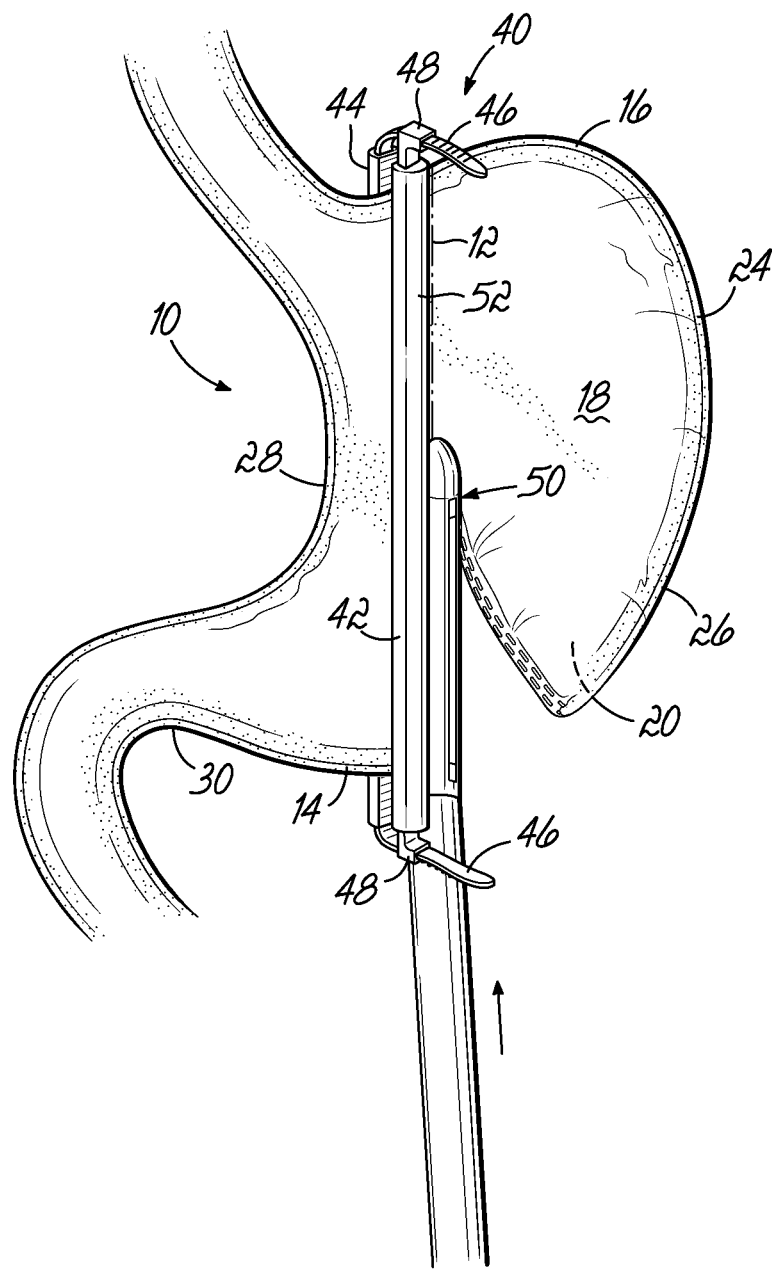
FIG. 2D is an elevation view of a surgical stapler and the resection line guide of FIG. 2A during resection of a portion of the stomach.

Once the resection line guide 40 is properly positioned, the surgeon may then cut and staple (e.g., using a stapler conventionally used in gastrectomy procedures) the tissue using the resection line guide 40 as a track along the entire segment or a significant part of the segment until complete resection of the stomach 10 occurs, as illustrated in FIGS. 2C and 2D. In this regard, an aspect of the stapling device (such as an outer edge thereof), schematically shown as stapling device 50, may abut or engage the resection line guide 40 along an alignment surface 52 to facilitate an improved resection line. For example, the outer edges of one or both of the clamp members 42, 44 may operate as an alignment surface 52 configured to securely engage the stapling device 50 and thereby provide an improved resection line 12. This may be by an abutting engagement. Alternatively, one or both of the clamp members 42, 44 may have a first connector and the stapling device 50 may have a second connector, wherein the first and second connectors are configured to movably couple the resection line guide 40 with the stapling device 50 during the resection (not shown). By way of example, the guide 40 may include connection features (not shown) such as a weak magnetic feature to attract the stapling device 50, a channel that couples with a projection on the stapling device 50 that slides into the channel, etc. FIG. 2D illustrates the application of the stapling device 50 to the stomach 10 along the resection line guide 40. As conventional staplers are generally well known in the art, such staplers will not be described herein in further detail.

Figure 2E:
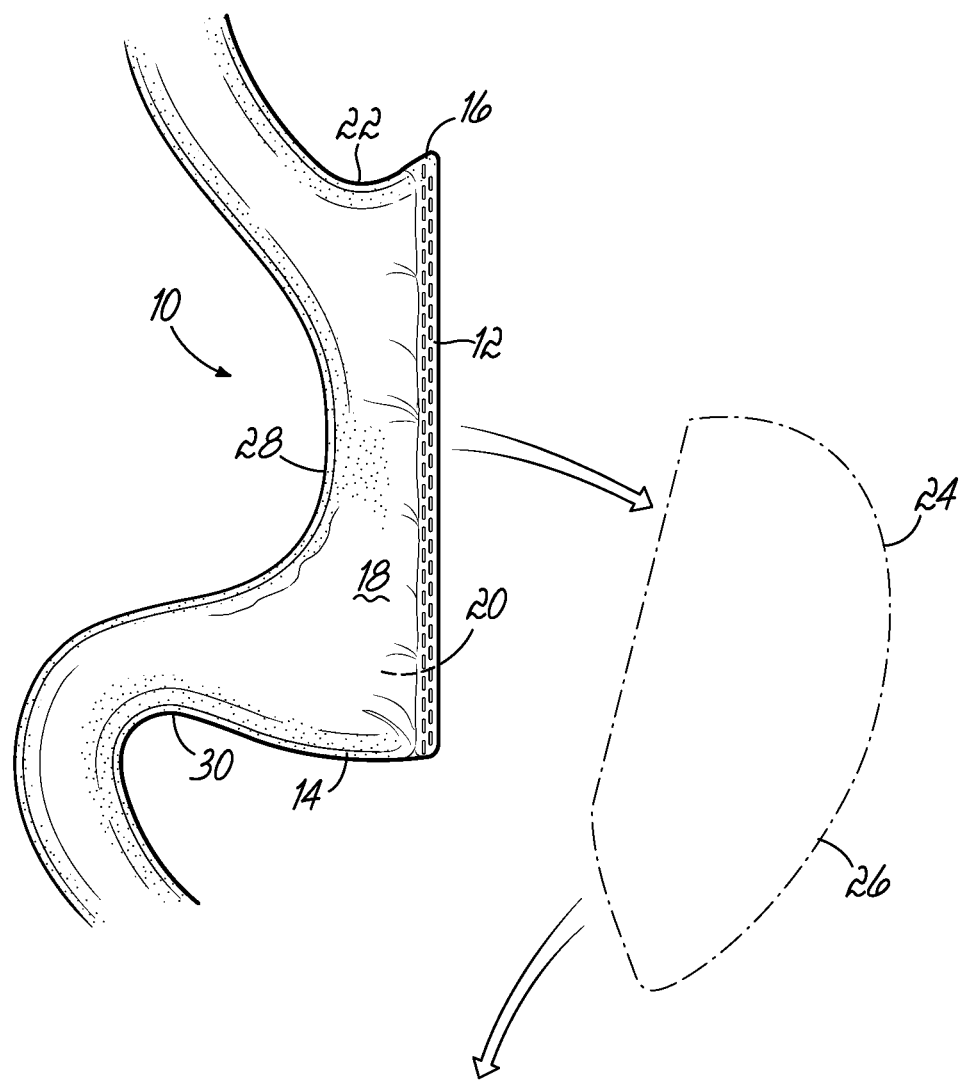
FIG. 2E depicts the stomach anatomy resulting from a vertical sleeve gastrectomy.

As noted above, the resection line guide 40 may be secured to the stomach 10 so that it does not migrate or move once the surgeon begins stapling (e.g., the second clamping stage). Furthermore, the resection line guide 40 may be generally positioned so that it does not interfere with the activation of the stapling device 50 and ideal formation of each individual staple. As illustrated in FIGS. 2A-2E, the use of the resection line guide 40 aids in creating an ideal gastric sleeve pouch size and shape (FIG. 2E). In an embodiment such as one described above where the flexible ratchet includes a release mechanism, the surgeon may engage the release mechanism after completing the resection of the stomach 10. This allows the tab 46 to be released from the bore 48 such that the tab 46 may be moved back through and free of the bore 48. Consequently, the two clamp members 42, 44 may be separated, and the resection line guide 40 may be removed from the abdominal cavity.

Figure 3A:
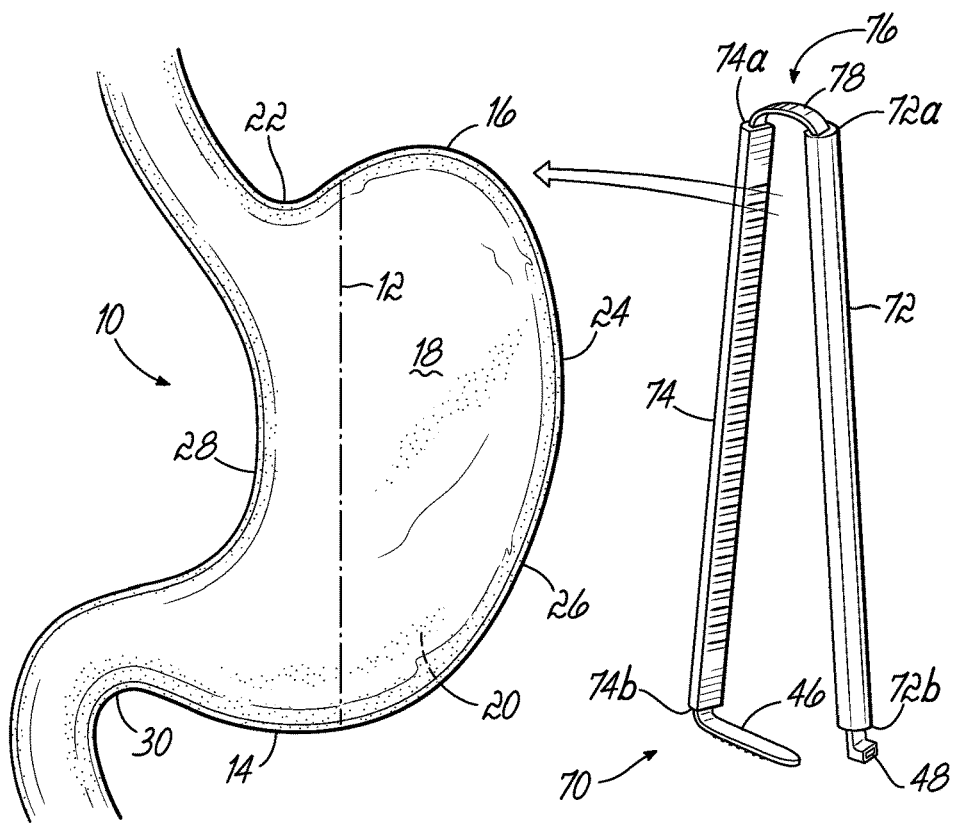
FIG. 3A is an elevation view of a resection line guide according to another embodiment.
Figure 3B:
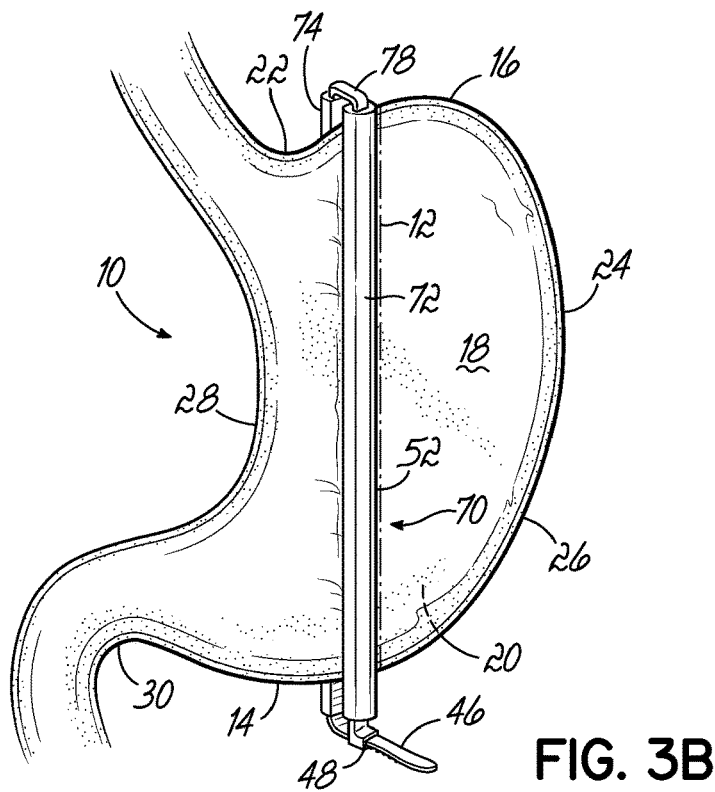
FIG. 3B is an elevation view of the resection line guide of FIG. 3A positioned on the stomach.

In an alternative embodiment, the resection line guide may have an articulated configuration for providing relative movement between the clamp members. In one embodiment, for example, a hinge may be provided at one of the proximal or distal ends of the clamp members to provide pivotable relative movement therebetween. Such an embodiment is illustrated in FIGS. 3A and 3B, where the hinge may be configured as a living hinge. In this regard, a resection line guide 70 includes a first clamp member 72 generally positionable on the anterior side 18 of the stomach 10 and a second clamp member 74 generally positionable on the posterior side 20 of the stomach 10, where the first clamp member 72 and the second clamp member 74 may be operatively coupled to effectuate a clamping force on the stomach 10. In this embodiment, the clamp members 72, 74 may be configured to be coupled at both the proximal and distal ends 14, 16 of the stomach 10. More particularly, the distal ends of the clamp members 72, 74 may be configured as a hinge joint 76. As noted above, the hinge joint 76 may be configured as a living hinge formed by a flexible band 78 having a first end coupled to the first clamp member 72 adjacent a distal end 72a thereof and a second end coupled to the second clamp member 74 adjacent a distal end 74a thereof. With such a living hinge, pivotal movement between the clamp members 72, 74 may be achieved. As illustrated in FIG. 3A, the proximal end 74b of the second clamp member 74 may be received through the proximal end 72b of the first clamp member 72. More particularly and similar to that above, the proximal end 74b of the second clamp member 74 may include a serrated tab 46 and the proximal end 72b of the first clamp member 72 may include a passage or bore 48 having an opening through which the serrated tab 46 may pass. While this embodiment is illustrated with the hinge joint 76 at the distal ends of the clamp members 72, 74, it should be appreciated that in an alternative embodiment, the hinge joint 76 may be at the proximal ends of the clamp members 72, 74 and the serrated tab 46/bore 48 may be at the distal ends of the clamp members 72, 74 (not shown). Other arrangements may also be possible.

The placement of the resection line guide 70 around the stomach 10 is illustrated in FIG. 3B. In this regard, using laparoscopic instruments, the surgeon may manipulate the resection line guide 70 across the stomach 10 so that the first clamp member 72 is generally positioned along the anterior side 18 of the stomach 10 and the second clamp member 74 is generally positioned along the posterior side 20 of the stomach 10. The distal ends 72a, 74a of the clamp members 72, 74 may generally extend beyond the distal end 16 of the stomach 10 and the proximal ends 72b, 74b of the clamp members 72, 74 may generally extend beyond the proximal end 14 of the stomach 10. The flexible band 78 between the clamp members 72, 74 may loop or extend around the distal end 16 of the stomach 10, as illustrated in FIG. 3B. The clamp members 72, 74 may be manipulated so as to provide a clamping force on the stomach 10.

More particularly, the clamp members 72, 74 may be pivoted relative to each other in order to position the resection line guide 70 relative to the stomach 10. To create a clamping force on the stomach 10, the proximal end 72b of the first clamp member 72 and the proximal end 72b of the second clamp member 74 may be coupled. For example, the serrated tab 46 may be pulled through the bore 48 at the proximal end 72b of the first clamp member 72, such as with conventional graspers. The securement of the resection line guide 70 to the stomach 10 may be achieved using the two-stage clamping process as described above. More particularly, the tab 46 may be pulled through bore 48 so as to generate a clamping force on the stomach 10 less than the threshold clamping force. This first-stage clamping force is configured and selected to provide a certain amount of resistance to movement of the resection line guide 70 relative to the stomach 10. This resistance is configured to prevent undesirable or unintentional movements of the resection line guide 70, but yet permit the surgeon to move the resection line guide 70 to a desired position relative to the stomach 10 without significant difficulty. In the second clamping stage, and with the resection line guide 70 in the desired location relative to the stomach 10, the clamping force of the resection line guide 70 may be increased above the threshold clamping force to effectively prevent or minimize the resection line guide 70 from moving relative to the stomach 10. The upper limit to which the resection line guide 70 may be clamped is selected so as to avoid any damage to the underlying tissue being clamped. This may be achieved in this embodiment, for example, by pulling the tab 46 further through the bore 48.

When the resection line guide 70 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the guide prior to stapling and cutting the stomach 10. Once the resection line guide 70 is finally positioned, the surgeon may then cut and staple the tissue using the resection line guide 70 as a track along the entire segment or a significant part of the segment until complete resection of the stomach 10 occurs. In this regard, the stapling device 50 may abut or engage the resection line guide 70 along an alignment surface to facilitate an improved resection line, similar to that shown above in FIG. 2D.

Figure 3C:
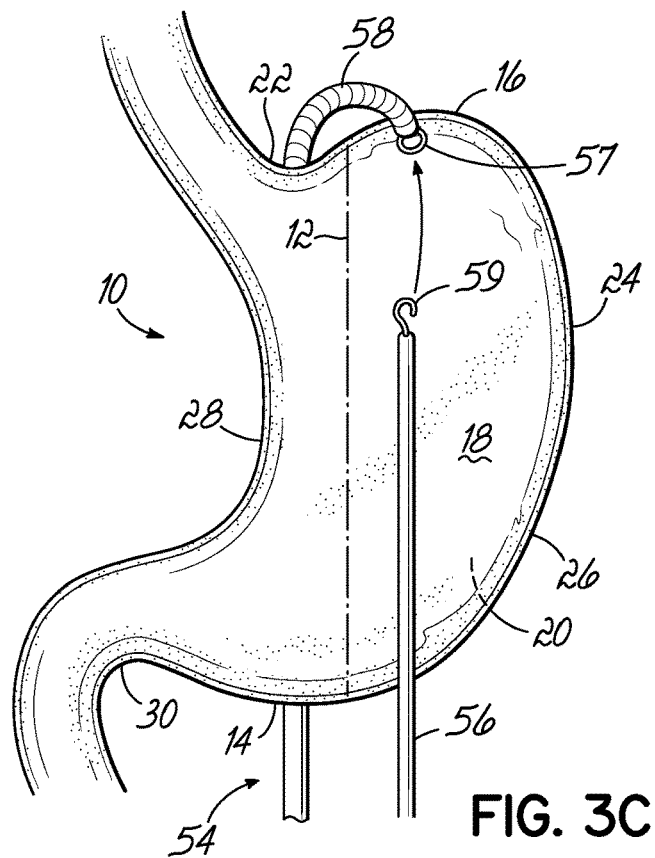
FIG. 3C is an elevation view of a section of a resection line guide according to another embodiment.
Figure 3D:
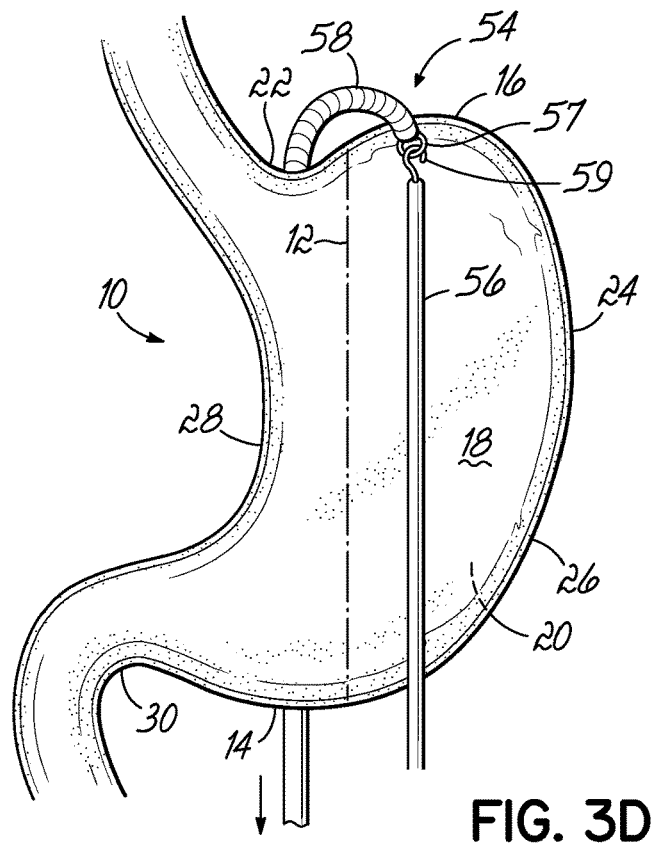
FIG. 3D is an elevation view of the section of a resection line guide of FIG. 3C positioned around the stomach.

In another embodiment of an articulated configuration, the hinge that connects the first and second clamping members may take the form of a selectively formable hinge which may, for example, be formed internal to the abdominal cavity to provide pivotable relative movement between the clamp members. Such an embodiment is illustrated in FIGS. 3C and 3D. In this regard and as shown in FIG. 3C, a resection line guide 54 includes a first clamp member 56 generally positionable on the anterior side 18 of the stomach 10 and a second clamp member 58 generally positionable on the posterior side 20 of the stomach 10, where the first clamp member 56 and the second clamp member 58 may be operatively coupled to effectuate a clamping force on the stomach 10. In this embodiment, the clamp members 56, 58 may be configured to be coupled at both the proximal and distal ends 14, 16 of the stomach 10 (although the proximal end connection is not shown). More particularly, the distal ends of the first and second clamp members 56, 58 may be configured as a formable hinge joint. In this regard, the distal end of the second clamp member 58 may include a ring or eyelet 57 having an opening, and the distal end of the first clamp member 56 may include a hook 59. With the hook 59 positioned within the eyelet 57, the hinge joint is assembled and pivotal movement between the clamp members 56, 58 may be achieved. Though not shown in FIG. 3C, the proximal ends of the clamp members 56, 58 may be configured to be coupled. By way of example and without limitation, the proximal end of the second clamp member 58 may include a serrated tab and the proximal end of the first clamp member 56 may include a passage or bore having an opening through which the serrated tab may pass, similar to that above. Other types of connections at the proximal ends are also possible.

The placement of the resection line guide 54 around the stomach 10 is illustrated in FIG. 3D. In this regard, using laparoscopic instruments, the second clamp member 58 may be inserted under (posterior to) the stomach 10 so that the distal end of the second clamp member 58 generally extends beyond the distal end 16 of the stomach 10 and the proximal end generally extends beyond the proximal end 14 of the stomach 10. Next, the first clamp member 56 may be inserted over (anterior to) the stomach 10 using laparoscopic instruments, for example, so that the distal end of the first clamp member 56 generally extends beyond the distal end 16 of the stomach 10 and the proximal end generally extends beyond the proximal end 14 of the stomach 10. In an advantageous aspect of this embodiment, the distal end of the second clamp member 58 may be configured to flex or bend so that the distal end extends upwardly and around the distal end 16 of the stomach 10. With the distal end of the second clamp member 58 now essentially positioned on the anterior side 18 of the stomach 10, the hook 59 at the distal end of the first clamp member 56 may be engaged within the eyelet 57, thereby forming the hinge joint. This may be accomplished, for example, with conventional graspers (not shown). Being able to assemble the resection line guide 54 inside the abdominal cavity may be advantageous in that it may allow for smaller trocars to be used because the entire guide does not have to fit simultaneously through a single trocar.

With the hinge joint complete, the clamp members 56, 58 may be pivoted relative to each in order to position the resection line guide 54 relative to the stomach 10. To create a clamping force on the stomach 10, the proximal end of the first clamp member 56 and the proximal end of the second clamp member 58 may be coupled (not shown). The securement of the resection line guide 54 to the stomach 10 may be achieved using the two-stage clamping process as described above. The first-stage clamping force is less than a threshold clamping force and is configured and selected to provide a certain amount of resistance to movement of the resection line guide 54 relative to the stomach 10. This resistance is configured to prevent undesirable or unintentional movements of the resection line guide 54, but yet permit the surgeon to move the resection line guide 54 to a desired position relative to the stomach 10 without significant difficulty. In the second clamping stage, and with the resection line guide 54 in the desired location relative to the stomach 10, the clamping force of the resection line guide 54 may be increased above the threshold clamping force to effectively prevent or minimize the resection line guide 54 from moving relative to the stomach 10. The upper limit to which the resection line guide 54 may be clamped is selected so as to avoid any damage to the underlying tissue being clamped.

When the resection line guide 54 is placed on the stomach 10 (e.g., in the first clamping stage as described above), the surgeon has a clear visualization of the intended results of the vertical sleeve gastrectomy prior to actually performing the division of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 54 prior to stapling and cutting the stomach 10. Once the resection line guide 54 is finally positioned, the surgeon may then cut and staple the tissue using the resection line guide 54 as a track along the entire segment or a significant part of the segment until complete resection of the stomach 10 occurs. In this regard, the stapling device 50 may abut or engage the resection line guide 54 along an alignment surface to facilitate an improved resection line, similar to that shown above in FIG. 2D.

Figure 3E:
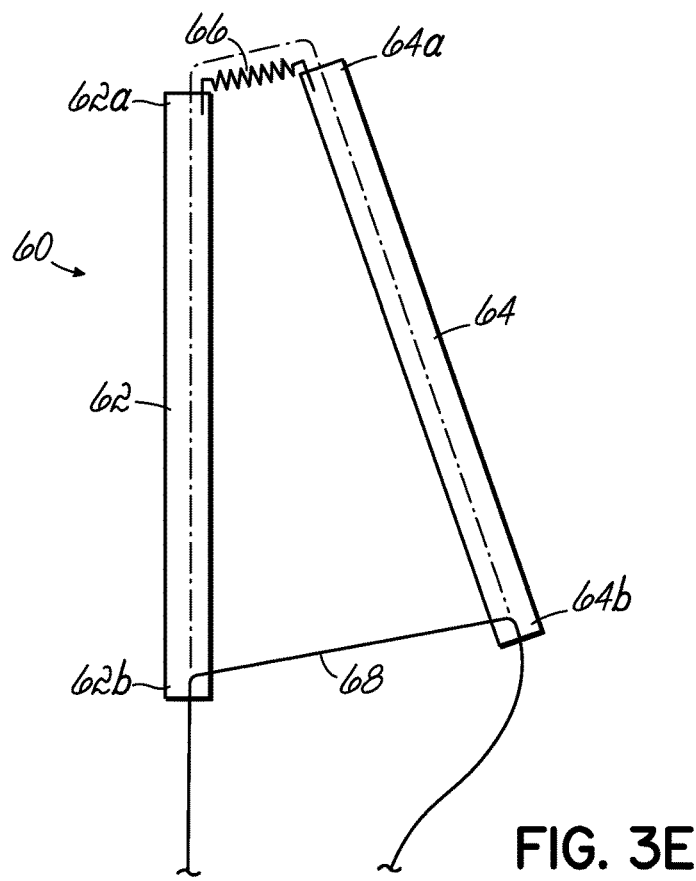
FIG. 3E is an elevation view of a resection line guide according to another embodiment.
Figure 3F:
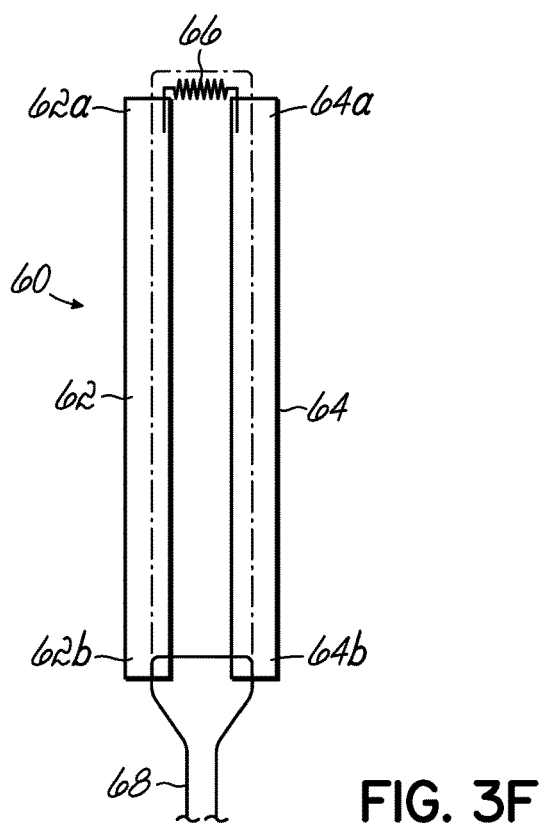
FIG. 3F is an elevation view of the resection line guide of FIG. 3E after the resection line guide has been tensioned.

In another embodiment of an articulated configuration, the hinge that connects the first and second clamping members may be a spring hinge. Such an embodiment is schematically illustrated in FIGS. 3E and 3F. In this regard and as shown in FIG. 3E, a resection line guide 60 includes a first clamp member 62 generally positionable on the anterior side 18 of the stomach 10 and a second clamp member 64 generally positionable on the posterior side 20 of the stomach 10, where the first clamp member 62 and the second clamp member 64 may be operatively coupled to effectuate a clamping force on the stomach 10. In this embodiment, the clamp members 62, 64 may be configured to be coupled at both the proximal and distal ends 14, 16 of the stomach 10. More particularly, the distal ends of the clamp members 62, 64 may be configured as a hinge joint. In this regard, the distal ends 62a, 64a of the clamp members 56, 58 may be coupled by the spring hinge 66, which allows for pivotal movement between the clamp members 62, 64. Spring hinges are generally well known in the art and thus will not be described in further detail herein. As illustrated in FIG. 3E, the proximal ends 62b, 64b of the clamp members 62, 64 may be configured to be coupled. More particularly, the proximal ends 62b, 64b may be coupled by a flexible member 68. Aspects of the flexible member according to the present embodiment are described in more detail below. Other types of connections at the proximal ends of the first and second clamp members 62, 64 are also possible. While this embodiment is illustrated with the hinge joint at the distal ends of the clamp members 62, 64 and the flexible member 68 at the proximal ends of the clamp members 62, 64, it should be appreciated that in an alternative embodiment (not shown), the hinge joint may couple the proximal ends of the clamp members 62, 64 and the flexible member 68 may couple the distal ends of the clamp members 62, 64.

Though not shown, but as readily understood by one of ordinary skill in the art based on the present description, the resection line guide 60 may be placed around the stomach 10. In this regard, using laparoscopic instruments, the surgeon may manipulate the resection line guide 60 across the stomach 10 so that the first clamp member 62 is generally positioned along the anterior side 18 of the stomach 10 and the second clamp member 64 is generally positioned along the posterior side 20 of the stomach 10. The distal ends 62a, 64a of the clamp members 62, 64 generally extend beyond the distal end 16 of the stomach 10 and the proximal ends 62b, 64b of the clamp members 62, 64 generally extend beyond the proximal end 14 of the stomach 10. The spring hinge 66 between the first and second clamp members 62, 64 may extend around the distal end 16 of the stomach 10. With the resection line guide 60 placed around the stomach 10, the clamp members 62, 64 may be pivoted relative to each in order to position the resection line guide 60 relative to the stomach 10. This may be done, for example, with conventional graspers. To create a clamping force on the stomach 10 (and as is explained in further detail below), the ends of the flexible member 68 may be pulled, which tensions the flexible member 68 and decreases the length of the flexible member 68 that is between the clamp members 62, 64. As the ends of the flexible member 68 are pulled, the proximal ends 62b, 64b of the clamp members 62, 64 move towards each other, and the clamp members 62, 64 begin to provide a clamping force on the stomach 10.

The securement of the resection line guide 60 to the stomach 10 may be achieved using the two-stage clamping process as described above. The first-stage clamping force is less than a threshold clamping force and is configured and selected to provide a certain amount of resistance to movement of the resection line guide 60 relative to the stomach 10. This resistance is configured to prevent undesirable or unintentional movements of the resection line guide 60, but yet permit the surgeon to move the resection line guide 60 to a desired position relative to the stomach 10 without significant difficulty. In the second clamping stage, and with the resection line guide 60 in the desired location relative to the stomach 10, the clamping force of the resection line guide 60 may be increased above the threshold clamping force to effectively prevent or minimize the resection line guide 60 from moving relative to the stomach 10. The upper limit to which the resection line guide 60 may be clamped is selected so as to avoid any damage to the underlying tissue being clamped. This may be achieved by pulling further on the ends of the flexible member 68, which increases the tension on the flexible member 68 and increases the clamping force provided by the clamp members 62, 64.

When the resection line guide 60 is placed on the stomach 10 (e.g., in the first clamping stage as described above), the surgeon has a clear visualization of the intended results of the vertical sleeve gastrectomy prior to actually performing the division of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 60 prior to stapling and cutting the stomach 10. Once the resection line guide 60 is finally positioned, the surgeon may then cut and staple the tissue using the resection line guide 60 as a track along the entire segment or a significant part of the segment until complete resection of the stomach 10 occurs. In this regard, the stapling device 50 may abut or engage the resection line guide 60 along an alignment surface to facilitate an improved resection line, similar to that shown above in FIG. 2D.

While the embodiment described in FIGS. 3E and 3F had the flexible member 68 extending only through the proximal ends 62b, 64b of the clamp members 62, 64, in an alternative embodiment, the flexible member 68 may extend through substantially the full length of the clamp members 62, 64 such that it extends between the distal ends 62a, 64a of the clamp members 62, 64 along with the spring hinge 66. This arrangement of the flexible member 68 is shown in phantom in FIGS. 3E and 3F. This type of arrangement of the flexible member 68 is also described in more detail below. The operation of this alternative embodiment is similar to that described above for FIGS. 3E and 3F.

Figures 4A, 4B:
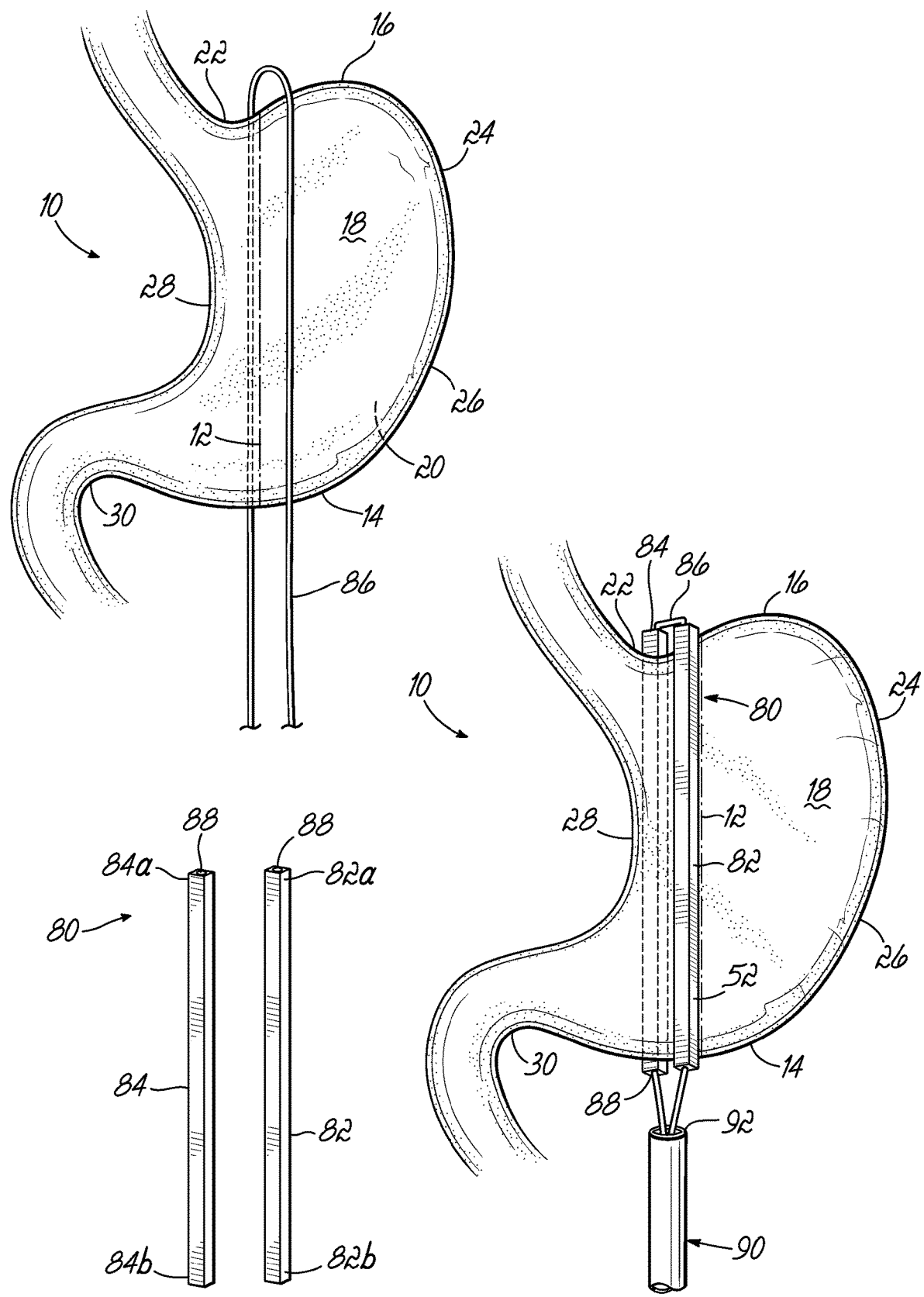
FIG. 4A is an elevation view of a resection line guide according to another embodiment.
FIG. 4B is an elevation view of the resection line guide of FIG. 4A positioned on the stomach.
Figure 4C:
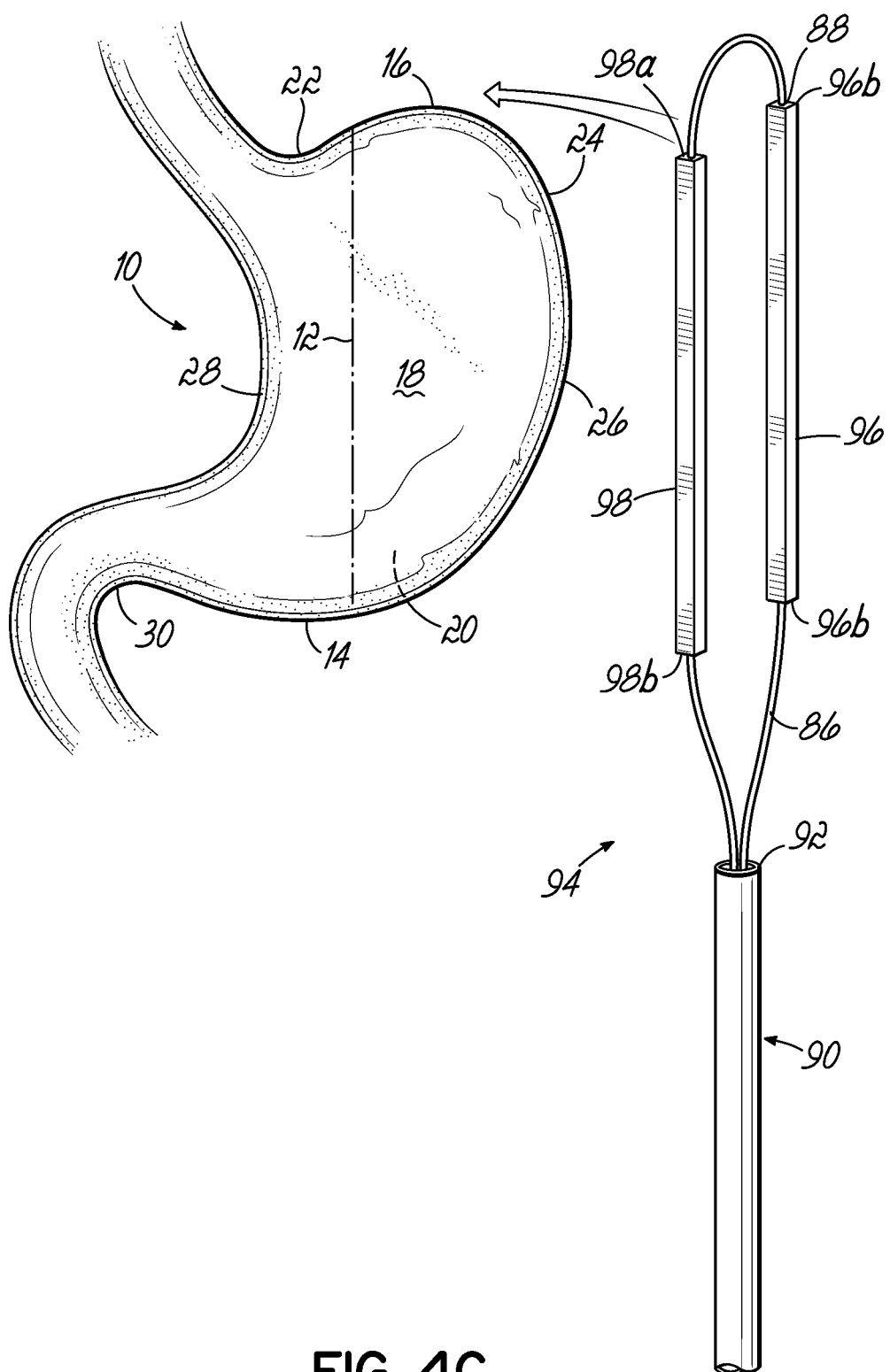
FIG. 4C is an elevation view of a resection line guide according to another embodiment.

In yet another embodiment, the resection line guide may have a pair of clamp members coupled by an elongate flexible member capable of being tensioned so as to produce a clamping force on an anatomical structure, such as stomach 10. FIGS. 4A-4C illustrate such an embodiment. In this regard and as shown in FIG. 4A, the resection line guide 80 includes a first clamp member 82 generally positionable on the anterior side 18 of the stomach 10 and a second clamp member 84 generally positionable on the posterior side 20 of the stomach 10, where the first clamp member 82 and the second clamp member 84 may be operatively coupled by a flexible member 86 to effectuate a clamping force on the stomach 10. In an exemplary embodiment, the flexible member 86 may include a flexible cable. However, other flexible members are contemplated, as noted below. In one embodiment, the clamp members 82, 84 may be configured as hollow bodies having a generally rectangular cross section and a length in a longitudinal direction which may exceed the length of the stomach 10 along the resection line 12. In an alternative embodiment, however, the clamp members 82, 84 may be generally solid. Additionally, the cross-sectional shape of the clamp members may also differ, as is noted below. In an exemplary embodiment, each of the clamp members 82, 84 may be a unity, monolithic member. However, in an alternative embodiment, the clamp members 82, 84 may be formed from a plurality of individual clamp segments that collectively form a clamp member. Such an embodiment, which is discussed below in greater detail, may allow the length of a clamp member to be easily varied.

In an exemplary embodiment, each of the clamp members 82, 84 may include openings 88 at their distal ends 82a, 84a and proximal ends 82b, 84b (or through bores in the case of solid clamp members) so as to allow the flexible member 86 to extend through and along the length of the clamp members 82, 84. In this configuration, the clamp members 82, 84 are essentially threaded onto the flexible member 86. In this configuration, the clamp members 82, 84 are also generally movable relative to the flexible member 86, such as along the length thereof. In an alternative embodiment, the flexible member 86 does not have to extend through (e.g., internal of) the clamp members 82, 84, but may extend along an outer surface of the clamp members 82, 84, such as through eyelets or the like positioned along a surface of the clamp members 82, 84 (not shown). In a further alternative, both clamp members 82, 84 do not have to be movable along the flexible member 86. For example, in one embodiment, one of the clamp members 82, 84 may be fixed relative to the flexible member 86 and the other of the clamp members 82, 84 may be movable relative to the flexible member 86.

FIGS. 4A and 4B illustrate the placement of the resection line guide 80 around the stomach 10. In this regard, using standard laparoscopic instruments and graspers, the surgeon may manipulate the flexible member 86 around the distal end 16 of the stomach 10 without having one or both clamp members 82, 84 thereon. The surgeon may then thread or manipulate the second clamp member 84 onto an end of the flexible member 86 and slide the second clamp member 84 along the flexible member 86 until the second clamp member 84 is generally positioned on the posterior side 20 of the stomach 10. In this regard, the distal end 84a may generally extend beyond the distal end 16 of the stomach 10 and the proximal end 84b may generally extend beyond the proximal end 14 of the stomach 10. Next, the surgeon may thread or manipulate the first clamp member 82 onto the flexible member 86 such that the first clamp member 82 is generally positioned on the anterior side 18 of the stomach 10. For example, the first clamp member 82 may be threaded or manipulated onto the other end of the flexible member 86. In this regard, the distal end 82a may generally extend beyond the distal end 16 of the stomach 10 and the proximal end 82b may generally extend beyond the proximal end 14 of the stomach 10. The order of applying the clamp members onto the flexible members may be reversed. Being able to assemble the resection line guide 80 inside the abdominal cavity may be advantageous in that it may allow for smaller trocars to be used because the entire guide does not have to fit simultaneously through a single trocar.

While the embodiment shown in FIG. 4A generally assembles the resection line guide 80 inside the abdominal cavity, in an alternative embodiment, as illustrated in FIG. 4C, the resection line guide 94 may be pre-assembled and then inserted into the abdominal cavity as a unit. In this regard, using standard laparoscopic instruments and graspers, the surgeon may manipulate the guide 94 across the stomach 10 so that the first clamp member 96 is generally positioned along the anterior side 18 of the stomach 10 and the second clamp member 98 is generally positioned along the posterior side 20 of the stomach 10. The distal ends 96a, 98a of the clamp members 96, 98 generally extend beyond the distal end 16 of the stomach 10 and the proximal ends 96b, 98b of the clamp members 96, 98 generally extend beyond the proximal end 14 of the stomach 10. The section of the flexible member 86 between the clamp members 96, 98 may be loop or extend around the distal end 16 of the stomach 10, as illustrated in FIG. 4B. The clamp members 96, 98 may be manipulated so as to provide a clamping force on the stomach 10. This clamping may be achieved by tensioning the flexible member 86.

In this regard, the resection line guides 80, 94 may include a device for tensioning the flexible member 86 thereby providing a clamping force on the anatomical structure, such as the stomach 10 (the process being described below with reference to resection line guide 80). In this regard, as the flexible member 86 is tensioned, the distance between the two clamp members 82, 84 decreases so as to impose a clamping force onto the stomach 10 captured therebetween. In one embodiment, for example, a tensioning device may include a tube 90 that operates in conjunction with the flexible member 86 and clamp members 82, 84 to generate a clamping force between the clamp members 82, 84. To this end, the flexible member 86 may extend through the tube 90 such that, for example, the ends thereof may be positioned outside the body, and thereby be more easily manipulated by the surgeon. The ends of the flexible member 86 may also remain within the abdominal cavity. In any event, the surgeon may then pull on the ends of the flexible member 86 while the end 92 of the tube 90 pushes against the proximal ends 82b, 84b of the clamp members 82, 84, which are not permitted to pass into the tube 90. When the flexible member 86 is initially pulled, slack in the flexible member 86 is thereby taken up and the clamp members 82, 84 move towards each other. As the clamp members 82, 84 move towards each other, the clamping force on the stomach 10 begins to increase along the length of the clamp members 82, 84. In addition, the length of the intermediate segment of the flexible member 86 between the clamp members 82, 84 decreases. Moreover, tensioning the flexible member 86 also generally aligns the clamp members 82, 84. For example, tension in the flexible member 86 may generally vertically align the clamp members 82, 84 relative to the stomach 10. The clamp members 82, 84 may slide along the flexible member 86 during this tensioning.

The securement of the resection line guides 80, 94 to the stomach 10 may be achieved using the two-stage clamping process as described above. More particularly, the flexible member 86 may be pulled so as to generate a clamping force on the stomach 10 less than the threshold clamping force. Again, this first-stage clamping force is configured and selected to provide a certain amount of resistance to movement of the resection line guide 80 relative to the stomach 10. This resistance is configured to prevent undesirable or unintentional movements of the resection line guide 80, but yet permit the surgeon to move the resection line guide 80 to a desired position relative to the stomach 10 without significant difficulty. In the second clamping stage, and with the resection line guide 80 in the desired location relative to the stomach 10, the clamping force of the resection line guide 80 may be increased above the threshold clamping force to effectively prevent or minimize the resection line guide 80 from moving relative to the stomach 10. The upper limit to which the resection line guide 80 may be clamped is selected so as to avoid any damage to the underlying tissue being clamped. This may be achieved in this embodiment by pulling the ends of the flexible member 86 while pushing further against the proximal ends 82b, 84b of the clamp members 82, 84 using the tube 90.

When the resection line guide 80 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 80 prior to stapling and cutting the stomach 10. Once the resection line guide 80 is finally positioned (e.g., the second clamping stage as described above), the surgeon may then cut and staple the tissue using the resection line guide 80 as a track along the entire segment or a significant part of the segment until complete resection of the stomach 10 occurs. In this regard, the stapling device 50 may abut or engage the resection line guide 80 along an alignment surface to facilitate an improved resection line, similar to that shown above in FIG. 2D.

Figure 5A:
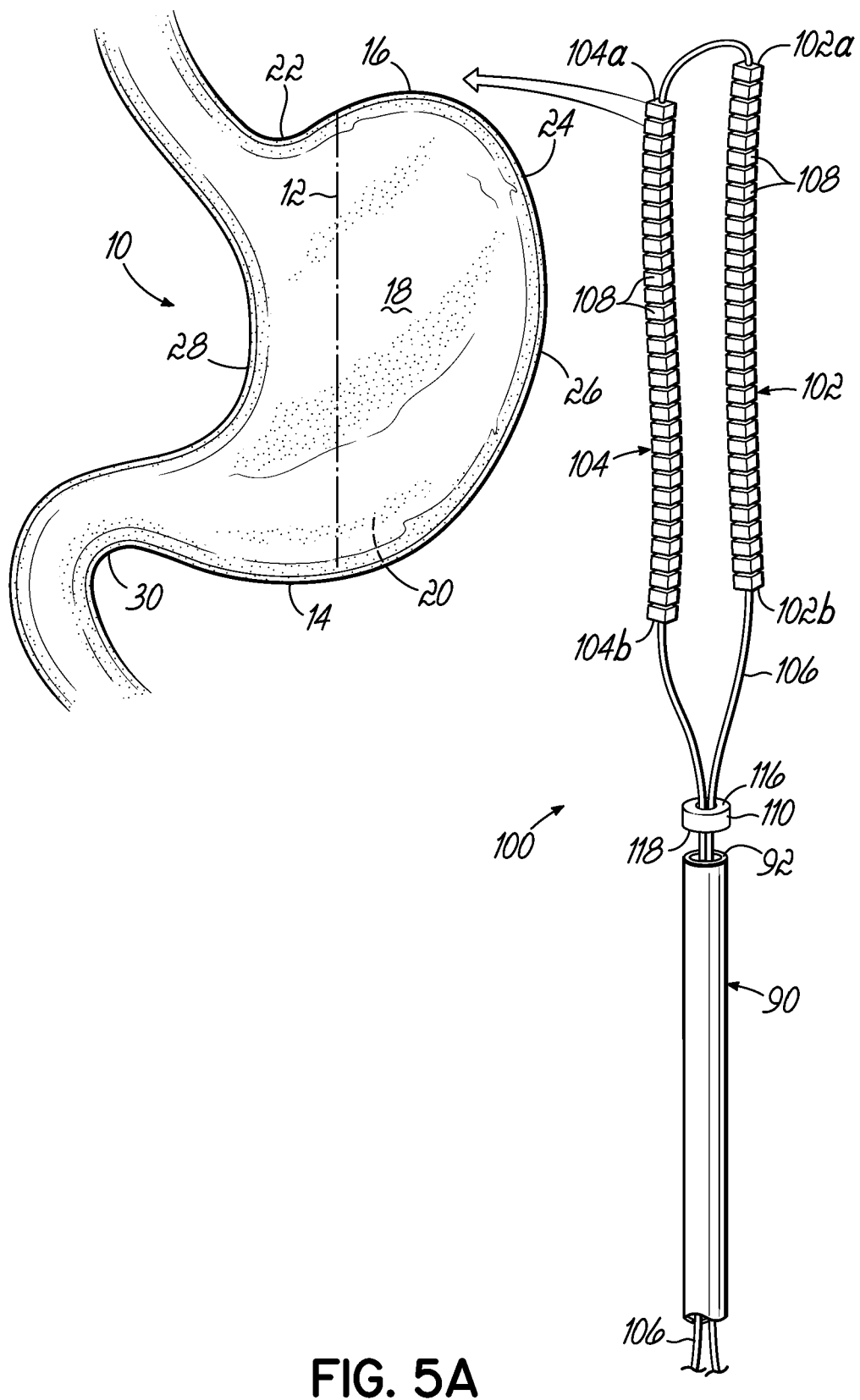
FIG. 5A is an elevation view of a resection line guide according to another embodiment.

In another alternative embodiment, and as alluded to above, a resection line guide may have clamp members formed from a plurality of clamp segments in order to allow the length of the clamp members to be more easily varied to fit a certain application. The figures shown in FIGS. 5A-5E illustrate such an embodiment. In this regard and as shown in FIG. 5A, the resection line guide 100 includes a first clamp member 102 generally positionable on the anterior side 18 of the stomach 10 and a second clamp member 104 generally positionable on the posterior side 20 of the stomach 10, where the first clamp member 102 and the second clamp member 104 may be operatively coupled by a flexible member 106 to effectuate a clamping force on the stomach 10. In an exemplary embodiment, the flexible member 106 may include a flexible cable, however, alternative embodiments of the flexible member, as described below, may also be used. As noted above, the clamp members 102, 104 may be formed from a plurality of clamp segments 108 serially arranged in order to form the clamp members 102, 104. In one embodiment, the clamp segments 108 may be configured as hollow bodies having a generally rectangular cross section and a length in a longitudinal direction which may be significantly less than the length of the stomach 10 along the resection line 12. In an alternative embodiment, however, the clamp segments 108 may be generally solid. Additionally, the cross-sectional shape of the clamp segments 108 may also differ, as described below.

In an exemplary embodiment, each of the clamp segments 108 may include openings at their distal ends and proximal ends (or through bores in the case of solid clamp members) so as to allow the flexible member 106 to extend through the clamp segments 108. In this configuration, the clamp segments 108 are essentially threaded onto the flexible member 106 and are also generally movable relative to the flexible member 106, such as along the length thereof. In an alternative embodiment, the flexible member 106 does not have to extend through (e.g., internal of) the clamp segments 108, but may extend along an outer surface of the clamp segments 108, such as through eyelets or the like along a surface of the clamp segments 108 (not shown). Adjacent clamp segments 108 of the first and second clamp members 102, 104 may be configured to couple to each other, such as using a tape or other type of fastener. Alternatively, adjacent clamp segments 108 may simply be configured to abut each other without any fixed connection therebetween. For example, each adjacent segment may include a confronting, generally planar faces which abut against each other when the flexible member 106 is tensioned.

In still a further alternative embodiment, adjacent clamp segments 108 of the clamp members 102, 104 may be configured to abut each other, and include an interlock configuration between the two adjacent clamp segments. For example, FIG. 5F illustrates two adjacent clamp segments 108a and 108b including an interlock configuration. In this regard, clamp segment 108a includes a projection 108c that extends from the main body of the clamp segment 108a, and clamp segment 108b includes a recess 108d that extends into the main body of the clamp segment 108b. When the flexible member 106 is tensioned, the adjacent clamp segments 108a, 108b engage each other through abutting contact. More particularly, however, when the flexible member 106 is tensioned, the projection 108c is positioned within the recess 108d to provide the interlock. The interlock between adjacent clamp segments 108 may more firmly stabilize the clamp members 102, 104 during use but yet also allow for a variable length.

Figure 5B:
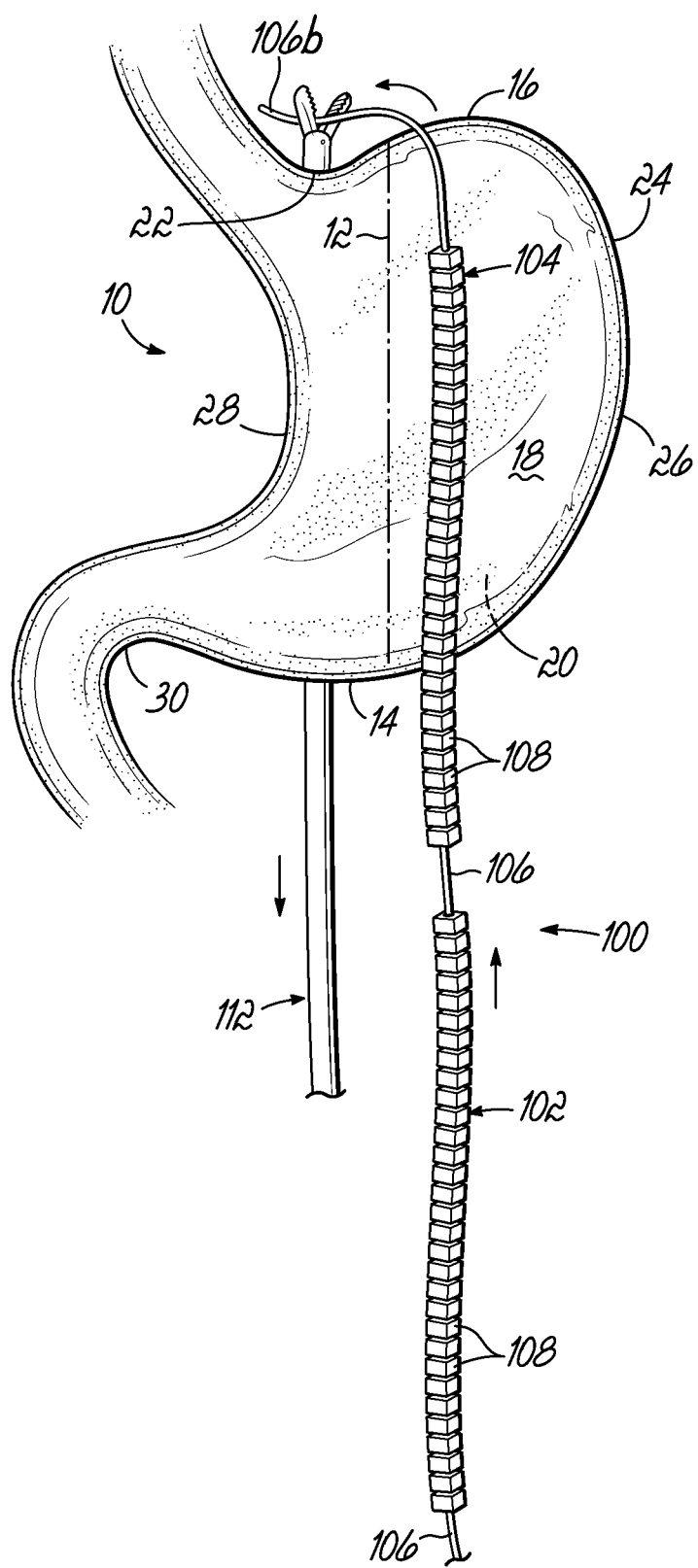
FIG. 5B is an elevation view of a part of the placement of the resection line guide of FIG. 5A around a stomach.
Figure 5C:
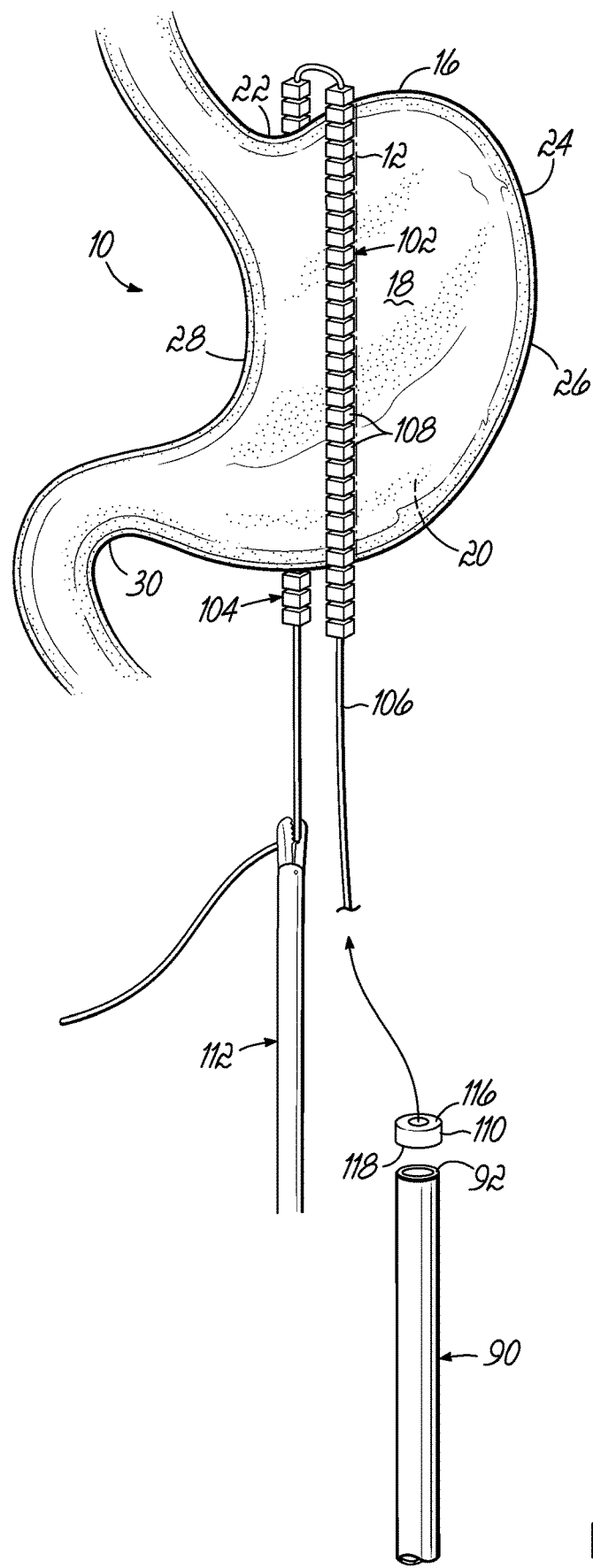
FIG. 5C is an elevation view of a part of the placement of the resection line guide of FIG. 5A around the stomach.

FIGS. 5B and 5C illustrate the placement of the resection line guide 100 around the stomach 10 in accordance with another embodiment. In this regard, using standard laparoscopic instruments and graspers, the surgeon may manipulate a leading end 106b of the flexible member 106 over the stomach 10 along the anterior side 18 and pull it around to the posterior side 20 of the stomach 10, such as with a grasper 112. The leading end 106b of the flexible member 106 may then be pulled around the stomach 10 until the second clamp member 104 is generally positioned on the posterior side 20 of the stomach 10 and the first clamp member 102 is generally positioned on the anterior side 18 of the stomach 10, as shown in FIG. 5C. At this point, should there be any need to vary the length of either of the first or second clamp members 102, 104, clamp segments 108 may be added or removed to provide the desired length to the clamp members 102, 104. For example, in order to add a segment, a new clamp segment 108 may be threaded onto an end (dictated by which clamp member is having its length adjusted) of the flexible member 106 and slid along the length thereof to position the segment in the desired location.

In one embodiment, the distal end 104a of the second clamp member 104 may generally extend beyond the distal end 16 of the stomach 10 and the proximal end 104b of the second clamp member 104 may generally extend beyond the proximal end 14 of the stomach 10. Similarly, the distal end 102a of the first clamp member 102 may generally extend beyond the distal end 16 of the stomach 10 and the proximal end 102b of the first clamp member 102 may generally extend beyond the proximal end 14 of the stomach 10. It should be realized that while most of the clamp members 102, 104 (e.g., but for slight adjustments in length) may be pre-assembled before the resection line guide 100 is inserted into the abdominal cavity, in an alternative embodiment, the flexible member 106 may be positioned around the stomach 10 first and then the clamp members 102, 104 assembled onto the flexible member 106, in a manner similar to that described above in FIG. 4A. Being able to assemble the resection line guide 100 inside the abdominal cavity may be advantageous in that it may allow for smaller trocars to be used because the entire guide does not have to fit simultaneously through a single trocar. In any event, the clamp members 102, 104 may be manipulated so as to provide a clamping force on the stomach 10. This clamping force may be achieved by tensioning the flexible member 106.

In this regard, the resection line guide 100 may include a device for tensioning the flexible member 106, thereby providing a clamping force on the anatomical structure, such as the stomach 10. In one embodiment, for example, a tensioning device may include a cinch ring 110 and a cinch tube 90 that are configured to operate in conjunction with the flexible member 106 and the clamp members 102, 104 to generate a clamping force between the clamp members 102, 104. To this end, the flexible member 106 may extend through the cinch ring 110 and tube 90 such that, for example, the ends 106a, 106b thereof may be positioned outside the body, and thereby more easily manipulated by the surgeon. The ends 106a, 106b may also remain in the abdominal cavity but be positioned proximal of the cinch ring 110 and tube 90. The surgeon may then pull on the ends 106a, 106b of the flexible member 106 while the end 92 of the tube 90 pushes against the proximal end 114 of the cinch ring 110. Eventually, the distal end 116 of the cinch ring 110 will engage against the proximal ends 102b, 104b of the clamp members 102, 104, which are not permitted to pass through the cinch ring 110. When the flexible member 106 is initially pulled, slack in the flexible member 106 is thereby taken up and the clamping force on the stomach 10 begins to increase, as illustrated in FIG. 5D. The clamp members 102, 104, and the clamp segments 108 that form these members, may slide along the flexible member 106 during this tensioning. The cinch ring 110 is configured to maintain tension in the flexible member 106 once it is applied. For example, the cinch ring 110 may be a rubber ring or the like such that friction maintains the tension in the flexible member 106. The cinch ring 110 may take other forms to maintain the tension in the flexible member 106.

The securement of the resection line guide 100 to the stomach 10 may be achieved using the two-stage clamping process as described above. More particularly, the flexible member 106 may be pulled so as to generate a clamping force on the stomach 10 less than the threshold clamping force. Again, this first-stage clamping force is configured and selected to provide a certain amount of resistance to movement of the resection line guide 100 relative to the stomach 10. This resistance is configured to prevent undesirable or unintentional movements of the resection line guide 100, but yet permit the surgeon to move the resection line guide 100 to a desired position relative to the stomach 10 without significant difficulty. In the second clamping stage, and with the resection line guide 100 in the desired location relative to the stomach 10, the clamping force of the resection line guide 100 may be increased above the threshold clamping force to effectively prevent or minimize the resection line guide 100 from moving relative to the stomach 10, as shown in FIG. 5E. The upper limit to which the guide 100 may be clamped is selected so as to avoid any damage to the underlying tissue being clamped. This may be achieved in this embodiment by pulling the ends 106a, 106b of the flexible member 106 while pushing against the proximal ends 102b, 104b of the clamp members 102, 104 using the tube 90 and cinch ring 110.

When the resection line guide 100 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide prior to stapling and cutting the stomach 10. Once the resection line guide 100 is finally positioned (e.g., the second clamping stage as described above), the surgeon may then cut and staple the tissue using the resection line guide 100 as a track along the entire segment or a significant part of the segment until complete resection of the stomach 10 occurs. In this regard, the stapling device 50 may abut or engage the resection line guide 100 along an alignment surface to facilitate an improved resection line, similar to that shown above in FIG. 2D.

Figure 6:
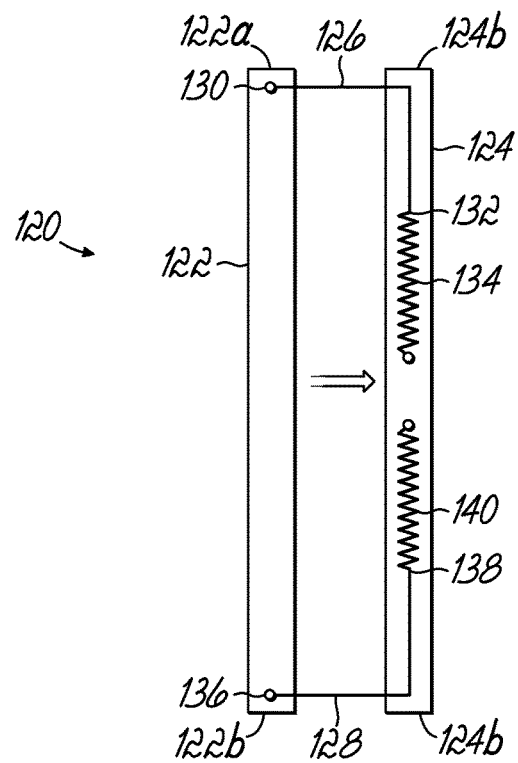
FIG. 6 depicts a schematic of a resection line guide according to another embodiment.

FIG. 6 illustrates another embodiment of a resection line guide in accordance with an embodiment where the clamp members may include a biasing mechanism that biases the clamp members toward one another, thereby generating a clamping force when the guide is placed about an anatomical structure. In this regard, a resection line guide 120 includes a first clamp member 122 generally positionable on the anterior side 18 of the stomach 10 and a second clamp member 124 generally positionable on the posterior side 20 of the stomach 10, where the first clamp member 122 and the second clamp member 124 may be operatively coupled to effectuate a clamping force on the stomach 10. In an exemplary embodiment, the first and second clamp members 122, 124 may be coupled by a first flexible member 126 and a second flexible member 128. More particularly, the first flexible member 126 may have a first end 130 fixed to the first clamp member 122 adjacent the distal end 122a thereof and pass out of the first clamp member 122 adjacent the distal end 122a. The flexible member 126 may then pass into the second clamp member 124 adjacent a distal end 124a thereof and extend along at least a portion of the second clamp member 124 toward the proximal end 124b thereof. A second end 132 of the flexible member 126 may be fixed to the second clamp member 124 by a biasing device 134, which when activated creates a tension in the first flexible member 126. The biasing device 134 may be generally positioned adjacent a central portion of the clamp member 124. Other positions, however, are possible. In an exemplary embodiment, the biasing device 134 may include a spring, an elastic deformable block (e.g., a rubber block), or other device capable of being biased so as to generate a tension in the first flexible member 126. In an alternate embodiment, the length of the flexible members 126, 128 that is between the clamp members 122, 124 may be externally controlled. For example, the flexible members 126, 128 may be externally manipulated to cause the clamp members 122, 124 to be separated by about 2 to 6 cm, while keeping the clamp members 122, 124 generally parallel. Consequently, the surgeon would not separate the clamp members 122, 124 laparoscopically.

In a similar manner, the second flexible member 128 may have a first end 136 fixed to the first clamp member 122 adjacent the proximal end 122b thereof and pass out of the first clamp member 122 adjacent the proximal end 122b. The flexible member 128 may then pass into the second clamp member 124 adjacent a proximal end 124b thereof and extend along at least a portion of the second clamp member 124 toward the distal end 124a thereof. A second end 138 of the flexible member 128 is fixed to the second clamp member 124 by a biasing device 140, which when activated creates a tension in the second flexible member 128. The biasing device 140 may be generally positioned adjacent a central portion of the clamp member 124. Other positions, however, are possible. It should be appreciated that the flexible members and biasing devices may be provided in a different arrangement as that shown in FIG. 6. For example, in an alternative embodiment, the biasing devices may be located in the first clamp member 122. In still a further alternative embodiment, one biasing device may be located in the first clamp member 122 and the second biasing device may be located in the second clamp member 124. Other arrangements may also be possible.

In a manner similar to that described above but not shown, after the stomach 10 has been effectively mobilized along the greater curvature 26, the resection line guide 120 may be inserted into the abdominal cavity through a surgical trocar and positioned along the stomach 10. Once inside the abdominal cavity, the surgeon may spread the first and second clamp members 122, 124 apart from each other using standard laparoscopic instruments and graspers, for example. In this regard, the clamp members 122, 124 may include attachment points or tabs (not shown) that facilitate grasping the clamp members by the laparoscopic instruments. As the clamp members 122, 124 move apart, the biasing devices 134, 140 activate (or they are pre-activated) to create a biasing force in a direction that directs the clamp members 122, 124 toward each other. This biasing force, however, may be overcome by the surgeon using the graspers in order to allow the surgeon to locate the resection line guide 120 on the stomach 10, where the first clamp member 122 generally extends along the anterior side 18 of the stomach 10 and the second clamp member 124 generally extends along the posterior side 20 of the stomach 10. When the desired position of the resection line 12 is reached, the surgeon may slowly release the hold on the clamp members 122, 124 with the graspers. Due to the bias of the biasing devices 134, 140, the clamp members 122, 124 move toward each other and generate a clamping force on the tissue between the members.

The biasing devices 134, 140 may be selected to provide a clamping force effective to prevent or minimize the resection line guide 120 from moving relative to the stomach 10. Due the particular design of this embodiment, there may only be a single stage of clamping to secure the resection line guide 120 on the stomach 10. The upper limit to which the resection line guide 120 may be clamped is selected so as to avoid any damage to the underlying tissue being clamped. This clamping force may be controlled by properly selecting the biasing generated by the biasing devices 134, 140. For example, when the biasing devices 134, 140 are configured as springs, the spring constants may be selected to provide the desired clamping force.

When the resection line guide 120 is initially placed on the stomach 10, the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 120 prior to stapling and cutting the stomach 10. For example, the laparoscopic graspers may be used to separate the clamp members 122, 124 and thereby allow the resection line guide 120 to be moved to an alternate position. In any event, once the resection line guide 120 is finally positioned, the surgeon may then cut and staple the tissue using the resection line guide 120 as a track along the entire segment or a significant part of the segment until complete resection of the stomach 10 occurs. In this regard, the stapling device 50 may abut or engage the resection line guide 120 along an alignment surface to facilitate an improved resection line, similar to that shown above in FIG. 2D.

Figure 7:
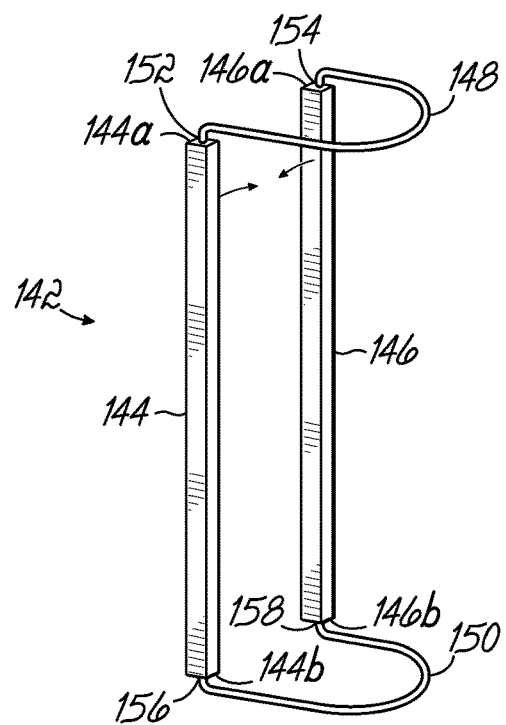
FIG. 7 is a perspective view of a resection line guide according to another embodiment.

Similar to the embodiment shown in FIG. 6, FIG. 7 illustrates another embodiment of a resection line guide in accordance with an embodiment where the clamp members may include a biasing mechanism that biases the clamp members toward one another to generate a clamping force when the guide is placed about an anatomical structure. In this embodiment, a resection line guide 142 includes a first clamp member 144 generally positionable on the anterior side 18 of the stomach 10 and a second clamp member 146 generally positionable on the posterior side 20 of the stomach 10, where the first clamp member 144 and the second clamp member 146 may be operatively coupled to effectuate a clamping force on the stomach 10. In an exemplary embodiment, the first and second clamp members 144, 146 may be coupled by a first member 148 and a second member 150. More particularly, the first member 148 may have a first end 152 coupled to the first clamp member 148 adjacent the distal end 144*a* thereof and a second end 154 coupled to the second clamp member 146 adjacent the distal end 146*a* thereof. In a similar manner, the second member 150 may have a first end 156 coupled to the first clamp member 144 adjacent the proximal end 144*b* thereof and a second end 158 coupled to the second clamp member 146 adjacent the proximal end 146*b* thereof. In accordance with this embodiment, the first and second members 144, 146 may be configured to be biased so as to generate a clamping force between the clamp members.

In one embodiment, for example, the first and second members 148, 150 may be configured as elastic bands (e.g., rubber bands) such that when the bands are pulled apart, tension is created within the members 148, 150 that tends to drive the clamp members 144, 146 toward each other. In another embodiment, the first and second members 144, 146 may be formed as shape memory elements. Shape memory elements have a set shape that they essentially "remember" such that when the shape elements are deformed, they generate a return force directing the element back to its set or remembered shape. By way of example and without limitation, the shape memory elements may take the form of nitinol (NiTi) wires, bands, cables or such wires, bands or cables made of other shape memory materials. The shape memory elements may be those described in U.S. Patent Application Publication No. 2009/0012545, which is hereby incorporated by reference herein in its entirety. The shape memory elements may also take other forms.

In a manner similar to that described above, after the stomach 10 has been effectively mobilized along the greater curvature 26, the resection line guide 142 may be inserted into the abdominal cavity through a surgical trocar and positioned along the stomach 10. Once inside the abdominal cavity, the surgeon may spread the first and second clamp members 144, 146 apart from each other using standard laparoscopic instruments and graspers, for example. In this regard, the clamp members 144, 146 may include attachment points (not shown) that facilitate grasping the clamp members 144, 146 by the laparoscopic instruments. As the clamp members 144, 146 move apart, the first and second members 148, 150 generate a biasing force in a direction that directs the clamp members 144, 146 toward each other. This biasing force, however, may be overcome by the surgeon using the graspers in order to allow the surgeon to locate the resection line guide 142 on the stomach 10, where the first clamp member 144 generally extends along the anterior side 18 of the stomach 10 and the second clamp member 146 generally extends along the posterior side 20 of the stomach 10. When the desired position of the resection line 12 is reached, the surgeon may slowly release the hold on the clamp members 144, 146 with the graspers. Due to the bias of the members 148, 150, the clamp members 144, 146 move toward each other and generate a clamping force on the tissue between the members.

The biasing force from the members 148, 150 may be selected to provide a clamping force effective to prevent or minimize the resection line guide 142 from moving relative to the stomach 10. Due the particular design of this embodiment, there may only be a single stage of clamping to secure the resection line guide 142 on the stomach 10. The upper limit to which the resection line guide 142 may be clamped is selected so as to avoid any damage to the underlying tissue being clamped. This clamping force may be controlled by properly selecting the biasing generated by the members 148, 150. For example, when the first and second members 148, 150 are formed from shape memory elements, the set position of the elements may be selected in a manner that controls the ultimate clamping force of the clamp members 144, 146.

When the resection line guide 142 is initially placed on the stomach 10, the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 142 prior to stapling and cutting the stomach 10. For example, the laparoscopic graspers may be used to separate the clamp members 144, 146 and thereby allow the resection line guide 142 to be moved to an alternate position. In any event, once the resection line guide 142 is finally positioned, the surgeon may then cut and staple the tissue using the resection line guide 142 as a track along the entire segment or a significant part of the segment until complete resection of the stomach occurs. In this regard, the stapling device 50 may abut or engage the resection line guide 142 along an alignment surface to facilitate an improved resection line, similar to that shown above in FIG. 2D.

Figure 8A:
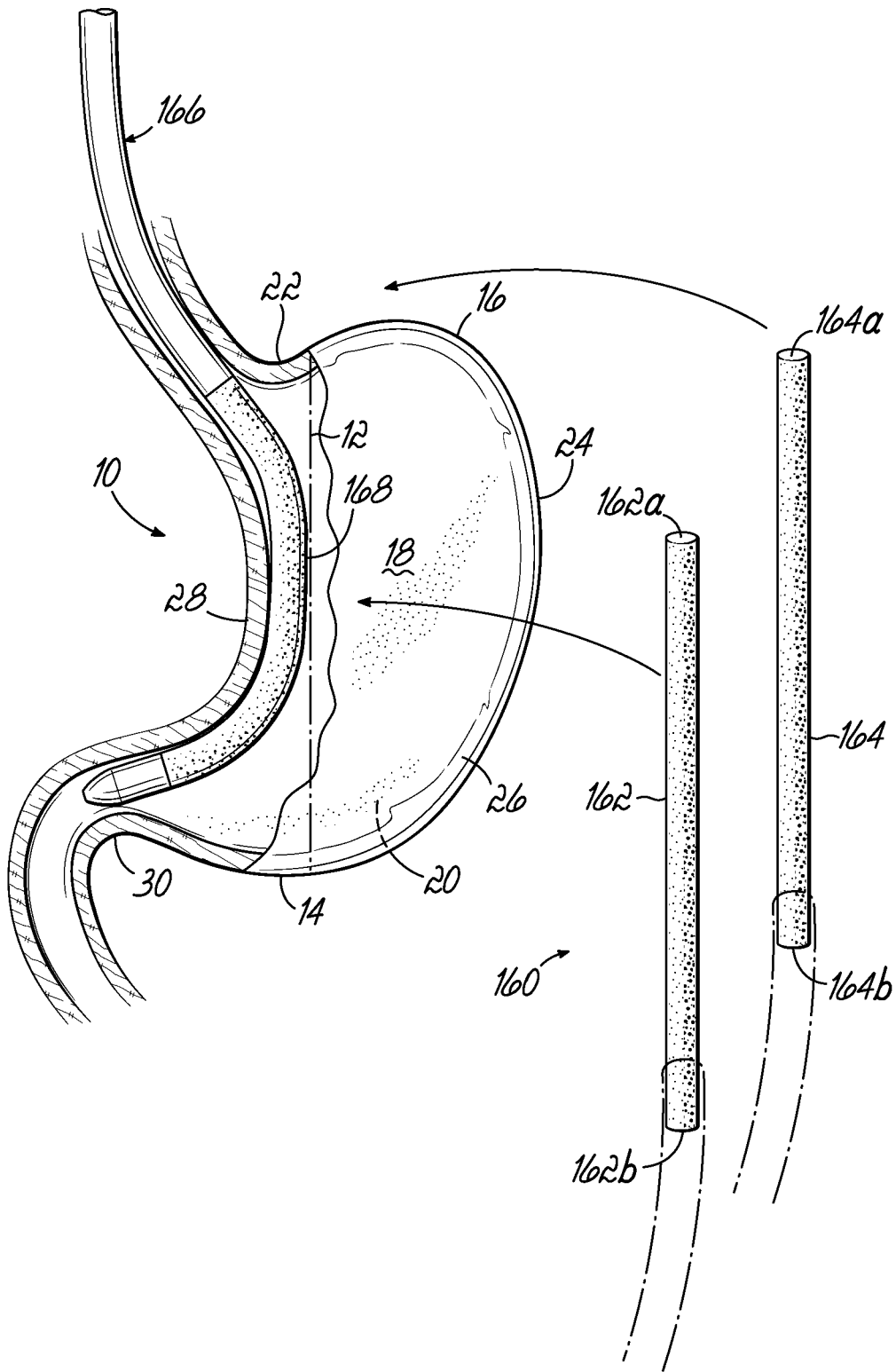
FIG. 8A is an elevation view of a resection line guide according to another embodiment.
Figure 8B:
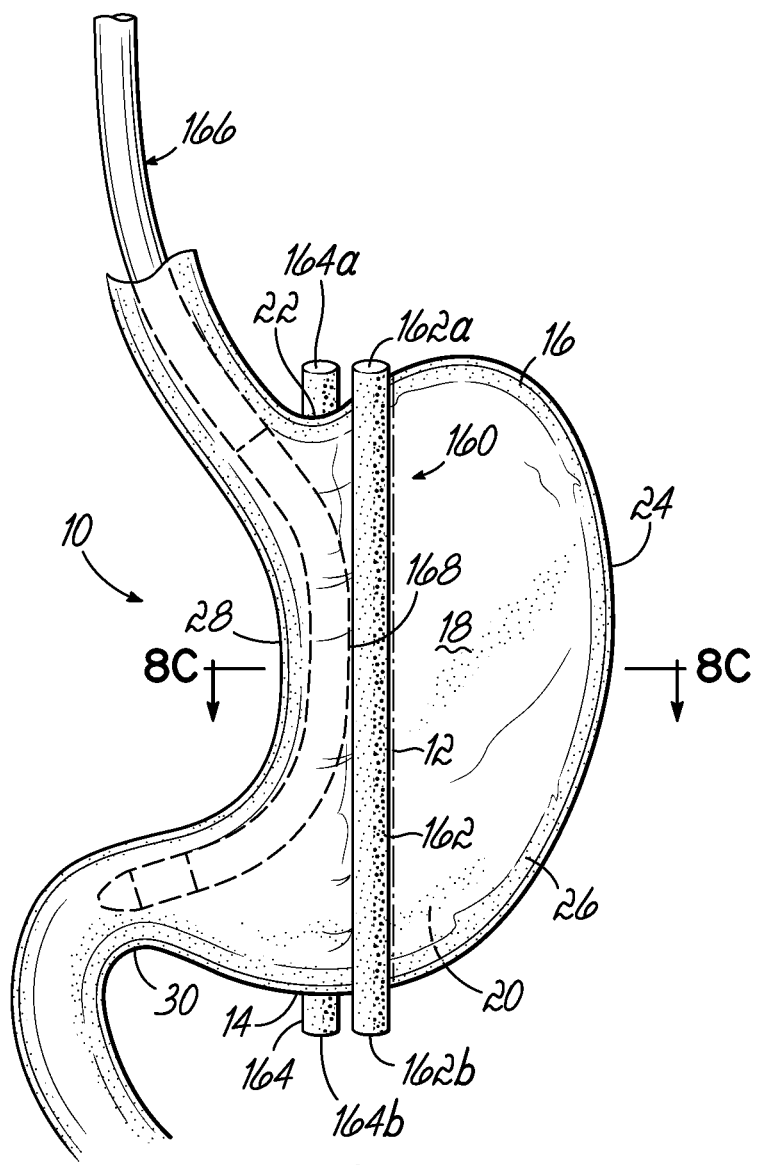
FIG. 8B is an elevation view of the resection line guide of FIG. 8A placed around a stomach.
Figure 8C:
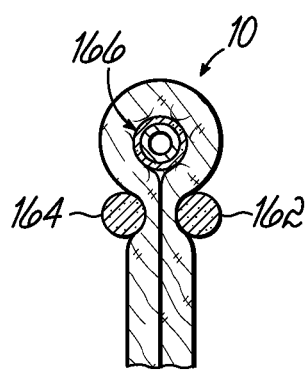
FIG. 8C is a cross-sectional view of the resection line guide shown in FIG. 8B.

In yet another embodiment, a resection line guide may include a pair of clamp members having magnetic characteristics or features to produce a clamping force on an anatomical structure, such as stomach 10. FIGS. 8A-8C illustrate such an embodiment. In this regard and as shown in FIG. 8A, a resection line guide 160 includes a first clamp member 162 generally positionable on the anterior side 18 of the stomach 10 and a second clamp member 164 generally positionable on the posterior side 20 of the stomach 10, where the first clamp member 162 and the second clamp member 164 may be configured to effectuate a clamping force on the stomach 10. More particularly, clamp members 162, 164 are configured to magnetically couple to each other to provide a clamping force on the stomach 10. In this regard, the clamp members 162, 164 may be magnetized using methods known in the art. For example, the clamp members 162, 164 may be coated in a ferromagnetic metal or other ferromagnetic material. As an alternative, the clamp members 162, 164 may contain a ferromagnetic metal or other ferromagnetic material. The ferromagnetic metal or other material may span the entire length of the clamp members 162, 164 or may only cover a portion of their entire length. In an exemplary embodiment, the clamp members 162, 164 may be formed as elongate members made of a ferromagnetic metal having a generally cylindrical cross-section and a length generally exceeding that of the stomach 10. However, other arrangements are possible as described below.

FIG. 8B illustrates the resection line guide 160 placed on the stomach 10. In this regard, using standard laparoscopic instruments and graspers, the surgeon may insert the second clamp member 164 into the abdominal cavity and position the second clamp member 164 generally on the posterior side 20 of the stomach 10. More particularly, the distal end 164a may generally extend beyond the distal end 16 of the stomach 10 and the proximal end 164b may generally extend beyond the proximal end 14 of the stomach 10. Next, the surgeon may insert the first clamp member 162 into the abdominal cavity and position the first clamp member 162 generally on the anterior side 18 of the stomach 10. In this regard, the distal end 162a may generally extend beyond the distal end 16 of the stomach 10 and the proximal end 162b may generally extend beyond the proximal end 14 of the stomach 10. Being able to assemble the resection line guide 160 inside the abdominal cavity may be advantageous in that it may allow for smaller trocars to be used because the entire guide does not have to fit simultaneously through a single trocar. In any event, as the clamp members 162, 164 are brought together, a magnetic force developed between the two clamp members 162, 164 tends to drive the clamp members toward each other, similar to the biasing force in FIGS. 6 and 7 above. This magnetic force, however, may be overcome by the surgeon using the graspers in order to allow the surgeon to locate the resection line guide 160 on the stomach 10. When the desired position of the resection line 12 is reached, the surgeon may slowly release the hold on one of both of the clamp members 162, 164 with the graspers. Due to the magnetic attraction, the clamp members 162, 164 move toward each other and generate a clamping force on the tissue between the members.

The magnetic force may be selected to provide a clamping force effective to prevent or minimize the resection line guide 160 from moving relative to the stomach 10. Due the particular design of this embodiment, there may only be a single stage of clamping to secure the resection line guide 160 on the stomach 10. The upper limit to which the guide 160 may be clamped is selected so as to avoid any damage to the underlying tissue being clamped. This clamping force may be controlled by properly selecting the magnetic characteristics of the clamp members 162, 164. Those of ordinary skill in the art will understand how to configure the magnetic characteristics of the clamp members 162, 164 in order to achieve a desired clamping force.

When the resection line guide 160 is initially placed on the stomach 10, the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 160 prior to stapling and cutting the stomach 10. For example, the laparoscopic graspers may be used to separate and move the clamp members 162, 164 and thereby allow the resection line guide 160 to be moved to an alternate position. In any event, once the resection line guide 160 is finally positioned, the surgeon may then cut and staple the tissue using the resection line guide 160 as a track along the entire segment or a significant part of the segment until complete resection of the stomach 10 occurs. In this regard, the stapling device 50 may abut or engage the resection line guide 160 along an alignment surface to facilitate an improved resection line, similar to that shown above in FIG. 2D.

In an alternative embodiment, the resection line guide 160 may be used in combination with a bougie 166, which is generally known in the art and facilitates placement of the resection line guide 160 along the intended resection line 12. In this regard, the surgeon may position the bougie 166 inside the stomach 10 by insertion through the mouth, for example (FIG. 8A). With the bougie 166 so positioned, it defines an alignment surface 168 which may be used to properly position the first and second clamp members 162, 164 along the intended resection line 12, as described above. In a further alternative embodiment, the bougie 166 may include magnetic features that provide a magnetic attraction force between the bougie 166 and one or both of the clamp members 162, 164. For example, the bougie 166 may be coated in a ferromagnetic metal or other ferromagnetic material. Alternatively, the bougie 166 may contain a ferromagnetic metal or other ferromagnetic material. The ferromagnetic metal or other material may span the entire length of the bougie or may only cover a portion of the entire length of the bougie. In these embodiments, the clamp member 162, 164 may be attracted solely to the bougie 166 in order to generate the clamping force to secure the resection line guide 160 to the stomach 10. In an alternative embodiment, however, the clamp members 162, 164 may be magnetically attracted to both the bougie 166 and the other clamp member. In a still further alternative embodiment, only one of the clamp members may be magnetically attracted to the bougie 166 and the other clamp member may be attracted solely to the other clamp member. Those of ordinary skill in the art may recognize other arrangements for generating a clamping force using magnetic attraction of the clamp members and a bougie.

Figure 9A:
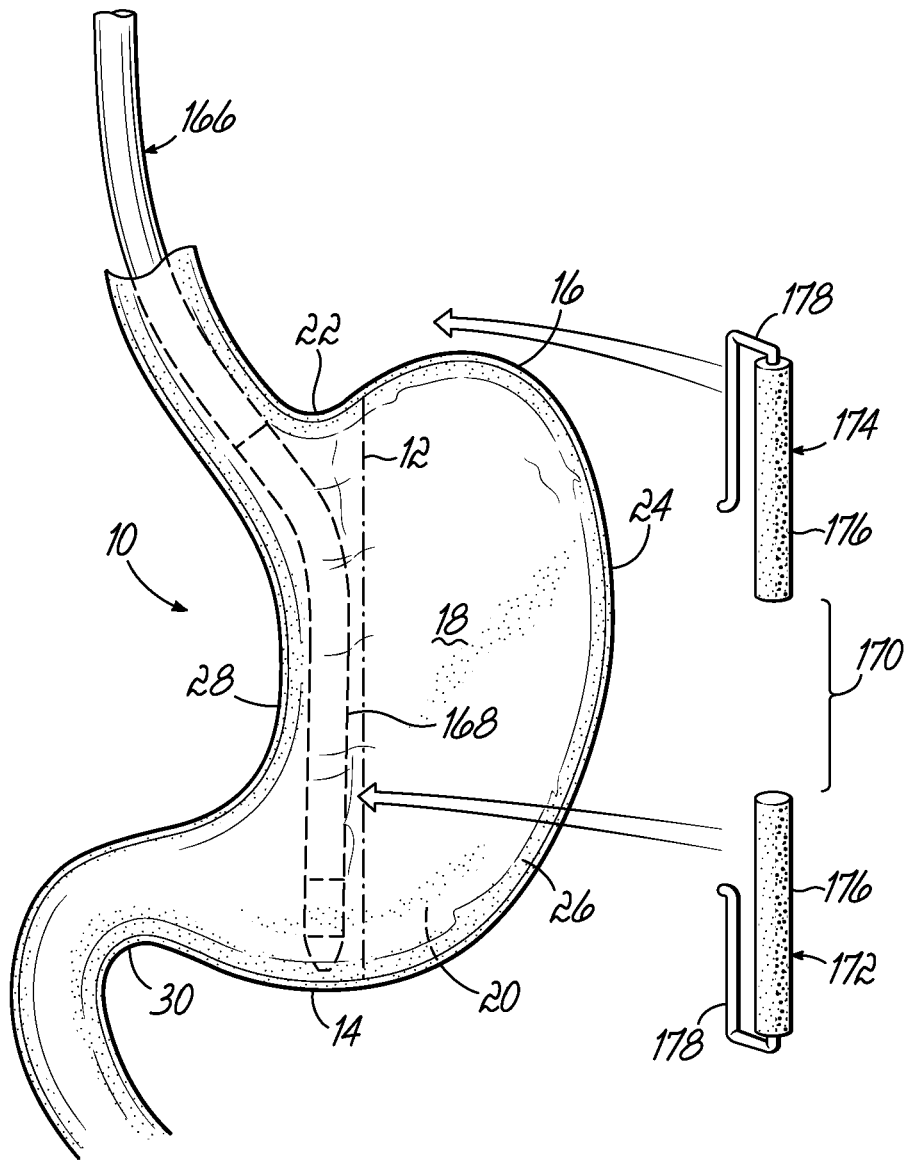
FIG. 9A is an elevation view of a resection line guide according to another embodiment.
Figure 9B:
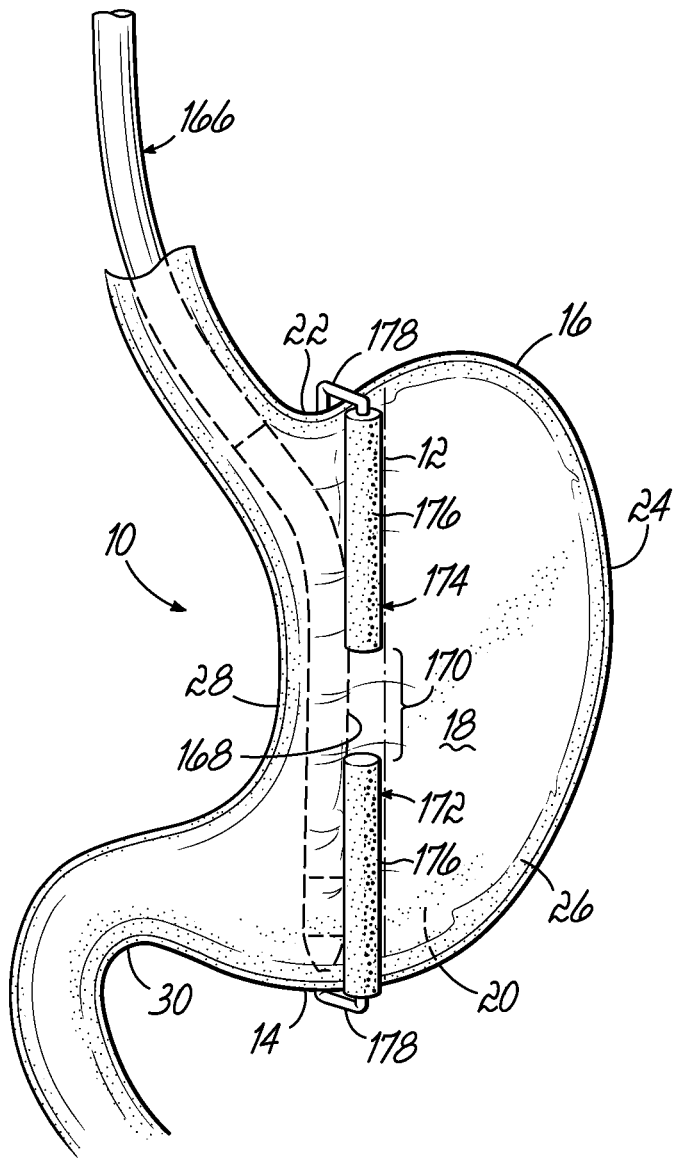
FIG. 9B is an elevation view of the resection line guide of FIG. 9A placed around a stomach.

FIGS. 9A and 9B illustrate another embodiment of a resection line guide utilizing magnetic attraction forces that facilitate locating the clamp members and/or that facilitate generating a clamping force on an anatomical structure, such as stomach 10. This embodiment differs from other embodiments in that each clamp member does not extend along the anatomical structure for substantially the full length of the intended resection line 12. In this regard, and as illustrated in FIGS. 9A and 9B, the resection line guide 170 includes a pair of retaining clips 172 and 174. Each retaining clip 172, 174 includes a guide portion 176 and a resilient arm 178 extending from guide portion 176 and in general parallel relation thereto (e.g., so as to form a u-shaped profile). The resilient arm 178 may be formed from metal, plastic or other materials suitable for a biological environment and capable of providing a resilient clamping force with guide portion 176. In this embodiment, the guide portions 176 may be magnetized using methods known in the art. For example, the guide portions 176 may be coated in a ferromagnetic metal or other ferromagnetic material. As an alternative, the guide portions 176 may contain a ferromagnetic metal or other ferromagnetic material. The ferromagnetic metal or other material may span the entire length of the guide portions 176 or may only cover a portion of their entire length. The length and width of the retaining clips 172, 174 may be varied according to surgeon preference and the procedure in which they are intended to be used. By way of example and without limitation, the width may range from 0.5 to 1 cm, and the length may range from 2 to 10 cm.

FIG. 9B illustrates the resection line guide 170 placed on the stomach 10. In this regard, the surgeon may position the bougie 166 inside the stomach 10 by insertion through the mouth, for example. With the bougie 166 so positioned, it defines an alignment surface 168 which may be used to properly position the first and second retaining clips 172 and 174 along the intended resection line 12. Using standard laparoscopic instruments and graspers, the surgeon may insert the first retaining clip 172 into the abdominal cavity and position the first retaining clip 172 at the proximal end 14 of the stomach 10. In this regard, the guide portion 176 is generally positioned on the anterior side 18 of the stomach 10 and the resilient arm 178 extends around the proximal end 14 and is generally positioned along the posterior side 20 of the stomach 10. In a similar manner, the second retaining clip 174 may be positioned at the distal end 16 of the stomach 10. The resiliency of the arm 178 generates a clamping force so as to secure the retaining clip 172 to the stomach 10. In addition to this, however, a magnetic force develops between the guide portion 176 of the retaining clip 172 and the bougie 166. This magnetic force, however, may be overcome by the surgeon using the graspers in order to allow the surgeon to locate the retaining clip 172 on the stomach 10. When the desired position of the resection line 12 is reached, the surgeon may slowly release the hold on the retaining clip 172 with the graspers. Due to the magnetic attraction, the guide portion 176 and the bougie 166 move toward each other and generate a clamping force on the tissue therebetween. Once placed on the stomach 10 and mated with the bougie 166, the surgeon may adjust the axial position of the retaining clip 172 relative to the retaining clip 174 to flatten the stomach and provide a flat, straight stapling surface.

The magnetic force may be selected to provide a clamping force effective to prevent or minimize the resection line guide 170 from moving relative to the stomach 10. Similar to previous embodiments, there may be a two-stage clamping process for securing the resection line guide 170 on the stomach 10. In this regard, the guide portion 176 and the resilient arm 178 may be configured to generate a clamping force on the stomach 10 less than the threshold clamping force. This first-stage clamping force is configured and selected to provide a certain amount of resistance to movement of the resection line guide 170 relative to the stomach 10 (e.g., movement of the retaining clips 172, 174 along the stomach 10). This resistance is configured to prevent undesirable or unintentional movements of the resection line guide 170, but yet permit the surgeon to move the resection line guide 170 to a desired position relative to the stomach 10 without significant difficulty. In the second clamping stage, the clamping force of the resection line guide 170 may be increased above the threshold clamping force due to the magnetic forces developed between the guide portions 176 and the bougie 166. The upper limit to which the resection line guide 170 may be clamped is selected so as to avoid any damage to the underlying tissue being clamped.

When the resection line guide 170 is initially placed on the stomach 10, the surgeon has a clear visualization of the intended results of the vertical sleeve gastrectomy prior to actually performing the resection of the stomach 10 at the resection line 12. Although the resection line guide 170 may not extend across substantially the full length of the resection line 12, the two retaining clips 172, 174, and more specifically, the guide portions 176 thereof, may provide an effective visualization of the intended resection line 12, by demonstrating the beginning and ending portions of the resection line 12. By way of example, the two retaining clips 172, 174 may collectively extend between about 20% and about 100% of the resection line 12, and preferably between 40% and 100% of the resection line. Hence, the surgeon has a sufficiently good indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the retaining clips 172, 174 prior to stapling and cutting the stomach 10. For example, the laparoscopic graspers may be used to separate and move the retaining clips 172, 174 and thereby allow the resection line guide 170 to be moved to an alternate position. In any event, once the resection line guide 170 is finally positioned, the surgeon may then cut and staple the tissue using the resection line guide 170 as a track along a significant part of the segment until complete resection of the stomach 10 occurs. In this regard, the stapling device 50 may abut or engage the resection line guide 170 along an alignment surface to facilitate an improved resection line, similar to that shown above in FIG. 2D.

It should be appreciated that the resection line guides described above may be modified in several ways, but remain within the scope and spirit of the present invention. In this regard, embodiments of the present invention may include a light source configured to cooperate with a light collector or sensor to provide an indication of tissue thickness. In reference to FIGS. 10A-10C, a resection line guide 180 includes a first clamp member 182 and a second clamp member 184 coupled by a living hinge 186, similar to that shown in FIGS. 3A and 3B above. When placed on the stomach 10, the second clamp member 184 may be generally positioned on the posterior side 20 of the stomach 10, and the first clamp member 182 may be generally positioned on the anterior side 18 of the stomach 10. In accordance with this embodiment, at least a portion of the second clamp member 184 may be made from a transparent or material, such as a transparent plastic like polycarbonate or other suitable biocompatible material, and include one or more light sources 188 configured to emit light into the tissue being clamped. In one embodiment, for example, the light sources may include a series of LEDs spaced along the second clamp member 184. It should be appreciated, however, that the light source can be other suitable sources for emitting light. At least a portion of the light from the light source 188 is transmitted through the stomach tissue and is received at the first clamp member 182. At least a portion of the first clamp member 182 may be transparent and include one or more light sensors 190 configured to measure the amount of light being received. As can be appreciated by one of ordinary skill in the art, the amount of light received at the sensors 190 may have a determinable correlation to the thickness of the tissue through which the light is transmitted. In this regard, the resection line guide 180 may be operatively coupled to a controller or other processor (not shown) capable of determining the tissue thickness based upon the amount of light emitted by the light source 188 and that received by sensors 190. Such a thickness determination may aid the surgeon in choosing the proper staple size along the resection line 12.

In embodiments of the present invention that include a flexible member for tensioning the clamp members, it should be appreciated that the flexible member may take several forms. By way of example and without limitation, the flexible member may include a wire, suture, thread, chain, or other elongate flexible member. The flexible member may be made of metal, plastic, or any other material that is suitable for a biological environment. The flexible member may be, for example, a braided cable. The flexible member should be capable of a radius of bend of approximately 0.030 inches and further be generally resistant to kinking, knotting, etc. Additionally, the flexible member should be able to accommodate a tensile load sufficient to generate a clamping force (pressure) above the maximum clamping force expected to be imposed during a procedure. By way of example, the flexible member should be able to accommodate a tensile load sufficient to create a clamping force of about 12 g/mm$^2$ on the anatomical structure. For example, the flexible member should be able to accommodate a tensile load of between about 25 to 50 lbs. In an exemplary embodiment, the flexible member may be a multi-strand stainless steel cable or a polymer, such as vectran.

Figure 11A:
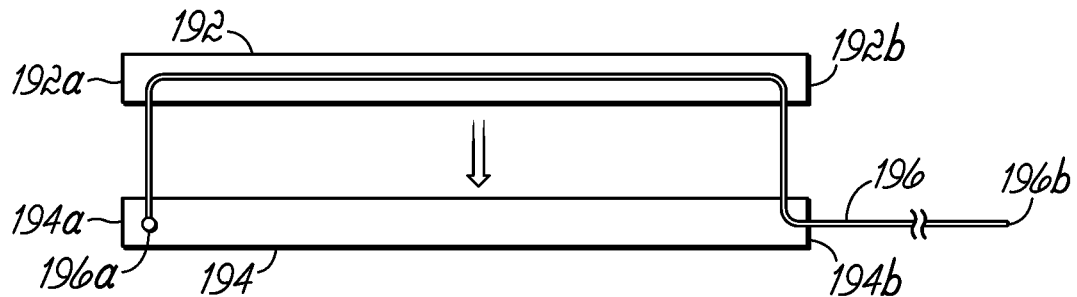
FIGS. 11A-11F depict schematics of a resection line guide including one or more flexible members according to various embodiment.
Figure 11B:
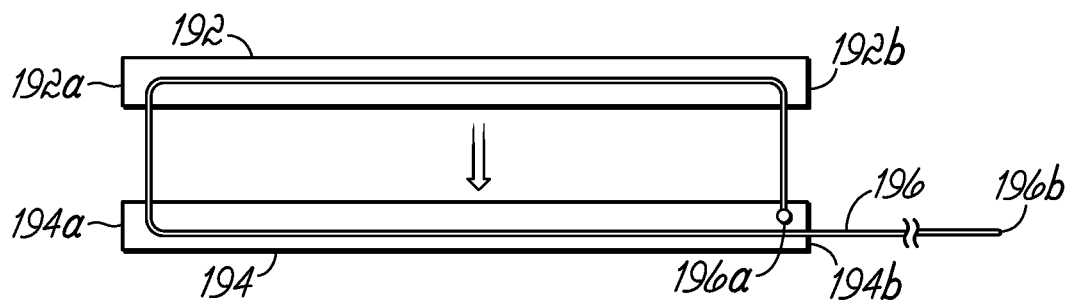
Figure 11C:
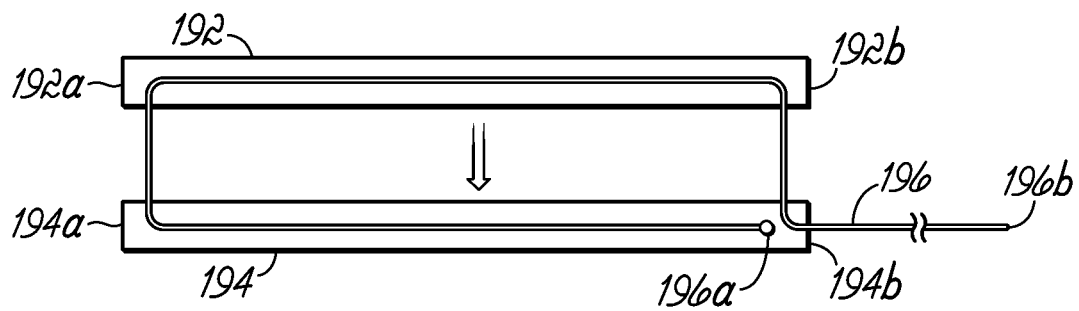

In addition to the above, there may be several alternative arrangements of the flexible member relative to the clamp members in the disclosed resection line guides. In this regard, FIGS. 11A-11C are schematic illustrations of exemplary configurations of two clamp members 192, 194 and a flexible member 196 configured to be tensioned so as provide a clamping force between the clamp members 192, 194. In FIG. 11A, the flexible member 196 has a first end 196a which is fixed to clamp member 194 adjacent a distal end 194a thereof and passes through the second clamp member 194 adjacent the distal end 194a. Flexible member 196 then passes through the first clamp member 192 adjacent a distal end 192a thereof and through and out of the first clamp member 192 adjacent a proximal end 192b thereof. The second end 196b of the flexible member 196 may be positioned outside the body and pulled or otherwise manipulated by the surgeon so as to increase the tension in the flexible member 196, and thereby generate a clamping force between clamp members 192, 194.

In FIG. 11B, the flexible member 196 has a first end 196a which is fixed to the second clamp member 194 adjacent the proximal end 194b thereof and passes through the second clamp member 194 adjacent the proximal end 194b thereof. The flexible member 196 then passes through the first clamp member 194 adjacent a proximal end 192b thereof, through the first clamp member 192, out of the first clamp member 192 adjacent the distal end 192a thereof, into the second clamp member 194 adjacent the distal end 194a thereof, through the second clamp member 194, and out the proximal end 194b of clamp member 194. The second end 196b of the flexible member 196 may be positioned outside the body and pulled or otherwise manipulated by the surgeon so as to increase the tension in the flexible member 196, and thereby generate a clamping force between the clamp members 192, 194. In FIG. 11C, the flexible member 196 is fixed to the second clamp member 194 adjacent a proximal end 194b thereof and extends along the length of the second clamp member 194 toward the distal end 194a. The flexible member 196 passes out of the second clamp member 194 adjacent the distal end 194a thereof and passes into the first clamp member 192 adjacent the distal end 192a thereof. The flexible member 196 extends along the length of the first clamp member 192 and out of the first clamp member 192 adjacent the proximal end 192b thereof. The flexible member 196 then passes back into the second clamp member 194 adjacent the proximal end 194b thereof and out the proximal end 194b of second clamp member 194. The second end 194b may be positioned outside the body and pulled or otherwise manipulated by the surgeon so as to increase the tension in the flexible member 196, and thereby generate a clamping force between the clamp members 192, 194.

Figure 11D:
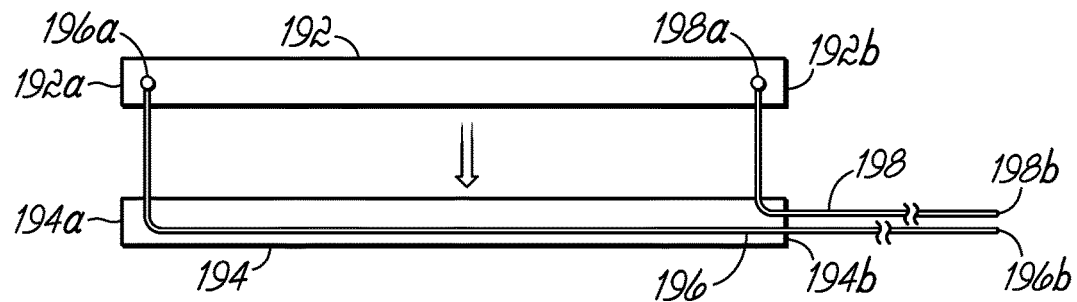
Figure 11E:
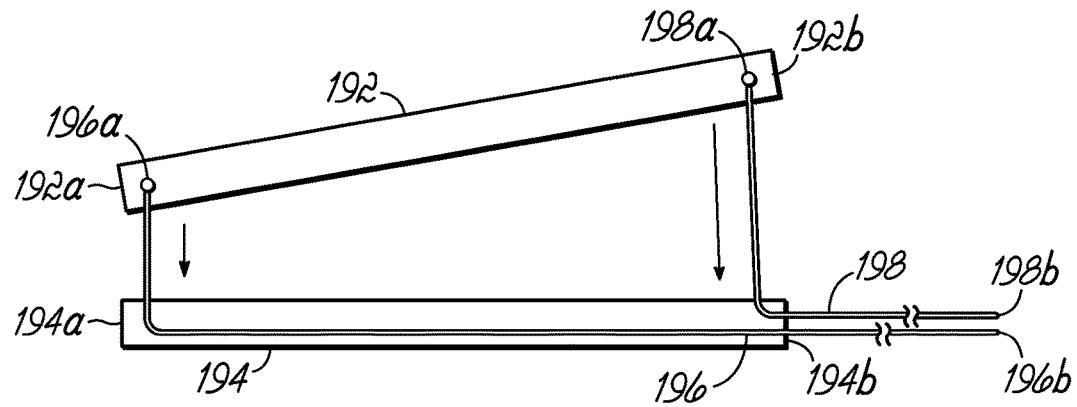
Figure 11F:
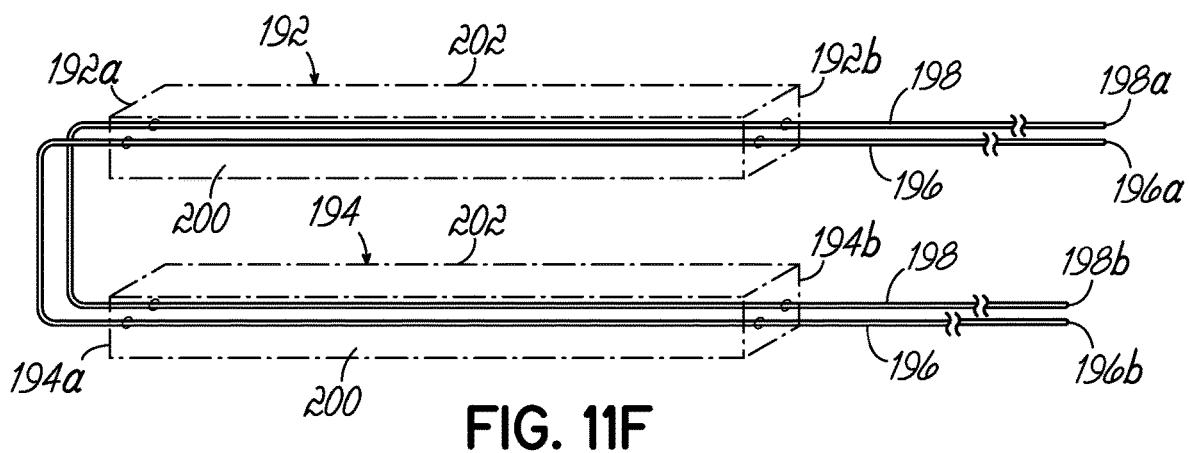

In alternative embodiments, there may be more than one flexible member used to tension the two clamp members so as to generate a clamping force therebetween. In this regard, FIGS. 11D-11E are schematic illustrations of exemplary configurations of two clamp members 192, 194 and two flexible members 196, 198 configured to be tensioned so as provide a clamping force between the clamp members 192, 194. In FIG. 11D, a first flexible member 196 has a first end 196a fixed to the first clamp member 192 adjacent the distal end 192a thereof and passes out of the first clamp member 192 adjacent the distal end 192a thereof. The first flexible member 196 then passes into the second clamp member 194 adjacent a distal end 194a thereof and extends along the second clamp member 194 and out of the proximal end 194b thereof. The second end 194b of the first flexible member 196 may be positioned outside the body. The arrangement further includes a second flexible member 198 having a first end 198a fixed to the first clamp member 192 adjacent the proximal end 192b thereof and passes out of the first clamp member 192 adjacent the proximal end 192b thereof. The second flexible member 198 then passes into the second clamp member 194 adjacent a proximal end 194b thereof and passes out of the proximal end 194b thereof. The second end 198b of the second flexible member 198 may be positioned outside the body.

With this arrangement, the second ends 196b, 198b may be pulled or otherwise manipulated by the surgeon so as to increase the tension in the flexible members 196, 198 and thereby generate a clamping force between the clamp members 192, 194. In one aspect, this arrangement advantageously provides for independent control of the clamping force of the proximal and the distal ends of the resection line guide. In this regard, increasing the tension in the first flexible member 196 will draw the distal ends 192a, 194a of clamp members 192, 194 towards each other. As the distance between the distal ends 192a, 194a decreases, the clamping force at the distal end of the resection line guide increases. In a similar manner, increasing the tension in the second flexible member 198 will draw the proximal ends 192b, 194b of clamp members 192, 194 towards each other. As the distance between the proximal ends 192b, 194b decreases, the clamping force at the proximal end of the resection line guide increases. FIG. 11E illustrates the resection line guide according to the embodiment in FIG. 11D where the distance between the distal ends 192a, 194a of the clamp members 192, 194 is less than the distance between the proximal ends 192b, 194b creating an overall shape of the resection line guide that is generally trapezoidal. In other words, the clamp members 192, 194 may be in non-parallel relation. Consequently, the clamping force at the distal end of the resection line guide may be greater than the clamping force at the proximal end of the resection line guide when the resection line guide is placed around an anatomical structure. This ability to independently control the clamping force along the proximal and distal ends of the resection line guide may be advantageous in certain applications. For instance, independently controlling the clamping force along the proximal and distal ends of the resection line guide may be advantageous where the tissue thickness of the anatomical structure varies along the length of the resection line. By way of example, the distal end 14 of the stomach 10 generally has a thickness less than that of the proximal end 16 of the stomach 10. Accordingly, the ranges of clamping force used in the two-stage clamping process, as described above, may vary at the distal and proximal ends 14, 16 of the stomach 10. Using a resection line guide capable of providing a varying clamping force along the length of, for example, the stomach 10 may aid in creating an improved resection line.

In reference to FIG. 11E, a first flexible member 196 is coupled to first and second clamp members 192, 194 in a manner similar to that described above for resection line guides 80, 94. However, this embodiment further includes a second flexible member 198 coupled to the first and second clamp members 192, 194 in a manner similar to that described above for guides 80, 94. Notably, the first flexible member 196 extends through the first and second clamp members 192, 194 adjacent a first edge 200 thereof and the second flexible member 198 extends through the first and second clamp members 192, 194 adjacent a second edge 202 thereof. This arrangement advantageously provides for independent control of the right and the left sides of the resection line guide. In this regard, increasing the tension in the first flexible member 196 will increase the clamping force at the left side of the resection line guide. In a similar manner, increasing the tension in the second flexible member 198 will increase the clamping force at the right side of the resection line guide. This ability to control the clamping force along the right and left sides of the resection line guide may be advantageous in certain applications.

In addition to the above, while the length of the clamp members have been described as generally exceeding the length of the anatomical structure being clamped (e.g., stomach, lung, kidney, liver, etc.), the invention is not so limited. More particularly, the lengths of the clamping members may vary depending on the specific application to be greater or less than the length of the anatomical structure being clamped. Additionally, the first and second clamp members do not have to be of equal lengths, but may have different lengths. In exemplary embodiments, the two clamp members may be formed from plastic, metal, or other materials suitable for providing a clamping force in a biological environment (i.e., must be biologically compatible). The clamp members may be configured to distribute the clamping force provided to the anatomical structure across the length of the clamp members. The clamp members may be generally rigid. As noted above, the clamp members may be hollow, solid, partially hollow, or have other configurations. In the embodiments discussed herein, the two clamp members are illustrated as elongate members having a certain cross-section. However, the clamp members may have a variety of cross-sectional shapes, some of which are illustrated in FIGS. 12A-12E. By way of example, the two clamp members 204, 206 may have cross-sectional shapes that are rectangular (FIG. 12A), cylindrical (FIG. 12B), V-shaped (FIG. 12C), half-moon (FIG. 12D-E), or wavy (FIG. 12G). The two clamp members 204, 206 may have the same or different cross-sectional shapes. For example, FIG. 12F illustrates an embodiment where the clamp member 204 may have a crescent cross-sectional shape, while the clamp member 206 may have a half-moon cross-sectional shape. As previously noted above, the two clamp members may be formed as a unitary member or may be formed from a plurality of clamp segments as previously described.

In addition to the above, the surfaces of the clamp members that engage with the anatomical structure may be textured to enhance the securement of the resection line guide to the anatomical structure. For example, these surfaces may include a traction pattern that facilitates the resistance of movement of the resection line guide relative to the underlying tissue. The traction pattern may be formed, for example, by ridges and grooves. The ridges and grooves may be directed generally in the axial direction, the longitudinal direction, or in crisscrossed pattern. The surfaces may be roughened, for example, with various post-processing methods generally known in the art. Other textured patterns may also be possible.

Figure 13C:
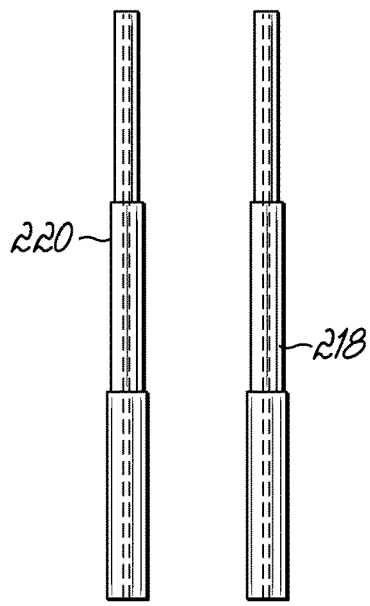
Figure 13D:
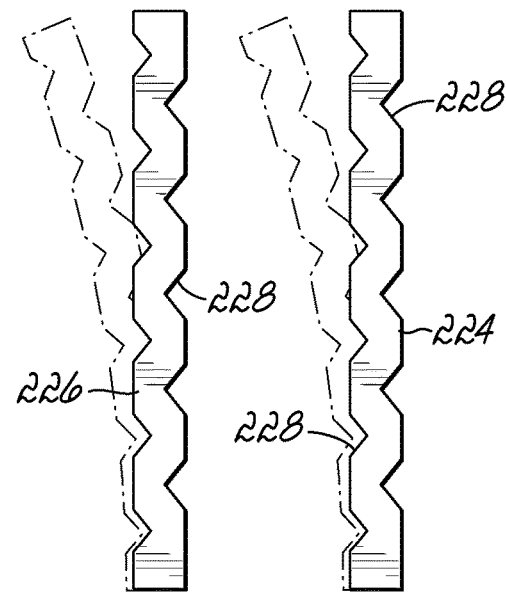

Additionally, while the embodiments above show the clamp members as being generally straight (i.e., so as to produce a generally straight resection line), the invention is not so limited. In this regard, the two clamp members may have a longitudinal shape other than straight. This may be beneficial where the surgeon wants to create a non-linear resection line. For example, the surgeon may want to create a curved resection line that reflects the lesser curvature 28 of the stomach 10. To accomplish this, FIG. 13A illustrates an alternative embodiment where the two clamp members 208, 210 may be generally arcuate or curved so as to generally correspond to the shape of the lesser curvature 28 of the stomach 10. In another alternative embodiment, two clamp members 212, 214 may be made of segments connected by a tape 216 or other spine generally running the length of the two clamp members 212, 214. With the tape 216 on the side of the segments facing anatomical right, the sides of the segments facing the anatomical left may generally bend and flex outwardly, as illustrated in FIG. 13B. Further, the segments may be sized based on a staple cartridge. By way of example, if the segments were between about 50 mm and about 60 mm in length, a curved resection line may be made by using one 60 mm staple cartridge per segment. In yet another alternative embodiment, the two clamp members 218, 220 may have a telescopic configuration (e.g., nested sections), as illustrated in FIG. 13C, such that the length of the two clamp members 218, 220 may be easily varied to meet the needs of a specific application. In still another alternative embodiment illustrated in FIG. 13D, the two clamp members 224, 226 may be configured to be rigid in the longitudinal direction but malleable in a transverse direction. In this regard, the clamp members 224, 226 may include a series of cut-outs or notches 228 that facilitate flexing or bending of the clamp members 224, 226 in a generally transverse direction (e.g., left and right in the reference frame of FIG. 13D). Although not shown, the clamp members 224, 226 may include a mechanism allowing for external control of the transverse movement of the clamp members 224, 226. In this regard, each clamp member 224, 226 may have one or more control lines coupled to one or more locations along the clamp members 224, 226 that allow the clamp members to be flexed in a certain manner. For example, the control lines may include flexible, or rigid, or semi-rigid cables. In an embodiment where the clamp members 224, 226 include two flexible members according to the arrangement in FIG. 11E, tightening one of the flexible members may cause the clamp members 224, 226 to flex.

The device for tensioning the flexible member should provide a sufficient clamping force for securing the guide onto the anatomical structure. In this regard, the tensioning device should be configured to implement the two-stage clamping described above. A variety of tensioning devices may be used to provide a tension in the flexible member in order to secure the resection line guide onto the anatomical structure. As noted above, for example, a cinch tube can be used in conjunction with the flexible member and clamp members to generate a tension in the flexible member. In an alternative embodiment, a tensioning mechanism for tightening the flexible member may include a tightener having a plunger, where the plunger may be lifted to slide the flexible member through and may be released to hold the flexible member in place. For example, the tensioning device may be configured to move over and rest on the clamp members, such as at a proximal end thereof. Holding the clamp members together in this way may provide increased tension or secure the clamp members in order to generate the clamping force.

Figure 13E:
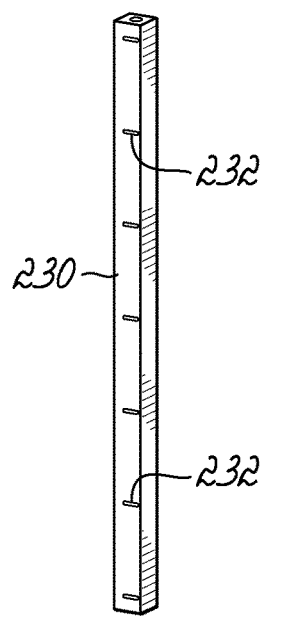
FIGS. 13E-13H are elevation views of a clamp member of a resection line guide according to various embodiments.

In another aspect, certain embodiments of the present invention may provide an indication of the length of the resection line. In procedures where laparoscopic linear cutter staplers are used, knowing the length of the resection line may aid the surgeon in planning the number of stapler applications that will be used to accomplish the resection. FIG. 13E illustrates an exemplary embodiment of a clamp member 230 (only one shown) having a series of markings 232 along the length of a clamp member 230 configured to provide an indication of distance. These markings 232 may be used to mark off distance, for example, in centimeters. Alternatively, the markings 232 may be used to mark off or estimate the number of staple firings that will be needed to resection the anatomical structure. In vertical sleeve gastrectomy procedures, staple cartridges of 60 mm are commonly used. As a result, markings 232 spaced 60 mm apart may be used along the clamp member 230. Using these markings, the surgeon may quickly assess how many staple cartridges will be needed to complete the resection.

Figure 13F:
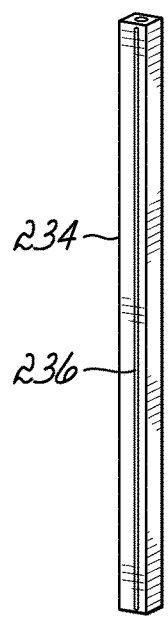
Figure 13G:
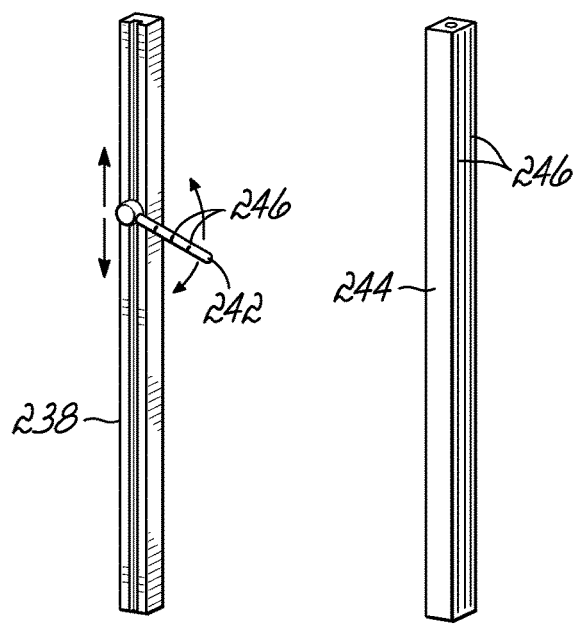

In yet another aspect, certain embodiments of the present invention may provide an indication of the distance from the resection line guide to certain anatomical landmarks. Because anatomical landmarks are typically referred to when establishing the ideal resection line, it may be beneficial to know, or be able to more accurately estimate, the distance of the resection line guide to those landmarks. In this regard, a clamp member of a resection line guide may have a fixed and known width (e.g., 1 cm in width). Because the resection line is frequently 1 cm away from the gastroesophageal junction 22, using a 1 cm wide clamp member that rests against the gastroesophageal junction 22 would assure a proper spacing from this anatomical landmark. As an alternative example, the clamp member may have markings indicating a specific width. In an exemplary embodiment, as illustrated in FIG. 13F, a clamp member 234 may be wider than 1 cm where a marking 236 may be included along the length of the clamp member 234 indicating a width of 1 cm, such as from one of the side edges thereof. In another embodiment, the resection line guide may include an adjustable measuring device capable of providing a physical scale for determining or estimating distance from the resection line guide. FIG. 13G illustrates an embodiment where a clamp member 238 includes a measuring arm 240 coupled to the clamp member 238. In one embodiment, the measuring arm 240 may be movably coupled, e.g., such as pivotally coupled to the clamp member 238. In one embodiment, the measuring arm 240 may have a known and pre-determined length.

Alternatively, the measuring arm 240 may include markings 246 indicating distance. This would allow the surgeon to pivot the measuring arm 240 away from the clamp member 238 and use the measuring arm 240 to determine or estimate the distance from the resection line guide to various anatomical landmarks. By way of example and without limitation, a pivotable arm may have a length of about 2 cm to about 6 cm. In one embodiment, the length of the measuring arm 240 may be variable. More than one of these components may be used the clamp member 238. Additionally, or in the alternative, the measuring arm may be movable, e.g., slidable, along the length of the clamp member 238, as is illustrated in FIG. 13G. For example, the measuring arm 240 may slide within a longitudinal groove in the clamp member 38. In an alternative embodiment, electronic distance measurement may be possible. For instance, a reference point may be established on a clamp member and the other reference point may be associated with a laparoscopic instrument. In this way, as the instrument moves within the abdomen, electronic feedback may be provided to indicate the distance between the two reference points. In this regard, the clamp member and instrument may be operatively coupled to a controller to provide the distance measurement.

Figure 13H:
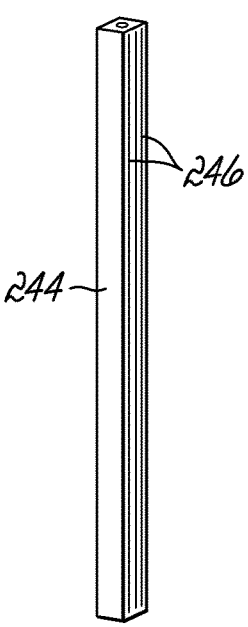

Certain embodiments of the present invention may provide an indication of the thickness of the anatomical structure to be stapled. This may be accomplished using a variety of methods. In a previously discussed embodiment, a light source is used to indicate the thickness of an anatomical structure. In another embodiment, for example, a clamp member 244 may include longitudinal markings 246 indicating the distance from the lower edge of the clamp member facing the anatomical structure to be resected. FIG. 13H illustrates three longitudinal markings 246 along a side wall of a clamp member 244. These markings may be, for example, markings of distance or markings based on staple leg lengths. In practice, different staple leg lengths often have corresponding colors depending on their manufacturer. The markings, and their spacing, may be based on these colors to indicate what staple size should be used. By way of example, blue, green, and black lines may be used to indicate staple leg lengths of 3.5 mm, 4.1 mm, and 4.4 mm, respectively. A surgeon may use the markings as a scale on which to base a determination or estimate of the thickness of the tissue of the anatomical structure. By way of example, the surgeon may compare the thickness of tissue that has already been, for example, stapled with the distances indicated by the longitudinal markings. The surgeon may then choose a staple leg length for the next application of the stapler based on the estimate of the tissue thickness at that location along the anatomical structure. As an alternate method of indicating thickness using a resection line guide with two clamp members connected by a flexible member, an indicator window may be used showing an indicator bar that moves based on the length of flexible member between the clamp members. This may be used for a single flexible member or for two thicknesses based on a flexible member at each of the distal and proximal ends of the resection line guide. In another embodiment, the resection line guide may be capable of measuring the distance between clamp members using ultrasound. Further, in an embodiment where the resection line guide is capable of providing a varying clamping force along the length of the anatomical structure, an indication of the distance between the two clamp members at the distal and proximal ends of the resection line guide may indicate tissue thickness at the distal and proximal ends 14, 16 of the stomach 10.

Certain embodiments of the present invention may be capable of measuring the clamping force provided by the resection line guide. This may be accomplished using any suitable method known in the art. An embodiment of a resection line guide may include a flexible member and a strain gauge to measure the amount of strain on the flexible member. In embodiments where the guide is applying varying pressure on the anatomical structure, there may be more than one device capable of measuring the clamping force. In another embodiment, PVDF piezoelectric film or Mylar film may be included in the resection line guide.

In another aspect of the present invention, and with reference to FIGS. 14-18, the surgeon may operate one of the guides above, including one or both clamp members, during a gastrectomy procedure, for example, with another mechanical device that is coupled to the guide. To that end and in one embodiment, a medical device 400 includes a resection line guide 402, which may be one of the guides described above, operatively coupled to a manipulator 404. As shown, the manipulator 404 includes an elongate member or shaft 408 coupled to a handpiece, such as a pistol-grip device 406, at one end and the resection line guide 402 at the other end thereof. As will be described below, during a surgical procedure, the resection line guide 402 and a portion of the shaft 408 may be inserted into the patient, such as via a trocar. The surgeon may then manipulate the resection line guide 402 and/or articulate the resection line guide 402 relative to the manipulator 404 to perform the procedure. Thus, embodiments of the present invention may include mechanisms for effectuating a surgical procedure with the resection line guide 402 and for allowing the resection line guide 402 to articulate relative to the shaft 408.

Figure 29:
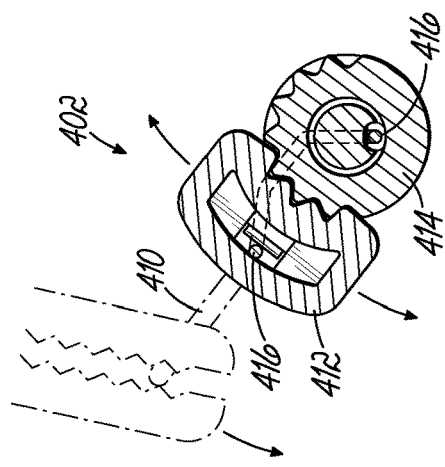
FIG. 29 is a schematic cross-sectional view of the resection line guide of FIG. 16 depicting manipulation thereof.
Figure 24B:
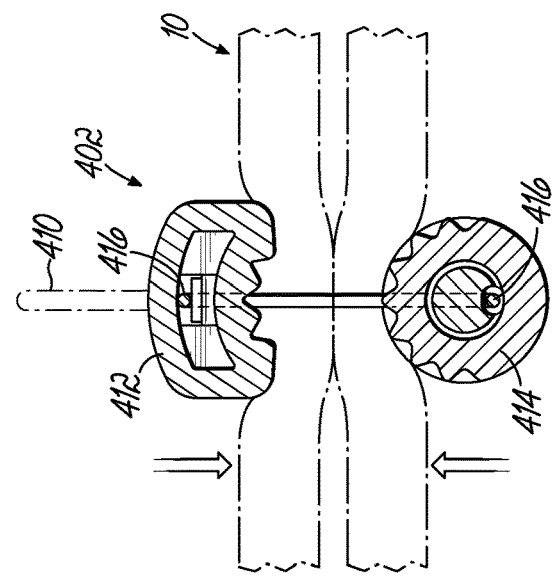
FIG. 24B is another schematic cross-sectional view of the resection line guide of FIG. 16 in a closed position.
Figure 23B:
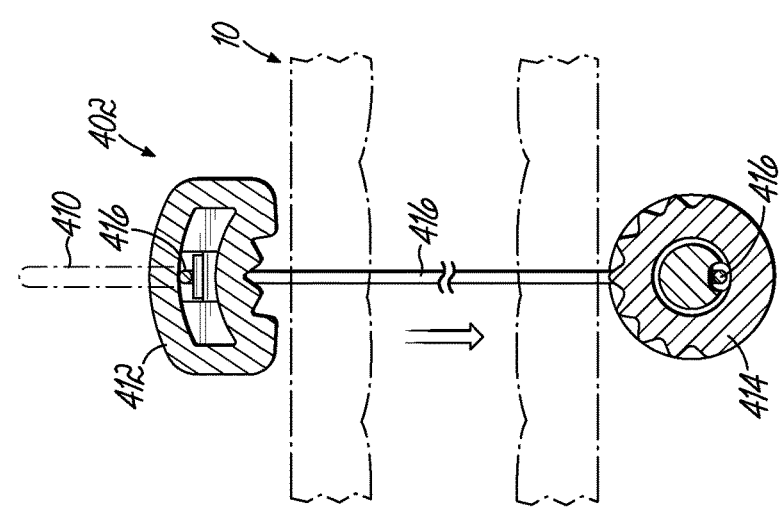
FIG. 23B is another schematic cross-sectional view of the resection line guide of FIG. 16 in an opened position.

With reference to FIGS. 14-18, the resection line guide 402 includes clamp members 412, 414 that are movably coupled together via a flexible member 416. The flexible member 416 passes through hollow portions of the clamp members 412, 414 so that, for example, the clamp member 412 may be separated from or brought closer to the clamp member 414. In this regard, an anchor 417 fixes a first end of the flexible member 416 to the clamp member 414 adjacent a proximal end thereof, and the flexible member 416 passes out of a bore adjacent a proximal end of the clamp member 414 into the clamp member 412 adjacent a proximal end thereof. Flexible member 416 passes through and out of the clamp member 412 adjacent a distal end thereof. Flexible member 416 then passes into the clamp member 414 adjacent a distal end thereof and through the clamp member 414 into the shaft 408. Retraction of the flexible member 416 moves at least one of the clamp members 412, 414 as is shown generally by arrow 418 in FIGS. 15A and 16 and described below. The clamp members 412, 414 may have mating surfaces, as shown in FIGS. 23B, 24B, and 29. In the present embodiment, the mating surfaces are illustrated as the ridged surfaces on the clamp members 412, 414. The ridged surface on the clamp member 412 is capable of mating with the ridged surface on the clamp member 414 in multiple locations. This effectively allows for rotation of the resection line guide 402 about an axis parallel to the clamp members 412, 414. When the resection line guide 402 is rotated about an axis parallel to the clamp members 412, 414, the flexible member 416 may exit the proximal end of the clamp member 414 at an angle, as is shown in FIG. 29. To reduce stress on the flexible member 416 if this happens, the bore 413 (labeled in FIG. 27B) adjacent a proximal end of the clamp member 414 creates an arcuate path for the flexible member 416 on the side of the clamp member 414 facing the clamp member 412. This arcuate path allows the flexible member 416 to more gradually angle towards the proximal end of the clamp member 412. The resection line guide 402 may include other bores similar to the bore 413 on one or both of the proximal and distal ends of one or both of the clamp members 412, 414.

The resection line guide 402 may include a tab 410, which extends from the clamp member 412 by which the surgeon may manipulate the orientation of the resection line guide 402. It will be appreciated that a tab may also be mounted on the clamp member 414. This may allow for more controlled separation of the clamp members 412, 414. Alternatively, instead of a tab on one or both of the clamp members 412, 414, another element capable of being engaged by a laparoscopic instrument may extend from or be mounted to one or both of the clamp members 412, 414. By way of example, a flexible cable or a coupling area may be attached or formed in one of the clamp members 412, 414 with which a laparoscopic instrument may engage. By way of further example, a coupling area may include a magnet or may be a recess in which a laparoscopic instrument may be configured to clip or snap. The resection line guide 402 may include one of the exemplary resection line guides described above, such as, for example, those shown in FIGS. 3E, 4B, and 5A. To at least those ends, the manipulator 404 includes mechanisms that the surgeon may manipulate to independently move the resection line guide 402 to open and close the clamp members 412, 414 and/or to pivot the resection line guide 402 relative to the manipulator 404, as is described in detail below.

Figure 17A:
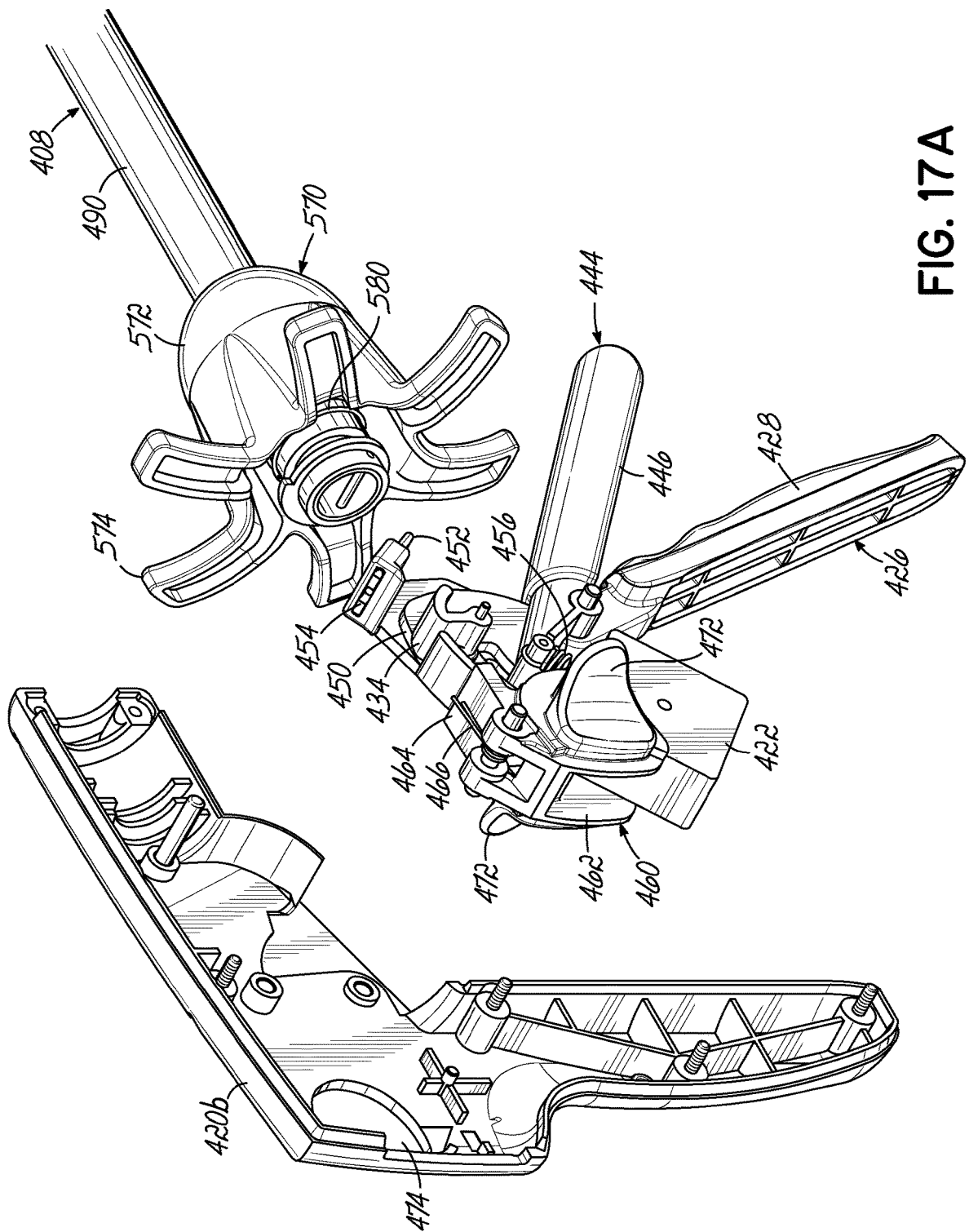
FIG. 17A is a partially exploded view of the medical device of FIG. 14.
Figure 17B:
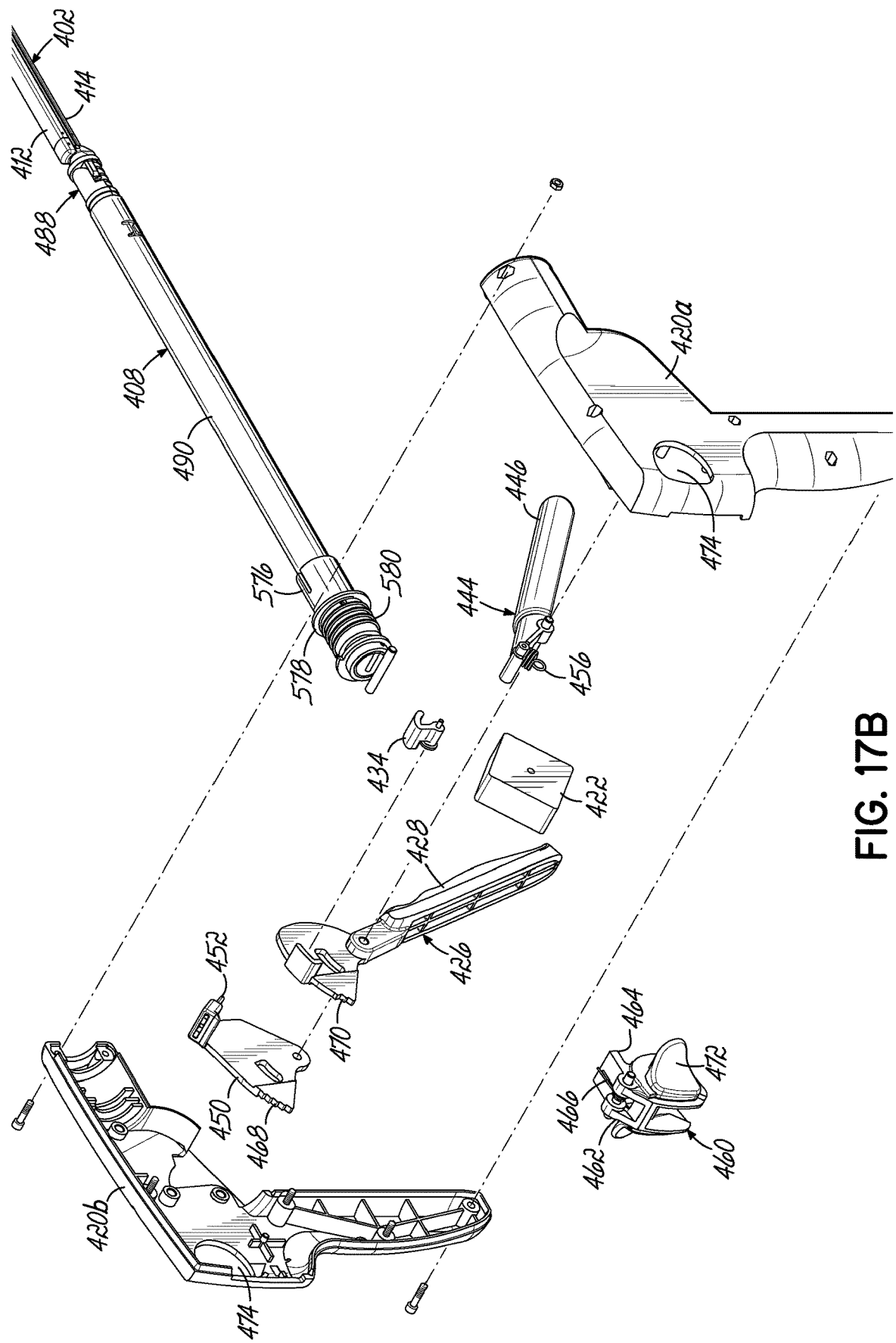
FIG. 17B is an exploded view of the medical device of FIG. 14.
Figure 18:
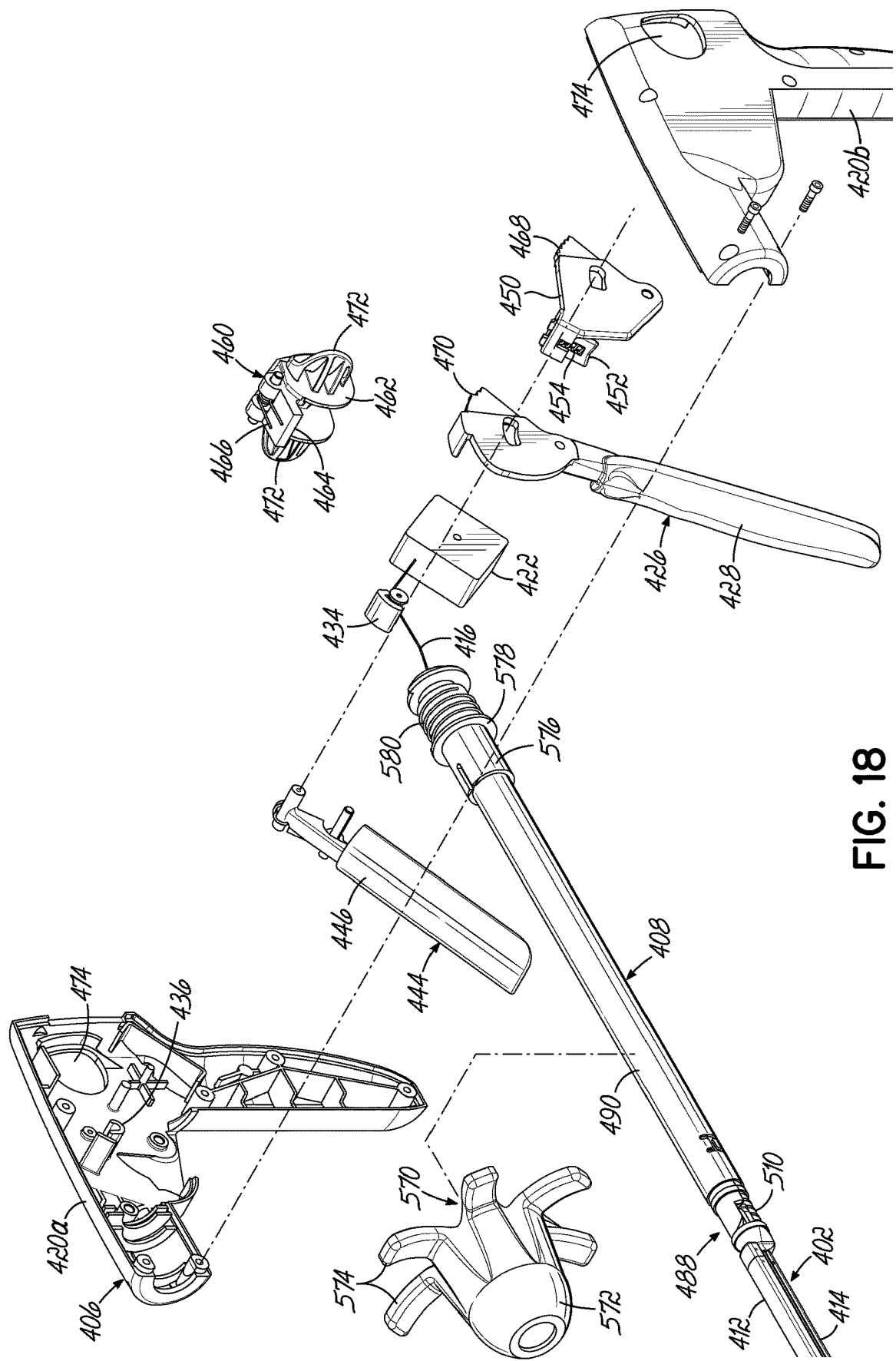
FIG. 18 is an exploded view of the medical device of FIG. 14.
Figure 18A:
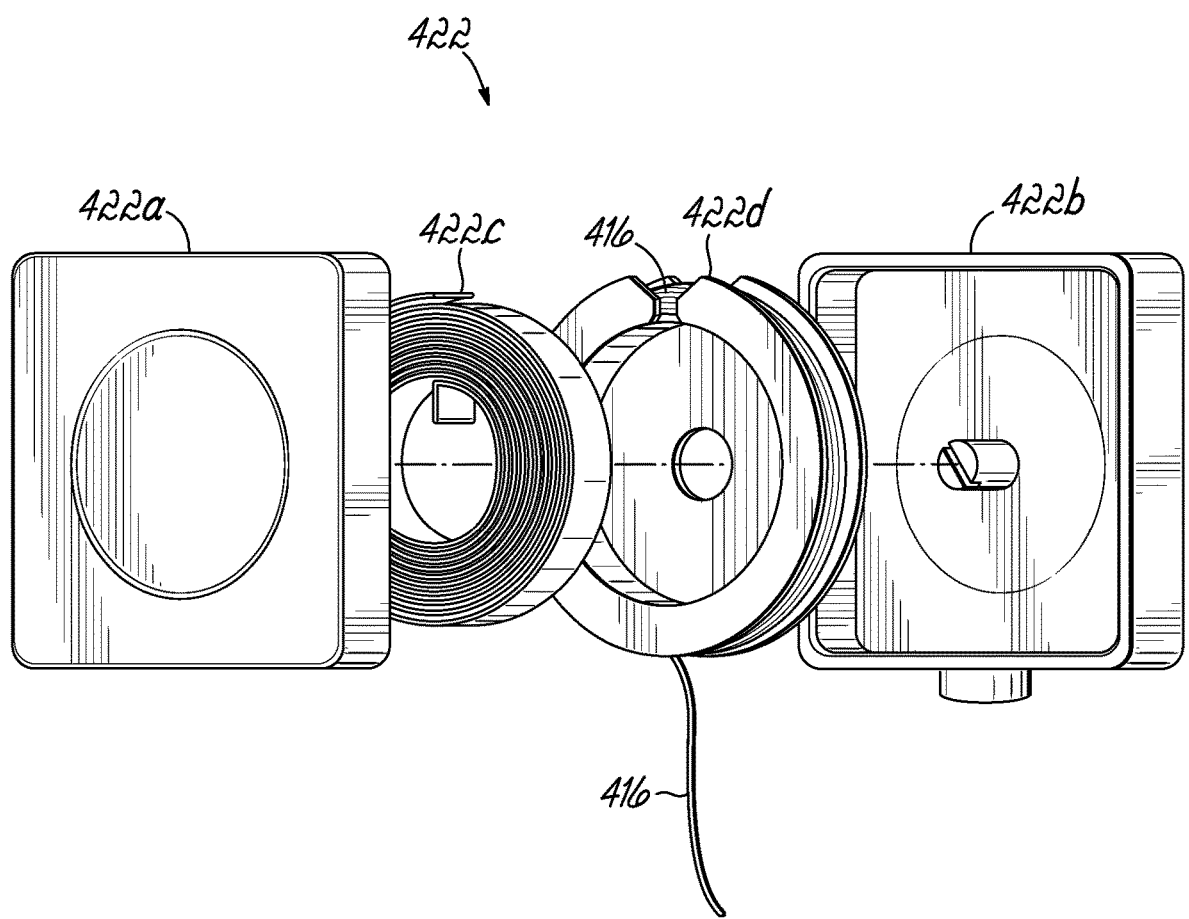
FIG. 18A is an exploded view of an exemplary spring reel, shown in FIG. 18.

With reference to FIGS. 14, 15A, 15B, 17A, 17B, and 18, in one embodiment, the manipulator 404 includes a case or housing formed by halves 420a, 420b that contains mechanisms for operation of the medical device 400. In this regard, the flexible member 416 extends from shaft 408 and is fixed to a spring reel 422. As is shown in FIG. 18A, the spring reel 422 may include a case or housing formed by halves 422a, 422b that contains a spiral spring 422c and a spool 422d of the flexible member 416 onto which the flexible member 416 may be wound and unwound. The spring reel 422 may have a force constant of 0.1 to 1 lb. The spring reel 422 is therefore configured to release a length of the flexible member 416 and/or take up a length of the flexible member 416 as is generally understood by one of ordinary skill in the art.

According to one aspect, for manipulating the resection line guide 402 to effectuate treatment, the manipulator 404 includes a brake mechanism 426 that is capable of frictionally capturing the flexible member 416 to prevent its unintentional movement relative to the brake mechanism 426, such as unintentional extension of the flexible member 416 from the spring reel 422. To that end, as is shown in FIGS. 17A, 17B, and 18, the brake mechanism 426 includes a brake lever 428 that is pivotally coupled relative to the housing 420a, 420b (as is indicated by arrow 430) and operatively positioned to clamp the flexible member 416 at one end. The brake lever 428 projects from the housing 420a, 420b so that it may be manipulated by the surgeon. It will be appreciated that the surgeon may operate the brake lever 428 with one or more fingers during operation of the medical device 400 between a disengaged position (FIG. 19) in which the brake mechanism 426 does not restrict movement of the flexible member 416 and an engaged position (FIGS. 20A and 20B) in which the brake mechanism 426 contacts the flexible member 416.

In one embodiment, and with reference to FIGS. 17A, 17B, and 18, the brake mechanism 426 further includes a brake arm 434 and a brake plate 436. The brake arm 434 is pivotally coupled between the housings 420a, 420b and positioned to be engaged by the brake lever 428 when pivoted according to the arrow 440 as is generally shown at 438 in FIG. 19, the operation of which is described below. In the embodiment shown, the brake plate 436 is integrally formed in the housing 420*a*. However, embodiments are not limited to integral formation as the brake plate 436 may be separately formed and then secured to one or both housings 420*a*, 420*b* via an adhesive, tack welding, or like means of attachment. The brake plate 436 may have a generally J-shaped cross-section that receives a portion of the brake arm 434 therein when the brake arm 434 is driven by the movement of the brake lever 428.

With reference to FIGS. 14, 15A, 15B, 17A, 17B, and 18, the mechanisms operating the resection line guide 402 may, in addition or alternatively to the brake mechanism 426, include a clamping mechanism 444 that is capable of applying a force generally crosswise or perpendicular to the flexible member 416 when the clamping mechanism 444 is engaged. In this way, the clamping mechanism 444 tensions the flexible member 416. By applying a force to the flexible member 416 in a crosswise direction, the clamp members 412, 414 (shown in FIGS. 15A and 15B) may be moved toward one another and, as is described below, may apply a clamping force to tissue situated between the clamp members 412, 414.

In one embodiment, the clamping mechanism 444 includes a clamping lever 446 that is pivotally coupled between housings 420*a*, 420*b*. The clamping lever 446 extends from the housings 420*a*, 420*b* and may be manipulated by the surgeon to engage the clamping mechanism 444. While the clamping lever 446 may be independently operated by the surgeon relative to the brake lever 428, in one embodiment, engaging the brake mechanism 426 may also initiate some slight engagement of the clamping mechanism 444. For example, the surgeon may independently operate the brake lever 428 and the clamping lever 446 or engagement of the brake mechanism 426 may also engage the clamping mechanism 444 at a low level. Thus, full depression of the brake lever 428 may cause slight movement of the clamping lever 446.

Portions of the clamping lever 446 pass through portions of the brake mechanism 426 and are slidably coupled to a clamping bracket 450 that includes a mechanism for limiting the magnitude of the force placed on the flexible member 416. In one embodiment, clamping mechanism 444 includes a limiter finger or plate 452 slidably secured to the clamping bracket 450 and operably coupled to a limiter spring 454. The limiter spring 454 biases the limiter plate 452 in an extended direction toward the flexible member 416 (best shown in FIG. 19) relative to the clamping bracket 450. It will be appreciated that the surgeon may operate the clamping lever 446 with one or more fingers during operation of the medical device 400 between a disengaged position (FIG. 19) in which the clamping mechanism 444 does not significantly tension the flexible member 416 and an engaged position (FIGS. 21A and 21B) in which the clamping mechanism 444 tensions the flexible member 416 by displacing the flexible member 416 from its original path. In particular, when the clamping lever 446 is in the engaged position, the limiter plate 452 forcibly contacts the flexible member 416 and deflects the flexible member 416 from its original path. This deflection thereby increases the tension in the flexible member 416. When engaged with the flexible member 416, the limiter plate 452 may compress the limiter spring 454 and so the limiter spring 454 may limit the maximum force applied to the flexible member 416 by the clamping mechanism 444.

Figure 20A:
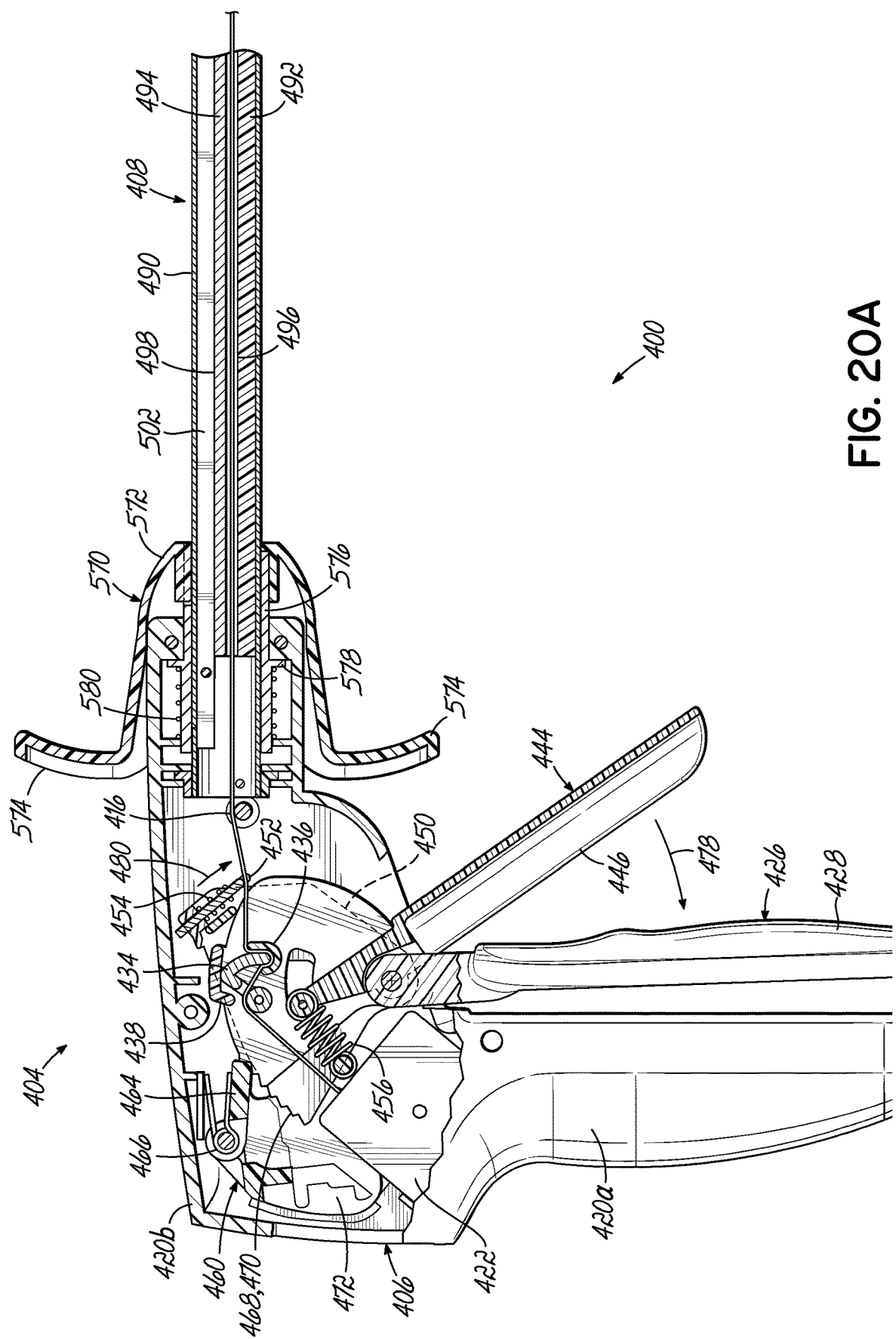
FIGS. 20A, 20B, and 20C are partial cross-sectional views of the manipulator of FIG. 19 depicting engagement of a mechanism according to an embodiment.
Figure 20B:
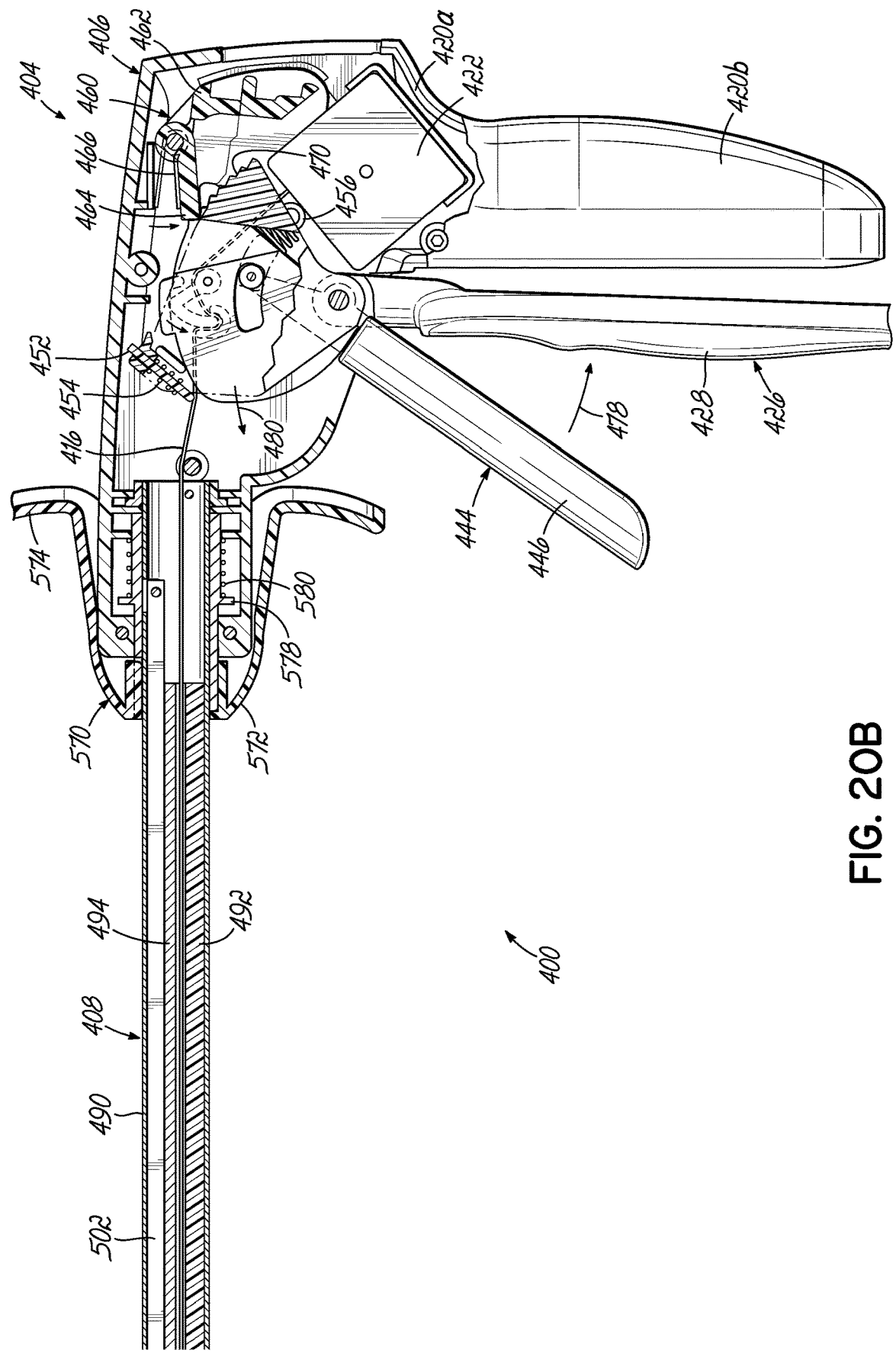
Figure 20C:
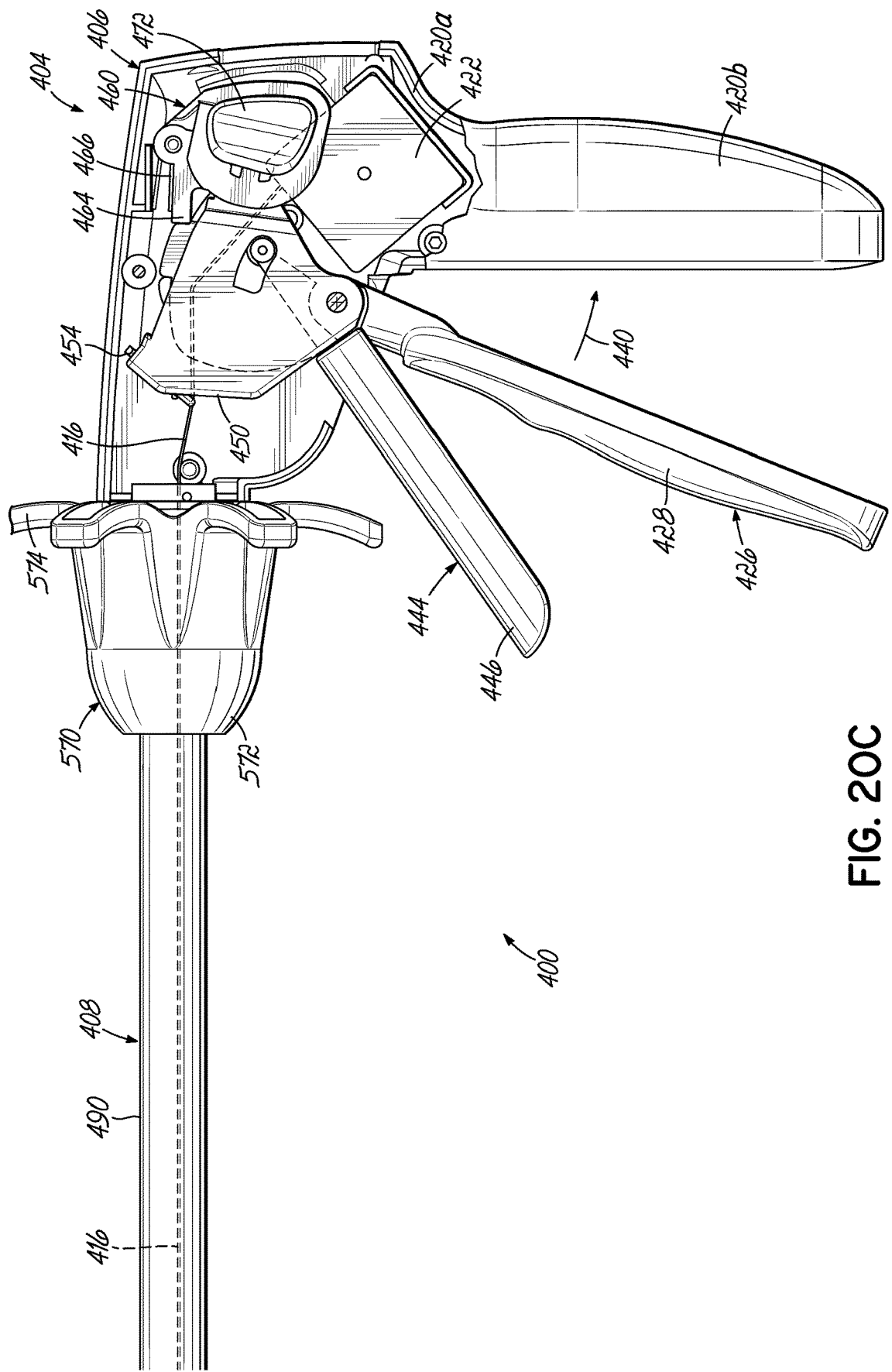

In one embodiment and with reference to FIGS. 19, 20A, and 20B, one or both of the brake mechanism 426 and the clamping mechanism 444 may be biased toward their disengaged positions. In this regard, as the surgeon releases one or both of the brake lever 428 and the clamping lever 446, each of the levers 428, 446 may spontaneously return to their disengaged positions. At this point, the flexible member 416 may freely extend from the spring reel 422. In one embodiment, a spring 456 is coupled directly to the clamping lever 446 at one end and is indirectly coupled to the brake lever 428 proximate the clamping lever 446. The spring 456 is coupled to the housing 420*a*, 420*b* at the other end thereof. The spring 456 biases one or both of the brake lever 428 and the clamping lever 446 toward their disengaged positions. For example, movement of the brake lever 428 and/or the clamping lever 446 toward the flexible member 416 causes the spring 456 to be extended or biased, as can be seen by comparison of FIGS. 19 and 20A. Release of the brake lever 428 and/or the clamping lever 446 may allow the spring 456 to return to a less biased or unbiased state and automatically disengage the respective brake mechanism 426 and/or the clamping mechanism 444.

In one embodiment, and with reference to FIGS. 14, 15A, 15B, and 17A-19, the housing 420*a*, 420*b* may also include a stop and release mechanism 460. The stop and release mechanism 460 may engage either or both of the brake mechanism 426 and the clamping mechanism 444 when one or both are engaged with the flexible member 416. In this regard and with reference to FIGS. 17A, 17B, and 18, the stop and release mechanism 460 may include a frame 462. A stop block 464 is pivotably secured to the frame 462 and is held in a stop position by a spring 466 (the stop position is shown best in FIG. 19).

As shown best in FIGS. 17A and 17B, the stop and release mechanism 460 may include a plurality of serrations 468 on the clamping bracket 450 and a plurality of serrations 470 on the brake lever 428. The stop block 464 may engage the serrations 468 and/or the serrations 470 when the surgeon manipulates the corresponding lever 428 and 446, as is described below. Once the stop block 464 is engaged with one serration 468 and/or one serration 470, the stop and release mechanism 460 maintains the brake mechanism 426 and/or the clamping mechanism 444 in the engaged position and thus counteracts the bias of the spring 456. That is, the combination of the stop block 464 and the serrations 468, 470 operates as a positive stop for the brake mechanism 426 and the clamping mechanism 444. Having multiple serrations 468, 470 allows the surgeon to independently adjust the force on the flexible member 416 from the brake mechanism 426 and adjust the force on the flexible member 416 from the clamping mechanism 444. For example, with reference to FIGS. 17A, 17B, 21A, and 21B, while not being limited to any particular quantity, the stop and release mechanism 460 may include at least three positive stop positions for the brake mechanism 426 in view of the three serrations 470 on the brake lever 428. The stop and release mechanism 460 may include at least five positive stop positions for the clamping mechanism 444 in view of the five serrations 468 on the clamping lever 446.

Once the desired level force for each of the mechanisms 426, 444 is determined by selection of the serration 468, 470 with which the stop block 464 engages, the stop and release mechanism 460 allows the surgeon to let go of the levers 446 and 428 while maintaining the mechanisms 426 and/or 444 engaged with the flexible member 416. Advantageously, the stop and release mechanism 460 reduces hand fatigue while maintaining the mechanisms 426 and 444 engaged with the flexible member 416, because the surgeon is not required to maintain pressure on each of these mechanisms to maintain engagement with the flexible member 416.

In one embodiment, and with reference to FIGS. 17A, 17B, and 18, the stop and release mechanism 460 further includes a release lever 472 that protrudes beyond the housing 420a, 420b through an opening 474 therein. The surgeon may selectively disengage the stop block 464 by pressing the release lever 472. In this regard, the surgeon may press on the release lever 472, such as with a thumb, with a sufficient force to counteract the bias produced by the spring 466. At that threshold force, the stop block 464 rotates out of contact with the serrations 468, 470 to a release position (shown best in FIG. 22). The spring 456 then spontaneously acts to disengage each of the brake mechanism 426 and/or the clamping mechanism 444.

In an exemplary embodiment, the operation of each of the brake mechanism 426, the clamping mechanism 444, and the stop and release mechanism 460 will be described in conjunction with operation of the resection line guide 402 during a surgical procedure. In particular, after the stomach has been effectively mobilized along its greater curve, the surgeon may manipulate the medical device 400 to insert the resection line guide 402 and at least a portion of the shaft 408 into the abdominal cavity through a surgical trocar. The surgeon may separate the clamp members 412, 414, for example, by grasping the tab 410 with a laparoscopic instrument. Because the first end of the flexible member 416 is fixed to the anchor 417, separating the clamp members 412, 414 causes the spring reel 422 to release a length of the flexible member 416, which slides through the clamp members 412, 414.

The surgeon may secure the resection line guide 402 in position by manually moving the clamp member 412 towards the clamp member 414. As the distance between the clamp members 412, 414 decreases, the spring reel 422 takes up any slack in the flexible member 416. When the spring reel 422 takes up slack in the flexible member 416, the clamp members 412, 414 may generally vertically align relative to the stomach 10. At this point, the clamp members 412, 414 may begin to provide a clamping force on the stomach 10. In this regard, the resection line guide 402 provides a clamping force sufficient to ensure that the clamp members 412, 414 do not migrate after being positioned.

With reference to FIGS. 19-24B, following insertion of the medical device 400 and positioning of the resection line guide 402 around tissue, such as the stomach 10 (shown in FIGS. 23A, 23B, 24A, and 24B), the surgeon may initially activate the brake mechanism 426. To do so, the surgeon grasps the housing 420a, 420b and squeezes the brake lever 428 toward the pistol grip as is indicated by arrow 440 in FIG. 19. As the surgeon squeezes the brake lever 428, the brake arm 434 rotates toward the brake plate 436, as indicated by the arrow 476. In a predetermined orientation of the brake lever 428, and with reference to FIGS. 20A and 20B, the brake arm 434 engages the flexible member 416 and captures it between the brake arm 434 and the brake plate 436. The engagement of the brake mechanism 426 may cause a slight retraction of the flexible member 416 and a correspondingly small movement of the clamp member 412 toward the clamp member 414. It will be appreciated that in this orientation of the brake lever 428, the stop block 464 may engage one serration 470 to provide a positive stop to the brake mechanism 426. As such, should the surgeon let go of the brake lever 428, the spring 456 (even though in an extended or biased condition) is unable to overcome the positive stop of the stop and release mechanism 460 and so the brake mechanism 426 remains frictionally engaged with the flexible member 416. In this position, the flexible member 416 may not move or slide in either direction between the brake arm 434 and the brake plate 436. Even though the brake mechanism 426 is engaged, the clamp members 412 and 414 may be separated by the stomach 10 (shown in phantom line in FIGS. 23A and 23B). The brake mechanism 426 may be engaged at other points during the medical procedure. By way of example, the surgeon may engage the brake mechanism 426 after separating the clamp members 412, 414 when positioning the resection line guide 402 around the stomach 10. This would allow the surgeon to manipulate the clamp members 412, 414 without the force from the spring reel 422 acting on the flexible member 416.

The securement of the resection line guide 402 to the stomach 10 may be achieved using the two-stage clamping process as described above. More particularly, the flexible member 416 may be pulled so as to generate a clamping force on the stomach 10 less than the threshold clamping force. Again, this first-stage clamping force is configured and selected to provide a certain amount of resistance to movement of the resection line guide 402 relative to the stomach 10. This resistance is configured to prevent undesirable or unintentional movements of the resection line guide 402, but yet permit the surgeon to move the resection line guide 402 to a desired position relative to the stomach 10 without significant difficulty. This may be achieved in this embodiment when the spring reel 422 takes up the slack in the flexible member 416 and the brake mechanism 426 is engaged. In the second clamping stage, and with the resection line guide 402 in the desired location relative to the stomach 10, the clamping force of the resection line guide 402 may be increased above the threshold clamping force to effectively prevent or minimize the resection line guide 402 from moving relative to the stomach 10. The upper limit to which the resection line guide 402 may be clamped is selected so as to avoid any damage to the underlying tissue being clamped. This may be achieved in this embodiment by engaging the clamping mechanism 444, as described below.

With reference now to FIGS. 20A, 20B, 21A, and 21B, following engagement of the brake mechanism 426, if additional tension on the flexible member 416 is desired, the surgeon may engage the clamping mechanism 444. To do so, the surgeon may squeeze the clamping lever 446 in the direction of the arrow 478 or toward the pistol grip. Movement of the clamping lever 446 rotates the clamping bracket 450 so that the limiter plate 452 rotates into contact with the flexible member 416 as is indicated by arrow 480 in FIG. 20. Because the limiter plate 452 only just begins to contact the flexible member 416, as shown in FIGS. 20A and 20B, there may be only limited retraction of the flexible member 416 from the resection line guide 402 and so the clamp member 412 as shown in FIG. 23A may not move.

Figure 21A:
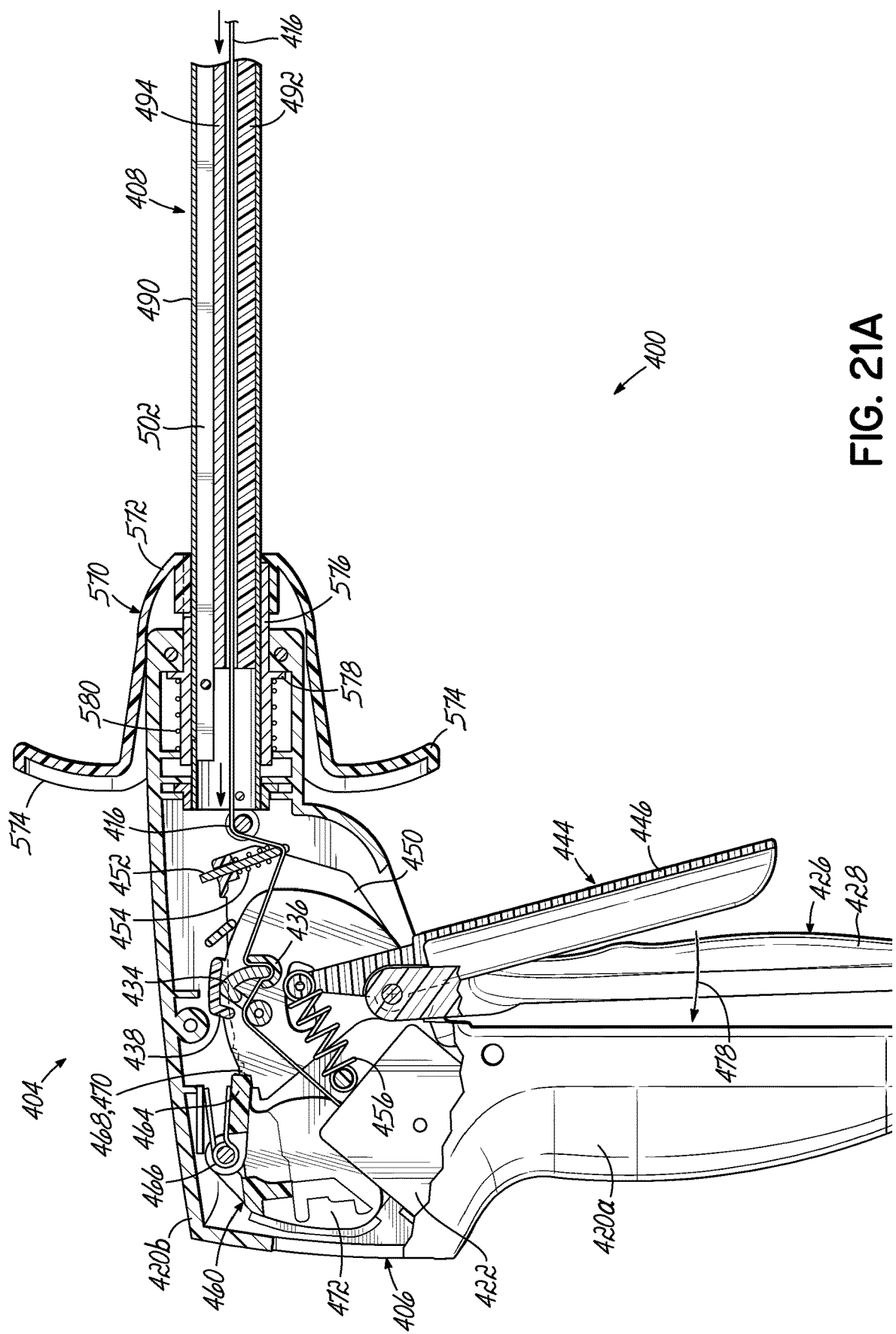
FIGS. 21A and 21B are partial cross-sectional views of the manipulator of FIG. 19 depicting engagement of a mechanism according to an embodiment.
Figure 21B:
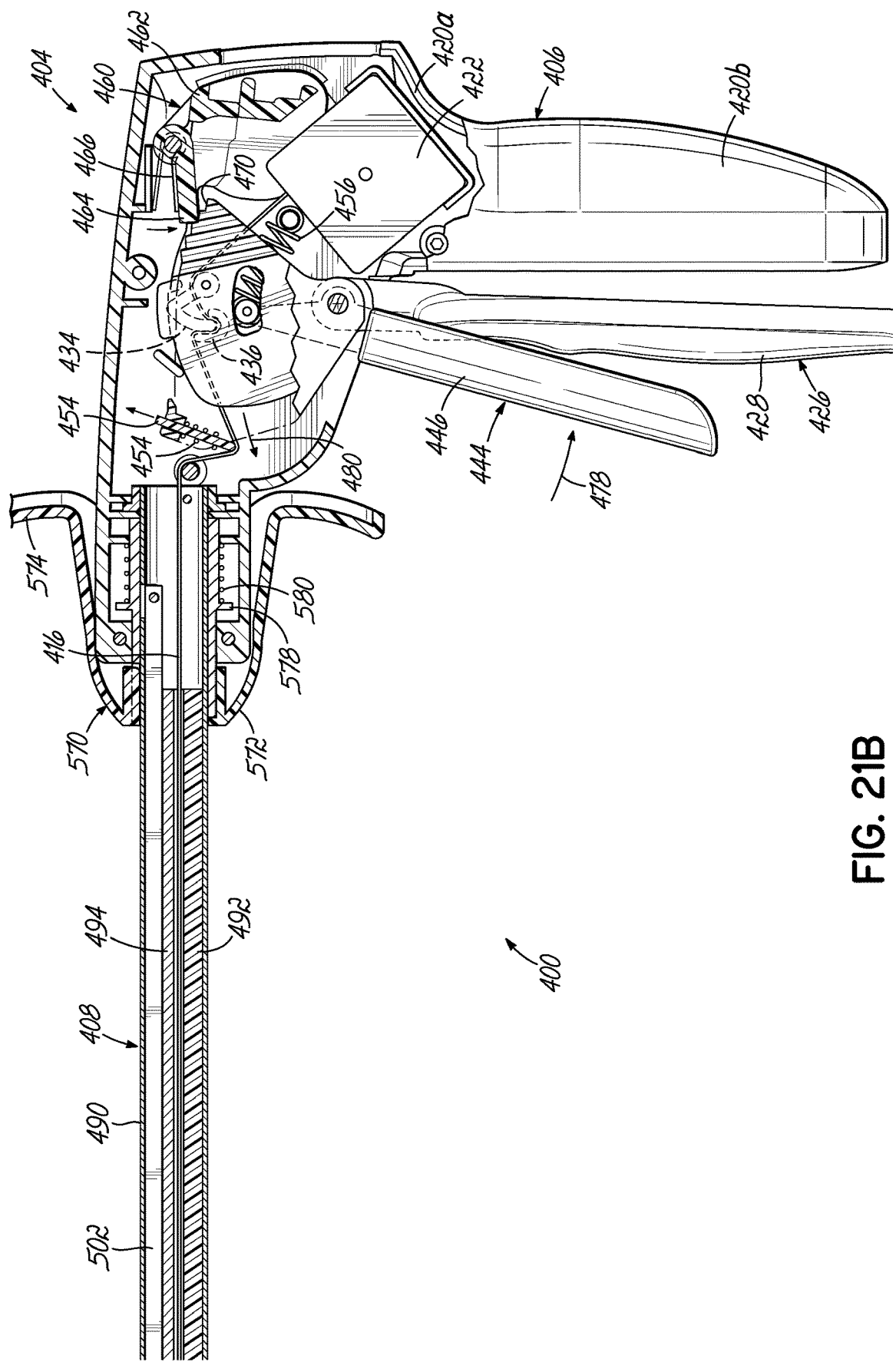

With reference to FIGS. 21A, 21B, 23A, and 23B, movement of the clamp member 412 toward the clamp member 414 as is indicated by arrow 482 may be achieved if the surgeon continues to squeeze the clamping lever 446 toward the pistol grip as indicated by arrow 478 in FIGS. 21A and 21B. As shown, squeezing the clamping lever 446 rotates the limiter plate 452 into contact with the flexible member 416 and causes the flexible member 416 to be displaced from its original path. Because the brake mechanism 426 is engaged, the flexible member 416 may not be pulled from the spring reel 422.

Instead, and with reference to FIGS. 21A, 21B, 24A, and 24B, the flexible member 416 is retracted from the resection line guide 402 as is indicated by arrows 482. Accordingly, squeezing the clamping lever 446 into the position shown in FIGS. 21A and 21B may cause the clamp member 412 to forcibly move toward the clamp member 414 and provide a clamping force on the stomach 10 therebetween. The surgeon may adjust the tension on the flexible member 416, and therefore adjust the clamping force on the stomach 10, by further squeezing the clamping lever 446. As described above, the clamping mechanism 444 limits the maximum clamping force of the resection line guide 402 on the stomach 10. Accordingly, and with continued reference to FIGS. 21A and 21B, further squeezing of the clamping lever 446, at some predetermined point, produces a maximum clamping force on the stomach 10 beyond which further movement of the clamping lever 446 produces little, if any, increase in tension on the flexible member 416. That is, once the maximum tension on the flexible member 416 is achieved, further squeezing of the clamping lever 446 produces little, if any, deflection of the flexible member 416 by the limiter plate 452. The limiter plate 452 and the limiter spring 454 in combination with the rotational stroke of the clamping lever 446 prevent excessive tension on the flexible member 416 and so prevent damaging the stomach 10 during the procedure.

With reference now to FIGS. 21A and 21B, squeezing the clamping lever 446 further extends the spring 456 and rotates the clamping bracket 450 into a position in which a serration 468 engages the stop block 464. Under the bias produced by the spring 466, the stop block 464 in contact with the serration 468 forms a positive stop of the clamping mechanism 444. Should the surgeon let go of the clamping lever 446, the stop and release mechanism 460 prevents the bias in the spring 456 from releasing the clamping mechanism 444. Any tension on the flexible member 416 produced by the clamping mechanism 444 is thereby maintained by the stop and release mechanism 460 and specifically by the positive stop produced between the stop block 464 and one serration 468. Further rotation of the clamping bracket 450, such as when the surgeon increases the clamping force, further engages the stop block 464 with successive serrations 468. Successively higher clamping forces on the stomach 10 are thereby maintained should the surgeon let go of the clamping lever 446.

When the resection line guide 402 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 402 prior to stapling and cutting the stomach 10. Once the resection line guide 402 is finally positioned (e.g., the second clamping stage as described above), the surgeon may then cut and staple the tissue using the resection line guide 402 as a track along the entire segment or a significant part of the segment until complete resection of the stomach 10 occurs. In this regard, a stapling device may abut or engage the resection line guide 402 along an alignment surface to facilitate an improved resection line, similar to that shown above in FIG. 2D.

Figure 22:
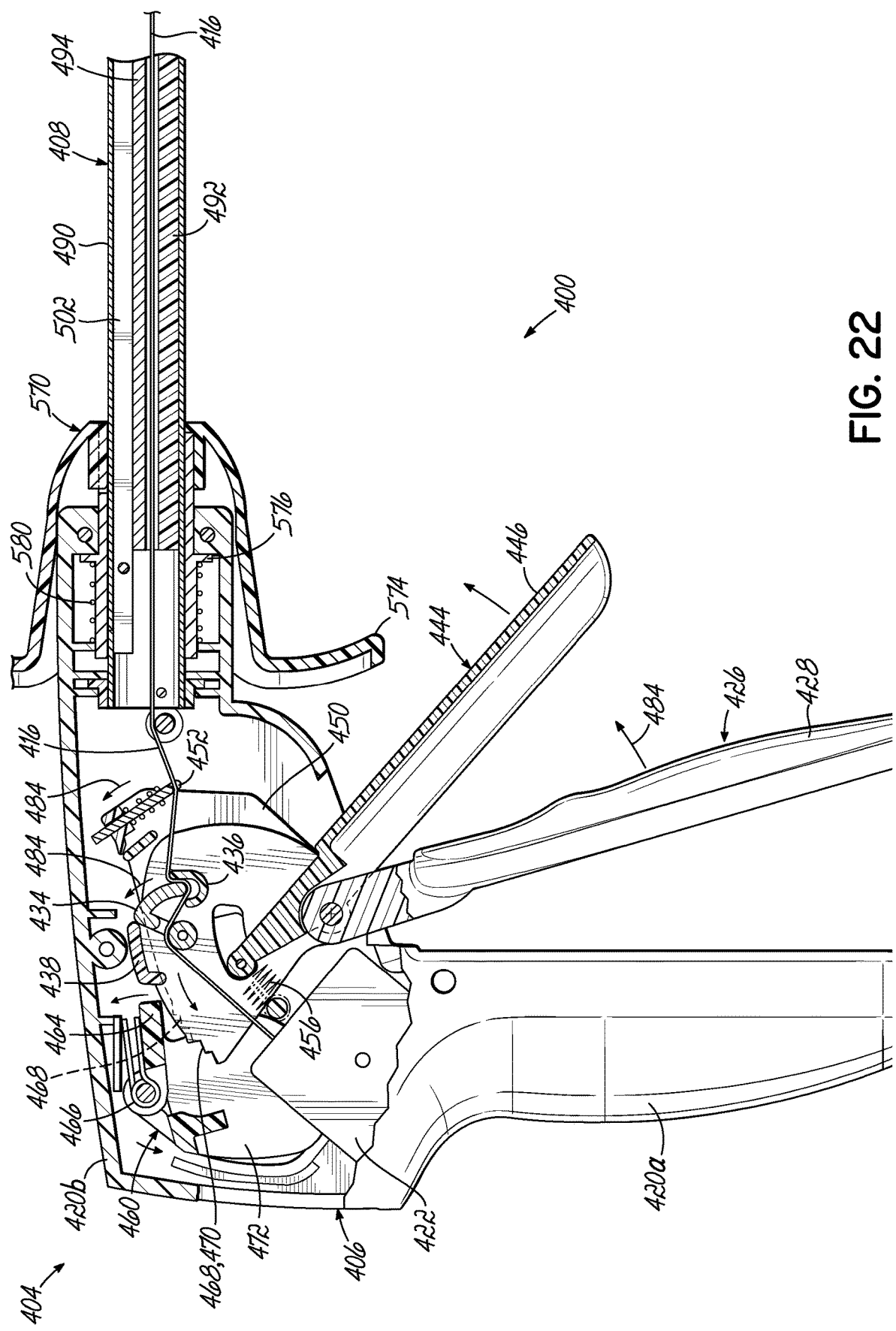
FIG. 22 is a partial cross-sectional view of the manipulator of FIG. 19 depicting release of the mechanisms according to an embodiment.

With reference to FIG. 22 and after the resection of stomach 10, each of the brake mechanism 426 and the clamping mechanism 444 may be released. In this regard, the surgeon may press the release lever 472. As described above, sufficient pressure on the release lever 472 overcomes the bias of the spring 466 and rotates the stop block 464 out of engagement with serrations 468, 470. Once the stop block 464 clears the serrations 468, 470, the spring 456 that was extended when the surgeon squeezed the levers 428 and 446 disengages the brake mechanism 426 and the clamping mechanism 444. The spring 456 moves each of the mechanisms according to arrows 484. As a result, the limiter plate 452 rotates away from contact with the flexible member 416. Similarly, the brake arm 434 rotates away from the flexible member 416 and out of engagement with the brake plate 436. Once each of the mechanisms 426 and 444 is released, a length of the flexible member 416 may be freed from the spring reel 422 and the clamp member 412 may be separated from the clamp member 414 to release the stomach 10. This movement may be the reverse of the movement of the clamp member 412 during clamping of the stomach 10. It will be appreciated that moving the clamp member 412 away from the clamp member 414 may be achieved by pulling on the tab 410 with a laparoscopic instrument.

With reference to FIGS. 14 and 25-29, in one embodiment, the medical device 400 includes a joint 488 movably coupling the shaft 408 to the resection line guide 402. The joint 488 allows the shaft 408 to articulate relative to the resection line guide 402. In addition to articulating, the joint 488 is lockable so that once the resection line guide 402 is properly positioned, it may be fixed in relative orientation to the shaft 408. To do so, in one embodiment, the manipulator 404 includes a mechanism for locking and unlocking the joint 488. The surgeon may therefore rotate and position the resection line guide 402 at any time during the procedure during which the resection line guide 402 is located in the patient and then lock the resection line guide 402 relative to the shaft 408 without having direct access to the joint itself.

To these and other ends, as shown in FIG. 25, in one embodiment, the shaft 408 includes a tubular housing 490 that encloses a cable guide 492 and a lever guide 494. As shown, the cable guide 492 and lever guide 494 each have semi-circular cross-sections that when assembled fill the tubular housing 490 and enhance the rigidity of the shaft 408. The cable guide 492 defines a channel 496 that extends axially and is open to each end of the cable guide 492. When the cable and lever guides 492, 494 are assembled within the housing 490, the channel 496 defines a passage that is open to each end of the shaft 408. The channel 496 receives the flexible member 416. The cable guide 492 may have a plurality of fins and corresponding trenches or grooves 510 formed at or near the location of the joint 488. This configuration may provide some flexibility in the shaft 408 at or near the joint 488.

With continued reference to FIG. 25, the lever guide 494 defines a slot 498 that extends axially along a circumferential surface of the lever guide 494. As shown, the length of the slot 498 may be less than the full length of the lever guide 494. The slot 498 may be open to only one end of the lever guide 494 and, although not shown in FIG. 25, the slot 498 opens to a bore 500 (shown in FIG. 28) at the other end of the lever guide 494. The slot 498 receives an elongated member or release lever 502 having a through-hole 504 at one end and a cutout 506 at the other end thereof. The cutout 506 defines a tab 508 at one end of the release lever 502. When the release lever 502 is received in the slot 498, the tab 508 aligns with the bore 500. The through-hole 504 is exposed at one end of the shaft 408 and is configured to cooperate with a locking/unlocking mechanism on the pistol-grip device 406, described below. The lever guide 494 may include a tongue-like projection 512 extending along the longitudinal axis of the lever guide 494. The tongue 512 may define a cutout 514 between the cable guide 492 and lever guide 494 when they are assembled. The cutout 514 movably receives a portion of the resection line guide 402, described below. As shown in FIG. 28, a post 516 extends substantially perpendicular to the longitudinal axis of the lever guide 494 and provides a point around which the shaft 408 and the resection line guide 402 pivot relative to one another, as is indicated by the arrows 518 in FIG. 28. In one embodiment, the lever guide 494 includes a notch 554 that cooperates with a pair of bendable tabs 556 in the housing 490. The housing 490 includes a window 558 which cooperates with a release mechanism coupled to the pistol-grip device 406 described below.

With continued reference to FIGS. 25, 27A, 27B, and 28, in one embodiment, the cable and lever guides 492, 494 house a locking mechanism 540 that may include a locking pin 542 and a locking spring 544. The locking pin 542 is a generally rectangular body having a tip 546 extending from one end and a slot 548 formed in one surface. As shown, the locking spring 544 cooperates with the end of the locking pin 542 opposite the tip 546 and so extends generally coincident with the axis of the locking pin 542. The locking pin 542 and the locking spring 544 may be movably contained within the bore 500. The locking spring 544 cooperates with the bore 500 to bias the locking pin 542 in the direction of the resection line guide 402. The slot 548 of the locking pin 542 receives the tab 508 of the release lever 502 when the locking mechanism 540 is positioned in the bore 500 and the release lever 502 is placed in the slot 498. The tip 546 of the locking pin 542 extends into the cutout 514 and interacts with a portion of the resection line guide 402, described below.

Figure 27A:
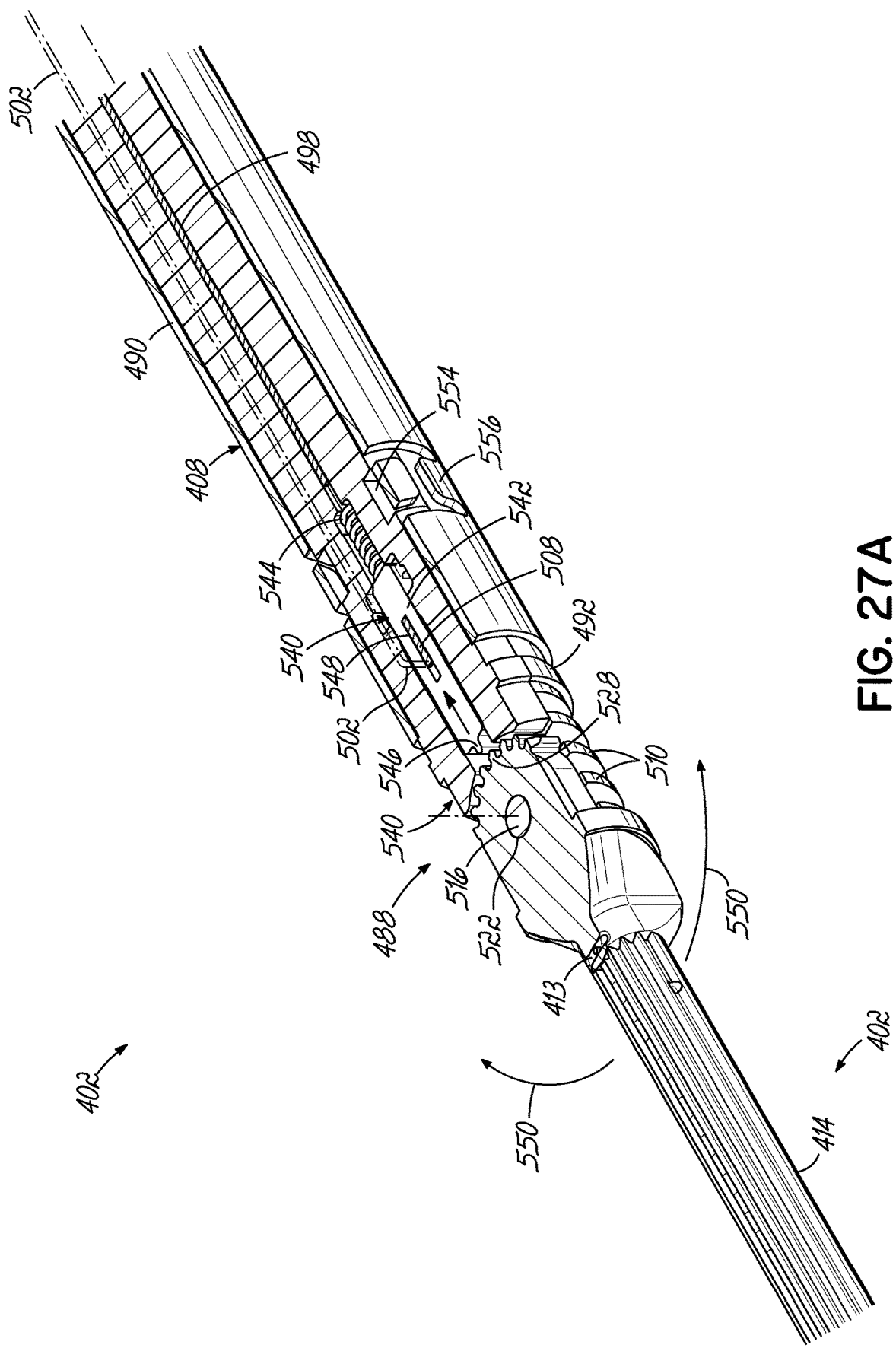
FIGS. 27A and 27B are enlarged cross-sectional views of a joint according to an embodiment.
Figure 27B:
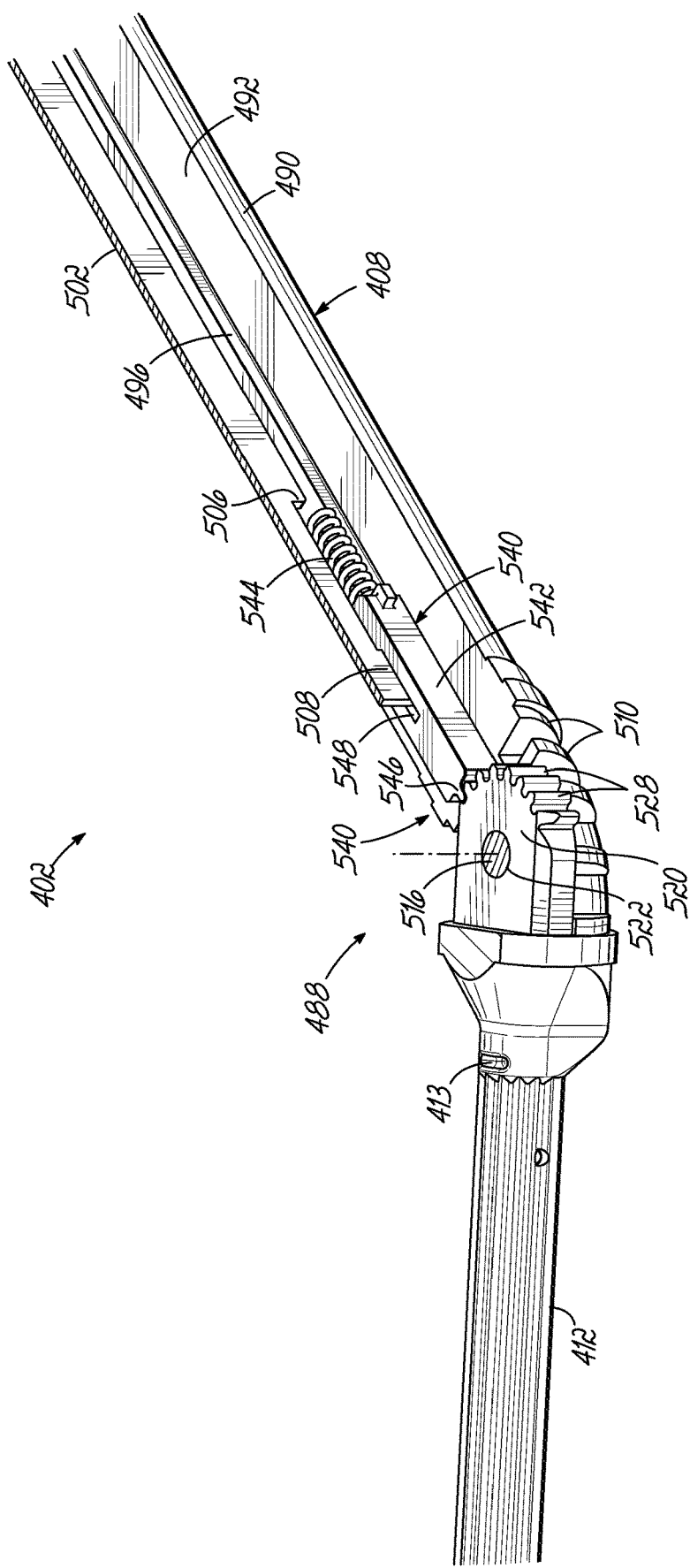

With continued reference to FIGS. 25, 27A, and 27B, in one embodiment, the clamp member 414 includes a tongue 520. A bore 522 extends through the tongue 520 generally perpendicularly to the longitudinal axis of the resection line guide 402. A plurality of gear-like teeth 528 generally define an arcuate-shaped end 526 of the tongue 520. With reference to FIGS. 25 and 28, in one embodiment, the joint 488 includes a centering spring 560. As shown, the centering spring 560 extends across the joint 488 into recesses in each of the shaft 408 and the clamp member 414 and is configured to elastically bend as loads that may be applied by the surgeon. As described below, the centering spring 560 resists relative movement between the shaft 408 and the resection line guide 402.

When the joint 488 is assembled, the cutout 514 of the shaft 408 receives the tongue 520 of the clamp member 414 with the post 516 residing in the bore 522. The tip 546 on the locking pin 542 cooperates with the teeth 528 on the tongue 520 of the resection line guide 402. By this arrangement as shown in FIG. 27B, the resection line guide 402 and the shaft 408 may not move relative to one another and are locked in position. It will be appreciated that the locking spring 544 biases the locking pin 542, specifically the tip 546, into the teeth 528 (best shown in FIG. 27B). As such, the locking mechanism 540 provides a normally-locked configuration. That is, only when the locking pin 542 is retracted against the bias of the locking spring 544 to clear the teeth 528 is the shaft 408 pivotable relative to the resection line guide 402.

In this regard and with reference to FIGS. 27A, 27B, and 28, the release lever 502 cooperates with the locking pin 542. Specifically, the tab 508 cooperates with the slot 548. Sliding movement of the release lever 502 in the direction of the arrow 552 in FIG. 28 counteracts the bias in the spring 544 and so slides the locking pin 542 within the bore 500 to compress the locking spring 544. The tip 546 is withdrawn from cooperation with the teeth 528 such that the joint 488 is unlocked. The resection line guide 402 may then be pivoted relative to the shaft 408 about the post 516 as is illustrated by way of comparison in FIGS. 27A and 27B with movement indicated by arrows 550.

In one embodiment, this pivoting action of the resection line guide 402 relative to the shaft 408 must be accompanied by a sufficient level force to bend the centering spring 560. In addition, once the resection line guide 402 is brought into position in which the centering spring 560 is flexed or biased, the locking mechanism 460 must be activated to lock in the nonlinear orientation against the bias produced by the centering spring 560. In the absence the locking mechanism 460 to lock-in the relative positions of the resection line guide 402 and the shaft 408, the bias in the centering spring 560 will return the resection line guide 402 and the shaft 408 into a linear orientation in which the centering spring 560 is unbiased. Further in this regard, the linear orientation between the resection line guide 402 and the shaft 408 may be obtained by releasing the locking mechanism 460 in the absence of any forces on either of the resection line guide 402 or the shaft 408, the centering spring 560 tending to linearly re-orient the resection line guide 402 and the shaft 408.

Figure 26:
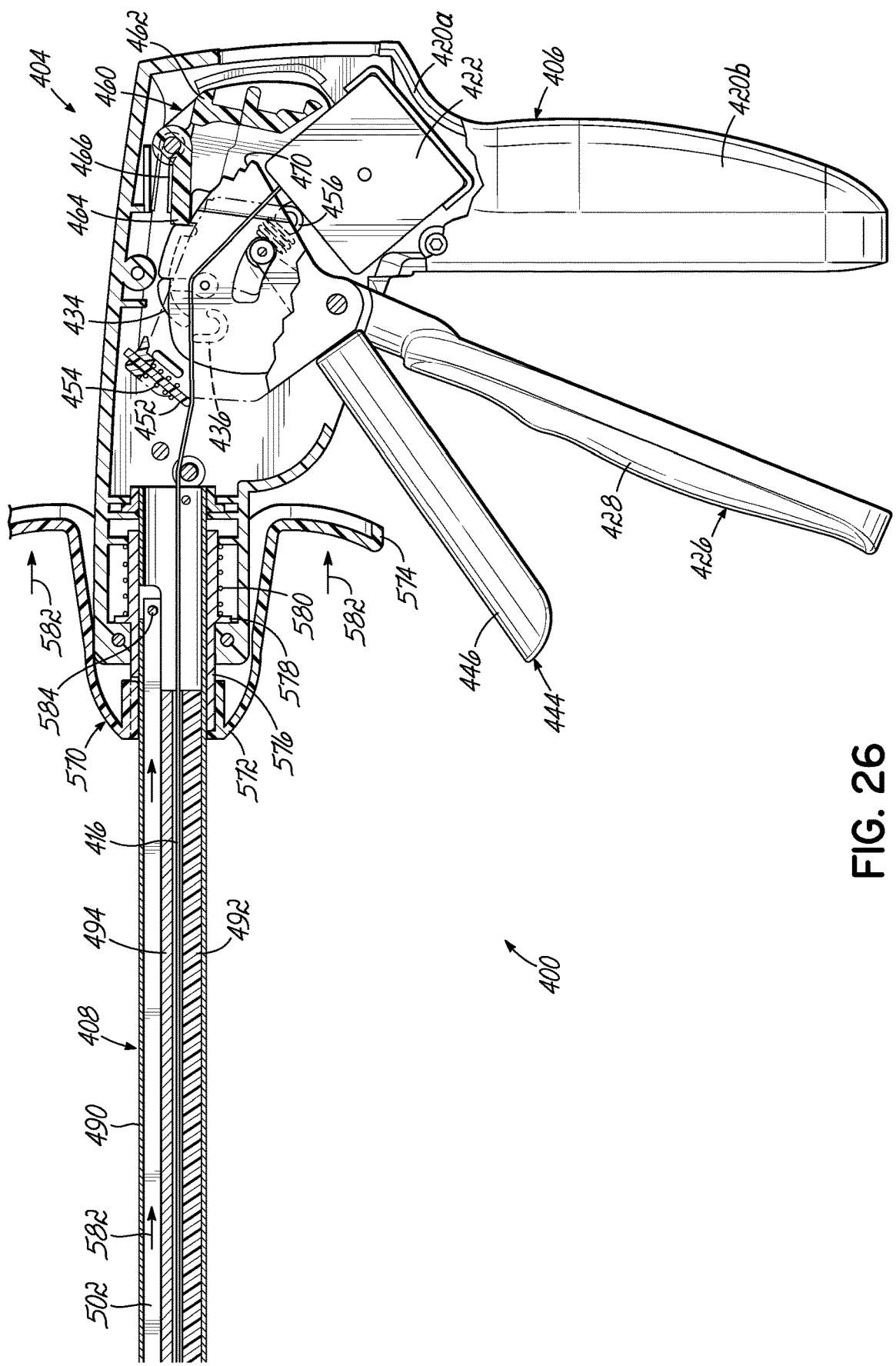
FIG. 26 is a partial cross-sectional view of a manipulator of the medical device of FIG. 14 depicting engagement of a mechanism according to an embodiment.

In one embodiment and with reference to FIGS. 14, 15A, 15B, 18, and 26, as described above, the manipulator 404 includes a mechanism by which the surgeon may control the articulation of the resection line guide 402 relative to the shaft 408. To that end, the manipulator 404 may include a release mechanism 570 coupled to the release lever 502 (shown in FIG. 26). The release mechanism 570 remains exposed during a procedure so that the surgeon may lock and unlock the joint 488. In one embodiment, as shown in FIG. 26, the release mechanism 570 includes a shroud 572 having a plurality of tabs 574 extending radially therefrom. The housing 420a, 420b slidably receives the shroud 572 at the junction of the shaft 408 with the pistol-grip device 406. The shroud 572 is coupled with a sleeve 576 that generally corresponds to the outer diameter of the tubular housing 490.

With reference to FIGS. 17A, 17B and 18, the sleeve 576 includes a flange 578 extending generally radially therefrom. The release mechanism 570 further includes a coil spring 580 between the flange 578 and the housing 420a, 420b. The sleeve 576 further includes a pin 584 (shown in FIG. 26) that is coupled to the release lever 502, for example, via the bore 504.

As shown in FIG. 26, during an operation, the surgeon may decide to rotate the resection line guide 402 relative to the shaft 408 at the joint 488. To do so, the surgeon may pull the shroud 572 by the tabs 574 in the direction indicated by arrow 582 with a sufficient amount of force to compress the spring 580. By this movement, the sleeve 576 pulls the release lever 502 in the direction indicated by arrow 582.

With reference to FIG. 25, as is described above, movement of the release lever 502 in this direction compresses the spring 544 and moves the locking pin 542 out of engagement with the teeth 528. Accordingly, movement of the shroud 572 unlocks the joint 488. The surgeon may then reposition the resection line guide 402 as necessary. Once repositioned, the surgeon may release the shroud 572. As a result, the coil spring 580 expands causing the release lever 502 and consequently the locking pin 542 to return to its locked position. In this manner, the surgeon may remotely lock and unlock the joint 488 during a procedure to reposition the resection line guide 402 relative to the shaft 408. It will be appreciated that the coil spring 580, like the locking spring 544, provides a normally-locked condition of the locking mechanism 540 proximate the joint 488. It will be appreciated that when the surgeon pivots the resection line guide 402 relative to the shaft 408, the path length for the flexible member 416 increases. In this case, the spring reel 422 may release a length of the flexible member 416 to compensate for the longer path length. If the spring reel 422 is prevented from releasing an additional length of the flexible member 416, for example, if the brake mechanism 426 is engaged, the distance between clamp members 412, 414 may decrease.

In another embodiment and with reference now to FIGS. 30-34B, a medical device 600 performs substantially the same procedure as the medical device 400 described above. To that end, the medical device 600 includes a resection line guide 602, which may be one of the guides described above, operatively coupled to a manipulator 604. As shown, the manipulator 604 includes an elongate member or shaft 608 coupled to a handpiece, such as a pistol-grip device 606, at one end and the resection line guide 602 at the other end thereof. As described above with respect to the medical device 400, during a surgical procedure, the resection line guide 602 and a portion of the shaft 608 may be inserted into the patient, such as via a surgical trocar. The surgeon may then manipulate the resection line guide 602 and/or articulate the resection line guide 602 relative to the manipulator 604 to perform the procedure. Thus, embodiments of the present invention may include mechanisms for allowing the resection line guide 602 to articulate relative to the shaft 608 and for effectuating a surgical procedure with the resection line guide 602.

Figure 30:
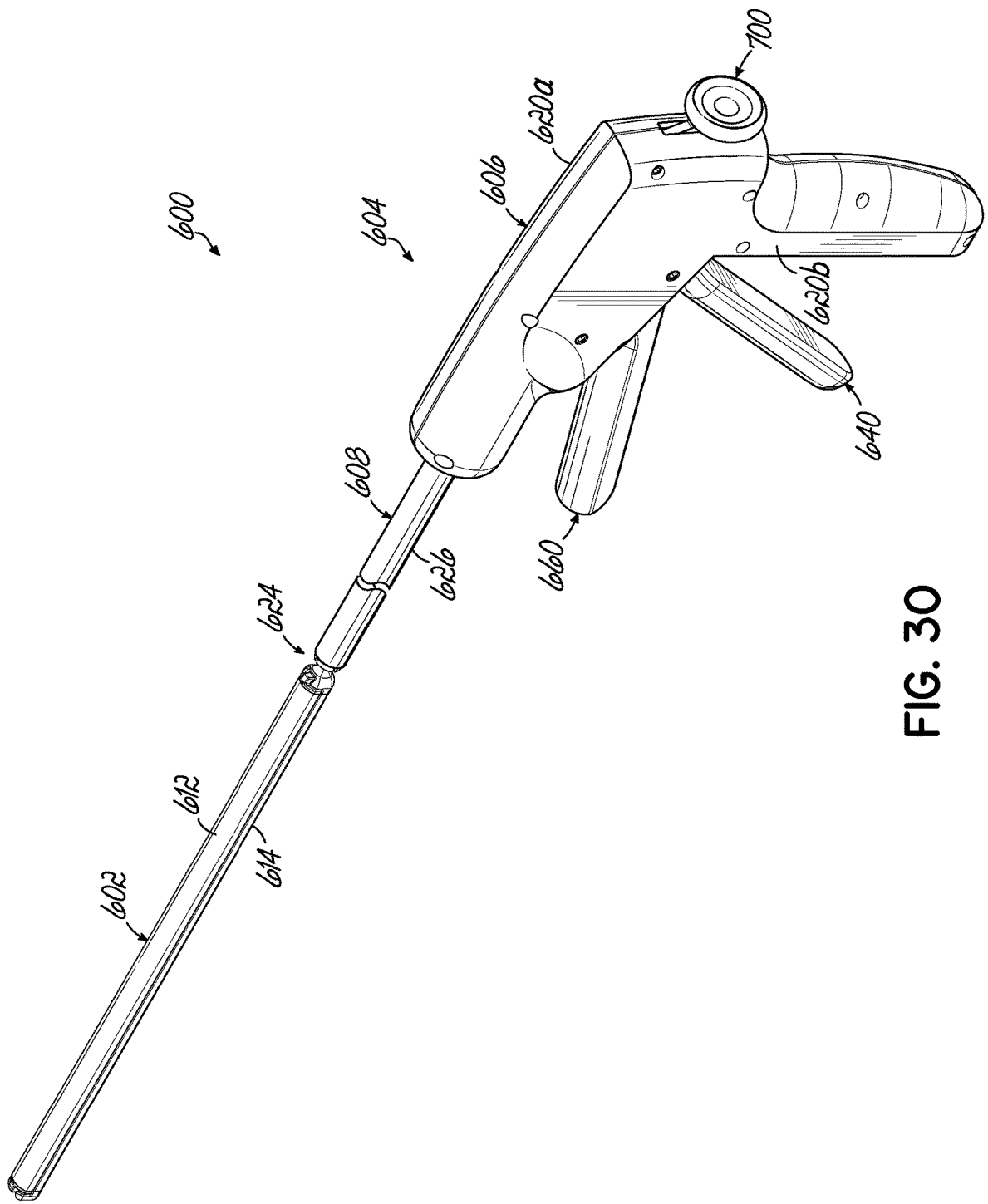
FIG. 30 is a perspective view of a medical device for use in a medical procedure according to one embodiment.

With reference to FIGS. 30, 33D, and 34C, the resection line guide 602 includes clamp members 612, 614 that are movably coupled together via a flexible member 616. The flexible member 616 passes through hollow portions of the clamp members 612, 614 so that, for example, the clamp member 612 may be separated from or brought closer to the clamp member 614. In this regard, an anchor 617 fixes a first end of the flexible member 616 to the clamp member 614 adjacent a distal end thereof. Flexible member 616 passes into the clamp member 612 adjacent a distal end thereto and out of the clamp member 612 adjacent a proximal end thereto. Flexible member 616 then passes into the clamp member 614 adjacent a proximal end thereto and into the shaft 608. Retraction of the flexible member 616 moves at least one of the clamp members 612, 614 as is shown generally by arrow 618 in FIG. 34C and described below. The resection line guide 602 may include one of the exemplary resection line guides described above, such as, for example, those shown in FIGS. 3E, 4B, and 5A. To at least those ends, the manipulator 604 includes mechanisms that the surgeon may manipulate to independently move the resection line guide 602 to open and close the clamp members 612, 614 and/or to pivot the resection line guide 602 relative to the manipulator 604, as is described in detail below.

Figure 31:
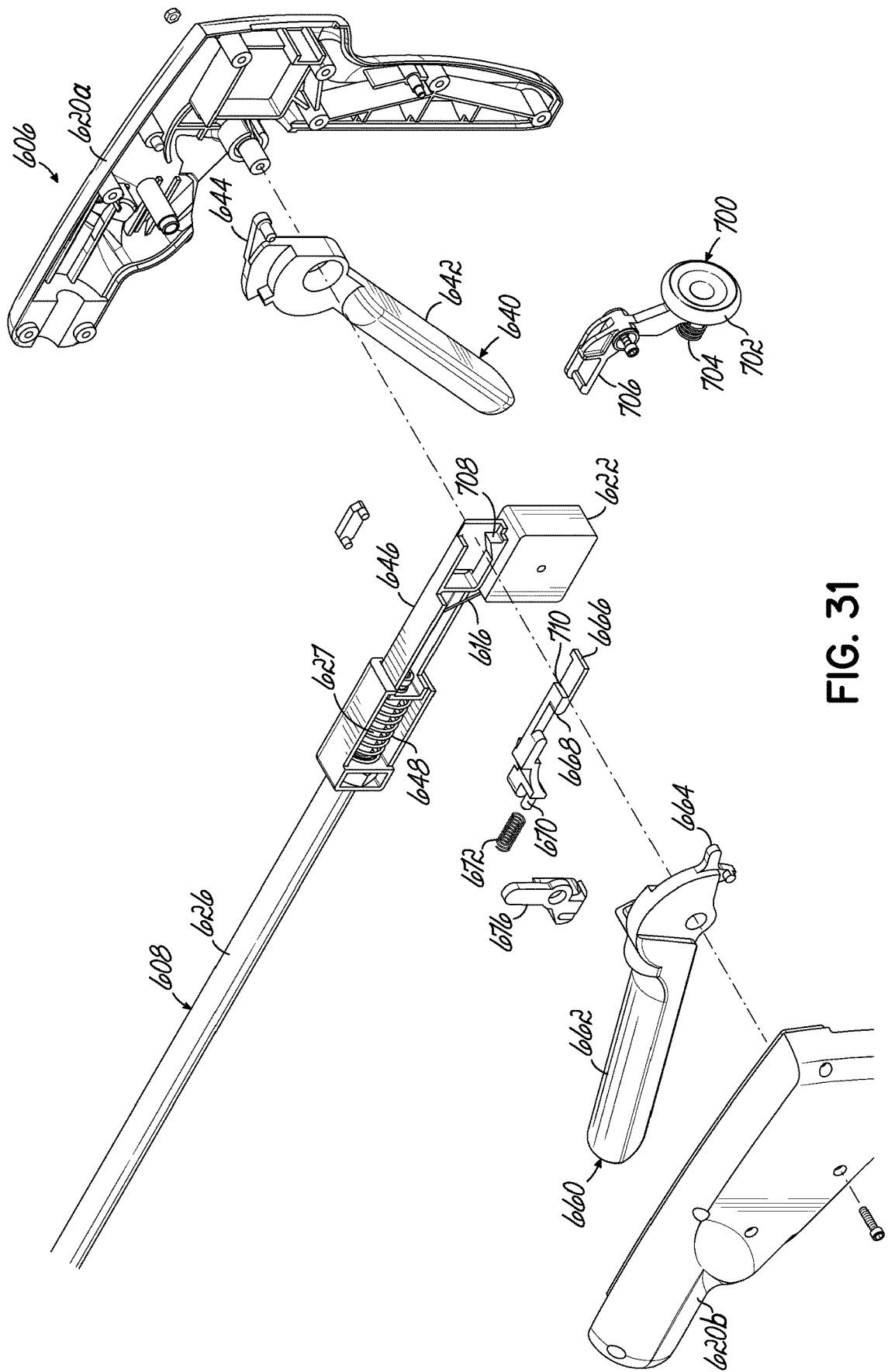
FIG. 31 is an exploded perspective view of a manipulator of the medical device of FIG. 30.
Figure 32A:
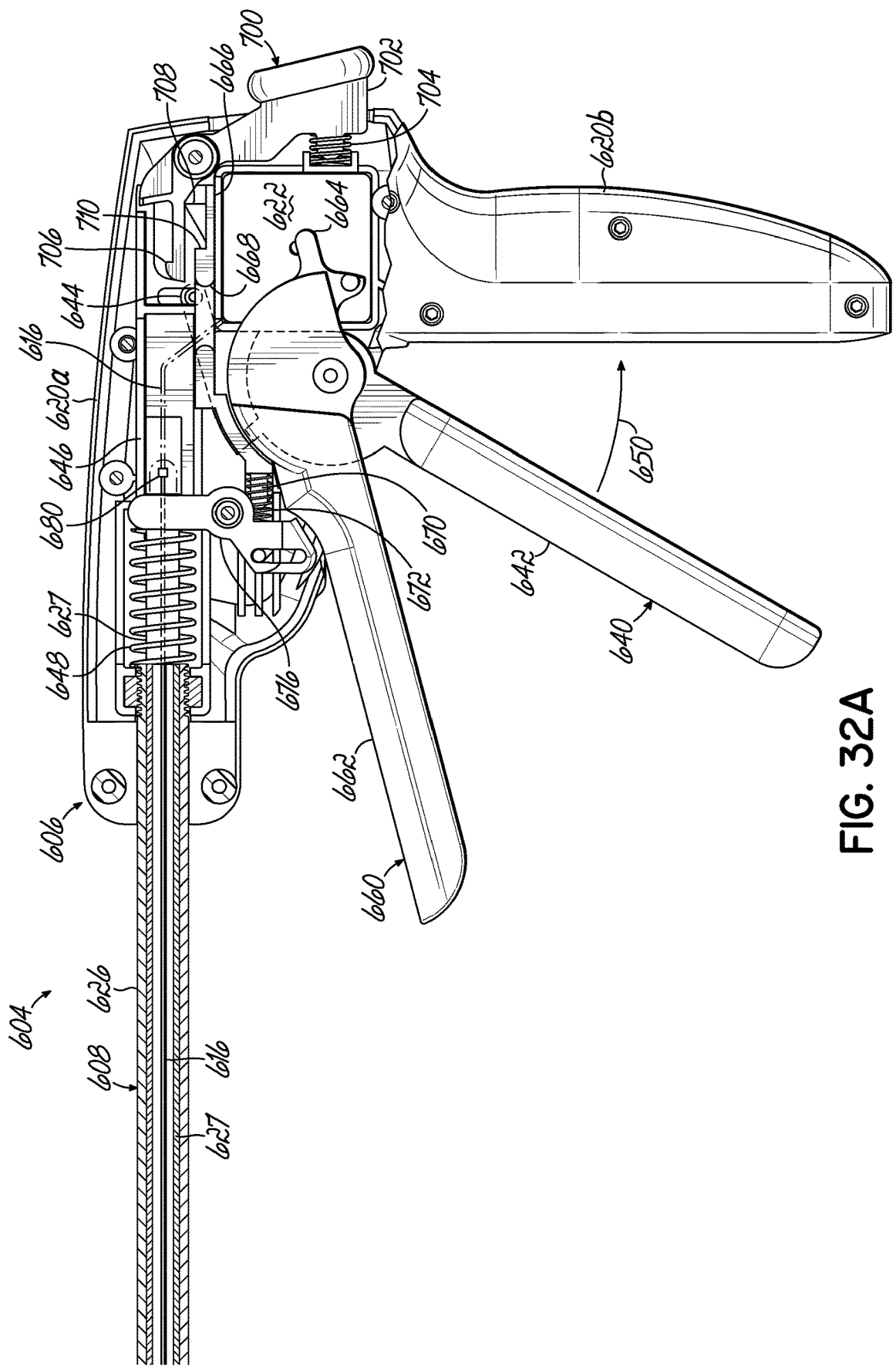
FIGS. 32A and 32B are partial cross-sectional views of the manipulator of the medical device of FIG. 30 depicting engagement of a mechanism according to an embodiment.
Figure 32B:
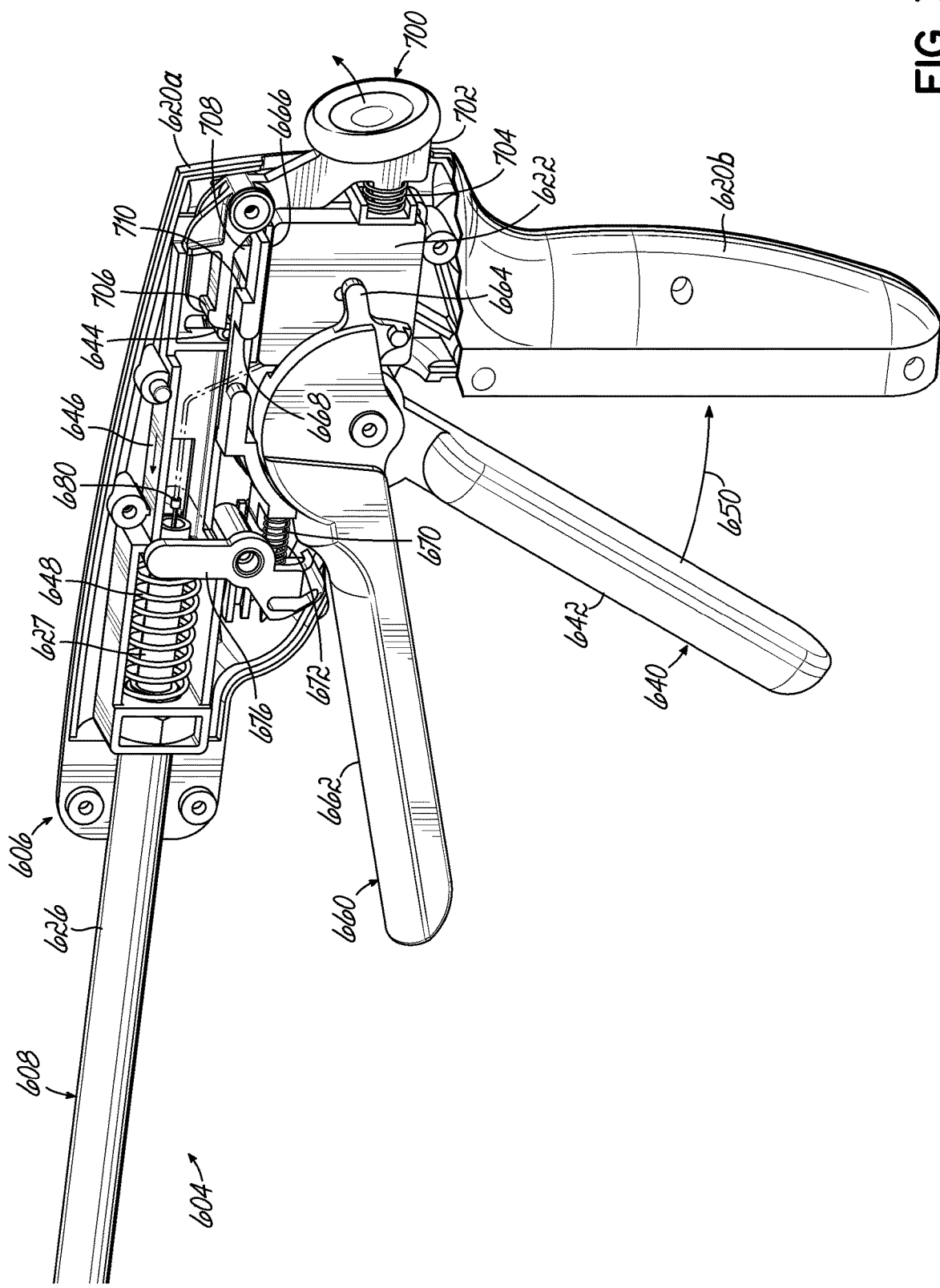

With reference to FIGS. 31, 32A, and 32B, in one embodiment, the manipulator 604 includes a case or housing formed by halves 620a, 620b that contains mechanisms for operation of the medical device 600. The flexible member 616 extends from shaft 608 and is fixed to a spring reel 622 (shown best in FIG. 32A), which may contain a spool of the flexible member 616 onto which the flexible member 616 may be wound and unwound. The spring reel 622 may be similar to the spring reel 422 shown in FIG. 18A. The spring reel 622 is contained within the housing 620a, 602b and releases and/or retracts a length of the flexible member 616. For example, the spring reel 622 may simply keep the flexible member 616 taut during the procedure. In other words, any slack in the flexible member 616 may be spontaneously taken up by the spring reel 622.

Figure 32C:
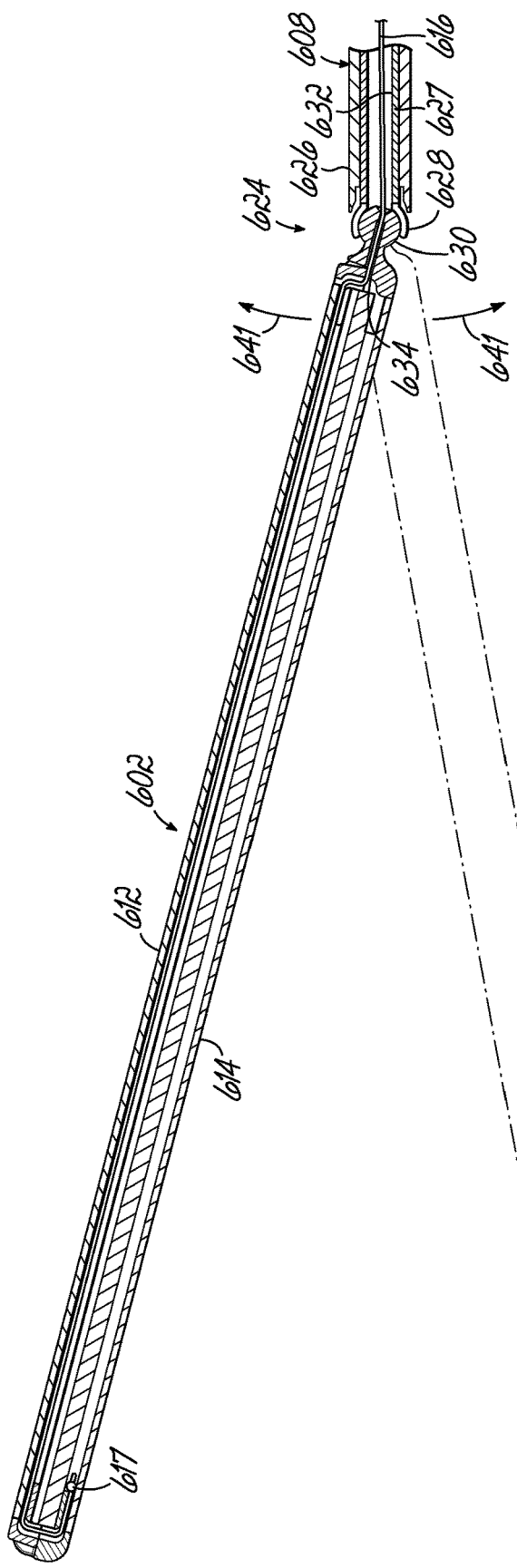
FIG. 32C is a cross-sectional view of a resection line guide of the medical device of FIG. 30.

With reference to FIGS. 30 and 32C, in one embodiment, the medical device 600 includes a joint 624 movably coupling the shaft 608 to the resection line guide 602. As shown, the joint 624 may be a ball-and-socket type joint. The joint 624 allows the shaft 608 to articulate relative to the resection line guide 602 (exemplary motion is shown in phantom line in FIG. 32C). The joint 624 is lockable so that, once the resection line guide 602 is properly positioned, the resection line guide 602 may be fixed in relative orientation to the shaft 608. To do so, in one embodiment, the manipulator 604 includes a mechanism for locking and unlocking the joint 624. The surgeon may therefore rotate and position the resection line guide 602 at any time during which the resection line guide 602 is located in the patient and then lock the resection line guide 602 relative to the shaft 608 without having direct access to the joint 624.

Figure 33C:
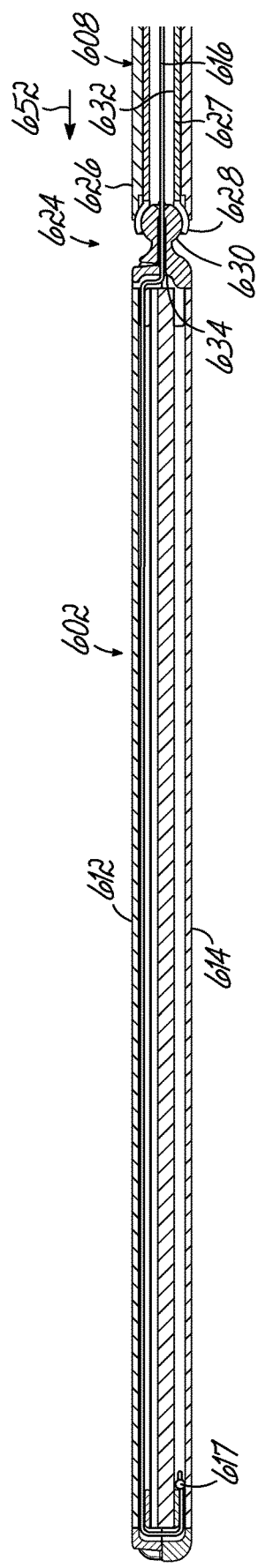
FIG. 33C is a cross-sectional view of a resection line guide of the medical device of FIG. 30.

To these and other ends, as shown in FIGS. 30-32C, in one embodiment, the shaft 608 includes a guide tube 626 that encloses an inner guide tube 627 having a socket 628. The socket 628 forms one portion of the ball-and-socket joint 624 and pivotally captures a ball 630 that forms another portion of the ball-and-socket joint 624. The ball 630 may extend from the clamp member 614. As shown in FIGS. 32A, 32B, and 33C, the inner guide tube 627 defines a longitudinally extending bore 632 through the shaft 608 through which the flexible member 616 passes. Similarly, the ball 630 defines a bore 634. The flexible member 616 passes through the bore 632 and through the joint 624 via the bore 634 in the ball 630.

In one embodiment and with reference to FIGS. 31, 32A, and 32B, the pistol-grip device 606 includes a mechanism by which the surgeon may lock the orientation of the resection line guide 602 relative to the shaft 608. That is, the joint 624 may be locked to inhibit unintentional movement between the resection line guide 602 and the shaft 608. To that end, the manipulator 604 may include an articulation locking mechanism 640 to lock the joint 624. In one embodiment, the articulation locking mechanism 640 includes an articulation locking lever 642 that is pivotally mounted within the housing 620a, 620b and extends therefrom so as to be operable by the surgeon, such as with one or more fingers.

The articulation locking lever 642 includes an actuation arm 644 that transfers load from the locking lever 642 to the guide tube 626 via a compression bracket 646, which acts as a plunger against a spring 648. As shown in FIGS. 32A and 32B, the compression bracket 646 and spring 648 generally align with the longitudinal axis of the shaft 608. Once compressed, the pressure from the spring 648 pushes the guide tube 626 axially away from the pistol-grip device 606. The inner guide tube 627 remains stationary during axial movement of the guide tube 626. In other words, the guide tubes 626, 627 move relative to one another. By this movement, the guide tube 626 forcibly engages the socket 628 to lock the ball 630 in position.

Figure 14:
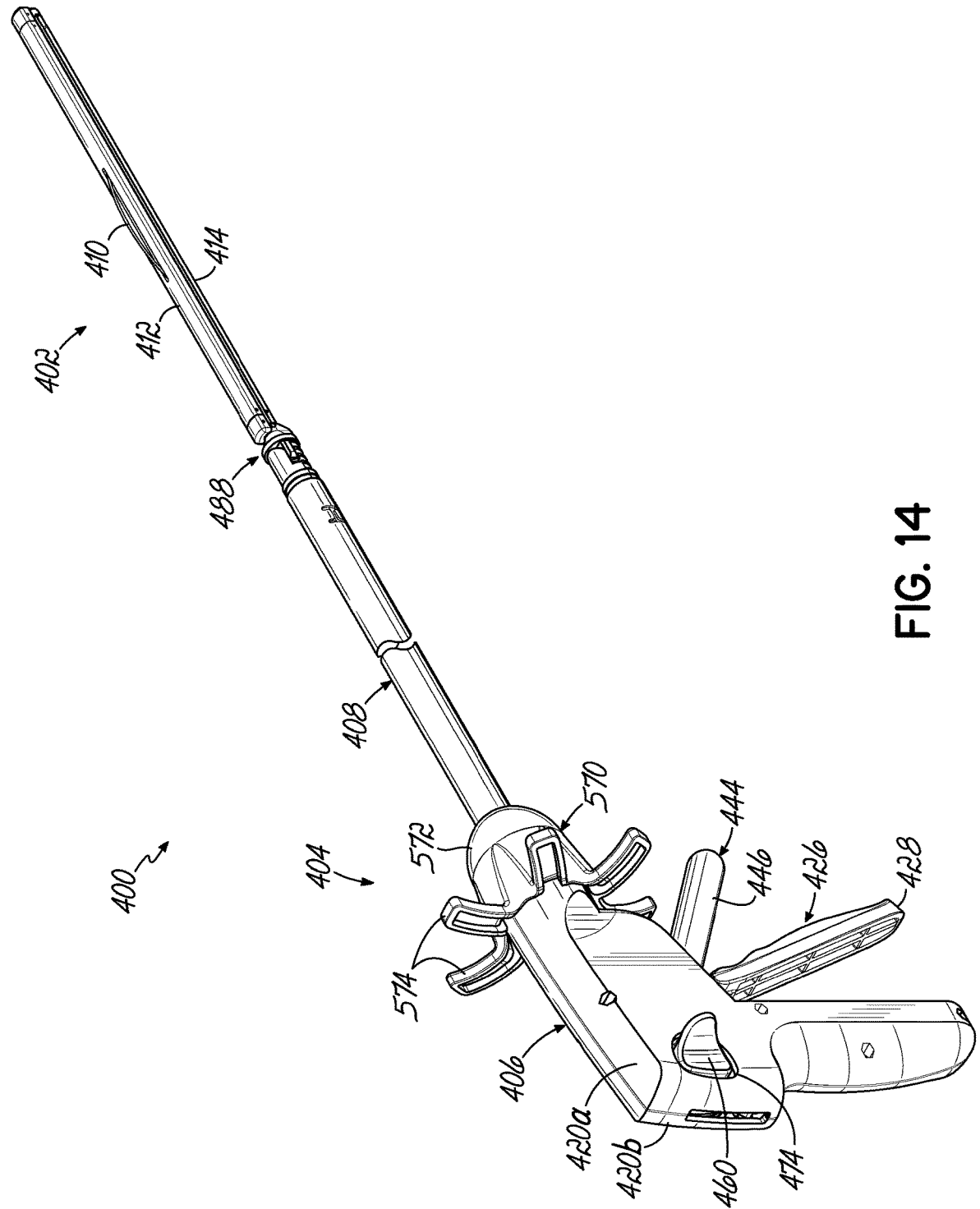
FIG. 14 is a perspective view of a medical device for use in a medical procedure according to one embodiment.
Figure 15A:
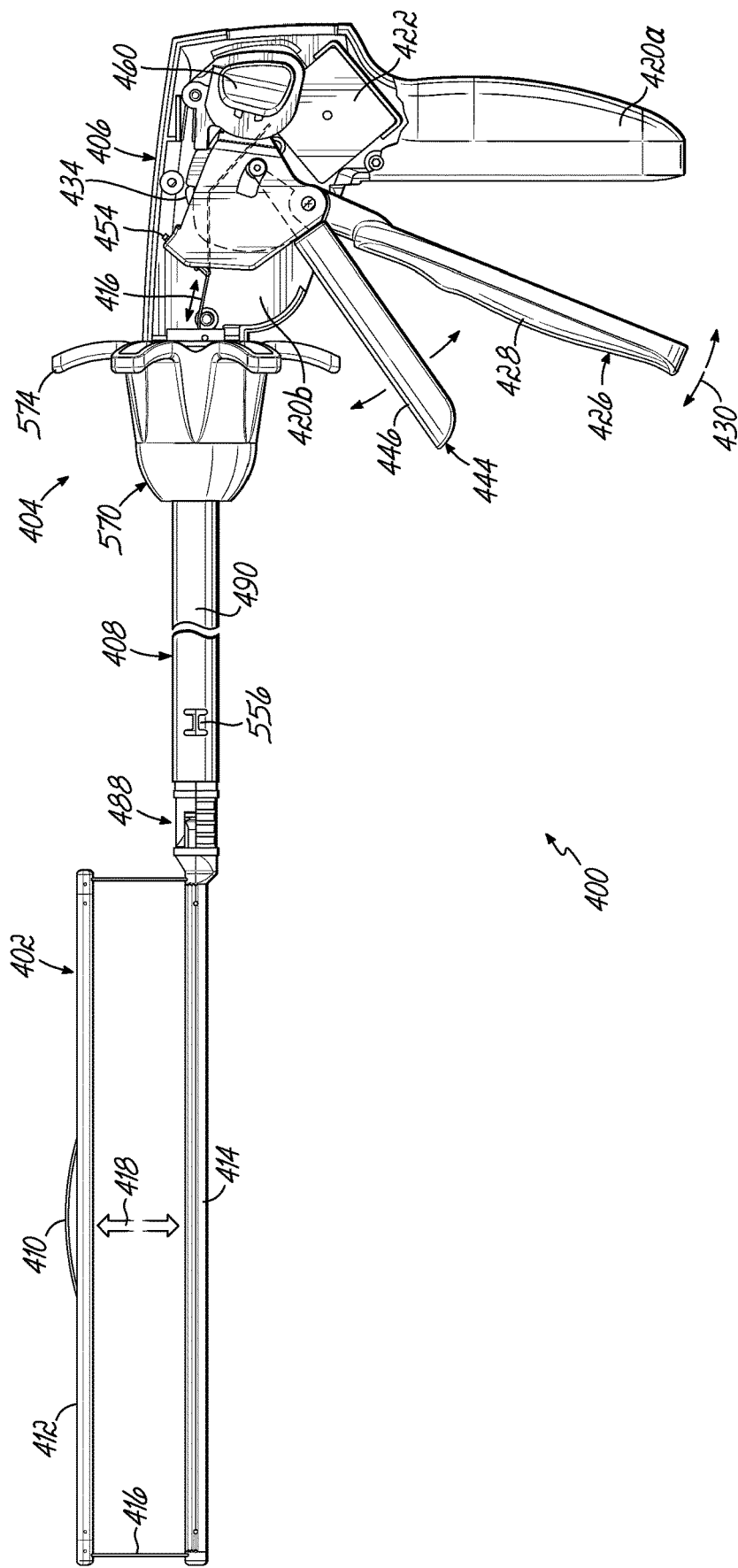
FIGS. 15A and 15B are partial sectional elevation views of the medical device of FIG. 14 with a resection line guide shown in an opened position and a closed position, respectively.
Figure 15B:
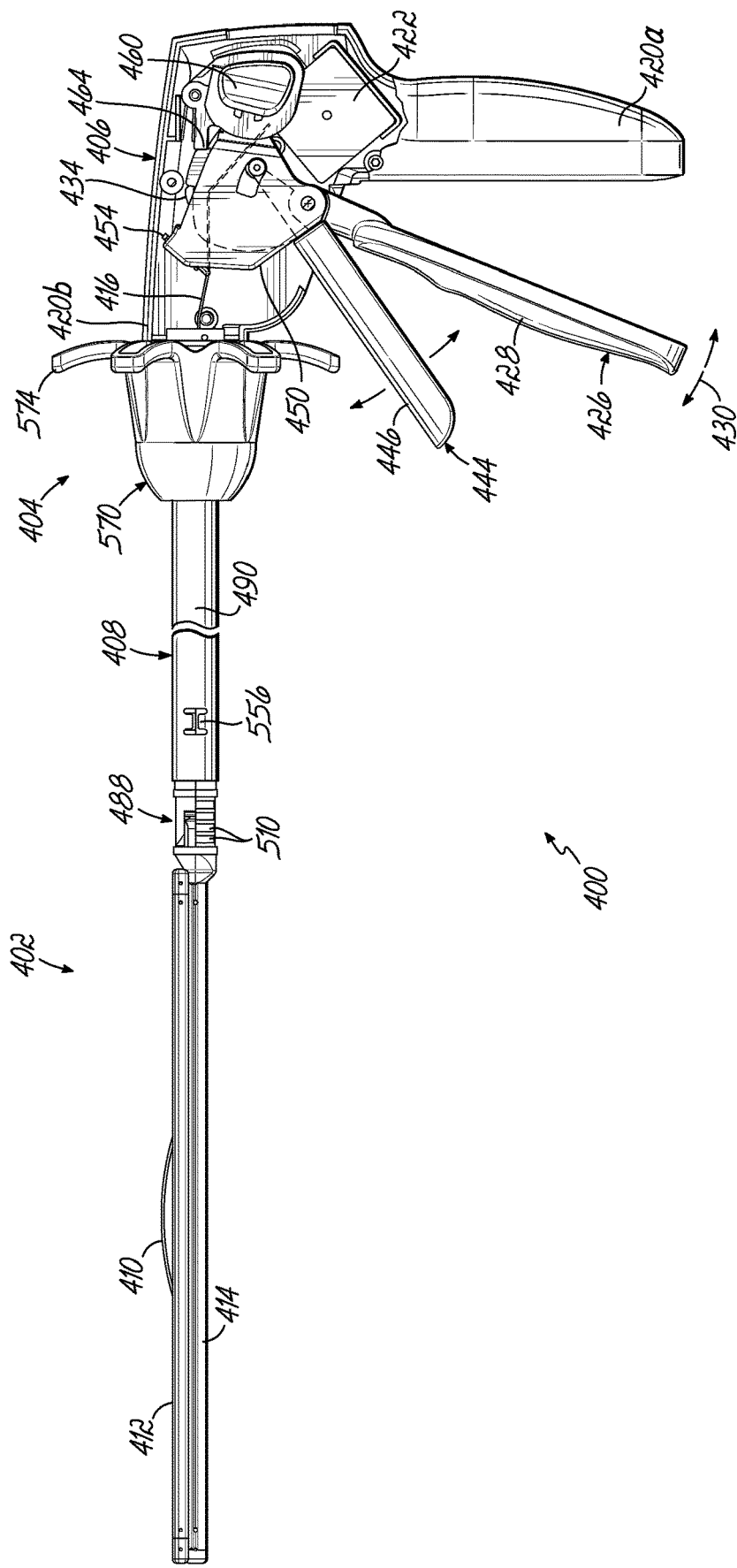
Figure 16:
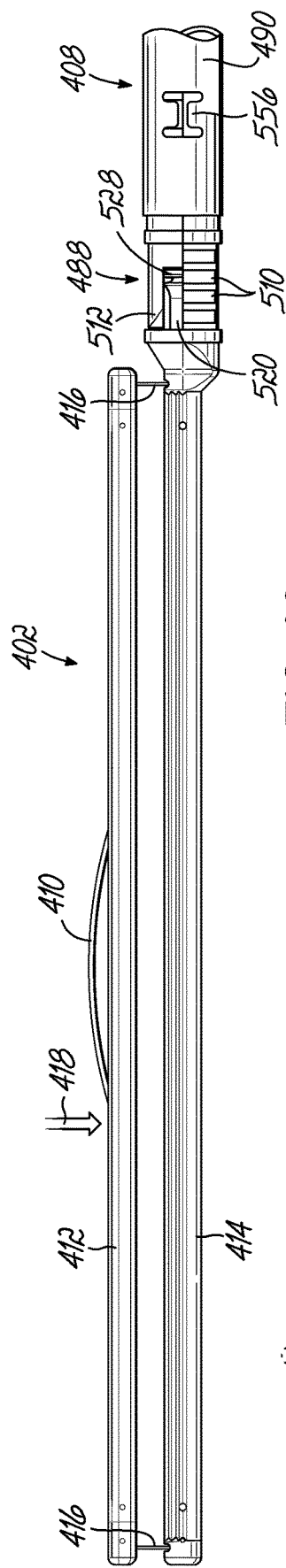
FIG. 16 is an enlarged elevation view of the resection line guide of the medical device of FIG. 14.

According to another aspect and with regard to the mechanisms for effectuating operation of the clamp members 612, 614, and with reference to FIGS. 31, 32A, and 32B, in one embodiment, the manipulator 604 includes a mechanism for tensioning the flexible member 616 similar to the clamping mechanism 444 shown in FIG. 14 and described above. To that end, the manipulator 604 may include a clamping mechanism 660 to forcibly retract the flexible member 616 from the resection line guide 602 and thereby forcibly retract the clamp member 612 toward the clamp member 614. The surgeon may therefore clamp tissue between the clamp members 612, 614 by operating the clamping mechanism 660.

As shown, in one embodiment, the clamping mechanism 660 includes a number of components including a clamping lever 662 that is pivotally mounted within the housing 620a, 620b proximate the locking lever 642. As with the locking lever 642, the surgeon may squeeze the clamping lever 662 during a procedure, as is described below. The clamping lever 662 includes an actuator arm 664 that transfers the load applied by the surgeon on the clamping lever 662 to a clamping bracket 666, which is slidably received within the housing 620a, 620b. The clamping bracket 666 includes a notch 668 which receives the actuator arm 664 as the surgeon squeezes the clamping lever 662. The clamping bracket 666 further includes a stud 670 onto which a clamping spring 672 is mounted. Translational movement of the clamping bracket 666 compresses the clamping spring 672 against a lever arm 676. The lever arm 676 is pivotally mounted within the housing 620a, 620b and is operably coupled to the clamping spring 672 proximate the location at which the flexible member 616 extends from the inner guide tube 627.

A bead 680 (shown in FIG. 32A) is fixedly attached to the flexible member 616 proximate the lever arm 676. The bead 680 may be a generally enlarged portion of the flexible member 616 or other enlarged discontinuity that is crimped, for example, on the flexible member 616 by which the flexible member 616 may be frictionally engaged. While a bead is shown in FIG. 32A, it will be appreciated that other structures may be securely fastened to the flexible member 616. A bead catcher 682 (shown best in FIG. 34B) is operably coupled to the lever arm 676 and is positioned to frictionally engage the bead 680 during rotational action of the lever arm 676. The bead catcher 682 translates in a direction generally away from the resection line guide 602 along a path that is generally coincident with the axis of the shaft 608 and, in doing so, pulls on or retracts the flexible member 616 from the resection line guide 602. It will be appreciated that any slack in the flexible member 616 during retraction from the resection line guide 602 may be taken up by the spring reel 622.

In one embodiment, and with reference to FIGS. 31, 32A, and 32B, the manipulator 604 may include a stop and release mechanism 700 by which one or both of the locking mechanism 640 and the clamping mechanism 660 may be locked in their engaged positions and then later released. To that end, in one embodiment, the stop and release mechanism 700 includes a release lever 702 (shown in the form of a button) that projects from the housing 620a, 620b, for example, from a backside of the pistol-grip device 606. The surgeon may therefore operate the lever 702 with a thumb or a forefinger.

As shown in FIG. 32A, the release lever 702 may be pivotally mounted within the housing 620a, 620b and operably coupled to a spring 704 which biases the lever 702 in an outwardly direction from the pistol-grip device 606. The release lever 702 may include a locking finger 706 that is positioned proximate each of the compression bracket 646 and the clamping bracket 666. The spring 704 biases the locking finger 706 into engagement with each of the compression bracket 646 and the clamping bracket 666 during manipulation of one or both of the clamping lever 662 and the locking lever 642.

The stop and release mechanism 700 may further include a first stop 708 on the compression bracket 646 and a second stop 710 on the clamping bracket 666. The locking finger 706 engages the first stop 708 of the compression bracket 646 as the locking lever 642 is compressed in the direction of the arrow 650. The locking finger 706 is shown engaged with the first stop 708 in FIGS. 33A and 33B as the locking lever 642 reaches the housing 620a, 620b. The locking finger 706 engages the second stop 710 of the clamping bracket 666 as the clamping lever 662 is compressed in the direction of the arrow 684. The locking finger 706 is shown engaged with the second stop 710 (and the first stop 708) in FIG. 34A as the clamping lever 662 reaches a position proximate the locking lever 642 and the housing 620a, 620b.

Figure 34A:
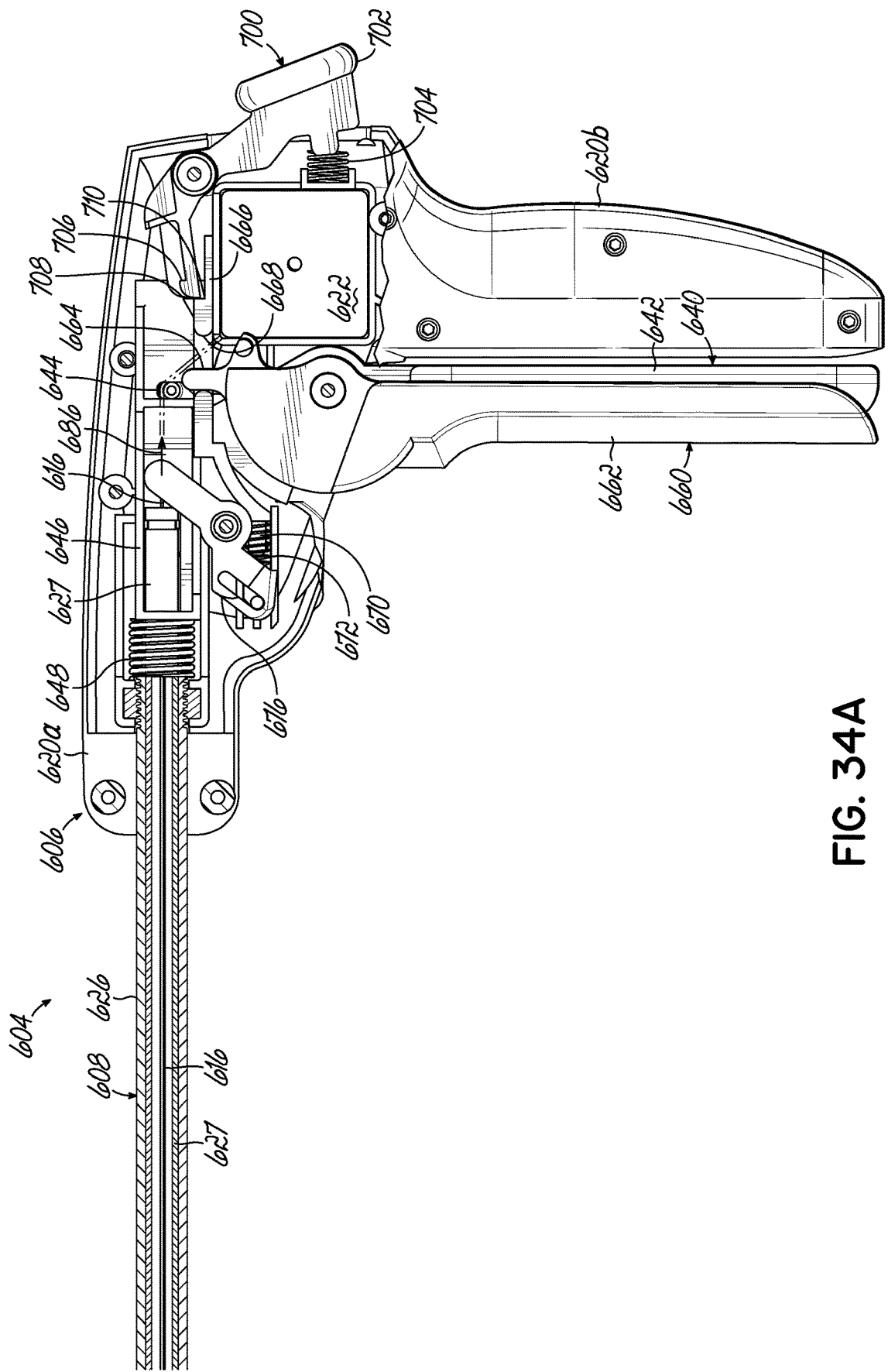
FIGS. 34A and 34B are partial cross-sectional views of the manipulator of the medical device of FIG. 30 depicting engagement of a mechanism according to an embodiment.

With continued reference to FIG. 34A, in one embodiment of the stop and release mechanism 700, a height dimension of the first stop 708 is greater than a height dimension of the second stop 710. It will be appreciated that this configuration allows the locking mechanism 640 to engage with the locking finger 706 first and also allows the locking mechanism 640 to remain engaged with the locking finger 706 even after the clamping mechanism 660 is released. In other words, gradual depression of the release lever 702 releases the clamping mechanism 660 first and only after additional depression of the release lever 702 is the locking mechanism 640 released. When the locking finger 706 is engaged with the stops 708 and 710, the surgeon may let go of each of the levers 642, 662 and the mechanisms 640, 660 will remain engaged. Advantageously, the stop and release mechanism 700 may reduce hand fatigue while also allowing the surgeon the freedom to perform other procedures while the mechanisms 640, 660 remain engaged.

With reference now to FIGS. 32A-32C and 33D, during a procedure and after insertion of the medical device 600 into a patient, the surgeon may orient the resection line guide 602 relative to the shaft 608 as is generally shown by the arrows 641 in FIG. 32C. The surgeon may also orient the clamp members 612, 614 proximate the stomach 10, as is shown in FIG. 33D. The surgeon may then fix the joint 624 relative to the shaft 608 by engaging the locking mechanism 640. It will be appreciated that orienting the clamp members 612, 614 and fixing the joint 624 may be reversed and/or may be repeated multiple times until the surgeon is satisfied that the clamp members 612, 614 are properly oriented relative to the stomach 10.

Figure 33A:
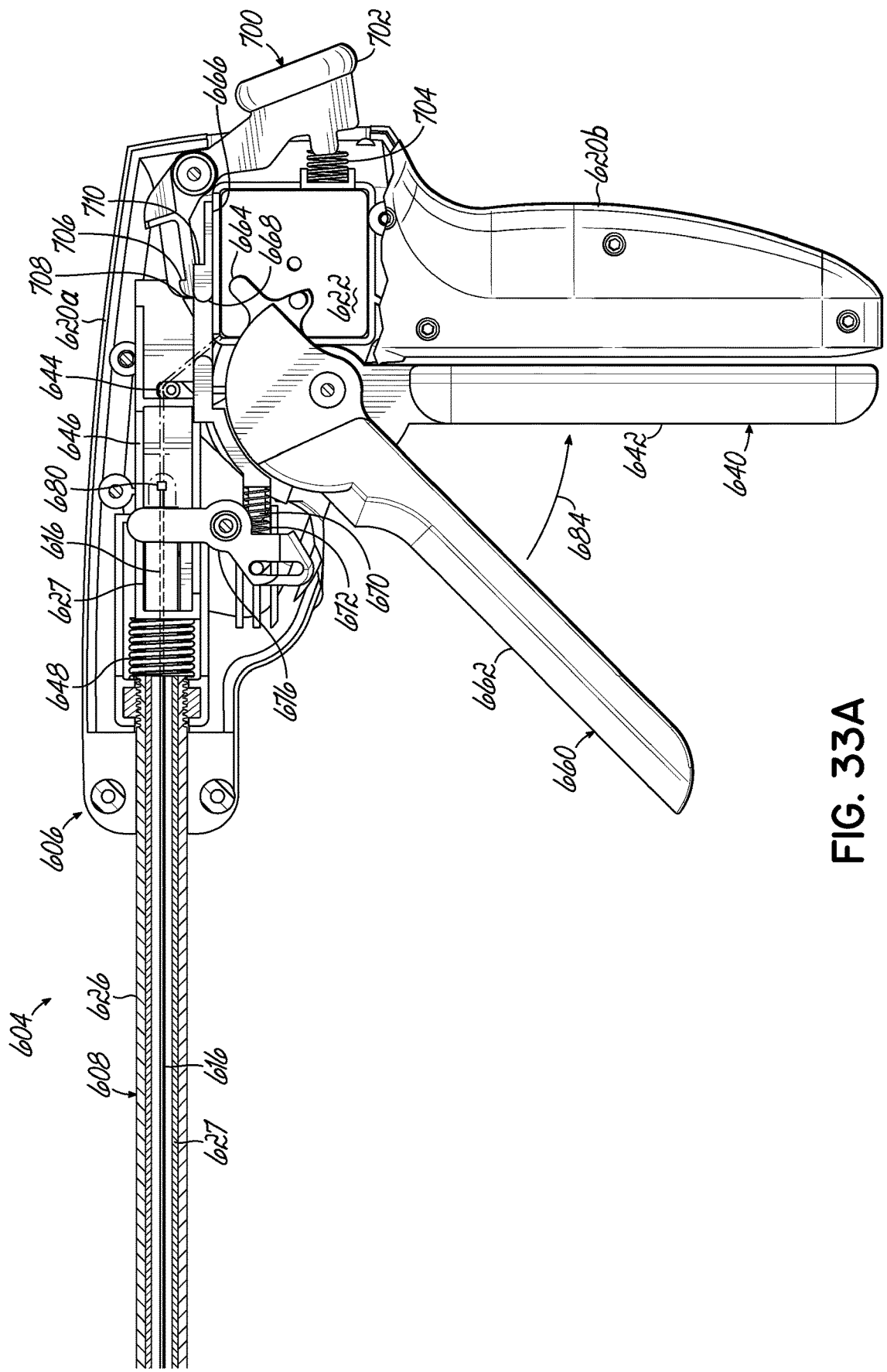
FIGS. 33A and 33B are partial cross-sectional views of the manipulator of the medical device of FIG. 30 depicting engagement of a mechanism according to an embodiment.
Figure 33B:
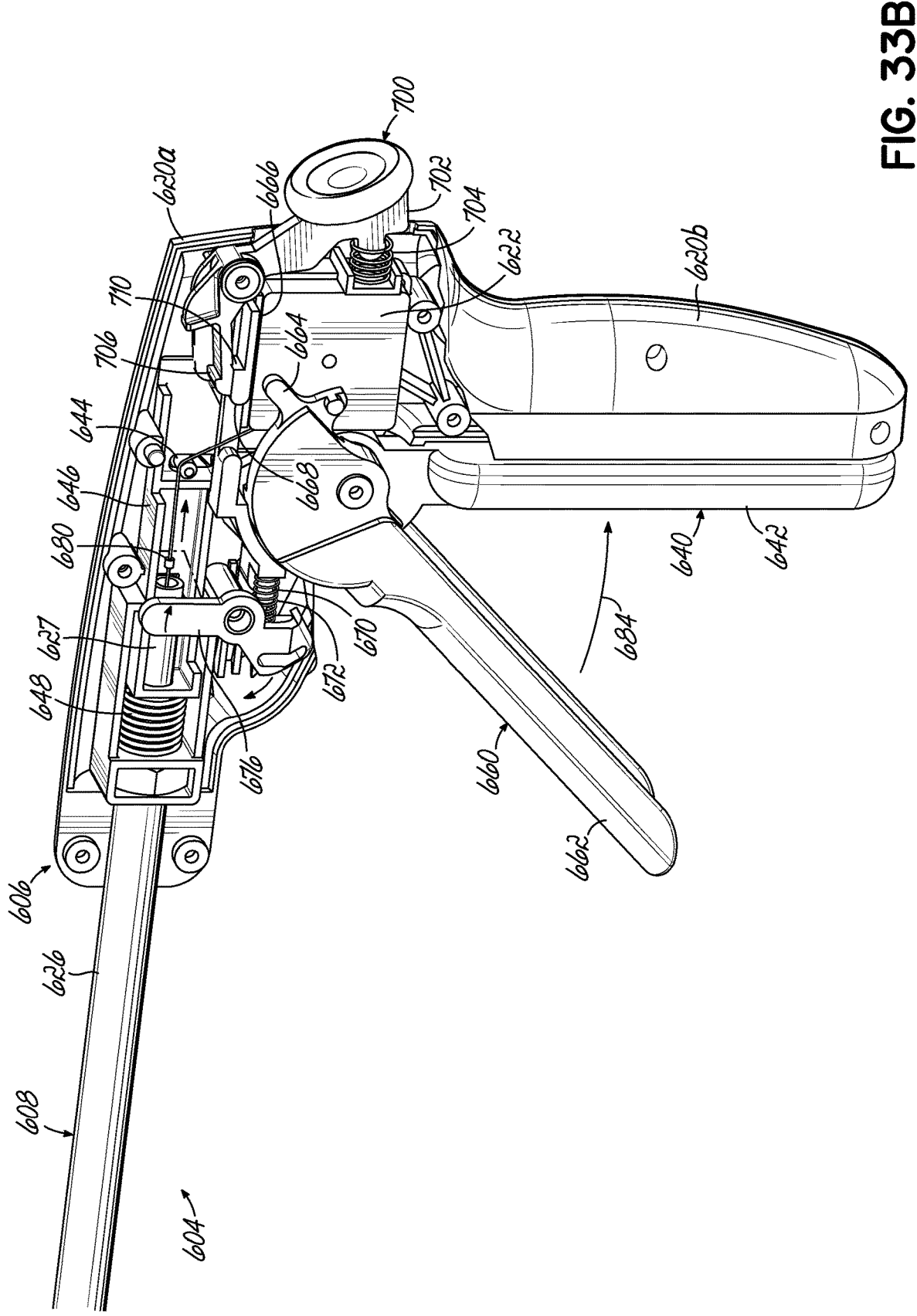

Once properly oriented, the surgeon squeezes the locking lever 642 in the direction of the arrow 650 as shown in FIGS. 32A and 32B. This motion drives the actuation arm 644 into the compression bracket 646 which in turn compresses the spring 648, as is shown in FIGS. 33A and 33B. With reference to FIG. 33C, the load from the spring 648 drives the guide tube 626 axially in the direction of the arrow 652 and into the socket 628. The compression force from the guide tube 626 on the socket 628 causes the socket 628 to compress and frictionally engage the ball 630. The frictional engagement between the ball 630 and the socket 628 inhibits relative movement of the ball 630 and thus locks the joint 624. In this manner, the resection line guide 602 is fixed in position relative to the shaft 608 and resists forces encountered during the procedure that would otherwise change the orientation of the shaft 608 relative to the resection line guide 602 and move the resection line guide 602 out of the desired position.

In one embodiment, compressing the locking lever 642 toward the housing 620a, 620b pushes the compression bracket 646 in the direction of the shaft 608 to a position in which the locking finger 706 engages the first stop 708. With reference to FIGS. 33A and 33B, when the first stop 708 is engaged, if the surgeon lets go of the locking lever 642, the stop and release mechanism 700 will maintain the locking mechanism 640 in its engaged position, and the joint 624 will remain locked.

The operation the clamping mechanism 660 will be described in conjunction with operation of the resection line guide 602 during a surgical procedure. After the resection line guide 602 is position as is described above and the stomach has been effectively mobilized along its greater curve, the surgeon may separate the clamp members 612, 614, for example, by pulling the clamp member 612 with a laparoscopic instrument. Because the first end of the flexible member 616 is fixed to the anchor 617, separating the clamp members 612, 614 causes the spring reel 622 to release a length of the flexible member 616, which slides through the clamp members 612, 614. After positioning the resection line guide around the stomach 10, the surgeon may secure the resection line guide 602 in position by manually moving the clamp member 612 towards the clamp member 614. As the distance between the clamp members 612, 614 decreases, the spring reel 622 takes up any slack in the flexible member 616. When the spring reel 622 takes up slack in the flexible member 616, the clamp members 612, 614 may generally vertically align relative to the stomach 10. At this point, the clamp members 612, 614 may begin to provide a clamping force on the stomach 10.

The securement of the resection line guide 602 to the stomach 10 may be achieved using the two-stage clamping process as described above. More particularly, the flexible member 616 may be pulled so as to generate a clamping force on the stomach 10 less than the threshold clamping force. Again, this first-stage clamping force is configured and selected to provide a certain amount of resistance to movement of the resection line guide 602 relative to the stomach 10. This resistance is configured to prevent undesirable or unintentional movements of the resection line guide 602, but yet permit the surgeon to move the resection line guide 602 to a desired position relative to the stomach 10 without significant difficulty. This may be achieved in this embodiment when the spring reel 622 takes up the slack in the flexible member 616, described above. In the second clamping stage, and with the resection line guide 602 in the desired location relative to the stomach 10, the clamping force of the resection line guide 602 may be increased above the threshold clamping force to effectively prevent or minimize the resection line guide 602 from moving relative to the stomach 10. The upper limit to which the resection line guide 602 may be clamped is selected so as to avoid any damage to the underlying tissue being clamped. This may be achieved in this embodiment by engaging the clamping mechanism 660, as described below.

From the configuration of the manipulator 604 shown in FIG. 33A (with the configuration of the resection line guide 602 shown in FIG. 33D), the surgeon may squeeze the clamping lever 662 in the direction of the arrow 684 in FIGS. 33A and 33B. When the surgeon squeezes the clamping lever 662, the actuator arm 664 enters the notch 668 of the clamping bracket 666 and forces the clamping bracket 666 generally parallel to the longitudinal axis of the shaft 608. By this sliding motion of the clamping bracket 666, the spring 672 is compressed against the lever arm 676 causing it to pivot and pull the bead catcher against the bead 680. Further squeezing of the clamping lever 662 pulls the flexible member 616 through the inner guide tube 627 substantially coincident with the longitudinal axis of the inner guide tube 627 as is generally indicated by arrow 686 in FIG. 34A. This motion causes retraction of the flexible member from the resection line guide 602.

In that regard, the retraction of the flexible member 616 according to the arrow 686 in FIG. 34A is translated into a similar retraction of the flexible member 616 in the resection line guide 602 as is indicated by the arrow 686 in FIG. 34C. Retraction of the flexible member 616 causes the clamp member 612 to forcibly collapse the stomach 10 against the clamp member 614 according to the arrow 618. The stomach 10 may then be clamped as is shown in FIG. 34C. The surgeon may then proceed to cut and staple the stomach 10 relying on the resection line guide 602 to provide the staple line as described above.

Figure 34B:
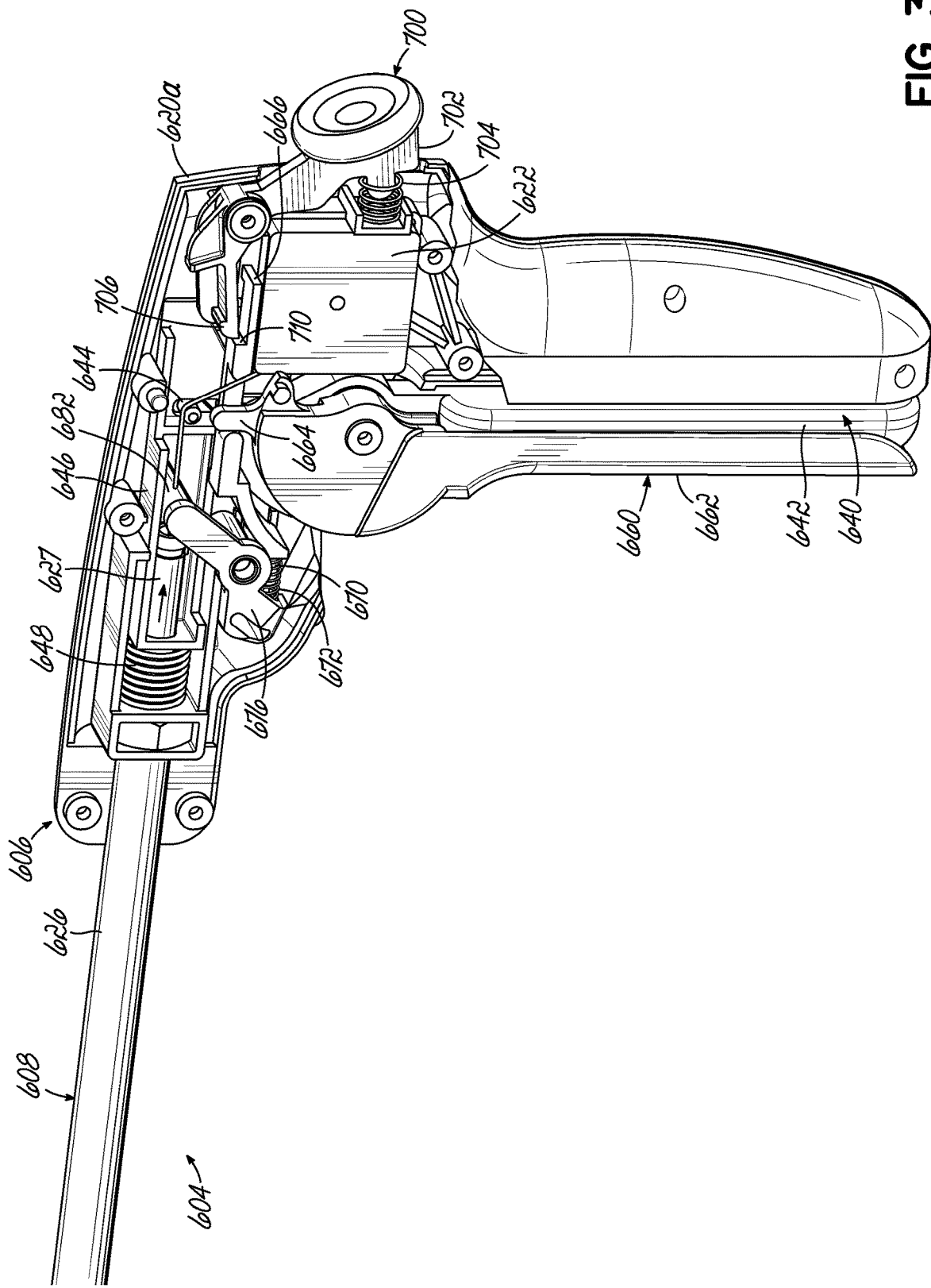

In one embodiment and with reference to FIGS. 34A and 34B, compressing the clamping lever 662 toward the housing 620a, 620b pushes the clamping bracket 666 in the direction of the shaft 608 to a position in which the locking finger 706 engages the second stop 710. If the surgeon lets go of the clamping lever 662, the stop and release mechanism 700 will maintain the clamping mechanism 660 in its engaged position. The surgeon may then let go of the clamping lever 662 and the tension on the flexible member 616 will be maintained.

When the resection line guide 602 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 602 prior to stapling and cutting the stomach 10. Once the resection line guide 602 is finally positioned (e.g., the second clamping stage as described above), the surgeon may then cut and staple the tissue using the resection line guide 602 as a track along the entire segment or a significant part of the segment until complete resection of the stomach 10 occurs. In this regard, a stapling device may abut or engage the resection line guide 602 along an alignment surface to facilitate an improved resection line, similar to that shown above in FIG. 2D.

With reference to FIGS. 34A and 34B, after the resection line 12 is complete, in one embodiment, the surgeon may disengage each of the locking mechanism 640 and the clamping mechanism 660 by activating the stop and release mechanism 700. In particular, the surgeon may depress the release lever 702 with a sufficient force to overcome the outwardly directed bias produced by the spring 704 (and any friction between the stops 708, 710 and the locking finger 706). Pressing on the release lever 702 rotates the locking finger 706 away from the first stop 708 and the second stop 710. Once the locking finger 706 clears the first stop 708 and the second stop 710, the springs 648 and 672, which are compressed, may spontaneously expand (unless the surgeon grasps the levers 642, 662 to control the disengagement) thereby disengaging each of the locking mechanism 640 and the clamping mechanism 660. By way of example, the springs 648 and 672 push the locking lever 642 and the clamping lever 662 from their engaged positions shown in FIG. 34A to their disengaged positions shown in FIG. 32B.

In another embodiment and with reference now to FIGS. 35-38, a medical device 800 performs substantially the same procedure as the medical devices 400 and 600, described above. To that end, the medical device 800 includes a resection line guide 802, which may be one of the guides described above, operatively coupled to a manipulator 804. As shown, the manipulator 804 includes an elongate member or shaft 808 coupled to a handpiece 806 at one end and the resection line guide 802 at the other end thereof. As described above with respect to the medical devices 400 and 600, during a surgical procedure, the resection line guide 802 and a portion of the shaft 808 may be inserted into the patient, such as via a surgical trocar. The surgeon may then manipulate the resection line guide 802 and/or articulate the resection line guide 802 relative to the manipulator 804 to perform the procedure. Thus, embodiments of the present invention may include mechanisms for allowing the resection line guide 802 to articulate relative to the shaft 808 (as is generally depicted by a cone 810 in FIG. 35) and for effectuating a surgical procedure with the resection line guide 802. To at least those ends, the manipulator 804 includes mechanisms that the surgeon may manipulate to independently move the resection line guide 802 to clamp tissue and/or to pivot the resection line guide 802 relative to the manipulator 804, as is described in detail below.

Figure 35:
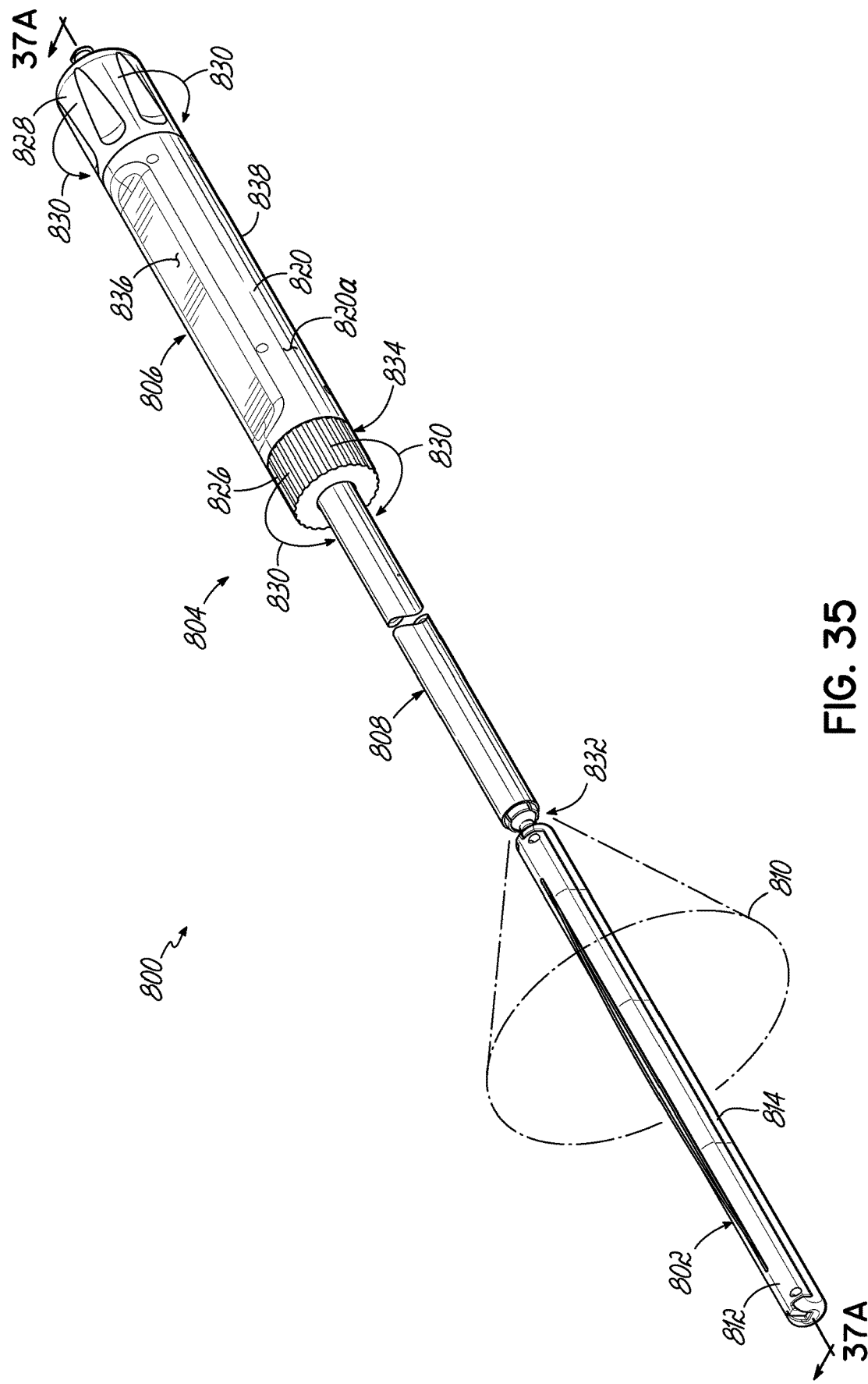
FIG. 35 is a perspective view of a medical device for use in a medical procedure according to one embodiment.
Figure 36:
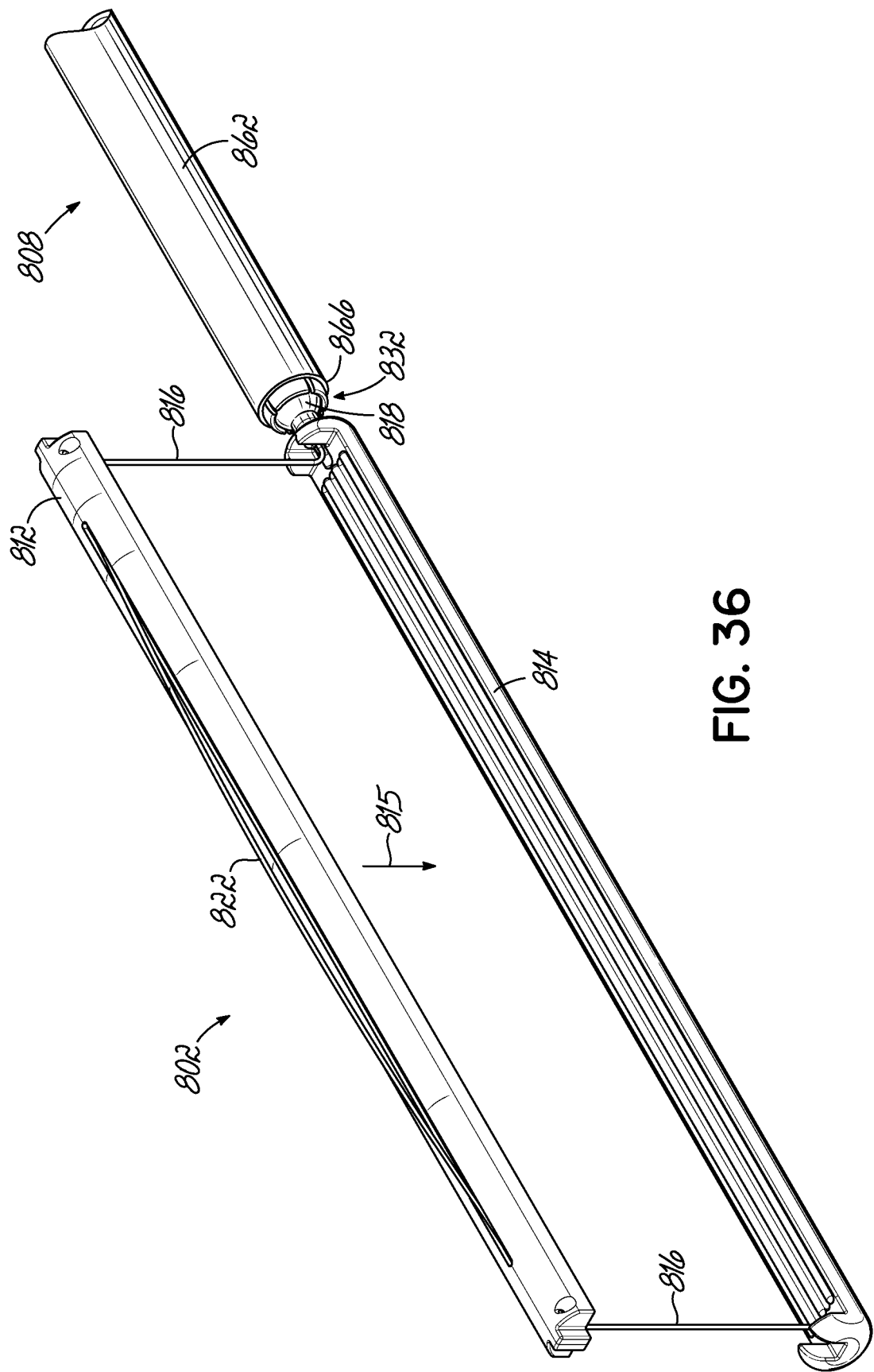
FIG. 36 is a perspective view of a resection line guide of the medical device of FIG. 35 with the resection line guide shown in an opened position.

With reference to FIGS. 35, 36, and 37A, the resection line guide 802 includes clamp members 812, 814 that are movably coupled together via a flexible member 816 (shown in FIG. 36). The flexible member 816 passes through hollow portions of the clamp members 812, 814 so that, for example, the clamp member 812 may be separated from or brought closer to the clamp member 814 during a surgical procedure. In this regard, an anchor 817 fixes a first end of the flexible member 816 to the clamp member 814 adjacent a distal end thereof. Flexible member 816 passes into the clamp member 812 adjacent a distal end thereto and out of the clamp member 812 adjacent a proximal end thereto. Flexible member 816 then passes into the clamp member 814 adjacent a proximal end thereto and into the shaft 808. Retraction of the flexible member 816 from the resection line guide 802 moves at least one of the clamp members 812, 814 as is shown generally by the arrow 815 in FIG. 36 and described below. By way of example only, and without limitation, the resection line guide 802 may include one of the exemplary resection line guides described above, such as, for example, those shown in FIGS. 3E, 4B, and 5A. In the exemplary embodiment shown, the clamp member 814 includes a ball 818, which forms a portion of a joint 832 with the shaft 808 and through which the flexible member 816 passes into the resection line guide 802.

In one embodiment, the resection line guide 802 includes a tab 822. As shown in FIG. 36, the tab 822 extends from the clamp member 812 and allows the surgeon to more easily position the resection line guide 802 during initial placement and during removal following surgery. In the exemplary embodiment, the tab 822 is cable configured to accept surgical grippers, though it will be appreciated that the clamp member 812 may include other features to which the surgeon may more easily grasp and by which the surgeon may manipulate the resection line guide 802.

With reference to FIGS. 35, 37A, and 37B, in one embodiment, the manipulator 804 includes a main body 820 having opposed operating knobs 826, 828 for manipulating portions of the medical device 800. The main body 820 may include housing halves 820a, 820b (labeled in FIG. 35). Each knob 826, 828 is independently rotatable relative to the main body 820 as is indicated by arrows 830 in FIG. 35. In one aspect, the surgeon may lock and unlock the orientation of the resection line guide 802 relative to the shaft 808 with one of the knobs 826, 828. In another aspect, the surgeon may control the extension and retraction of the flexible member 816 from the resection line guide 802 to move clamp member 812, 814 with the other of the knobs 826, 828.

With regard to the former aspect, in one embodiment, the joint 832 movably couples the resection line guide 802 to the shaft 808. For example, the joint 832 may be a ball-and-socket type joint which allows relative pivotal motion between the shaft 808 and the resection line guide 802 as is indicated by cone 810 in FIG. 35. By rotating the knob 826, for example, the surgeon may operate a mechanism located in at least the manipulator 804 to selectively lock and unlock the joint 832. Unlocking the joint 832 allows the surgeon to change the relative orientation of the shaft 808 and the resection line guide 802. The surgeon may use another laparoscopic instrument, such as a surgical gripper, to change the orientation of the resection line guide 802, or the surgeon may push the resection line guide 802 or shaft 808 against another object, such as tissue or the surgical trocar, to provide the desired change in relative orientation. Once positioned, locking the joint 832 fixes a desired orientation between the resection line guide 802 and the shaft 808.

To that end, in one embodiment, the manipulator 804 includes a locking mechanism 834 that the surgeon may utilize to lock the orientation between the shaft 808 and the resection line guide 802. In the exemplary embodiment, the locking mechanism 834 allows for selective locking and unlocking of the joint 832 and includes the knob 826 that cooperates with the main body 820.

With reference to FIGS. 35 and 37A, the main body 820 may have a roughly cylindrical shape with flats 836, 838 for ease of handling and gripping. A main bore 840 extends from one end 842 to an opposite end 844 of the main body 820 and receives portions of the locking mechanism 834. In the exemplary embodiment shown, the main bore 840 extends along the longitudinal axis of the main body 820 and has a variable inside diameter to define a first channel 846 that receives a portion of the knob 826, a second channel 848 that receives a portion of the shaft 808, and a third channel 852 that receives a portion of the knob 828, each of which is described below.

With regard to the locking mechanism 834, the knob 826 includes an engagement portion 854 that couples the knob 826 to the main body 820. The knob 826 is accessible to the surgeon and is rotatable relative to the main body 820 by hand. A rim 856 projects radially outward from the engagement portion 854. The engagement portion 854 is rotably received in the bore 840 with the rim 856 projecting into the first channel 846. By this configuration, the knob 826 is prevented from being inadvertently separated from the main body 820 by providing an interference fit therebetween that resists forces tending to pull the knob 826 axially away from the main body 820 but allows the surgeon to rotate the knob 826.

In the exemplary embodiment shown, the knob 826 may have a toroidal shape with an inside surface 858. It will be appreciated that embodiments of the present invention are not limited to any particular shape of the knob 826 (or to the shape of the knob 828). The dimension of the inside surface 858 is sized to receive a portion of the shaft 808 therein. A portion of the inside surface 858 of the knob 826 may include a thread 860 that cooperates with a portion of the shaft 808. By rotating the knob 826, the thread 860 moves a portion of the shaft 808 so that the surgeon may lock and unlock the joint 832 as described below.

To that end, the shaft 808 includes an outer locking tube 862 and an inner guide tube 864. As shown, the flexible member 816 extends from the main body 820 through the inner guide tube 864 to the joint 832. The inner guide tube 864 has a socket 866 that receives the ball 818 and thus the socket 866 forms a portion of the joint 832. At its other end, the inner guide tube 864 includes a rim 868 that projects radially outward and is received in the second channel 848 of the bore 840. The inner guide tube 864 and outer tube 862 are slidable relative to one another along an axis of the shaft 808. This relative sliding motion facilitates the locking and unlocking of the joint 832.

Specifically, in the embodiment shown in FIGS. 37A and 37B, the outer tube 862 is slidable relative to the inner guide tube 864 along the axis of the shaft 808 as is indicated by the arrow 870. This motion may be produced by a thread 872 on the outer tube 862 that cooperates with the thread 860 on the knob 826. By rotating the knob 826, the thread 860 drives the thread 872 and provides an axially directed sliding motion of the outer tube 862 toward or away from the joint 832 while the inner tube 864 is held in a fixed axial position by interference between the rim 868 and the second channel 848.

As the outer tube 862 slides toward the joint 832, the outer tube 862 compresses the socket 866 of the inner tube 864 on the ball 818. The resulting compression of the socket 866 increases the frictional engagement in the joint 832 as the knob 826 is further rotated to tighten the thread 860 against the thread 872. The frictional contact between the ball 818 and the socket 866 resists relative motion between the resection line guide 802 and the shaft 808. The joint 832 is shown in the locked configuration with the outer tube 862 frictionally engaged with the socket 866 in FIG. 37A.

The joint 832 is shown in the unlocked configuration in FIG. 37B such that the resection line guide 802 may be pivotally adjusted, which is exemplified by arrows 874. To reach this configuration, the surgeon rotates the knob 826 in the opposite direction to that shown in FIG. 37A. This rotational direction of the knob 826 decreases the compression of the joint 832, retracts the outer tube 862 from contact with the socket 866, and thereby unlocks the joint 832. In summary, rotating the knob 826 in one direction locks the joint 832 in position, and rotation of the knob 826 in the other direction unlocks the joint 832.

Figure 38:
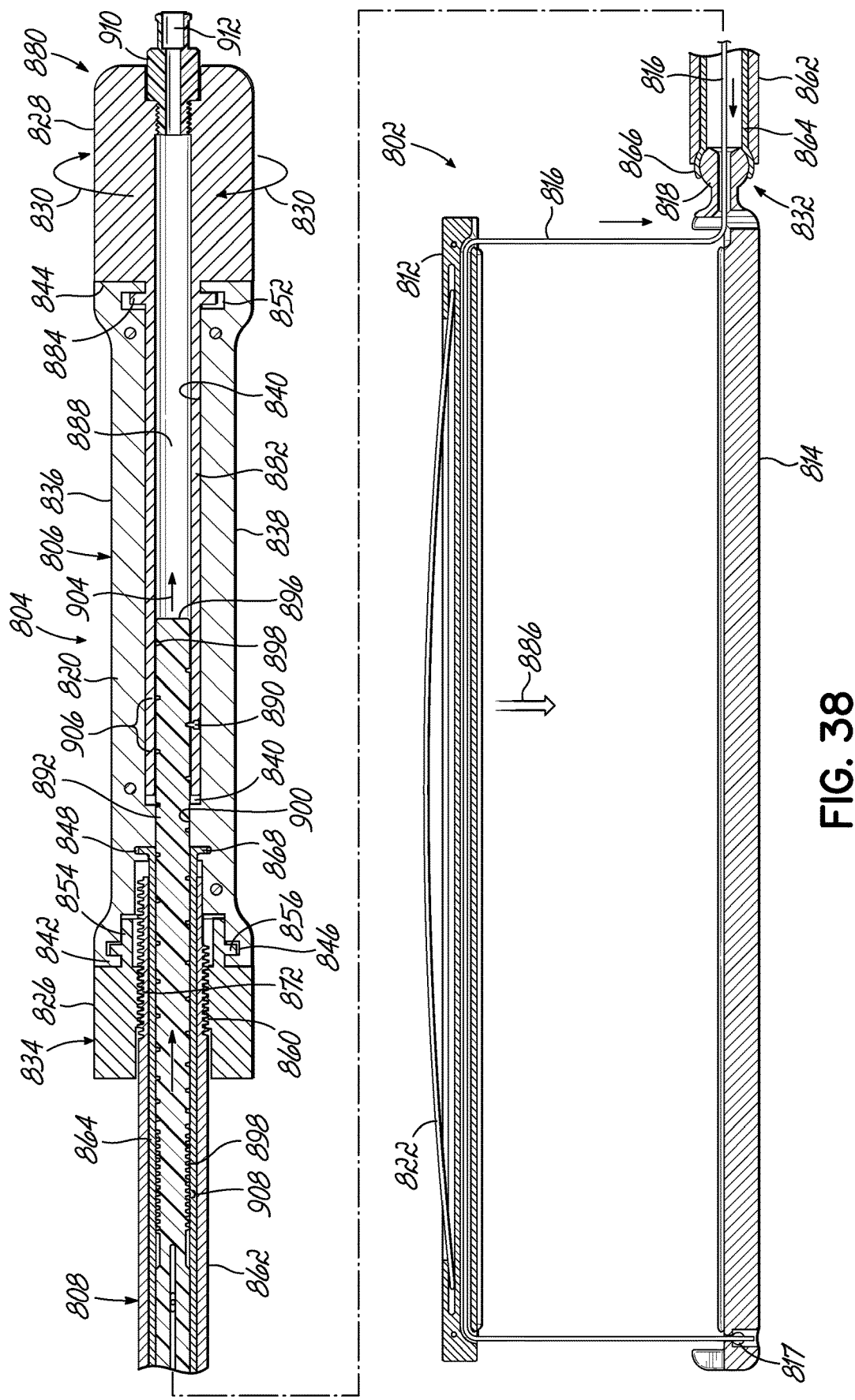
FIG. 38 is a cross-sectional view of the medical device of FIG. 38 depicting engagement of a mechanism according to an embodiment.

With regard to the latter aspect, that is, controlling the extension and retraction of the flexible member 816 to move the clamp members 812, 814, and with reference to FIGS. 35 and 38, the manipulator 804 includes a clamping mechanism 880. In one embodiment, the clamping mechanism 880 includes the knob 828. Generally, rotating the knob 828 in one direction extends the flexible member 816 from the manipulator 804 to allow the clamp members 812, 814 to separate. Rotating the knob 828 in the other direction retracts the flexible member 816 and causes the clamp members 812, 814 to move toward one another (as is generally indicated by arrow 886 in FIG. 38) or to clamp tissue therebetween.

To that end, the knob 828 includes an engagement portion 882. A rim 884 projects radially outward from the engagement portion 882. The engagement portion 882 is rotably received in the bore 840 with the rim 884 projecting into the third channel 852. By this configuration, the knob 828 is prevented from being inadvertently separated from the main body 820 by providing an interference fit therebetween. The knob 828 resists separation from the main body 820 in an axial direction away therefrom similar to the knob 826, described above.

The engagement portion 882 defines an inner bore 888. The engagement portion 882 of the knob 828 may extend the majority of the length of the main body 820. By way of example, the engagement portion 882 and the inner bore 888 may extend from 50% to 75% of the length of the main body 820 as determined by ends 894, 896. A narrow region 900 in the main bore 840 may separate the inner guide tube 864 from the inner bore 888. The narrow region 900 may reduce or eliminate fluid leakage between the inner guide tube 864 and the inner bore 888 or other portions of the main body 820. The knob 828, like the knob 826, is accessible to the surgeon and is rotatable relative to the main body 820 by hand.

In one embodiment, the clamping mechanism 880 includes a follower pin 890 that projects into the inner bore 888 and may be mounted in the engagement portion 882. Further, a cam rod 892 is slidably received in the main bore 840 of the main body 820 and is axially movable relative thereto when the clamping mechanism 880 is engaged. A second end of the flexible member 816 is secured to the cam rod 892 at one end 894 (shown in FIG. 37B) and so is retracted from the resection line guide 802 or extended from the main body 820 during manipulation of the clamping mechanism 880.

In particular, with reference to FIG. 38, the cam rod 892 is slidably received in the inner guide tube 864 and in the inner bore 888 of the engagement portion 882. To facilitate movement of the flexible member 816, the cam rod 892 has a helical groove 898 along at least a portion of its outer surface. The follower pin 890 in the engagement portion 882 is slidably received in the helical groove 898. Rotating the knob 828 rotates the engagement portion 882 and the follower pin 890. The follower pin 890 interacts with the groove 898 to forcibly slide the cam rod 892 in one direction or in the other direction relative to the main body 820. By this axial movement, the flexible member 816 is extended or retracted depending on the direction that the knob 828 is rotated. By way of example, rotation of the knob 828 in the clockwise direction forces the cam rod 892 in the direction of arrow 904 or toward the knob 828. This movement of the cam rod 892 retracts the flexible member 816 from the resection line guide 802.

In one embodiment, as is shown in FIG. 38, the helical groove 898 progressively tightens from one end 896 of the cam rod 892 to the opposite end 894 of the cam rod 892. In other words, the spacing or pitch between successive rotations of the groove 898 at the end 896 is generally indicated at 906. The spacing or pitch between successive rotations of the groove 898 toward the end 894 is generally indicated at 908. As shown, the spacing at end 896 is larger than the spacing of the groove 898 toward the end 894. As such, a single rotation of the knob 828 while the follower pin 890 is engaged with the groove 898 near the end 894 produces a greater axial displacement of the cam rod 892 than a single rotation of the knob 828 while the follower pin 890 is engaged with the groove 898 as the end 894 approaches.

By this configuration, the surgeon may be able to more quickly bring the clamp members 812, 814 from a fully opened configuration (as shown in FIG. 38) to collapse the stomach 10 and during which gross movement of the clamp members 812, 814 is tolerable or even desirable because it saves time. Once initially clamped, and with the follower pin 890 in the groove 898 closer to the end 894, the spacing 908 provides more refined, slower, axial translation of the cam rod 892. This finer movement may allow the surgeon to more finely adjust the position of the clamp members 812, 814 on the stomach 10 and so better control the clamping force. Once the procedure is complete, the spacing difference in the groove 898 allows the surgeon to uncompress the stomach 10 and quickly loosen the flexible member 816 so that the clamp members 812, 814 may be removed from the patient.

In one embodiment, and with reference to FIG. 38, the inner bore 888 of the knob 828 may be capped with a plug 910. The plug 910 may define a bore 912 that fluidly communicates with the inner bore 888 and with the cam rod 892. The surgeon, following a procedure and prior to the next procedure, may inject cleaning solution into the inner bore 888 via the plug 910. This may include removing the plug 910 and injecting the cleaning solution or may include inserting a syringe through the bore 912 and injecting the cleaning solution.

In an exemplary embodiment, the operation of each of the knobs 826, 828 will be described in conjunction with operation of the resection line guide 802 during a surgical procedure. In particular, after the stomach has been effectively mobilized along its greater curve, the surgeon may manipulate the medical device 800 to insert the resection line guide 802 and at least a portion of the shaft 808 into the abdominal cavity through a surgical trocar. If the joint 832 is unlocked, the surgeon may rotate the resection line guide 802 relative to the shaft 808. Once the resection line guide 802 is properly positioned, the surgeon may lock the joint 832 by rotating the knob 826 in a direction which forces the outer locking tube 862 into contact with the socket 866. It will be appreciated that the surgeon may repeat positioning the resection line guide 802, locking the joint 832, and unlocking the joint 832 to reposition the resection line guide 802 numerous times until the surgeon is satisfied that the resection line guide 802 is properly positioned.

The surgeon may separate the clamp members 812, 814, for example, by grasping and pulling the tab 822 with a laparoscopic instrument. Because the first end of the flexible member 816 is fixed to the anchor 817, separating the clamp members 812, 814 causes the flexible member 816 to slide through the clamp members 812, 814. After positioning the resection line guide 802 around the stomach 10, the surgeon may secure the resection line guide 802 in position by manually moving the clamp member 812 towards the clamp member 814. Once the resection line guide 802 is properly positioned with the clamp member 812, 814 on either side of the stomach 10, the surgeon may take up any slack in the flexible member 816 by rotating the knob 828 in a direction that draws the cam rod 892 into the main body 820 so as to pull the flexible member 816 from the resection line guide 802 and cause the clamp members 812, 814 to compress on the stomach 10. When the cam rod 892 takes up slack in the flexible member 816, the clamp members 812, 814 may generally vertically align relative to the stomach 10. At this point, the clamp members 812, 814 may begin to provide a clamping force on the stomach 10.

The securement of the resection line guide 802 to the stomach 10 may be achieved using the two-stage clamping process as described above. In an advantageous aspect of this embodiment, one mechanism may be used to provide the clamping force in both the first and second stages. More particularly, the flexible member 816 may be pulled so as to generate a clamping force on the stomach 10 less than the threshold clamping force. Again, this first-stage clamping force is configured and selected to provide a certain amount of resistance to movement of the resection line guide 802 relative to the stomach 10. This resistance is configured to prevent undesirable or unintentional movements of the resection line guide 802, but yet permit the surgeon to move the resection line guide 802 to a desired position relative to the stomach 10 without significant difficulty. This may be achieved in this embodiment by turning the knob 828 to move the cam rod 892, which takes up any slack in the flexible member 816. In the second clamping stage, and with the resection line guide 802 in the desired location relative to the stomach 10, the clamping force of the resection line guide 802 may be increased above the threshold clamping force to effectively prevent or minimize the resection line guide 802 from moving relative to the stomach 10. The upper limit to which the resection line guide 802 may be clamped is selected so as to avoid any damage to the underlying tissue being clamped. This may be achieved in this embodiment by further turning knob 828, as described below.

As the cam rod 892 is drawn into the main body 820, the rate at which the clamp members 812, 814 approach one another may slow as the follower pin 890 must trace the tighter spacing of the helical groove 898 as the cam rod 892 slides further into the inner bore 888. The surgeon may feel an increase in the torque required to rotate the knob 828 and so may make fine adjustments in the position of the knob 828 to control the clamping force on the stomach 10.

When the resection line guide 802 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach volume defined by the lesser curvature 28 and the resection line 12 will be prior to cutting tissue. If the surgeon is not satisfied with the indication of the expected stomach volume, the surgeon may adjust and manipulate the location and alignment of the resection line guide 802 prior to stapling and cutting the stomach 10. Once the resection line guide 802 is finally positioned (e.g., the second clamping stage as described above), the surgeon may then cut and staple the tissue using the resection line guide 802 as a track along the entire segment or a significant part of the segment until complete resection of the stomach 10 occurs. In this regard, a stapling device may abut or engage the resection line guide 802 along an alignment surface to facilitate an improved resection line, similar to that shown above in FIG. 2D.

Once the staple line is complete, the surgeon may rotate the knob 828 in the opposite direction to allow extension of the flexible member 816 into the resection line guide 802. If the clamp members 812, 814 do not spontaneously separate, the slack in the flexible member 816 may allow the surgeon to separate the clamp members 812, 814 with a tool by pulling on the tab 822. The surgeon may also rotate the knob 826 in the opposite direction to unlock the joint 832, which may aid in removing the resection line guide 802 from the abdominal cavity. The bore 840 may be cleaned by introducing a cleaning solution through the plug 910.

It should be appreciated that the medical devices described above may be modified in several ways, but remain within the scope and spirit of present invention. In embodiments of the present invention where an articulation joint is used, it should be appreciated that the articulation joint may take several forms. A previously discussed embodiment includes passive articulation at a joint using gear teeth and a locking tab. As an alternative, active articulation may be used. For example, a resection line guide may be pivotally connected to a shaft where the connection includes a turning gear, which, when turned, rotates the resection line guide. The turning gear may be connected to a separate component having gear teeth, where that component may be manipulated using one or more bands or cables.

Additional previously discussed embodiments include a freely rotating ball joint and a ball joint that can be locked using a locking tube. A ball joint may be locked using features other than a locking tube. In an embodiment, the surface of the ball may have a pattern of recessions that are capable of mating with the pattern of protrusions on the locking member surface in a variety of angles. When the locking member is in contact with the ball, the mating surfaces prevent the ball from rotating. In a further embodiment, a ball joint may be locked using a spring capable of being engaged and disengaged. Those of ordinary skill in the art may recognize still further embodiments that allow for articulation at a joint.

In embodiments of the present invention that allow for rotation of the clamp members relative to an axis parallel to the clamp members, it should be appreciated that the method of this rotation may take several forms. A previously discussed embodiment includes a resection line guide having two clamp members where the clamp members are capable of mating at multiple angles. In another embodiment, a resection line guide including a ball joint may be capable of free rotation. The resection line guide may be connected to the articulation ball through a resection line guide connector where the articulation ball encompasses the resection line guide connector but allows the resection line guide connector to rotate within the articulation ball. An alternative embodiment may include a resection line guide capable of rotation where the rotation may be locked. By way of example, a clamp member connected to a shaft may be made of two segments have interlocking surfaces connected by a pin. When the two segments are separated, the pin may allow the distal segment to rotate while preventing the two segments from coming completely apart. The rotation of the clamp members relative to an axis parallel to the clamp members may be provided using any other suitable method or mechanism known in the art.

Figure 39:
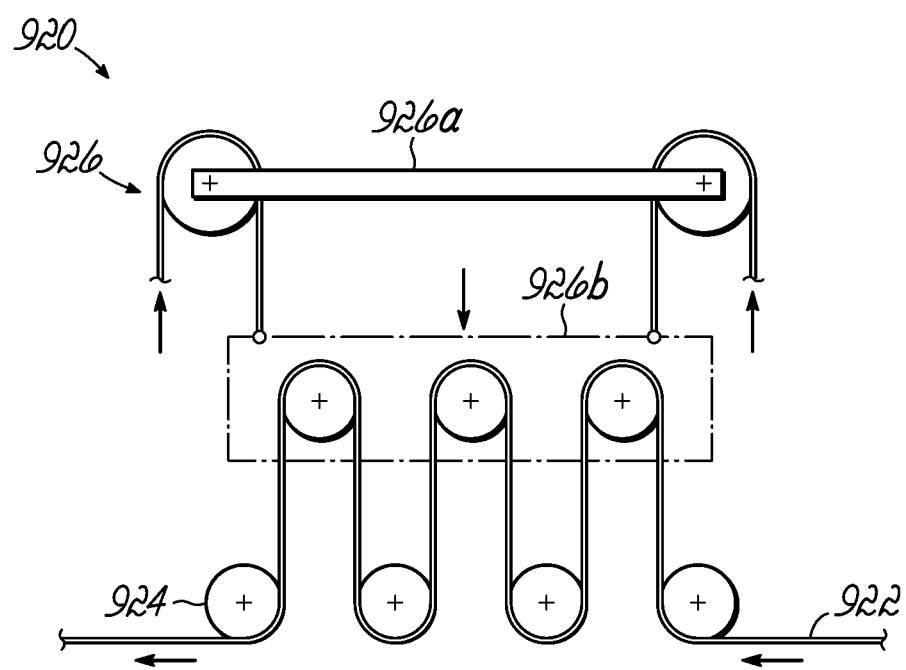
FIG. 39 is a schematic diagram of an accumulator according to one embodiment.

In embodiments of the present invention where tensioning a flexible member provides a clamping force on an anatomical structure, the flexible member may be manipulated in a variety of ways. Previously discussed embodiments include tensioning a flexible member a cinch tube, a cinch ring, a spring reel, and a slidable cam rod. In another embodiment, the flexible member may be connected to a manual reel, where the surgeon manually reels in the flexible member to tighten the resection line guide. Alternatively, the flexible member may be connected to a powered reel, where the surgeon controls a motor that causes the flexible member to be taken up. In another embodiment, the ends of the flexible member may be clamped together where the ends may be pulled through a shaft by a handle, similar to a feature used in a Rumel tourniquet. In another embodiment, the flexible cable connecting two clamp members could be connected to a rack, where the rack can be ratcheted and held in place by a pin that contacts the ridges of the rack. Alternatively, the rack could be moved by turning a gear that engages the ridges on the rack. In another embodiment, the rack could be powered by a motor. Another embodiment may include an accumulator to take up the flexible member. As is shown in FIG. 39, the accumulator 920 may include a flexible member 922 connected to and entwined in two sets of pins 924. When one end of the flexible member 922 is released or pulled from the accumulator 920, the sets of pins 924 move towards each other. The accumulator 920 may include a mechanism 926 that may be configured to increase or decrease the distance between the sets of pins 924. The mechanism 926 may include, for example, a torque shaft 926*a* and a carriage 926*b* that carries one of the sets of pins 924. When the mechanism 926 is engaged, the carriage may move to increase the distance between the sets of pins 924 causing the flexible member 922 to be drawn into the accumulator 920 (not shown). The length of the flexible member 922 able to be taken up or released by the accumulator 920 increases as more pins are used. Those of ordinary skill in the art may recognize still further embodiments that take up and add tension to the flexible member. The flexible member may be taken up using any suitable method known in the art. Additionally, a combination of methods may be utilized to take up the flexible member, which could allow for variation in the speed and control of the take up. For example, a rack and cam rod may be used together, where the flexible member is capable of being taken up by both moving the rack and moving the cam rod. The rack may be pulled for quick take up of the flexible member, and a knob may be spun to move the cam rod for a more controlled take up of the flexible member. Further, if more than one flexible member is used, the flexible members may have the same or independent take up and tensioning mechanisms.

In an aspect of the present invention, certain embodiments may provide an indication of the magnitude or level of the clamping force being provided by the resection line guide. A previously discussed embodiment including a cam rod capable of taking up a length of the flexible member provides the surgeon a tactile indication of the magnitude of the clamping force. In this regard, the torque required to move the cam rod may increase as the amount of flexible member taken up increases. In an alternate embodiment, a resection line guide or medical device may include a visual indicator. By way of example, a medical device may include an indicator window showing an indicator bar that moves as the clamping force decreases or increases. Another embodiment that is capable of measuring the clamping force may display the amount of clamping force or pressure the resection line guide is providing.

In a further advantageous aspect, certain embodiments of the present invention may include a mechanism that limits the clamping force. A previously discussed embodiment included a force limiter and force limiter spring that acted upon the flexible member to limit the force. In an embodiment including a clamping force indicator, a maximum clamping force may also be designated, which indicates to the surgeon the danger of exceeding that clamping force. In another embodiment, the length of flexible member able to be taken up may be limited. By way of example, in an embodiment where the flexible member may be taken up by moving a cam rod, the cam rod may be prevented from moving past a point where an unwanted amount of force is provided by the resection line guide. In an alternate embodiment, a slip-clutch feature may be included to prevent an element with a helical groove from moving past a certain point. Those of ordinary skill in the art may recognize still further embodiments that limit the clamping force provided by the resection line guide.

In an advantageous aspect, the resection line guide may be deployable around an anatomical structure. Further, where a medical device according to the present invention is used, the resection line guide may be separable from the manipulator (not shown). Where the resection line guide may be deployable, the trocar that had been used to place the resection line guide may be used for another purpose, such as inserting another laparoscopic instrument. The resection line guide may be detached at any suitable point in the procedure. In embodiments where two clamp members are connected to provide a clamping force, it is possible that the two clamp members will be placed in the abdominal cavity using two trocars. In a case like this, the surgeon may choose to detach the shaft of the instrument used to place one of the clamp members freeing up one trocar. The surgeon may keep one of the clamp members attached to the handle of the instrument used to place it, which could increase stability of the resection line guide and control over the stomach while stapling along the resection line guide. Alternatively, the surgeon could detach both clamp members leaving the resection line guide fully deployed on the stomach.

Methods of using embodiments of the present invention are discussed above. Broadly, embodiments of the present invention involving resection line guides may be placed inside an abdominal cavity, or other portion of the body, and placed around an anatomical structure to be at least partially resected. Once placed around the anatomical structure, the resection line guide may then be manipulated to provide a clamping force on the anatomical structure. The resection line guide may act as a physical guide that assists the surgeon in envisioning and creating a resection line. The surgeon may use the resection line guide as a spacer or as an aid in estimating the distance of the projected resection line to anatomical landmarks. In creating a staple resection line, the stapler may abut the resection line guide, which aids in creating the desired staple line. The surgeon may choose to resect the anatomical structure to the anatomical left or right of the resection line guide. Straight or curved resection lines may be created in procedures using a resection line guide according to the present invention. Embodiments of the present invention may also aid in control and manipulation of the anatomical structure during the resection. In other words, the resection line guide may act as both a clamp and a guide during the resection.

In another aspect, certain embodiments of the present invention may include two resection line guides positioned on an anatomical structure. In embodiments such as these, the two resection line guides may be positioned on each side of the desired resection line. This may increase the surgeon's control of the anatomical structure during the medical procedure, which may allow for an improved resection line.

Embodiments of the present invention including two clamp members coupled by a flexible member contemplate an amount of slack between the two clamp members when separated. The extent of the available slack affects the method of placing the resection line guide around the stomach. The clamp members may have, for example, about three to about five inches of slack at both the proximal and distal ends between the two clamp members when separated. In an embodiment such as this, the stomach may be mobilized and moved to the side while the bottom clamp member is put into place. The stomach may then be flipped over the bottom clamp member and the top clamp member may be manipulated over the stomach. Alternately, there may be, for example, about one to about three inches of slack between both ends of the clamp members when separated. In embodiments with this amount of slack, the stomach may be slid between the open clamp members using laparoscopic instruments.

While the present invention has been illustrated by a description of various preferred embodiments and while these embodiments have been described in some detail, it is not the intention of the inventor to restrict or in any way limit the scope of the appended claims to such detail. Though the embodiments described herein were primarily directed to a resection line guide, it is clear that many of the aspects of the present invention may be utilized with additional devices. By way of example, the embodiments described herein may operate as a surgical clamp or a stabilizing device independent of the aspects of the present invention that allow the embodiments to act as a guide to a medical instrument. Additional advantages and modifications will readily appear to those skilled in the art. The various features of the invention may be used alone or in any combination depending on the needs and preferences of the user.

What is claimed is:

1. A clamp for a medical procedure, the clamp comprising:
    a first clamp member having a first end and a second end;
    a second clamp member having a first end and a second end;
    a hinge, the hinge coupling the first ends of the first and second clamp members such that the first clamp member is pivotable relative to the second clamp member;
    a biasing member, the biasing member coupling the second ends of the first and second clamp members, wherein the biasing member is configured to apply a clamping force;
    a shaft, the shaft having a proximal end and a distal end, wherein the distal end of the shaft and the biasing member are fixedly coupled with at least one of the first clamp member or the second clamp member for a duration of the medical procedure; and
    an actuator, the actuator being operatively coupled with the biasing member such that the actuator selectively tensions the biasing member to provide the clamping force.

2. The clamp of claim 1, wherein the hinge is a spring.

3. The clamp of claim 2, wherein the spring is extensible such that the first end of the first clamp member and the first end of the second clamp member are spaced apart by a variable gap.

4. The clamp of claim 1, wherein each of the first clamp member and the second clamp member have a rigid unitary construction.

5. The clamp of claim 1, wherein the clamp is configured to have a first stage and a second stage, wherein the first stage comprises a first clamping force and the second stage comprises a second clamping force, and wherein the second clamping force is greater than the first clamping force.

6. The clamp of claim 5, wherein the biasing member is actuated to achieve the first clamping force and the second clamping force.

7. The clamp of claim 5, wherein the first clamping force is from about 0.5 g/mm$^2$ to about 4 g/mm$^2$ and the second clamping force is from about 4 g/mm$^2$ to about 12 g/mm$^2$.

8. The clamp of claim 1, wherein at least one of the first clamp member and the second clamp member include an alignment surface operably configured to engage a stapling device.

9. The clamp of claim 1, further comprising an indicator of tissue thickness.

10. The clamp of claim 1, further comprising a spring reel tensioning device.

11. The clamp of claim 1, further comprising a spring configured to limit the clamping force applied by the biasing member.

12. The clamp of claim 1, wherein adjusting a length of the biasing member adjusts the clamping force.

13. A clamp for a medical procedure, the clamp comprising:
    a first rigid clamp member having a first end and a second end;
    a second rigid clamp member having a first end and a second end;

a pin, the pin coupling the first ends of the first and second rigid clamp members such that the first rigid clamp member is pivotable relative to the second rigid clamp member and such that the first end of the first rigid clamp member is spaced apart from the first end of the second rigid clamp member with a variable gap;

a metal biasing member, the metal biasing member coupling the second ends of the first and second rigid clamp members, wherein the metal biasing member applies a clamping force;

a shaft, the shaft having a proximal end and a distal end, wherein the distal end of the shaft and the metal biasing member are fixedly coupled with at least one of the first rigid clamp member or the second rigid clamp member for a duration of the medical procedure; and an actuator, the actuator being operatively coupled with the metal biasing member such that the actuator selectively tensions the metal biasing member to provide the clamping force.

14. The clamp of claim 13, wherein the metal biasing member is a multi-strand stainless steel cable.

15. The clamp of claim 13, wherein the metal biasing member is selected from the group consisting of a flexible member, a chain, at least one link, and combinations thereof.

16. The clamp of claim 13, wherein the clamp is configured to have a first stage and a second stage, wherein the first stage comprises a first clamping force being from about 0.5 $g/mm^2$ to about 4 $g/mm^2$, and the second stage comprises a second clamping force being from about 4 $g/mm^2$ to about 12 $g/mm^2$.

17. A clamp for a medical procedure, the clamp comprising:

a first rigid clamp member having a proximal end and a distal end;

a second rigid clamp member having a proximal end and a distal end;

a hinge, the hinge coupling the distal ends of the first and second rigid clamp members such that the first rigid clamp member is pivotable relative to the second rigid clamp member and such that the proximal end of the first rigid clamp member is spaced apart from the proximal end of the second rigid clamp member with a variable gap;

a biasing member, the biasing member coupling the proximal ends of the first and second rigid clamp members, wherein the biasing member applies a clamping force;

a shaft, the shaft having a proximal end and a distal end, wherein the distal end of the shaft and the biasing member are fixedly coupled with at least one of the first rigid clamp member or the second rigid clamp member for a duration of the medical procedure; and an actuator, the actuator being operatively coupled with the biasing member such that the actuator selectively tensions the biasing member to provide the clamping force.

18. The clamp of claim 17, wherein the biasing member is selected from the group consisting of a flexible member, a chain, at least one link, and combinations thereof.

19. The clamp of claim 17, wherein the clamp is configured to have a first stage and a second stage, wherein the first stage comprises a first clamping force being from about 0.5 $g/mm^2$ to about 4 $g/mm^2$ and the second stage comprises a second clamping force being from about 4 $g/mm^2$ to about 12 $g/mm^2$.

* * * * *